US012582712B2

(12) United States Patent　　　　(10) Patent No.:　US 12,582,712 B2
Carven et al.　　　　　　　　　　　　(45) **Date of Patent:　*Mar. 24, 2026**

(54) METHOD OF MAKING ANTI-PRO/LATENT MYOSTATIN ANTIBODIES

(71) Applicant: Scholar Rock, Inc., Cambridge, MA (US)

(72) Inventors: Gregory J. Carven, Maynard, MA (US); Michelle Straub, Yarmouth, ME (US); Adriana Donovan, West Roxbury, MA (US); Katherine Jane Turner, Acton, MA (US)

(73) Assignee: Scholar Rock, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/814,221

(22) Filed: Jul. 21, 2022

(65) Prior Publication Data

US 2023/0190929 A1　　Jun. 22, 2023

Related U.S. Application Data

(63) Continuation of application No. 16/946,483, filed on Jun. 24, 2020, now Pat. No. 11,439,704, which is a continuation of application No. 15/760,393, filed as application No. PCT/US2016/052014 on Sep. 15, 2016, now Pat. No. 10,751,413.

(60) Provisional application No. 62/219,094, filed on Sep. 15, 2015.

(51) Int. Cl.

| | |
|---|---|
| *C07K 16/22* | (2006.01) |
| *A61K 39/395* | (2006.01) |
| *A61P 21/04* | (2006.01) |
| *A61P 21/06* | (2006.01) |
| *A61K 39/00* | (2006.01) |
| *A61P 9/00* | (2006.01) |
| *A61P 21/00* | (2006.01) |
| *C07K 14/475* | (2006.01) |

(52) U.S. Cl.

CPC ........ *A61K 39/395* (2013.01); *A61K 39/3955* (2013.01); *A61P 21/04* (2018.01); *A61P 21/06* (2018.01); *A61K 2039/505* (2013.01); *A61K 2039/545* (2013.01); *A61P 9/00* (2018.01); *A61P 21/00* (2018.01); *C07K 14/475* (2013.01); *C07K 16/22* (2013.01); *C07K 2317/24* (2013.01); *C07K 2317/33* (2013.01); *C07K 2317/92* (2013.01)

(58) Field of Classification Search

CPC ..... C07K 16/22; C07K 16/18; A61K 39/3955

See application file for complete search history.

(56) References Cited

U.S. PATENT DOCUMENTS

| | | | |
|---|---|---|---|
| 3,773,919 | A | 11/1973 | Boswell et al. |
| 4,485,045 | A | 11/1984 | Regen |
| 4,544,545 | A | 10/1985 | Ryan et al. |
| 4,816,397 | A | 3/1989 | Boss et al. |
| 4,816,567 | A | 3/1989 | Cabilly et al. |
| 5,013,556 | A | 5/1991 | Woodle et al. |
| 5,223,409 | A | 6/1993 | Ladner et al. |
| 5,981,568 | A | 11/1999 | Kunz et al. |
| 6,096,506 | A | 8/2000 | Lee et al. |
| 6,172,197 | B1 | 1/2001 | Mccafferty et al. |
| 6,291,158 | B1 | 9/2001 | Winter et al. |
| 6,582,915 | B1 | 6/2003 | Griffiths et al. |
| 6,593,081 | B1 | 7/2003 | Griffiths et al. |
| 6,656,475 | B1 | 12/2003 | Lee et al. |
| 6,696,245 | B2 | 2/2004 | Winter et al. |
| 6,858,208 | B2 | 2/2005 | Lee et al. |
| 7,083,784 | B2 | 8/2006 | Dall'acqua et al. |
| 7,138,501 | B2 | 11/2006 | Ruben et al. |
| 7,566,768 | B1 | 7/2009 | Lee et al. |
| 10,287,345 | B2 | 5/2019 | Donovan et al. |
| 10,307,480 | B2 | 6/2019 | Straub et al. |
| 10,751,413 | B2 | 8/2020 | Carven et al. |
| 10,882,904 | B2 | 1/2021 | Donovan et al. |
| 10,934,349 | B2 | 3/2021 | Pordy et al. |
| 10,946,036 | B2 | 3/2021 | Long et al. |
| 11,135,291 | B2 | 10/2021 | Straub et al. |
| 11,155,611 | B2 | 10/2021 | Donovan et al. |
| 11,439,704 | B2 * | 9/2022 | Carven ............... A61K 39/395 |
| 11,925,683 | B2 | 3/2024 | Straub et al. |
| 12,006,359 | B2 | 6/2024 | Donovan et al. |
| 2002/0157126 | A1 | 10/2002 | Lee et al. |
| 2003/0167492 | A1 | 9/2003 | Lee et al. |
| 2005/0049402 | A1 | 3/2005 | Babcook et al. |
| 2005/0143306 | A1 | 6/2005 | Junker et al. |
| 2006/0025340 | A1 | 2/2006 | Knopf et al. |

(Continued)

FOREIGN PATENT DOCUMENTS

| | | |
|---|---|---|
| AU | 2011244851 A1 | 11/2011 |
| CN | 103097415 A | 5/2013 |

(Continued)

OTHER PUBLICATIONS

Knappik et al., "Recombinant Antibody Expression and Purification", Chapter 203 (pp. 1929-1943) of The Protein Protocols Handbook, 2009.*
Amthor et al. "Lack of myostatin results in excessive muscle growth but impaired force generation," Proc Natl Acad Sci U S A. Feb. 6, 2007;104(6):1835-40.
Benjamini et al. (1991) Immunology: A Short Course, 2nd edition, p. 40 only.
Deguise et al. (2017) "New insights into SMA pathogenesis: immune dysfunction and neuroinflammation," Ann Clin Transl Neurol. 4(7):522-53.

(Continued)

*Primary Examiner* — Zachary C Howard

(74) *Attorney, Agent, or Firm* — Finnegan, Henderson, Farabow, Garrett & Dunner, LLP

(57) ABSTRACT

Aspects of the present disclosure relate to antibodies that specifically bind proMyostatin and/or latent Myostatin and uses thereof.

8 Claims, 40 Drawing Sheets

Specification includes a Sequence Listing.

(56) References Cited

U.S. PATENT DOCUMENTS

| | | |
|---|---|---|
| 2006/0216279 A1 | 9/2006 | Glass et al. |
| 2006/0263354 A1 | 11/2006 | Chin et al. |
| 2007/0087000 A1 | 4/2007 | Walsh et al. |
| 2007/0178095 A1 | 8/2007 | Smith et al. |
| 2007/0218067 A1 | 9/2007 | Buttner et al. |
| 2008/0119426 A1 | 5/2008 | Dale |
| 2008/0213251 A1 | 9/2008 | Sexton et al. |
| 2008/0299126 A1 | 12/2008 | Han et al. |
| 2009/0031435 A1 | 1/2009 | Stockwell et al. |
| 2009/0131638 A1 | 5/2009 | Davies et al. |
| 2009/0148436 A1 | 6/2009 | LaVallie et al. |
| 2009/0324590 A1 | 12/2009 | Kambadur et al. |
| 2010/0080811 A1 | 4/2010 | Davies et al. |
| 2010/0087631 A1 | 4/2010 | Han et al. |
| 2010/0166764 A1 | 7/2010 | Sayers et al. |
| 2010/0183616 A1 | 7/2010 | Green et al. |
| 2010/0221777 A1 | 9/2010 | Choe et al. |
| 2010/0331252 A1 | 12/2010 | Hamrick et al. |
| 2011/0165175 A1 | 7/2011 | Linhard et al. |
| 2011/0239317 A1 | 9/2011 | Lee et al. |
| 2011/0256132 A1 | 10/2011 | Ashman et al. |
| 2011/0293630 A1 | 12/2011 | Stitt et al. |
| 2013/0065820 A1 | 3/2013 | Bower et al. |
| 2013/0209489 A1 | 8/2013 | Han et al. |
| 2013/0216548 A1 | 8/2013 | Neijssen et al. |
| 2013/0230515 A1 | 9/2013 | Han et al. |
| 2013/0336982 A1 | 12/2013 | Mader et al. |
| 2014/0017262 A1 | 1/2014 | Sanicola-Nadel et al. |
| 2014/0023638 A1 | 1/2014 | Lavallie et al. |
| 2016/0074474 A1 | 3/2016 | Passini |
| 2016/0199458 A1 | 7/2016 | Knopf et al. |
| 2017/0198032 A1 | 7/2017 | Donovan et al. |
| 2017/0333558 A1 | 11/2017 | Straub et al. |
| 2021/0046180 A1 | 2/2021 | Carven et al. |
| 2021/0283166 A1 | 9/2021 | Long et al. |
| 2021/0332117 A1 | 10/2021 | Donovan et al. |
| 2022/0106390 A1 | 4/2022 | Donovan et al. |
| 2024/0002490 A1 | 1/2024 | Nomikos et al. |
| 2024/0368262 A1 | 11/2024 | Long et al. |
| 2024/0374718 A1 | 11/2024 | Straub et al. |
| 2024/0391989 A1 | 11/2024 | Donovan et al. |

FOREIGN PATENT DOCUMENTS

| | | | |
|---|---|---|---|
| EP | 0171496 A2 | 2/1986 |
| EP | 0173494 A2 | 3/1986 |
| EP | 2853898 A1 | 4/2015 |
| EP | 3922645 | 12/2021 |
| GB | 2177096 B | 5/1989 |
| JP | 2003-520839 | 7/2003 |
| JP | 2004-504826 | 2/2004 |
| JP | 2009-545313 | 12/2009 |
| JP | 2010-502633 | 1/2010 |
| JP | 2012-520887 | 9/2012 |
| JP | 2017536354 | 12/2017 |
| KR | 20070105685 A | 10/2007 |
| WO | WO 90/02809 A1 | 3/1990 |
| WO | WO 91/17271 A1 | 11/1991 |
| WO | WO 92/01047 A1 | 1/1992 |
| WO | WO 92/09690 A2 | 6/1992 |
| WO | WO 92/15679 A1 | 9/1992 |
| WO | WO 92/18619 A1 | 10/1992 |
| WO | WO 92/20791 A1 | 11/1992 |
| WO | WO 93/01288 A1 | 1/1993 |
| WO | WO 1996/001845 A2 | 1/1996 |
| WO | WO 00/53211 A2 | 9/2000 |
| WO | WO 2002/009641 A2 | 2/2002 |
| WO | WO 2002/085306 A2 | 10/2002 |
| WO | WO 2003/027248 A2 | 4/2003 |
| WO | WO 2004/009776 A1 | 1/2004 |
| WO | WO 2004/024890 A2 | 3/2004 |
| WO | WO 2004/037861 A2 | 5/2004 |
| WO | WO 2005/066204 A2 | 7/2005 |
| WO | WO 2005/084699 A1 | 9/2005 |
| WO | WO 2005/103081 A2 | 11/2005 |

| | | | |
|---|---|---|---|
| WO | WO 2005/115439 A2 | 12/2005 |
| WO | WO 2006/116269 A2 | 11/2006 |
| WO | WO 2007/024535 A2 | 3/2007 |
| WO | WO 2007/044411 A3 | 4/2007 |
| WO | WO 2007/047112 A2 | 4/2007 |
| WO | WO 2007/061995 A2 | 5/2007 |
| WO | WO 2008/030367 A2 | 3/2008 |
| WO | WO 2008/067480 A2 | 6/2008 |
| WO | WO 2008/119426 A1 | 10/2008 |
| WO | WO 2009/038760 A2 | 3/2009 |
| WO | WO 2010/070094 A1 | 6/2010 |
| WO | WO 2010/125003 A1 | 11/2010 |
| WO | WO 2010/144452 A1 | 12/2010 |
| WO | WO 2011/122011 A2 | 10/2011 |
| WO | WO 2011/150008 A1 | 12/2011 |
| WO | WO 2012/024242 A1 | 2/2012 |
| WO | WO 2013/071056 A2 | 5/2013 |
| WO | WO 2013/072902 A1 | 5/2013 |
| WO | WO 2013/074557 A1 | 5/2013 |
| WO | WO 2013/148284 A1 | 10/2013 |
| WO | WO 2013/165972 A2 | 11/2013 |
| WO | WO 2013/186719 A1 | 12/2013 |
| WO | WO 2014/074532 A2 | 5/2014 |
| WO | WO 2014/182676 A2 | 11/2014 |
| WO | WO 2015/070158 A1 | 5/2015 |
| WO | WO 2015/195094 A1 | 12/2015 |
| WO | WO 2016/073853 A1 | 5/2016 |
| WO | WO 2016/073879 A2 | 5/2016 |
| WO | WO 2016/073906 A2 | 5/2016 |
| WO | WO 2016/098357 A1 | 6/2016 |
| WO | WO 2016/168613 A1 | 10/2016 |
| WO | WO 2017/049011 A1 | 3/2017 |
| WO | WO 2017/104783 A1 | 6/2017 |
| WO | WO 2017/120523 A2 | 7/2017 |
| WO | WO 2017/218592 A1 | 12/2017 |
| WO | WO 2018/116201 A1 | 6/2018 |
| WO | WO 2018/129395 A1 | 7/2018 |
| WO | WO 2019/193204 A1 | 10/2019 |
| WO | WO 2020/160291 A2 | 8/2020 |
| WO | WO 2022/093724 A1 | 5/2022 |
| WO | WO 2022/164351 A1 | 8/2022 |
| WO | WO 2022/271867 A1 | 12/2022 |
| WO | WO 2023/215384 A2 | 9/2023 |
| WO | WO 2024/064842 A1 | 3/2024 |
| WO | WO 2024/138076 A1 | 6/2024 |

OTHER PUBLICATIONS

Jablonka et al. (2022) "Therapy development for spinal muscular atrophy: perspectives for muscular dystrophies and neurodegenerative disorders," Neurol Res Pract. 4(7):522-530.

Rindt et al. (2012) "Transgenic inactivation of murine myostatin does not decrease the severity of disease in a model of Spinal Muscular Atrophy," Neuromuscul Disord. 22(3):277-85.

Suh et al. (2020) "GDF11 promotes osteogenesis as opposed to MSTN, and follistatin, a MSTN/GDF11 inhibitor, increases muscle mass but weakens bone," Proc Natl Acad Sci U S A. 3;117(9):4910-4920.

Abdiche et al. "Antibodies Targeting Closely Adjacent or Minimally Overlapping Epitopes Can Displace One Another", PLoS One. Jan. 6, 2017;12(1):e0169535.

Abdiche et al. "High-throughput epitope binning assays on label-free array-based biosensors can yield exquisite epitope discrimination that facilitates the selection of monoclonal antibodies with functional activity", PLoS One. Mar. 20, 2014;9(3):e92451.

Al-Zaidy et al., "Follistatin Gene Therapy Improves Ambulation in Becker Muscular Dystrophy", J Neuromuscul Dis. 2015; 2(3):185-192.

Anonymous, "History of Changes for Study: NCT03921528", Jan. 13, 2020. URL:https://clinicaltrials.gov/ct2/history/NCT03921528?V_13=View#StudyPage Top (6 pgs.).

Anonymous, "NCT05115110: A Study to Investigate the Safety and Efficacy of RO7204239 in Combination With Risdiplam (RO7034067) in Ambulat Spinal Muscular Atrophy", Nov. 1, 2021 (Nov. 1, 2021), URL:https://clinicaltrials.gov/ct2/history/NCT05115110?V_1=View#StudyPage Top [retrieved from the internet on Mar. 18, 2022].

(56)  References Cited

OTHER PUBLICATIONS

Anonymous, "Scholar Rock Announces Positive Proof-of-Concept Data from TOPAZ Phase 2 Trial Interim Analysis of SRK-015 in Patients with Type 2 and Type 3 Spinal Muscular Atrophy" Business Wire, Oct. 27, 2020. (7pgs.).

Barrett et al., "A Randomized Phase 1 Safety, Pharmacokinetic and Pharmacodynamic Study of the Novel Myostatin Inhibitor Apitegromab (SRK-015): A Potential Treatment for Spinal Muscular Atrophy", May 8, 2021 vol. 38, No. 6, p. 3203-3222.

Bowerman et al., "UK SMA Research Consortium. Therapeutic strategies for spinal muscular atrophy: SMN and beyond", Dis Model Mech. 2017; 10(8):943-954.

Cambridge Mass et al., "Scholar Rock Announces Positive Interim Results from Phase 1 Trial of SRK-015 in Healthy Volunteers and Updates on Future Development Plans", Feb. 19, 2019. (3pgs.).

Castellana et al., "Resurrection of a clinical antibody: template proteogenomic de novo proteomic sequencing and reverse engineering of an anti-lymphotoxin-$\alpha$ antibody", Proteomics. Feb. 2011;11(3):395-405.

Chan et al., "Bone Geometry is Altered by Follistatin-Induced Muscle Growth in Young Adult Male Mice", JBMR Plus, 2021, 5(4):e10477 (12 pgs.).

Corey, "Nusinersen, an antisense oligonucleotide drug for spinal muscular atrophy", Nature Neuroscience, vol. 20, Feb. 13, 2017, pp. 497-499.

Crawford et al., "Apitegromab in Spinal Muscular Atrophy (SMA): An Analysis of Multiple Efficacy Endpoints in the TOPAZ Trial (P15-5.005)", American Academy of Neurology (May 3, 2022), vol. 98, No. 18 Supp.

Crawford et al., "Relationship of pharmacokinetics and pharmacodynamics to apitegromab efficacy in patients with later-onset spinal muscular atrophy (Types 2 and 3 SMA): Results from the TOPAZ study", Abstracts/Journal of Neurological Sciences Oct. 2021, vol. 429.

Extended European Search Report in EP23158609.0, mailed Aug. 8, 2023, 27 pages.

Gorgey et al., "Effects of spinal cord injury on body composition and metabolic profile—Part I" J Spinal Cord Med. 2014; 37(6):693-702.

Hagan, "When are mice considered old?", 2017, https://www.iax.org/news-and insights/jax-blog/2017/november/when-are-mice-considered-old.

Hua et al., "Enhancement of SMN2 Exon 7 inclusion by Antisense Oligonucleotides Targeting the Exon", PLOS Biology, Published Apr. 2007, vol. 5, pp. 0729-0742.

International Search Report and Written Opinion of the International Searching Authority received in PCT/US2021/056517, mailed Mar. 2, 2022 (23 pgs.).

International Search Report and Written Opinion of the International Searching Authority received in PCT/US2022/034588, mailed Jun. 10, 2022 (10 pgs.).

International Search Report and Written Opinion of the International Searching Authority received in PCT/US2023/020843, mailed Oct. 30, 2023 (21 pgs.).

Kubo et al., "A new method for SMN1 and hybrid SMN gene analysis in spinal muscular atrophy using long-range PCR followed by Sequencing", Journal of Human Genetics, Published Feb. 26, 2015, pp. 233-238.

Lee, "Myostatin: A Skeletal Muscle Chalone", Annu Rev Physiol., 2023, 10;85:269-291.

Markovits et al., The diversity of the immune response to the A2 domain of human factor VIII. Blood. Apr. 4, 2013;121(14):2785-95.

Opposition Proceedings in EP 3368069—Carpmaels submission, Feb. 9, 2024 (127 pgs.).

Opposition Proceedings in EP 3368069—Declaration of Ms. Ying Qian filed Feb. 9, 2024 (2pgs).

Opposition Proceedings in EP 3368069—DFMP submission pursuant to Rule 116 EPC, Feb. 9, 2024 (13 pgs.).

Opposition Proceedings in EP 3368069—Hoffmann Eitle comments under Rule 116 EPC, Feb. 9, 2024 (23 pgs.).

Opposition Proceedings in EP 3368069—Hoffmann Eitle Submission, Apr. 2, 2024 (23 pgs.).

Opposition Proceedings in EP 3368069—Second Declaration of Dr. Karen Chen (3 pgs.).

Passey et al., "Emerging therapies for the treatment of skeletal muscle wasting in chronic obstructive pulmonary disease", Pharmacol Ther. 2016; 166:56-70.

Place et al., "A Phase 2 Study to Evaluate the Efficacy and Safety of SRK-015 in Patients with Later-Onset Spinal Muscular Atrophy (TOPAZ): An Introduction" May 26, 2020. URL:https://scholarrock.com/wp-content/uploads/2020/09/MDA-2020-TOPAZ-SMA-Introduction.pdf [retrieved from internet on Dec. 20, 2021].

Place et al., "SMA—THERAPY P.253 Clinical Development of SRK-015, a Fully Human Anti-proMyostatin Monoclonal Antibody, for the Treatment of Later-Onset Spinal Muscular Atrophy," Abstracts/Neuromuscular Disorders, Elsevier Ltd., GB, vol. 30 (2020) (2 pgs.).

Place et al., "TOPAZ: Phase 2 study evaluating efficacy and safety of apitegromab in later-onset spinal muscular atrophy", EMBASE2021, Database accession No. EMB-635747941, Retrieved from the Internet: URL:Elsevier Science Publishers, Amsterdam, Nl 1-24 abstract; & PLACE et al., "TOPAZ: Phase 2 study evaluating efficacy and safety of apitegromab in later-onset spinal muscular atrophy", Journal of Neuromuscular Diseases 2021 IOS Press NLD, vol. 8, No. Suppl 1, 2021, p. S9 Conf 20210528 to 20210529 Virtual-16th Inte.

Pyatt et al., "A feasability study for the newborn screening of spinal muscular atrophy", Genetics in Medicine, Published Jul. 2006, vol. 8, pp. 428-435.

Saitoh et al., "Myostatin inhibitors as pharmacological treatment for muscle wasting and muscular dystrophy", Journal of Cachexia, Sarcopenia and Muscle - Clinical Reports, vol. 2, Issue 1, 2017, e00037 (10 pgs.).

Scholar Rock press release (2021): Scholar Rock Announces Positive 12-Month Top-Line Results From the TOPAZ Phase 2 Clinical Trial Evaluating Apitegromab in Patients With Type 2 and Type 3 Spinal Muscular Atrophy (SMA).

Scholar Rock stuns with positive results for SRK-015 in SMA patients (2020) (https://www.thepharmaletter.com/article/scholar-rock-stuns-with-positive- resultsfor-srk-015-in-smapatients#>:text= US%20clinical%2Dstage%20biotech%20Scholar,a%20public% 2Ooffering%20of%20shares.).

Second Written Opinion of the International Preliminary Examining Authority for PCT/US2017/012606 dated Jan. 3, 2018.

Sidis et al., "Biological activity of follistatin isoforms and follistatin-like-3 is dependent on differential cell surface binding and specificity for activin, myostatin, and bone morphogenetic proteins", Endocrinology. 2006; 147(7):3586-97.

Staels et al., "Fibrates and future PPARalpha agonists in the treatment of cardiovascular disease", Nat Clin Pract Cardiovasc Med. 2008, 5(9):542-53.

Trevogrumab: Statement on a Nonproprietary Name Adopted By the Usan Council (2015) (https://searchusan.amaassn.org/undefined/documentDownload?uri=%2Funstructured%2Fbinary%2Fusan%2Ftrevogrumab.pdf).

U.S. Appl. No. 62/486,934, filed Apr. 18, 2017.

Vai et al., "Bone and Spinal Muscular Atrophy", Bone. 2015; 79:116-20.

Wallner et al., "Inhibition of GDF8 (Myostatin) accelerates bone regeneration in diabetes mellitus type 2", Sci Rep. Aug. 29, 2017;7(1):9878 (11 pgs.).

Zhou et al., "Myostatin inhibition in combination with antisense oligonucleotide therapy improves outcomes in spinal muscular atrophy", J Cachexia Sarcopenia Muscle. 2020, 11(3):768-782.

Anderson et al., (2008) "Identification of a novel pool of extracellular pro myostatin in skeletal muscle", The Journal of Biological Chemistry, 283(11):7027-7035.

Anonymous (2005) "Human Myostatin ELISA—Prodomain specific", BioVendor Laboratory Medicine, Inc., XP055100354, Retrieved from the Internet: URL:http://deltaclon.es/pdf/RD193058100.pdf (10 pgs.).

(56) References Cited

OTHER PUBLICATIONS

Anonymous (2017) "SC 2. Anterolateral Systems—Deficits" [online]. Retrieved from: http://www.neuroanatomy.wisc.edu/sc97/text/p2/deficits.htm; on Jul. 11, 2017 (1 page).
Anonymous (2019) "GDF-11/BMP-11 Mouse anti-Human, Clone: 743833, R&D Systems(TM)" [online]. Retrieved from: http://www.fishersci.co.uk/shop/products/gdf-11bpm-11-mouse-anti-human-clone-743833-r-d-systems/15724724; on Feb. 28, 2019 (4 pgs.).
Australian Application No. 202010134, filed Jul. 27, 2020, for Scholar Rock, Inc.: Examination Report No. 1, issued Oct. 15, 2020.
Baranello et al., (2020) "Evaluation of body composition as a potential biomarker in spinal muscular atrophy", Muscle & Nerve, 61(4):530-534.
Benatar (2007) "Lost in translation: Treatment trials in the SOD1 mouse and in human ALS", Neurobiology of Disease, 26:1-13.
Bernardo et al. (2010) "Postnatal PPARdelta activation and myostatin inhibition exert distinct yet complimentary effects on the metabolic profile of obese insulin-resistant mice," PLoS One. 25;5(6):e11307.
Biovendor, Research and Diagnostics Products. Myostatin Propeptide Human, Chicken Polyclonal Antibody. Product Data Sheet 2 pgs. Apr. 11, 2013.
Bräuninger et al., (2003) "Epstein-Barr virus (EBV)-positive lymphoproliferations in post-transplant patients show immunoglobulin V gene mutation patterns suggesting interference of EBV with normal B cell differentiation processes", Eur J Immunol., 33(6):1593-1602.
Breitbart et al., (2013) "Highly specific detection of myostatin prodomain by an immunoradiometric sandwich assay in serum of healthy individuals and patients", PLoS One, 8(11):e80454 (10 pgs.).
Brown et al., (1996) "Tolerance of single, but not multiple, amino acid replacements in antibody VH CDR 2: a means of minimizing B cell wastage from somatic hypermutation?", J Immunol., 156(9):3285-3291.
Burch et al., (2017) "Reduced serum myostatin concentrations associated with genetic muscle disease progression", Journal of Neurology, 264(3):541-553.
Chen Declaration filed in opposition of EP Patent No. 3368069 on Apr. 27, 2022 ( 2pgs.).
Chen et al., "Considerations for Developing Combination Therapies in SMA", Cure SMA Researcher Meeting, Jun. 16, 2016.
Ciciliot et al., (2013) "Muscle type and fiber type specificity in muscle wasting", Int J Biochem Cell Biol., 45(10):2191-2199.
Cohen et al., (2015) "Muscle wasting in disease: molecular mechanisms and promising therapies", Nat Rev Drug Discov., 14(1):58-74.
Cully, (2014) "Beefing up the right splice variant to treat spinal muscular atrophy". Nat Rev Drug Discov 13, 725. https://doi.org/10.1038/nrd4445 (1 pg.).
Cure SMA Presentation filed in opposition of EP Patent No. 3368069 on Apr. 27, 2022 (86 pgs.).
Dagbay et al., (2020) "Structural basis of specific inhibition of extracellular activation of pro- or latent myostatin by the monoclonal antibody SRK-015", J. Biol. Chem., 295(16):5404-5418.
Dalbo et al., (2017) "Testosterone and trenbolone enanthate increase mature myostatin protein expression despite increasing skeletal muscle hypertrophy and satellite cell number in rodent muscle", Andrologia, 49(3):1-11.
Day et al., (2021) "Onasemnogene abeparvovec gene therapy for symptomatic infantile-onset spinal muscular atrophy in patients with two copies of SMN2 (STR1VE): an open-label, single-arm, multicentre, phase 3 trial", Lancet Neurol, 20:284-293.
Dibernardo et al., (2006) "Translating preclinical insights into effective human trials in ALS", Biochimica et Biophysica Acta, 1762:1139-1149.
D'ydewalle et al., (2015) "Spinal muscular atrophy therapeutics: where do we stand?", Neurotherapeutics, 12(2):303-316.
Egerman et al., (2015) "GDF11 Increases with Age and Inhibits Skeletal Muscle Regeneration", Cell Metabolism, 22(1):164-174.

European Patent Application No. 16828657.3, by Scholar Rock, Inc.: Supplementary European Search Report and Opinion, dated Mar. 20, 2019.
European Patent Application No. 20179533.3, by Scholar Rock, Inc.: Partial European Search Report, dated Mar. 31, 2021 (12 pgs.).
European Patent Application No. 20193425.4, by Scholar Rock, Inc.: European Search Report, dated Apr. 1, 2021 (9 pgs.).
Extended European Search Report in EP Application No. 21170667.6 dated Nov. 11, 2021.
Farrar et al. (2017) "Emerging therapies and challenges in spinal muscular atrophy" Ann Neural 81(3): 355-368. Published online Feb. 1, 20177. doi: 10.1002/ana.24864. Publication details included.
Feng et al., (2016) "Pharmacologically induced mouse model of adult spinal muscular atrophy to evaluate effectiveness of therapeutics after disease onset", Human Molecular Genetics, 25(5):964-975.
Ferrara et al., (2015) "Recombinant renewable polyclonal antibodies", MAbs, 7(1):32-41.
Fidler, (2016) "Scholar Rock Rolls Up $36M to Move Muscle Drug to Clinical Trials" https://xconomy.com/boston/2016/01/04/scholar-rock-rolls-up-36m-to-move-muscle-drug-to-clinical-trials/.
Ge et al., (2005) "GDF11 Forms a Bone Morphogenetic Protein 1-Activated Latent Complex That Can Modulate Nerve Growth Factor—Induced Differentiation of PC12 Cells", Molecular and Cellular Biology, 25(14):5846-5858.
Giangregorio et al., (2006) "Bone Loss and Muscle Atrophy in Spinal Cord Injury: Epidemiology, Fracture Prediction, and Rehabilitation Strategies", J Spinal Cord Med., 29(5):489-500.
Gogliotti et al., (2011) "Characterization of a commonly used mouse model of SMA reveals increased seizures susceptibility and heightened fear response in FVB/N mice", Neurobiol Dis. 43(1):142-151.
Gonzalez et al., (2005) "BMP-1/Tolloid-like Metalloproteases Process Endorepellin, the Angiostatic C-terminal Fragment of Perlecan", The Journal of Biological Chemistry, 280(8):7080-7087.
Graham et al., (2015) "A Soluble Myostatin Inhibitor Does Not Prevent Sublesional Muscle Atrophy 56 Days After Spinal Cord Injury in Mice", Medicine & Science in Sports & Exercise, Abstract No. 2219:587.
Guo et al., (2009) "Myostatin Inhibition in Muscle, but Not Adipose Tissue, Decreases Fat Mass and Improves Insulin Sensitivity", PLoS One, 4(3):e4937 (11 pgs.).
Heymsfield et al., (2021) "Effect of Bimagrumab vs Placebo on Body Fat Mass Among Adults With Type 2 Diabetes and Obesity: A Phase 2 Randomized Clinical Trial", 4(1):e2033457. doi: 10.1001/jamanetworkopen.2020.33457.
Holzbaur et al., (2006) "Myostatin inhibition slows muscle atrophy in rodent models of amyotrophic lateral sclerosis", Neurobiol Dis., 23(3):697-707.
Hori et al. (2022) "Elimination of plasma soluble antigen in cynomolgus monkeys by combining pH-dependent antigen binding and novel Fc engineering" MAbs. 14(1):2068213. doi: 10.1080/19420862.2022.2068213.
Igawa et al. (2013) "Engineered Monoclonal Antibody with Novel AntigenSweeping Activity In Vivo". PLoS One 8(5):e63236.
Iinternational Search Report for Application No. PCT/US2015/059557, dated May 19, 2016 (5 pgs.).
International Application No. PCT/US2016/043712, by Scholar Rock, Inc., International Search Report and Written Opinion, mailed Jan. 13, 2017.
International Application No. PCT/US2017/012606, by Scholar Rock, Inc., International Search Report and Written Opinion, mailed Jul. 24, 2017.
International Application No. PCT/US2017/012606, by Scholar Rock, Inc., Written Opinion mailed Jan. 3, 2018 (18 pgs.).
International Application No. PCT/US2017/037332, by Scholar Rock, Inc., International Search Report and Written Opinion, mailed Nov. 14, 2017.
International Application No. PCT/US2018/012686, by Scholar Rock, Inc., International Search Report and Written Opinion, mailed Apr. 3, 2018.
International Preliminary Report on Patentability for Application No. PCT/US2015/059468, dated May 9, 2017 (12 pgs.).

(56) References Cited

OTHER PUBLICATIONS

International Preliminary Report on Patentability for Application No. PCT/US2015/059515, dated May 9, 2017 (12 pgs.).

International Preliminary Report on Patentability for Application No. PCT/US2015/059557, dated May 9, 2017 (12 pgs.).

International Preliminary Report on Patentability for Application No. PCT/US2016/052014, dated Mar. 29, 2018 (11 pgs.).

International Search Report and Written Opinion for Application No. PCT/US2016/052014, dated Jan. 9, 2017 (17 pgs.).

International Search Report for Application No. PCT/US2015/059468, dated Apr. 4, 2016 (6 pgs.).

International Search Report for Application No. PCT/US2015/059515, dated Mar. 25, 2016 (8 pgs.).

Japanese Patent Application No. 2019-517209, filed Jun. 13, 2017, by Scholar Rock, Inc., Decision to Grant a Patent, mailed Dec. 8, 2020 (7 pgs.).

Jarecki Declaration filed in opposition of EP Patent No. 3368069 on Apr. 27, 2022 (2 pgs.).

Jarolim et al., (2013) "2013 AACC Annual Meeting Abstracts B-175 Determination of Cardiac Troponin with a Single-Molecule High-Sensitivity Assay and Outcomes in Patients with Stable Coronary Artery Disease: Analysis from PROVE IT-TIMI 22", XP055100559, Retrieved from the Internet: URL:http://www.aacc.org/events/Annual_Meeting/abstracts/Documents/AACC_13_AM_B175-B239.pdf (22 pgs.).

Jiang et al., (2019) "Genomic analysis of a spinal muscular atrophy (SMA) discordant family identifies a novel mutation in TLL2, an activator of growth differentiation factor 8 (myostatin): a case report", BMC Medical Genetics, 20(1):204.

Jobling et al. (2006) "Isoform-specific activation of latent transforming growth factor beta (LTGF-beta) by reactive oxygen species", Radiat Res. 166(6):839-48.

Kariya et al., (2014) "Requirement of enhanced Survival Motoneuron protein imposed during neuromuscular junction maturation", The Journal of Clinical Investigation, 124(2):785-800.

Latres et al., (2015) "Myostatin blockade with a fully human monoclonal antibody induces muscle hypertrophy and reverses muscle atrophy in young and aged mice", Skeletal Muscle, 5:34.

Latres et al., (2017) "Activin A more prominently regulates muscle mass in primates than does GDF8", Nature Communications, 8:15153.

Ling et al. (2012) "Severe neuromuscular denervation of clinically relevant muscles in a mouse model of spinal muscular atrophy" Human Molecular Genetics, vol. 21, No. 1, pp. 185-195.

Liu et al., (2014) "The Smn-Independent Beneficial Effect of Trichostatin A on an Intermediate Mouse Model of Spinal Muscular Atrophy", Plos One, 9(7):e101225.(9 pgs.).

Liu et al., (2016) Activin Receptor Type 118 Inhibition Improves Muscle Phenotype and Function in a Mouse Model of Spinal Muscular Atrophy, PLoS One 11 (11): e0166803, published Nov. 21, 2016.

Loffredo et al., (2013) "Growth differentiation factor 11 is a circulating factor that reverses age-related cardiac hypertrophy", Cell, 153(4):828-839.

Long et al., (2019) "Specific inhibition of myostatin activation is beneficial in mouse models of SMA therapy", Human Molecular Genetics, 28(7):1076-1089.

Mariot et al., (2017) "Downregulation of myostatin pathway in neuromuscular diseases may explain challenges of anti-myostatin therapeutic approaches", Nature Communications, 8(1):1859.

McPherron et al., (2010) "Metabolic Functions of Myostatin and GDF11", Immunol Endocr Metab Agents Med Chem., 10(4):217-231.

Morrison et al., (2009) "A soluble activin type IIB receptor improves function in a mouse model of amyotrophic lateral sclerosis", Exp Neurol, 217(2):258-268.

Mosler et al., (2012) "The anabolic steroid methandienone targets the hypothalamic-pituitary-testicular axis and myostatin signaling in a rat training model", Archives of Toxicology, 86(1):109-119.

Muramatsu et al., (2021) "Novel myostatin-specific antibody enhances muscle strength in muscle disease models" , Sci Rep, 11:2160, https://doi.org/10.1038/s41598-021-81669-8 (16 pgs.).

Naryshkin et al., (2014) "SMN2 splicing modifiers improve motor function and longevity in mice with spinal muscular atrophy" Science, vol. 345, Issue 6197, pp. 688-693, DOI: 10.1126/science.1250127.

Ojala et al., (2021) "In Search of a Cure: The Development of Therapeutics to Alter the Progression of Spinal Muscular Atrophy", Brain Sci., 11:194 (39 pgs.).

Opposition filed in EP Patent No. 3368069 on Apr. 28, 2021 (37 pgs.).

Opposition filed in EP Patent No. 3368069 on May 4, 2021 (89 pgs.).

Opposition Pre-summons Response filed in EP Patent No. 3368069 on Apr. 27, 2022 (33 pgs.).

Pandya et al., (2013) "Therapeutic neuroprotective agents for amyotrophic lateral sclerosis", Cell Mol Life Sci., 70(24):4729-4745.

Pirruccello-Straub et al., (2018) "Blocking extracellular activation of myostatin as a strategy for treating muscle wasting", Scientific Reports, 8(1):2292.

Pistilli et al., (2011) "Targeting Activin Type IIB Receptor to Improve Muscle Mass and Function in the mdx Mouse Model of Duchenne Muscular Dystrophy", Am J Pathol., 178(3):1287-1297.

Pubchem Substance No. CID 310264710 (trevogrumab); Create Date Feb. 5, 2016 [online]. Retrieved from: http://pubchem.ncbi.nlm.nih.gov/substance/310264710; on Feb. 5, 2020 (6 pgs.).

Reply to Examination Report dated Feb. 13, 2016 in EP Application No. 17732001.7, on May 31, 2019.

Request for early entry and processing of EP Application No. 17732001.7, on Jun. 1, 2018.

Response to Communication dated Jul. 31, 2018 in EP Application No. 17732001.7, on Dec. 10, 2018.

Rodino-Klapac et al., (2009) "Inhibition of myostatin with emphasis on follistatin as a therapy for muscle disease" Muscle Nerve 39(3):283-96. doi: 10.1002/mus.21244.

Rose et al., (2009) "Delivery of recombinant follistatin lessens disease severity in a mouse model of spinal muscular atrophy" Hum Mol Genet. Mar. 15, 2009; 18(6): 997-1005, Published online Dec. 12, 2008. doi: 10.1093/hmg/ddn426.

Roth et al., (2004) "Myostatin: a therapeutic target for skeletal muscle wasting" Curr Opin Clin Nutr Metab Care 7(3):259-63. doi: 10.1097/00075197-200405000-00004.

Schoch et al., (2015) "Charge-mediated influence of the antibody variable domain on FcRn-dependent pharmacokinetics", Proceedings of the National Academy of Sciences, vol. 112, No. 19, pp. 5997-6002.

ScholarRock Announcement (2015) "Scholar Rock Presents First Data for Niche Modulator Inhibiting Myostatin Activation and Announces SRK-015 as Lead Drug Program" (1 pg.).

ScholarRock.com (2016) "Scholar Rock discovered SRK-015, a selective and local inhibitor or latent myostatin activation for the treatment of primary myopathies" (1 pg.).

Sgoutas et al., (1992) "Effect of Lyophilization on Determinations of Lipoprotein(a) in Serum", Clin Chem., 38(7):1355-1360.

Shorrock et al., (2016) "Development and Translation of Therapies for Spinal Muscular Atrophy" EMJ Neurol. 4[1]:64-73.

Singapore Patent Application No. 11201805709R, filed Jan. 6, 2017, by Scholar Rock, Inc.: International Search Report and Written Opinion, mailed Oct. 11, 2019 (12 pgs.).

SMA Annual Conference "The 2016 Annual SMA Conference is here", https://www.curesma.org/the-2016-annual-sma-conference-is-here/ (3 pgs.).

SMA Researcher Meeting Summary: The Changing Landscape of SMA 2016 (5 pgs.).

Smith et al., (2013) "Myostatin inhibitors as therapies for muscle wasting associated with cancer and other disorders", Curr Opin Support Palliat Care, 7(4):352-360.

Smith et al., (2015) "Myostatin Neutralization Results in Preservation of Muscle Mass and Strength in Preclinical Models of Tumor-Induced Muscle Wasting", Mol Cancer Ther., 14(7):1661-1670.

Spinraza (Nusinersen) FDA label, Dec. 2016 (13 pgs.).

(56)     References Cited

OTHER PUBLICATIONS

Sumner et al. (2016) "Spinal Muscular Atrophy, Disease Mechanisms and Therapy", Academic Press, pp. 6, 15-19 and 351-356. Publication details included (22 pgs).

Sumner et al., (2009) "Inhibition of myostatin does not ameliorate disease features of severe spinal muscular atrophy mice", Human Molecular Genetics, 18(17):3145-3152.

Sumner et al., (2016) "Spinal Muscular Atrophy, Disease Mechanisms and Therapy", First edition, Academic Press, Chapters 15, 16, 21, and 23. Publication details included (91 pgs.).

Suragani et al., (2014) "Transforming growth factor-β superfamily ligand trap ACE-536 corrects anemia by promoting late-stage erythropoiesis", Nature Medicine, 20(4):408-414.

Szlama et al., (2013) "Latent myostatin has significant activity and this activity is controlled more efficiently by WFIKKN1 than by WFIKKN2", FEBS Journal, 280(16):3822-3839.

Unknown (2000) American Spinal Injury Association (ASIA) Impairment Scale, Standard Neurological Classification of Spinal Cord Injury (2 pgs.).

Unknown (2013) "Myostatin Propeptide Human, Chicken Polyclonal Antibody", BioVendor, Research and Diagnostic Products, Data Sheet (2 pgs.).

Wagner, (2020) "The elusive promise of myostatin inhibition for muscular dystrophy", Current Opinion in Neurology, 33(5):621-628.

Walker et al., Biochemistry and Biology of GDF11 and Myostatin: similarities, differences and questions for future investigation, Cir. Res. 118(7): 1125-1142, published Apr. 1, 2016.

Walter et al., (2021) "Improving Care and Empowering Adults Living with SMA: A Call to Action in the New Treatment Era", Journal of Neuromuscular Diseases, DOI 10.3233/JND-200611 (9 pgs.).

Wang (2000) "Lyophilization and development of solid protein pharmaceuticals", International Journal of Pharmaceutics, 203(1-2):1-60.

Whittemore et al., (2003) "Inhibition of myostatin in adult mice increases skeletal muscle mass and strength", Biochem Biophys Res Commun, 300(4):965-971.

Wintgens et al., (2012) "Plasma myostatin measured by a competitive ELISA using a highly specific antiserum", Clin Chim Acta., 413(15-16):1288-1294.

Wolfman et al., (2003) "Activation of latent myostatin by the BMP-1/tolloid family of metalloproteinases", Proc Natl Acad Sci U.S.A., 100(26):15842-15846.

Zhao et al., (2016) "Pharmacokinetics, pharmacodynamics, and efficacy of a small molecule SMN2 splicing modifier in mouse models of spinal muscular atrophy", Human Molecular Genetics, 25(10):1885-1899.

Bailey. "GIP analogues and the treatment of obesity-diabetes," Peptides. Mar. 2020;125:170202.

Bhattacharya et al. "Application of quantitative pharmacology approaches in bridging pharmacokinetics and pharmacodynamics of domagrozumab from adult healthy subjects to pediatric patients with Duchenne muscular disease", The Journal of Clinical Pharmacology. 2018;58(3):314-326.

Fock et al., "Diet and exercise in management of obesity and overweight," J Gastroenterol Hepatol. Dec. 2013; 28 Suppl 4:59-63.

Foster "Malonyl-CoA: the regulator of fatty acid synthesis and oxidation", J Clin Invest. 2012;122(6):1958-1959.

Golan et al. "LY2495655, an antimyostatin antibody, in pancreatic cancer: a randomized, phase 2 trial", Journal of Cachexia, Sarcopenia and Muscle. 2018;9(5):871-879.

Gonzalez Trotter et al. "34-OR: The Effect of Combined Activin A and Myostatin Blockade on Body Composition—A Phase 1 Trial. Diabetes", 2024;73(Supplement_1).

Hamrick. "The skeletal muscle secretome: an emerging player in muscle-bone crosstalk", Bonekey Rep. Apr. 11, 2012;1:60. (5 pgs.).

Hansen et al., "Incretin mimetics: a novel therapeutic option for patients with type 2 diabetes—a review," Diabetes Metab Syndr Obes. May 17, 2010;3:155-63.

Incretin mimetic drugs for type 2 diabetes—FDA, downloaded on Sep. 9, 2024 (1 pg.).

International Search Report and Written Opinion of the International Searching Authority received in PCT/US2023/085574, mailed May 7, 2024 (16 pgs.).

Kaufmann et al. "Observational study of spinal muscular atrophy type 2 and 3: functional outcomes over 1 year," Arch Neurol. Jun. 2011;68(6):779-86.

List of Incretin Mimetics (GLP-1 Agonists) (GLP-1 Analogues)—Drugs.com, downloaded Sep. 9, 2024.

Liu et al., "New practice in semaglutide on type-2 diabetes and obesity: clinical evidence and expectation", Frontiers of Medicine, Higher Education Press, Heidelberg, vol. 16, No. 1, Feb. 1, 2022, 17-24.

Miller et al. "The danger of weight loss in the elderly", J Nutr Health Aging. Aug.-Sep. 2008;12(7):487-91.

Muramatsu et al., "Novel myostatin-specific antibody enhances muscle strength in muscle disease models", Scientific Reports, vol. 11, No. 1, Jan. 25, 2021.

Nguyen, "Oral-033: Bimagrumab + Semaglutide Causes> 30% Fat Loss and 5% Lean Mass Increase in Obese Mice After 2 Weeks", Obesity, vol. 30, No. SI, Nov. 1, 2022, 4-54.

Oestreich et al. "Myostatin deficiency partially rescues the bone phenotype of osteogenesis imperfecta model mice", Osteoporos Int. Jan. 2016;27(1):161-70.

Opposition Proceedings in EP 3368069 Brief Communication from EPO Oct. 10, 2024(63 pgs.).

Singh et al."Translational pharmacokinetic/pharmacodynamic analysis of myo-029 antibody for muscular dystrophy", Clinical and Translational Science. 2016;9(6):302-310.

Tang et al. "Inhibiting myostatin signaling prevents femoral trabecular bone loss and microarchitecture deterioration in diet-induced obese rats", Exp Biol Med (Maywood). Feb. 2016;241(3):308-16.

Tao et al. "Genetic Inactivation of Pyruvate Dehydrogenase Kinases Improves Hepatic Insulin Resistance Induced Diabetes", Plos One. 2013, 8(8):1-8.

Wagner et al. "A phase I/II trial of MYO-029 in adult subjects with muscular dystrophy", Annals of Neurology. 2008;63(5):561-571.

Wagner et al. "Randomized phase 2 trial and open-label extension of domagrozumab in Duchenne muscular dystrophy", Neuromuscular Disorders. 2020;30(6):492-502.

Woodhouse et al. "A Phase 2 Randomized Study Investigating the Efficacy and Safety of Myostatin Antibody LY2495655 versus Placebo in Patients Undergoing Elective Total Hip Arthroplasty", The Journal of Frailty & Aging. 2016;5(1):62-70.

Yumuk et al. "European Guidelines for Obesity Management in Adults", Obes Facts Dec. 1, 2015; 8 (6):402-424.

Adams et al., "Comparison of the effects of body-weight-supported treadmill training and tilt-table standing on spasticity in individuals with chronic spinal cord injury," J Spinal Cord Med. 2011;34(5):488-94.

Ader, D., "Developing the patient-reported outcomes measurement information system (PROMIS)," Medical care 45.5 (2007): S1-S2.

Alfano et al., "Validity and reliability of the neuromuscular gross motor outcome," Pediatric Neurology 122 (2021): 21-26.

Altschul et al., "Basic local alignment search tool," Journal of molecular biology 215.3 (1990): 403-410.

Altschul et al., "Gapped BLAST and PSI-BLAST: a new generation of protein database search programs," Nucleic acids research 25.17 (1997): 3389-3402.

Alves et al., "Serum creatinine is a biomarker of progressive denervation in spinal muscular atrophy," Neurology 94.9 (2020): e921-e931.

Amato et al., "Treatment of sporadic inclusion body myositis with bimagrumab," Neurology 83.24 (2014): 2239-2246.

Ambery et al., "MEDI0382, a GLP-1 and glucagon receptor dual agonist, in obese or overweight patients with type 2 diabetes: a randomised, controlled, double-blind, ascending dose and phase 2a study," The Lancet 391.10140 (2018): 2607-2618.

Angal et al., "A single amino acid substitution abolishes the heterogeneity of chimeric mouse/human (IgG4) antibody," Molecular immunology 30.1 (1993): 105-108.

(56) References Cited

OTHER PUBLICATIONS

Annoussamy et al., "Natural history of Type 2 and 3 spinal muscular atrophy: 2-year NatHis-SMA study," Annals of Clinical and Translational Neurology 8.2 (2021): 359-373.

Applebaum et al., "Modified 30-second Sit to Stand test predicts falls in a cohort of institutionalized older veterans," Plos one 12.5 (2017): 1-13.

Aragon-Gawinska et al., "Nusinersen in patients older than 7 months with spinal muscular atrophy type 1: a cohort study," Neurology 91.14 (2018): e1312-e1318.

Aronne et al., "Continued treatment with tirzepatide for maintenance of weight reduction in adults with obesity: the SUR-MOUNT-4 randomized clinical trial," Jama, 331.1, (2024): 38-48.

Awano et al., "Spinal muscular atrophy: journeying from bench to bedside," Neurotherapeutics 11.4 (2014): 786-795.

Axente et al., "Clinical features and genetics in non-5q spinal muscular atrophy caused by acid ceramidase deficiency," Journal of Medicine and Life 14.3 (2021): 1-5.

Bahne et al., "Metformin-induced glucagon-like peptide-1 secretion contributes to the actions of metformin in type 2 diabetes," JCI insight, 3.23, (2018): 1-16.

Baranello et al., "Risdiplam in type 1 spinal muscular atrophy," New England Journal of Medicine 384.10 (2021): 915-923.

Bartels et al., "Fatigability in spinal muscular atrophy: validity and reliability of endurance shuttle tests," Orphanet Journal of Rare Diseases 15 (2020): 1-9.

Battaglino et al., "Spinal cord injury-induced osteoporosis: pathogenesis and emerging therapies," Curr Osteoporos Rep. Dec. 2012; 10(4):278-85.

Becker et al., "Myostatin antibody (LY2495655) in older weak fallers: a proof-of-concept, randomised, phase 2 trial," The Lancet Diabetes & Endocrinology. 2015;3(12):948-957.

Belhayara et al., "The metabolic syndrome: emerging novel insights regarding the relationship between the homeostasis model assessment of insulin resistance and other key predictive markers in young adults of Western Algeria," Nutrients 12.3 (2020): 1-13.

Bergen et al., "Myostatin as a mediator of sarcopenia versus homeostatic regulator of muscle mass: insights using a new mass spectrometry-based assay," Skeletal muscle 5 (2015): 1-16.

Bhattacharya et al., "Comparative analysis of silencing expression of myostatin (MSTN) and its two receptors (ACVR2A and ACVR2B) genes affecting growth traits in knock down chicken," Scientific reports 9.1 (2019): 1-13.

Bird et al., "Single-chain antigen-binding proteins," Science 242. 4877 (1988): 423-426.

Bolon et al., "STP position paper: recommended best practices for sampling, processing, and analysis of the peripheral nervous system (nerves and somatic and autonomic ganglia) during nonclinical toxicity studies," Toxicologic Pathology 46.4 (2018): 372-402.

Bolon et al., "STP position paper: recommended practices for sampling and processing the nervous system (brain, spinal cord, nerve, and eye) during nonclinical general toxicity studies," Toxicologic pathology 41.7 (2013): 1028-1048.

Brakemeier et al., "Assessment of bulbar function in adult patients with 5q-SMA type 2 and 3 under treatment with nusinersen," Brain Sciences 11.9 (2021): 1-9.

Butler et al., "Reversing type 1 diabetes with stem cell-derived islets: a step closer to the dream?" The Journal of Clinical Investigation 132.3 (2022): 1-2.

Cabri et al., "Therapeutic peptides targeting PPI in clinical development: Overview, mechanism of action and perspectives," Frontiers in Molecular Biosciences 8 (2021): 1-21.

Calder et al., "Small molecules in development for the treatment of spinal muscular atrophy: miniperspective," Journal of medicinal chemistry 59.22 (2016): 10067-10083.

Calucho et al., "Correlation between SMA type and SMN2 copy No. revisited: an analysis of 625 unrelated Spanish patients and a compilation of 2834 reported cases," Neuromuscular Disorders 28.3 (2018): 208-215.

Campbell et al., "Myostatin inhibitor ACE-031 treatment of ambulatory boys with Duchenne muscular dystrophy: results of a randomized, placebo-controlled clinical trial," Muscle & nerve 55.4 (2017): 458-464.

Cances et al., "Natural history of type 1 spinal muscular atrophy: a retrospective, global, multicenter study," Orphanet Journal of Rare Diseases 17.1 (2022): 1-11.

Cava et al., "Preserving healthy muscle during weight loss," Advances in nutrition 8.3 (2017): 511-519.

Cavagnaro, J., "Preclinical safety evaluation of biotechnology-derived pharmaceuticals," Nature Reviews Drug Discovery 1.6 (2002): 469-475.

Cedarbaum et al., "The ALSFRS-R: a revised ALS functional rating scale that incorporates assessments of respiratory function. Bdnf Als Study Group (Phase III)," Journal of the neurological sciences 169.1-2 (1999): 13-21.

Chen et al., "The development and validation of a dysphagia-specific quality-of-life questionnaire for patients with head and neck cancer: the MD Anderson dysphagia inventory," Archives of Otolaryngology-Head & Neck Surgery 127.7 (2001): 870-876.

Chiriboga et al., "Longer-Term treatment with nusinersen: results in Later-onset spinal muscular atrophy from the shine study (1661)," Neurology 94.15 Supplement (2020): 1-3.

Chiriboga et al., "Results from a phase 1 study of nusinersen (ISIS-SMNRx) in children with spinal muscular atrophy," Neurology 86.10 (2016): 890-897.

Chitramuthu et al., "Progranulin modulates zebrafish motoneuron development in vivo and rescues truncation defects associated with knockdown of Survival motor neuron 1," Molecular neurodegeneration 5 (2010): 1-13.

Clackson et al., "Making antibody fragments using phage display libraries," Nature 352.6336 (1991): 624- 628.

Coratti et al., "Age and baseline values predict 12 and 24-month functional changes in type 2 SMA," Neuromuscular Disorders 30.9 (2020): 756-764.

Coratti et al., "Clinical variability in spinal muscular atrophy type III," Annals of neurology 88.6 (2020): 1109- 1117.

Cornell, S., "A review of GLP-1 receptor agonists in type 2 diabetes: a focus on the mechanism of action of once-weekly agents," Journal of clinical pharmacy and therapeutics 45 (2020): 17-27.

Cote et al., "A sensitive and selective immunoassay for the quantitation of serum latent myostatin after in vivo administration of SRK-015, a selective inhibitor of myostatin activation," Slas Discovery: Advancing Life Sciences R&D 25.1 (2020): 95-103.

Crawford et al., "Apitegromab in SMA: An Analysis of Multiple Endpoints and PD Relationships to Efficacy in the TOPAZ Trial," Annual Congress of the World Muscle Society (Sep. 20, 2021), 1 pg.

Crawford et al., "TOPAZ extension: 24 month efficacy and safety of apitegromab in patients with later- onset Spinal Muscular Atrophy (type 2 and type 3 SMA)," presented at Cure SMA, Jun. 2022, 17 pages.

Dankbar et al., "Myostatin-a new player in inflammatory bone loss," Annals of the Rheumatic Diseases 70.Suppl 2 (2011): A75-A76.

Darras et al., "Nusinersen in later-onset spinal muscular atrophy: long-term results from the phase 1/2 studies," Neurology 92.21 (2019): e2492-e2506.

Darras et al., "Risdiplam-treated infants with type 1 spinal muscular atrophy versus historical controls," New England Journal of Medicine 385.5 (2021): 427-435.

David et al., "Identification of BMP9 and BMP10 as functional activators of the orphan activin receptor-like kinase 1 (ALK1) in endothelial cells," Blood 109.5 (2007): 1953-1961.

Day et al., "Advances and limitations for the treatment of spinal muscular atrophy," BMC pediatrics 22.1 (2022): 1-15.

De Onis et al., "The WHO Multicentre Growth Reference Study: planning, study design, and methodology," Food and nutrition bulletin 25 (2004): S15-S26.

Deng et al., "Drug Development progress in duchenne muscular dystrophy," Frontiers in Pharmacology 13 (2022): 1-20.

Ding et al., "BPI-3016, a novel long-acting hGLP-1 analogue for the treatment of Type 2 diabetes mellitus," Pharmacological Research 122 (2017): 130-139.

(56)        References Cited

OTHER PUBLICATIONS

Dinicolantonio et al., "Postprandial insulin assay as the earliest biomarker for diagnosing pre-diabetes, type 2 diabetes and increased cardiovascular risk," Open Heart 4.2 (2017): 1-4.

Du et al., "Metformin in therapeutic applications in human diseases: Its mechanism of action and clinical study," Molecular Biomedicine 3.1 (2022): 1-32.

Ducata et al., "Solution equilibrium titration for high-throughput affinity estimation of unpurified antibodies and antibody fragments," Journal of Biomolecular Screening 20.10 (2015): 1256-1267.

Dunaway Young et al., "Scoliosis surgery significantly impacts motor abilities in higher-functioning individuals with spinal muscular atrophy," Journal of Neuromuscular Diseases 7.2 (2020): 183-192.

Dunaway Young et al., "Six-minute walk test is reliable and valid in spinal muscular atrophy," Muscle & nerve 54.5 (2016): 836-842.

Duong et al., "Use of the children's hospital of philadelphia infant test of neuromuscular disorders (Chop Intend) in X-linked myotubular myopathy: content validity and psychometric performance," Journal of Neuromuscular Diseases 8.1 (2021): 63-77.

Dwivedi et al., "Validation of the Sydney Swallow Questionnaire (SSQ) in a cohort of head and neck cancer patients," Oral oncology 46.4 (2010): e10-e14.

Ellulu et al., "Obesity and inflammation: the linking mechanism and the complications," Archives of medical science 13.4 (2017): 851-863.

EMA (European Medicines Agency)., Zolgensma, European Public Assessment Report (Epar). EMA/200482/2020. (2020): 1-150.

Eppstein et al., "Biological activity of liposome-encapsulated murine interferon gamma is mediated by a cell membrane receptor," Proceedings of the National Academy of Sciences 82.11 (1985): 3688-3692.

Fallah et al., "Comparison of T1-weighted 2D Tse, 3D Spgr, and two-point 3D Dixon MRI for automated segmentation of visceral adipose tissue at 3 Tesla," Magnetic Resonance Materials in Physics, Biology and Medicine 30 (2017): 139-151.

Finkel et al., "Nusinersen versus sham control in infantile-onset spinal muscular atrophy," New England Journal of Medicine 377.18 (2017): 1723-1732.

Finkel et al., "Treatment of infantile-onset spinal muscular atrophy with nusinersen: a phase 2, open-label, dose-escalation study," The Lancet 388.10063 (2016): 3017-3026.

Frohlich et al., "GDF11 inhibits adipogenesis and improves mature adipocytes metabolic function via WNT/B-catenin and ALK5/SMAD2/3 pathways," Cell Proliferation 55.10 (2022): 1-15.

Garito et al., "Bimagrumab improves body composition and insulin sensitivity in insulin-resistant individuals," Diabetes, obesity and metabolism 20.1 (2018): 94-102.

Gascon et al., "Non-viral delivery systems in gene therapy," Chapter 1 in: Gene therapy-tools and potential applications. IntechOpen, (2013) 1-43.

Glanzman et al., "The Children's Hospital of Philadelphia infant test of neuromuscular disorders (Chop Intend): test development and reliability," Neuromuscular Disorders 20.3 (2010): 155-161.

Glanzman et al., "Validation of the Expanded Hammersmith Functional Motor Scale in spinal muscular atrophy type II and III," Journal of child neurology 26.12 (2011): 1499-1507.

Godoy-Matos et al., "NAFLD as a continuum: from obesity to metabolic syndrome and diabetes," Diabetology & metabolic syndrome 12 (2020): 1-20.

Golay, A., "Metformin and body weight," International Journal of Obesity 32.1 (2008): 61-72.

Gorgey et al., "Skeletal muscle atrophy and increased intramuscular fat after incomplete spinal cord injury," Spinal Cord. Apr. 2007;45(4):304-9.

Goyal et al., "Evaluation of TNF-a and IL-6 levels in obese and non-obese diabetics: pre-and postinsulin effects," North American journal of medical sciences 4.4 (2012): 180-184.

Graham et al., "A Soluble Activin Receptor IIB Fails to Prevent Muscle Atrophy in a Mouse Model of Spinal Cord Injury," J Neurotrauma. Jun. 1, 20165;33(12):1128-35.

Griffin et al., "Functional electrical stimulation cycling improves body composition, metabolic and neural factors in persons with spinal cord injury," J Electromyogr Kinesiol. Aug. 2009; 19(4):614-22.

Guidance for Industry: S6 Preclinical Safety Evaluation of Biotechnology-Derived Pharmaceuticals. FDA, Jul. 1997, 1-14.

Guidance for Industry: S9 Nonclinical Evaluation for Anticancer Pharmaceuticals. FDA, Mar. 2010, 1-12.

Guideline on development, production, characterization and specification for monoclonal antibodies and related products, European Medicines Agency, (2016): 1-13.

Gupta et al., "Myopathy associated with statins and SGLT2-a review of literature," Current problems in cardiology 46.4 (2021): 1-13.

Haley et al., "Assessing mobility in children using a computer adaptive testing version of the pediatric evaluation of disability inventory," Archives of Physical Medicine and Rehabilitation 86.5 (2005): 932-939.

Hanna et al., "Safety and efficacy of intravenous bimagrumab in inclusion body myositis (RESILIENT): a randomised, double-blind, placebo-controlled phase 2b trial," The Lancet Neurology 18.9 (2019): 834-844.

Harms et al., "Brown and beige fat: development, function and therapeutic potential," Nature medicine 19.10 (2013): 1252-1263.

Herweijer et al., "Progress and prospects: naked DNA gene transfer and therapy," Gene therapy 10.6 (2003): 453-458.

Holliger et al., "Diabodies": small bivalent and bispecific antibody fragments, Proceedings of the National Academy of Sciences 90.14 (1993): 6444-6448.

Hrebicek et al., "Detection of insulin resistance by simple quantitative insulin sensitivity check index QUICKI for epidemiological assessment and prevention," The Journal of Clinical Endocrinology & Metabolism 87.1 (2002): 144-147.

Hua et al., "Antisense correction of SMN2 splicing in the CNS rescues necrosis in a type Iii Sma mouse model," Genes & development 24.15 (2010): 1634-1644.

Hua et al., "Peripheral SMN restoration is essential for long-term rescue of a severe spinal muscular atrophy mouse model," Nature 478.7367 (2011): 123-126.

Huston et al., "Protein engineering of antibody binding sites: recovery of specific activity in an anti-digoxin single-chain Fv analogue produced in Escherichia coli," Proceedings of the National Academy of Sciences 85.16 (1988): 5879-5883.

Hwang et al., "Hepatic uptake and degradation of unilamellar sphingomyelin/cholesterol liposomes: a kinetic study," Proceedings of the National Academy of Sciences 77.7 (1980): 4030-4034.

Iannaccone et al., The PedsQL™ in pediatric patients with spinal muscular atrophy: feasibility, reliability, and validity of the pediatric quality of life inventory ™ generic core scales and neuromuscular module, Neuromuscular Disorders 19.12 (2009): 805-812.

Igawa et al., "pH-dependent antigen-binding antibodies as a novel therapeutic modality," Biochimica et Biophysica Acta 1844 (2014) 1943-1950.

Ito et al., "Skeletal muscle atrophy and short-term mortality in patients with acute exacerbation of idiopathic pulmonary fibrosis: an observational cohort study," Respiratory Investigation 61.4 (2023): 371-378.

Jedrzejowska, M., "Advances in newborn screening and presymptomatic diagnosis of spinal muscular atrophy," Degenerative Neurological and Neuromuscular Disease (2020): 39-47.

Jones et al., "A 30-s chair-stand test as a measure of lower body strength in community-residing older adults," Research quarterly for exercise and sport 70.2 (1999): 113-119.

Jones et al., "Validation of quantitative magnetic resonance for the determination of body composition of mice," International journal of body composition research 7.2 (2009): 67-72.

Karlin et al., "Applications and statistics for multiple high-scoring segments in molecular sequences," Proceedings of the National Academy of Sciences 90.12 (1993): 5873-5877.

(56)     References Cited

OTHER PUBLICATIONS

Karlin et al., "Methods for assessing the statistical significance of molecular sequence features by using general scoring schemes," Proceedings of the National Academy of Sciences 87.6 (1990): 2264-2268.

Kaufmann et al., "Prospective cohort study of spinal muscular atrophy types 2 and 3," Neurology 79.18 (2012): 1889-1897.

Kenward et al., "Small Sample Inference for Fixed Effects from Restricted Maximum Likelihood," 1997, Biometrics 53, pp. 983-997.

Kohler et al., "Continuous cultures of fused cells secreting antibody of predefined specificity," Nature 256.5517 (1975): 495-497.

Kong et al., "Impaired prenatal motor axon development necessitates early therapeutic intervention in severe SMA," Science translational medicine 13.578 (2021): 1-30.

Lakshman et al., "Measurement of myostatin concentrations in human serum: circulating concentrations in young and older men and effects of testosterone administration," Molecular and cellular endocrinology 302.1 (2009): 26-32.

Lander et al., "Appion: an integrated, database-driven pipeline to facilitate EM image processing," Journal of structural biology 166.1 (2009): 95-102.

Landfeldt et al., "Quality of life of patients with spinal muscular atrophy: a systematic review," european journal of paediatric neurology 23.3 (2019): 347-356.

Le Berre et al., "The psychometric properties of a modified sit-to-stand test with use of the upper extremities in institutionalized older adults," Perceptual and motor skills 123.1 (2016): 138-152.

Le Verche et al., "Skeletal Muscle in Spinal Muscular Atrophy As an Opportunity for Therapeutic Intervention," Chapter 21 in Spinal Muscular Atrophy: Disease Mechanisms and Therapy, (2017): 341-356.

Lee et al., "Regulation of muscle growth by multiple ligands signaling through activin type II receptors," Proceedings of the National Academy of Sciences 102.50 (2005): 18117-18122.

Lee et al., "Regulation of myostatin activity and muscle growth," Proceedings of the National Academy of Sciences 98.16 (2001): 9306-9311.

Lefebvre et al., "Identification and characterization of a spinal muscular atrophy-determining gene," Cell 80.1 (1995): 155-165.

Li et al., "Glutazumab, a novel long-lasting GLP-1/anti-GLP-1R antibody fusion protein, exerts anti-diabetic effects through targeting dual receptor binding sites," Biochemical Pharmacology 150 (2018): 46-53.

Lu et al., "Gdf11 gene transfer prevents high fat diet-induced obesity and improves metabolic homeostasis in obese and STZ-induced diabetic mice," Journal of Translational Medicine 17 (2019): 1-16.

MacDonald et al., "Denervation atrophy is independent from Akt and mTOR activation and is not rescued by myostatin inhibition," Dis Model Mech. Apr. 2014; 7(4):471-81.

Madeira et al., "The EMBL-EBI search and sequence analysis tools APIs in 2019," Nucleic acids research 47.W1 (2019): W636-W641.

Main et al., "The Hammersmith functional motor scale for children with spinal muscular atrophy: a scale to test ability and monitor progress in children with limited ambulation," European Journal of Paediatric Neurology 7.4 (2003): 155-159.

Malik et al., "Pediatric dose selection for therapeutic proteins," The Journal of Clinical Pharmacology 61 (2021): S193-S206.

Marks et al., "By-passing immunization: human antibodies from V-gene libraries displayed on phage," Journal of molecular biology 222.3 (1991): 581-597.

Mashhood et al., "Reproducibility of hepatic fat fraction measurement by magnetic resonance imaging," Journal of Magnetic Resonance Imaging 37.6 (2013): 1359-1370.

Mastaitis et al., "Myostatin Inhibition Synergizes with GLP-1R Agonism to Accelerate Weight Loss in Male, Obese Nonhuman Primates" (Abstract). Diabetes Jun. 20, 2023; 72 (Supplement1): 207-OR.

Matsuda et al., "Insulin sensitivity indices obtained from oral glucose tolerance testing: comparison with the euglycemic insulin clamp," Diabetes care 22.9 (1999): 1462-1470.

Mazzone et al., "Revised upper limb module for spinal muscular atrophy: development of a new module," Muscle & nerve 55.6 (2017): 869-874.

McAllister et al., "Modified 30-second sit-to-stand test: reliability and validity in older adults unable to complete traditional sit-to-stand testing," Journal of geriatric physical therapy 43.3 (2020): 153-158.

McHorney et al., "The SWAL-QOL and SWAL-CARE outcomes tool for oropharyngeal dysphagia in adults: III. Documentation of reliability and validity," Dysphagia 17 (2002): 97-114.

McPherron et al., "Regulation of skeletal muscle mass in mice by a new TGF-p superfamily member," Nature 387.6628 (1997): 83-90.

Meece, J., "The role of the pharmacist in managing type 2 diabetes with glucagon-like peptide-1 receptor agonists as add-on therapy," Advances in therapy 34 (2017): 638-657.

Mendell et al., "A phase 1/2a follistatin gene therapy trial for becker muscular dystrophy," Molecular Therapy 23.1 (2015): 192-201.

Mendell et al., "Five-year extension results of the phase 1 START trial of onasemnogene abeparvovec in spinal muscular atrophy," JAMA neurology 78.7 (2021): 834-841.

Mercuri et al., "Long-term progression in type II spinal muscular atrophy: a retrospective observational study," Neurology 93.13 (2019): e1241-e1247.

Mercuri et al., "Nusinersen versus sham control in later-onset spinal muscular atrophy," New England Journal of Medicine 378.7 (2018): 625-635.

Mercuri et al., "Patterns of disease progression in type 2 and 3 SMA: implications for clinical trials," Neuromuscular Disorders 26.2 (2016): 126-131.

Mercuri et al., "Spinal muscular atrophy-insights and challenges in the treatment era," Nature Reviews Neurology 16.12 (2020): 706-715.

Mercuri et al., "SUNFISH Part 2: Efficacy and Safety of Risdiplam (RG7916) in Patients with Type 2 or Non- Ambulant Type 3 Spinal Muscular Atrophy (SMA) (1260)," Neurology 94.15 Supplement (2020): 1-3.

Mercuri et al., "Longer-term treatment with nusinersen: Results in later-onset spinal muscular atrophy from the SHINE study," Neuromuscular Disorders p. 257 (2020): S121.

Mix et al., "Quality of life in SMA patients under treatment with nusinersen," Frontiers in neurology 12 (2021): 1-8.

Mokdad et al., "Prevalence of obesity, diabetes, and obesity-related health risk factors, 2001," Jama 289.1 (2003): 76-79.

Monani et al., "A single nucleotide difference that alters splicing patterns distinguishes the SMA gene SMN1 from the copy gene SMN2," Human molecular genetics 8.7 (1999): 1177-1183.

Monani, U., "Spinal muscular atrophy: a deficiency in a ubiquitous protein; a motor neuron-specific disease," Neuron 48.6 (2005): 885-896.

Montes et al., "Nusinersen improves walking distance and reduces fatigue in later-onset spinal muscular atrophy," Muscle & nerve 60.4 (2019): 409-414.

Morrison et al., "Chimeric human antibody molecules: mouse antigen-binding domains with human constant region domains," Proceedings of the National Academy of Sciences 81.21 (1984): 6851-6855.

Nadkarni et al., "Regulation of glucose homeostasis by GLP-1," Progress in molecular biology and translational science 121 (2014): 23-65.

Nakano et al., "Remogliflozin etabonate improves fatty liver disease in diet-induced obese male mice," Journal of Clinical and Experimental Hepatology 5.3 (2015): 190-198.

Nardone et al., "Inflammatory bowel diseases and sarcopenia: the role of inflammation and gut microbiota in the development of muscle failure," Frontiers in Immunology 12 (2021): 1-11.

National Cancer Institute, "Common Terminology Criteria for Adverse Events," Version 5.0, Published Nov. 2017, 1-147.

Nayerossadat et al., "Viral and nonviral delivery systems for gene delivery," Advanced biomedical research 1.2 (2012): 1-11.

(56) References Cited

OTHER PUBLICATIONS

Nomikos, "Clinical Development of SRK-015,a Fully Human Anti-proMyostatinMonoclonal Antibody, for the Treatment of Later-Onset Spinal Muscular Atrophy, " Poster presented on Oct. 1, 2020, Annual Congress of the World Muscle Society.

Nusinersen, Office of drug evaluation decisional memorandum, FDA, (2016), 22 pages.

O'Hagen et al., "An expanded version of the Hammersmith Functional Motor Scale for SMA II and III patients," Neuromuscular Disorders 17.9-10 (2007): 693-697.

Oskoui et al., "SUNFISH Part 2: 24-month efficacy and safety of risdiplam in patients with type 2 or non- ambulant type 3 spinal muscular atrophy (SMA)," Presented at MDA Clinical and Scientific Conference; Poster 80, (2021): 1-16.

Oskoui et al., "Two-year efficacy and safety of risdiplam in patients with type 2 or non-ambulant type 3 spinal muscular atrophy (SMA)," Journal of Neurology 270.5 (2023): 2531-2546.

Ozempic (semaglutide) injection, for subcutaneous use; prescribing information, Novo Nordisk A/S, Revised Dec. 2017, 1-44.

Padwal et al., "Using the Edmonton obesity staging system to predict mortality in a population-representative cohort of people with overweight and obesity," Cmaj 183.14 (2011): E1059-E1066.

Palacino et al., "SMN2 splice modulators enhance U1-pre-mRNA association and rescue SMA mice," Nature chemical biology 11.7 (2015): 511-517.

Pan et al., "Everestmab, a novel long-acting GLP-1/anti GLP-1R nanobody fusion protein, exerts potent anti- diabetic effects," Artificial cells, nanomedicine, and Biotechnology 48.1 (2020): 854-866.

Pane et al., "Neurological assessment of newborns with spinal muscular atrophy identified through neonatal screening," European Journal of Pediatrics 181.7 (2022): 2821-2829.

Passini et al., "Antisense oligonucleotides delivered to the mouse CNS ameliorate symptoms of severe spinal muscular atrophy," Science translational medicine 3.72 (2011): 1-21.

Passini et al., "CNS-targeted gene therapy improves survival and motor function in a mouse model of spinal muscular atrophy," The Journal of clinical investigation 120.4 (2010): 1253-1264.

Pasternak et al., "Rasch analysis of the Pediatric Evaluation of Disability Inventory-computer adaptive test (PEDI-CAT) item bank for children and young adults with spinal muscular atrophy," Muscle & nerve 54.6 (2016): 1097-1107.

Patil et al., "DNA-based therapeutics and DNA delivery systems: a comprehensive review," The AAPS journal 7 (2005): E61-E77.

Pechmann et al., "Evaluation of children with SMA type 1 under treatment with nusinersen within the expanded access program in Germany," Journal of neuromuscular diseases 5.2 (2018): 135-143.

Peeters et al., "Clinical and genetic diversity of SMN1-negative proximal spinal muscular atrophies," Brain 137.11 (2014): 2879-2896.

Pierzchlewicz et al., "Spinal muscular atrophy: the use of functional motor scales in the era of disease- modifying treatment," Child neurology open 8 (2021): 1-9.

Place et al., "Insights into the Potential Pharmacological Effects of Apitegromab in Health and Disease: Data from Preclinical and Clinical Studies," Annual Congress of the World Muscle Society (Sep. 20, 2021), 2 pgs.

Points to Consider in the Manufacture and Testing of Monoclonal Antibody Products for Human Use, Feb. 1997, 1-50.

Poljak, R., "Production and structure of diabodies," Structure 2.12 (1994): 1121-1123.

Prasad-Reddy et al., "A clinical review of GLP-1 receptor agonists: efficacy and safety in diabetes and beyond," Drugs in context 4 (2015): 1-19.

Ramsey et al., "Revised Hammersmith Scale for spinal muscular atrophy: A Sma specific clinical outcome assessment tool," PloS one 12.2 (2017): 1-19.

Ramsey et al., "Revised Hammersmith Scale for spinal muscular atrophy: Inter and intra-rater reliability and agreement," Plos one 17.12 (2022): 1-14.

Ratni et al., "Specific correction of alternative survival motor neuron 2 splicing by small molecules: discovery of a potential novel medicine to treat spinal muscular atrophy," Journal of medicinal chemistry 59.13 (2016): 6086-6100.

Ravenscroft et al., "Heterozygous loss-of-function variants significantly expand the phenotypes associated with loss of GDF11," Genetics in Medicine 23.10 (2021): 1889-1900.

Regolisti et al., "Management of congestion and diuretic resistance in heart failure," Nephrology@ Point of Care 2.1 (2016): e73-e87.

Rena et al., "The mechanisms of action of metformin," Diabetologia 60.9 (2017): 1577-1585.

Robberecht et al., "Biomarkers of metabolic syndrome: biochemical background and clinical significance," Metabolic syndrome and related disorders 14.2 (2016): 47-93.

Robbie et al., "Population pharmacokinetics of palivizumab, a humanized anti-respiratory syncytial virus monoclonal antibody, in adults and children," Antimicrobial agents and chemotherapy 56.9 (2012): 4927-4936.

Roberts et al., "Classifications in brief: American spinal injury association (ASIA) impairment scale," (2017): 1499-1504.

Rohou et al., "CTFFIND4: Fast and accurate defocus estimation from electron micrographs," Journal of structural biology 192.2 (2015): 216-221.

Rooks et al., "Bimagrumab vs optimized standard of care for treatment of sarcopenia in community-dwelling older adults: a randomized clinical trial," JAMA network open 3.10 (2020): 1-13.

Rooks et al., "Treatment of sarcopenia with bimagrumab: results from a phase II, randomized, controlled, proof-of-concept study," Journal of the American Geriatrics Society 65.9 (2017): 1988-1995.

Rosenbaum et al., "Low-dose leptin reverses skeletal muscle, autonomic, and neuroendocrine adaptations to maintenance of reduced weight," The Journal of clinical investigation 115.12 (2005): 3579-3586.

Rosenstock et al., "Efficacy and safety of a novel dual GIP and GLP-1 receptor agonist tirzepatide in patients with type 2 diabetes (SURPASS-1): a double-blind, randomised, phase 3 trial," The Lancet 398.10295 (2021): 143-155.

Rossi et al., "Predictors of ectopic fat accumulation in liver and pancreas in obese men and women," Obesity 19.9 (2011): 1747-1754.

Rouault et al., "Disease impact on general well-being and therapeutic expectations of European Type II and Type III spinal muscular atrophy patients," Neuromuscular Disorders 27.5 (2017): 428-438.

S11 Nonclinical Safety Testing in Support of Development of Paediatric Medicines, FDA, (2020): 1-43.

Salvi, J., "Columbia-suicide severity rating scale (C-SSRS)," Emergency medicine practice 21.5 (2019): CD3- CD4.

Saunders, K., "Conceptual approaches to modulating antibody effector functions and circulation half-life," Frontiers in immunology 10 (2019): 1-20.

Schiaffino et al., "Three myosin heavy chain isoforms in type 2 skeletal muscle fibres," Journal of Muscle Research & Cell Motility 10 (1989): 197-205.

Sengle et al., "Prodomains of transforming growth factor B (Tgfb) superfamily members specify different functions: extracellular matrix interactions and growth factor bioavailability," Journal of Biological Chemistry 286.7 (2011): 5087-5099.

Shields et al., "Predictive Model of Muscle Fatigue after Spinal Cord Injury in Humans," Muscle Nerve. Jul. 2006; 34(1): 84-91.

Smith et al., "GLP-1: Molecular mechanisms and outcomes of a complex signaling system," Neurochemistry international 128 (2019): 94-105.

Smith, G., "Filamentous fusion phage: novel expression vectors that display cloned antigens on the virion surface," Science 228.4705 (1985): 1315-1317.

Somiari et al., "Theory and in vivo application of electroporative gene delivery," Molecular Therapy 2.3 (2000): 178-187.

Sorzano et al., "XMIPP: a new generation of an open-source image processing package for electron microscopy," Journal of structural biology 148.2 (2004): 194-204.

(56) References Cited

OTHER PUBLICATIONS

Spungen et al., "Factors influencing body composition in persons with spinal cord injury: a cross-sectional study," J Appl Physiol 95: 2398-2407, 2003.

Stam et al., "Protocol for a phase II, monocentre, double-blind, placebo-controlled, cross-over trial to assess efficacy of pyridostigmine in patients with spinal muscular atrophy types 2-4 (SPACE trial)," BMJ open 8.7 (2018): 1-9.

Stanford et al., "Brown adipose tissue regulates glucose homeostasis and insulin sensitivity," The Journal of clinical investigation 123.1 (2012): 215-223.

Staunton et al., "Development of a Clinical Global Impression of Change (CGI-C) and a Caregiver Global Impression of Change (CaGI-C) measure for ambulant individuals with Duchenne muscular dystrophy," Health and Quality of Life Outcomes 19 (2021): 1-16.

Takeda et al., "Construction of chimaeric processed immunoglobulin genes containing mouse variable and human constant region sequences," Nature 314.6010 (1985): 452-454.

Tan et al., "Albumin-binding domain extends half-life of glucagon-like peptide-1," European Journal of Pharmacology 890 (2021): 173650.

Tanzeum® (albiglutide) for injection, for subcutaneous use prescribing information, GlaxoSmithKline LLC., Revised Aug. 2017, 1-60.

Teoh et al., "Inherited paediatric motor neuron disorders: beyond spinal muscular atrophy," Neural plasticity 2017.1 (2017): 6509493.

Thimm et al., "Assessment of health-related quality of life in adult spinal muscular atrophy under nusinersen treatment-a pilot study," Frontiers in neurology 12 (2022): 1-9.

Tulsky et al., "Overview of the spinal cord injury-quality of life (SCI-QOL) measurement system," The journal of spinal cord medicine 38.3 (2015): 257-269.

UniProt: the universal protein knowledgebase in 2021. Nucleic acids research 49, No. D1 (2021): D480-D489.

Vuillerot et al., "Responsiveness of the motor function measure in patients with spinal muscular atrophy," Archives of physical medicine and rehabilitation 94.8 (2013): 1555-1561.

Walker et al., "Exogenous GDF11, but not GDF8, reduces body weight and improves glucose homeostasis in mice," Scientific Reports. Vol. 10 (2020): 1-13.

Wan et al., "Health, wellbeing and lived experiences of adults with SMA: a scoping systematic review," Orphanet journal of rare diseases 15 (2020): 1-17.

Wang et al., "Reloading promotes recovery of disuse muscle loss by inhibiting TGFB pathway activation in rats after hind limb suspension," American Journal of Physical Medicine & Rehabilitation 96.6 (2017): 430-437.

Ward et al., "Binding activities of a repertoire of single immunoglobulin variable domains secreted from Escherichia coli," Nature 341.6242 (1989): 544-546.

Wawersik et al., "A novel, highly specific TGFB1 inhibiting antibody demonstrates antifibrotic activity without cardiotoxicity," Poster presented on Nov. 3, 2017, The American Society of Nephrology. 3 pgs.

Weiss et al., "Real-world weight change, adherence, and discontinuation among patients with type 2 diabetes initiating glucagon-like peptide-1 receptor agonists in the Uk," Bmj Open Diabetes Research and Care 10.1 (2022): 1-9.

Weststrate et al., "Evolution of bulbar function in spinal muscular atrophy type 1 treated with nusinersen," Developmental Medicine & Child Neurology 64.7 (2022): 907-914.

WHO Drug Information, vol. 34, No. 2, (2020): 272-273.

WHO Multicentre Growth Reference Study Group, "WHO Motor Development Study: windows of achievement for six gross motor development milestones," Acta paediatrica, Suppl. 450, (2006): 86-95.

Wijnhoven et al., "Assessment of gross motor development in the WHO Multicentre Growth Reference Study," Food and nutrition bulletin 25, Suppl 1 (2004): S37-S45.

Wilding et al., "Weight regain and cardiometabolic effects after withdrawal of semaglutide: the STEP 1 trial extension," Diabetes, Obesity and Metabolism 24.8 (2022): 1553-1564.

Williams et al., "Drug therapy in obesity: a review of current and emerging treatments," Diabetes Therapy 11.6 (2020): 1199-1216.

Williams et al., "Minimal clinically important differences of the expanded hammersmith functional motor scale in later-onset spinal muscular atrophy: results from the Phase 3 CHERISH trial," Presented at the 2019 AMCP Managed Care & Specialty Pharmacy Annual Meeting; San Diego, Ca, J Manag Care Spec Pharm. (2019): S54.

Wu et al., "Spinal cord injury causes brain inflammation associated with cognitive and affective changes: role of cell cycle pathways," J Neurosci. Aug. 1, 20143;34(33):10989-1006.

Wu et al., "Cell Cycle Activation Contributes to Increased Neuronal Activity in the Posterior Thalamic Nucleus and Associated Chronic Hyperesthesia after Rat Spinal Cord Contusion," Neurotherapeutics (2013) 10:520- 538.

Yang et al., "Systematic literature review of clinical and economic evidence for spinal muscular atrophy," Advances in therapy 39.5 (2022): 1915-1958.

Yao et al., "Quality of life of children with spinal muscular atrophy and their caregivers from the perspective of caregivers: a Chinese cross-sectional study," Orphanet journal of rare diseases 16 (2021): 1-13.

Yokoyama et al., "Quantitative insulin sensitivity check index and the reciprocal index of homeostasis model assessment are useful indexes of insulin resistance in type 2 diabetic patients with wide range of fasting plasma glucose," The Journal of Clinical Endocrinology & Metabolism 89.3 (2004): 1481-1484.

Zhang et al., "Pharmacological inhibition of myostatin suppresses systemic inflammation and muscle atrophy in mice with chronic kidney disease," The FASEB journal 25.5 (2011): 1653-1663.

Zhao et al., "Targeting fibrosis: Mechanisms and clinical trials," Signal transduction and targeted therapy, 2022, 7(1), 21 pages.

Zhou et al., "Reversal of cancer cachexia and muscle wasting by ActRIIB antagonism leads to prolonged survival," Cell 142.4 (2010): 531-543.

Dubowitz, "Chaos in Classification of The Spinal Muscular Atrophies of Childhood," Neuromuscular Disorders, 1991, vol. 1, No. 2, pp. 77-80.

Melson et al., "What is the pipeline for future medications for obesity?" International Journal of Obesity (2024): 1-19.

Monani et al., "Neurodegeneration in spinal muscular atrophy: from disease phenotype and animal models to therapeutic strategies and beyond," Future Neurol. Jan. 1, 2014;9(1):49-65.

Sproule, "Spinal Muscular Atrophy," Encyclopedia of the Neurological Sciences, vol. 4, pp. 281-285.

ASO, "Pharmacologic Strategy in the Treatment of Type 2 Diabetes According to the Degree of Obesity." Journal of the Japan Diabetes Society 63.7 (2020): 433-436.

Creative Biolabs, "Monoclonal Antibody Epitope Binning," Retrieved from the Internet: < https://www.creative- biolabs.com/Monoclonal-Antibody-Epitope-Binning.html>, Accessed on Nov. 27, 2020, 2 pages.

Iemura et al., "Direct binding of follistatin to a complex of bone-morphogenetic protein and its receptor inhibits ventral and epidermal cell fates in early Xenopus embryo," Proc Natl Acad Sci U S A. Aug. 4, 1998;95(16):9337-42.

Kadouh et al., "GLP-1 Analog Modulates Appetite, Taste Preference, Gut Hormones, and Regional Body Fat Stores in Adults with Obesity," J Clin Endocrinol Metab. May 1, 2020;105(5):1552-63.

Lee et al., "Regulation of GDF-11 and myostatin activity by GASP-1 and GASP-2." Proceedings of the National Academy of Sciences 110.39 (2013): E3713-E3722.

McCrimmon et al., "Effects of once-weekly semaglutide vs once-daily canagliflozin on body composition in type diabetes: a substudy of the SUSTAIN 8 randomised controlled clinical trial," Diabetologia. Mar. 2020;63(3):473- 485.

Place et al. "A phase 2 study to evaluate the efficacy and safety of SRK-015 in patients with later-onset spinal muscular atrophy (TOPAZ):

(56) References Cited

OTHER PUBLICATIONS

An Introduction," European Abstracts of the 6th Congress of the European Academy of Neurology 27, Suppl. 1 p. 103-522 , May 2020 (5 p. ).

Tsuchida et al., "Activin signaling as an emerging target for therapeutic interventions." Cell Communication and Signaling 7 (2009): 1-11.

Ueno et al., "Body Weight Reduction Caused by GLP-1 Receptor Agonists." Journal of the Japan Diabetes Society 60.9 (2017): 570-572.

* cited by examiner

Group 1: Vehicle Control
Group 2: Ab7 (25mg/kg)
Group 3: Ab1 (25mg/kg)
Group 4: Ab8 (25mg/kg)
Group 5: Ab9 (25mg/kg)

▨▨ Group 1: Vehicle Control

▧▧ Group 2: Ab7 (25mg/kg)

▭ Group 3: Ab1 (25mg/kg)

◫ Group 4: Ab8 (25mg/kg)

█ Group 5: Ab9 (25mg/kg)

- ⊙ - PBS
- □ - IgG ct1 (60 mg/kg/wk)
- △ - Ab1 (60 mg/kg/wk)
- ▽ - Ab1 (20 mg/kg/wk)
- ◇ - Ab1 (6 mg/kg/wk)
- ● - Ab1 (2 mg/kg/wk)

Gastrocnemius
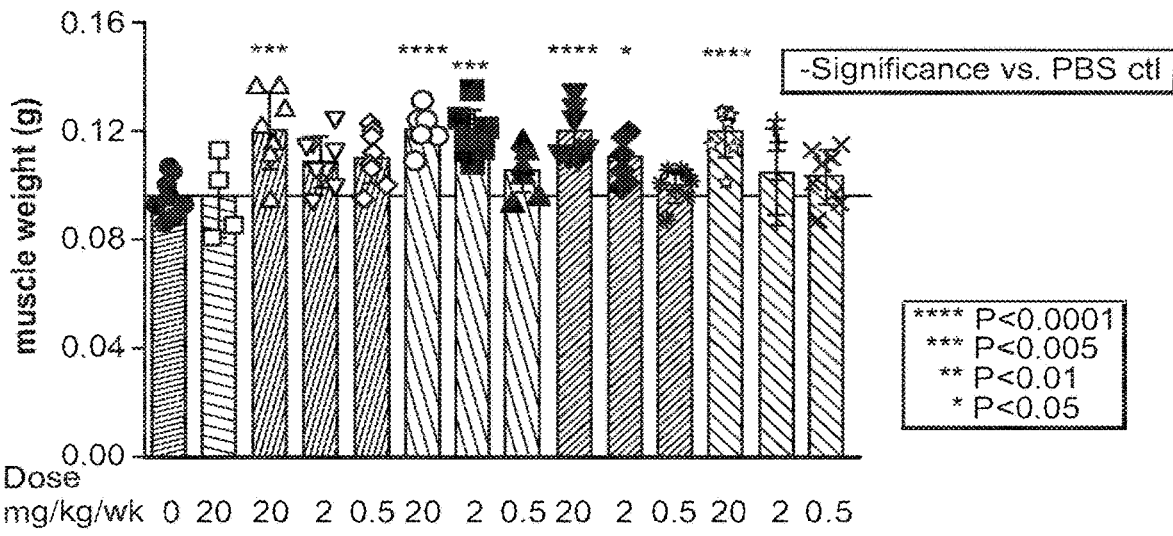
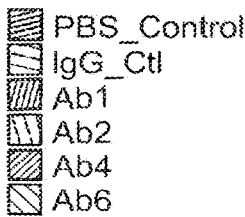
FIG. 18A
Quadriceps
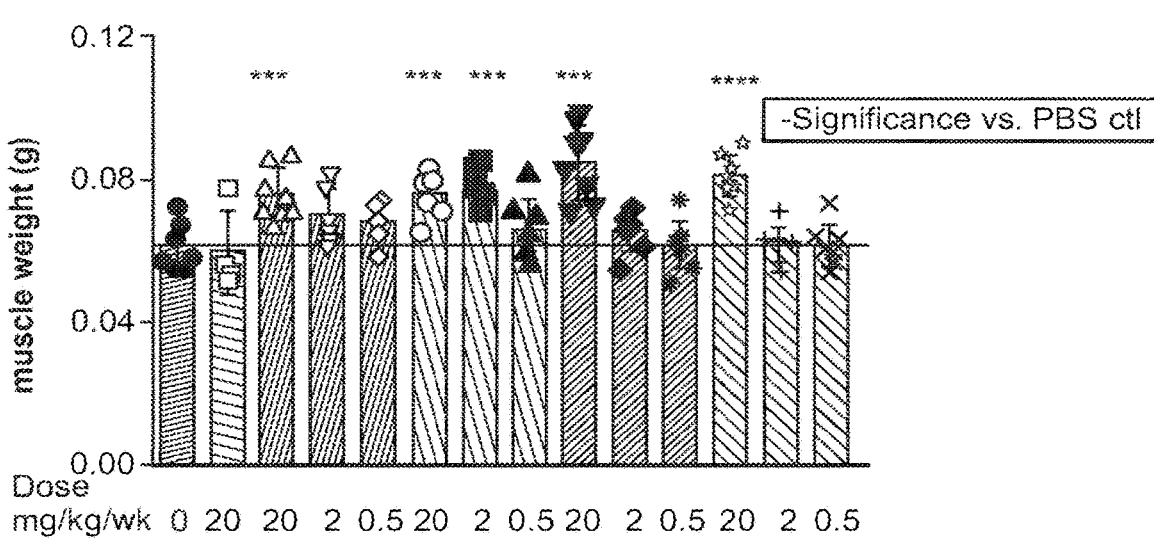
FIG. 18B

| Muscle | Ab | PBS_Ctl | 20 mg/kg/wk | 2 mg/kg/wk | 0.5 mg/kg/wk |
|---|---|---|---|---|---|
| Gastrocnemius | Ab1 | 0 | 25.1 | 13.0 | 14.9 |
| Gastrocnemius | Ab2 | 0 | 25.6 | 24.0 | 9.8 |
| Gastrocnemius | Ab4 | 0 | 25.0 | 15.0 | 3.1 |
| Gastrocnemius | Ab6 | 0 | 24.8 | 9.3 | 7.4 |
| Quadriceps | Ab1 | 0 | 23.9 | 13.9 | 10.8 |
| Quadriceps | Ab2 | 0 | 23.9 | 26.1 | 7.6 |
| Quadriceps | Ab4 | 0 | 37.8 | 6.4 | 0.2 |
| Quadriceps | Ab6 | 0 | 32.0 | 0.4 | 0.2 |

FIG. 18C

Pre-incubate antibody and proMyostatin proMyostatin

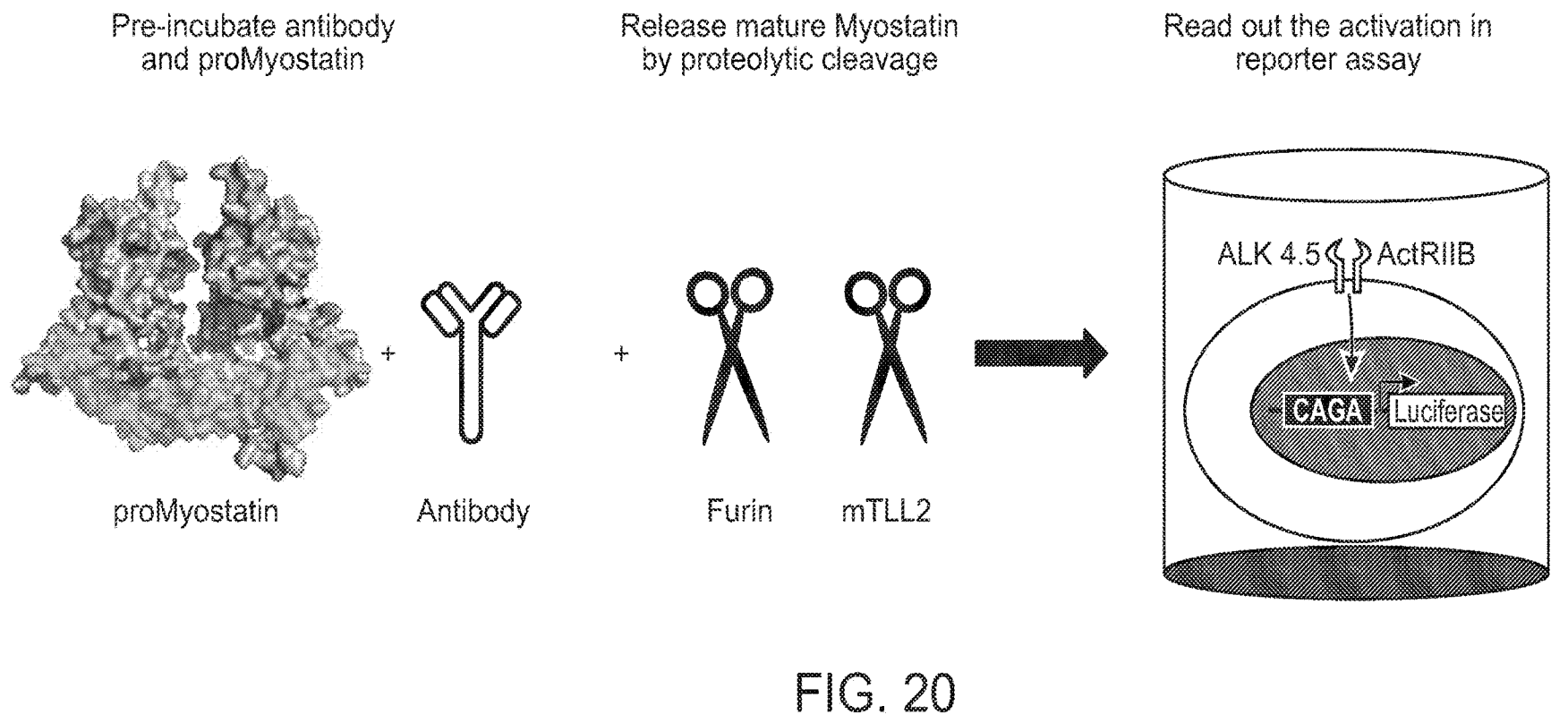

Antibody

Release mature Myostatin by proteolytic cleavage

Furin     mTLL2

Read out the activation in reporter assay

ALK 4,5 ActRIIB

CAGA Luciferase

FIG. 20

```
1   QVQLVESGGGVVQPGRSLRLSCAASGFTFSSYGMHWVRQAPGKGLEWVAVISYDGSNKYY    60
61  ADSVKGRFTISRDNSKNTLYLQMNSLRAEDTAVYYCARDLLVRFLEWSHYYGMDVWGQGT   120
121 TVTVSSASTKGPSVFPLAPCSRSTSESTAALGCLVKDYFPEPVTVSWNSGALTSGVHTFP   180
181 AVLQSSGLYSLSSVVTVPSSSLGTKTYTCNVDHKPSNTKVDKRVESKYGPPCPPCPAPEF   240
241 LGGPSVFLFPPKPKDTLMISRTPEVTCVVVDVSQEDPEVQFNWYVDGVEVHNAKTKPREE   300
301 QFNSTYRVVSVLTVLHQDWLNGKEYKCKVSNKGLPSSIEKTISKAKGQPREPQVYTLPPS   360
361 QEEMTKNQVSLTCLVKGFYPSDIAVEWESNGQPENNYKTTPPVLDSDGSFFLYSRLTVDK   420
421 SRWQEGNVFSCSVMHEALHNHYTQKSLSLSLG                              452
```

FIG. 21A

```
1   QSVLTQPPSASGTPGQRVTISCSGSGSSSNIGSNTVHWYQQLPGTAPKLLIYSDNQRPSGVP    60
61  DRFSGSKSGTSASLAISGLQSEDEADYYCAAWDDSLMGVEGGGTKLTVLGQPKAAPSVTL   120
121 FPPSSEELQANKATLVCLISDFYPGAVTVAWKADSSPVKAGVETTTPSKQSNNKYAASSY   180
181 LSLTPEQWKSHRSYSCQVTHEGSTVEKTVAPTECS                           215
```

FIG. 21B

Top 12 clones selected for further characterization

Ab1:                      4.8 nM

Ab4:                      0.47 nM          10-fold improved

Ab6:                      0.48 nM          10-fold improved

Best affy matured mAb:   <10 pM           >480-fold improvement

```
              FRAMEWORK 1                CDR1        FRAMEWORK 2
Ab1    QIQLVQSGGGVVQPGRSLRLSCAASGFTFSSYGMHWVRQAPGKGLEWVA
Ab3    QIQLVQSGGGVVQPGRSLRLSCAASGFAFSSYGMHWVRQAPGKGLEWVA
Ab5    QIQLVQSGGGVVQPGRSLRLSCAASGFAFSSYGMHWVRQAPGKGLEWVA

CDR2                 FRAMEWORK 3
Ab1    VISYDGSNKYYADSVKGRFTISRDNSKNTLYLQMNSLRAEDTAVYYCAR
Ab3    VISYDGSIKYYADSVKGRFTISRDNSKNTLYLQMNSLRAEDTAVYYCAR
Ab5    VISYDGNNKYYADSVKGRFTISRDNSKNTLYLQMNSLRAEDTAVYYCAR

CDR3             FRAMEWORK 4
Ab1    DLLVRFLEWSHYYGMDVWGQGTTVTVSS
Ab3    DLLVRFLEWSHKYGMDVWGQGTTVTVSS
Ab5    DLLVRFLEWSHKYGMDVWGQGTTVTVSS
```

FIG. 24A

```
              FRAMEWORK 1                CDR1         FRW2
Ab1    QPVLTQPPSASGTPGQRVTISCSGSSSNIGSNTVHWYQQLPGTAPKLLIY
Ab3    QPVLTQPPSASGTPGQRVTISCSGSTSNIGSNTVHWYQQLPGTAPKLLIY
Ab5    QPVLTQPPSASGTPGQRVTISCSGSSSNIGGNTVHWYQQLPGTAPKLLIY

CDR2           FRAMEWORK 3
Ab1    SDNQRPSGVPDRFSGSKSGTSASLVISGLQSDDEADYYC
Ab3    SDDQRPSGVPDRFSGSKSGTSASLVISGLQSDDEADYYC
Ab5    SDDQRPSGVPDRFSGSKSGTSASLVISGLQSDDEADYYC

CDR3        FRAMEWORK 4
Ab1    AAWDDSLNGVFGGGTKLTVL
Ab3    AAWDESLNGVFGGGTKLTVL
Ab5    AAWDESLNGVFGGGTKLTVL
```

FIG. 24B

Muscle Weight

* Sig vs. IgG Ctl
Sig vs. PBS Ctl

*Increased Duration of Muscle Mass Gain in
Mice treated with Ab2
% Change in Lean Mass vs. Day 0
Measured by qNMR, N=4 to 8 per group*

—□— Ab2

—■— IgG Control (5mg/kg)

—▨— AbMyo

\*    P < 0.01 (Ab2 vs. AbMyo)

+    P < 0.01 (Ab2 vs. IgG)

SEQUENCE LISTING

```
Sequence total quantity: 65
SEQ ID NO: 1           moltype = AA  length = 6
FEATURE                Location/Qualifiers
source                 1..6
                       mol_type = protein
                       organism = synthetic construct
                       note = Synthetic Polypeptide
SEQUENCE: 1
SSYGMH                                              6

SEQ ID NO: 2           moltype = AA  length = 10
FEATURE                Location/Qualifiers
source                 1..10
                       mol_type = protein
                       organism = synthetic construct
                       note = Synthetic Polypeptide
SEQUENCE: 2
GFTFSSYGMH                                          10

SEQ ID NO: 3           moltype = AA  length = 10
FEATURE                Location/Qualifiers
source                 1..10
                       mol_type = protein
                       organism = synthetic construct
                       note = Synthetic Polypeptide
SEQUENCE: 3
GFAFSSYGMH                                          10

SEQ ID NO: 4           moltype = AA  length = 17
FEATURE                Location/Qualifiers
source                 1..17
                       mol_type = protein
                       organism = synthetic construct
                       note = Synthetic Polypeptide
SEQUENCE: 4
VISYDGSNKY YADSVKG                                  17

SEQ ID NO: 5           moltype = AA  length = 7
FEATURE                Location/Qualifiers
source                 1..7
                       mol_type = protein
                       organism = synthetic construct
                       note = Synthetic Polypeptide
SEQUENCE: 5
ISYDGSN                                             7

SEQ ID NO: 6           moltype = AA  length = 17
FEATURE                Location/Qualifiers
```

-continued

```
source                    1..17
                          mol_type = protein
                          organism = synthetic construct
                          note = Synthetic Polypeptide
SEQUENCE: 6
VISYDGSIKY YADSVKG                                                    17

SEQ ID NO: 7              moltype = AA   length = 7
FEATURE                   Location/Qualifiers
source                    1..7
                          mol_type = protein
                          organism = synthetic construct
                          note = Synthetic Polypeptide
SEQUENCE: 7
ISYDGSI                                                               7

SEQ ID NO: 8              moltype = AA   length = 17
FEATURE                   Location/Qualifiers
source                    1..17
                          mol_type = protein
                          organism = synthetic construct
                          note = Synthetic Polypeptide
SEQUENCE: 8
VISYDGNNKY YADSVKG                                                    17

SEQ ID NO: 9              moltype = AA   length = 7
FEATURE                   Location/Qualifiers
source                    1..7
                          mol_type = protein
                          organism = synthetic construct
                          note = Synthetic Polypeptide
SEQUENCE: 9
ISYDGNN                                                               7

SEQ ID NO: 10             moltype = AA   length = 17
FEATURE                   Location/Qualifiers
source                    1..17
                          mol_type = protein
                          organism = synthetic construct
                          note = Synthetic Polypeptide
SEQUENCE: 10
DLLVRFLEWS HYYGMDV                                                    17

SEQ ID NO: 11             moltype = AA   length = 17
FEATURE                   Location/Qualifiers
source                    1..17
                          mol_type = protein
                          organism = synthetic construct
                          note = Synthetic Polypeptide
SEQUENCE: 11
DLLVRFLEWS HKYGMDV                                                    17

SEQ ID NO: 12             moltype = AA   length = 13
FEATURE                   Location/Qualifiers
source                    1..13
                          mol_type = protein
                          organism = synthetic construct
                          note = Synthetic Polypeptide
SEQUENCE: 12
SGSSSNIGSN TVH                                                        13

SEQ ID NO: 13             moltype = AA   length = 8
FEATURE                   Location/Qualifiers
source                    1..8
                          mol_type = protein
                          organism = synthetic construct
                          note = Synthetic Polypeptide
SEQUENCE: 13
SSNIGSNT                                                              8

SEQ ID NO: 14             moltype = AA   length = 13
FEATURE                   Location/Qualifiers
source                    1..13
                          mol_type = protein
                          organism = synthetic construct
                          note = Synthetic Polypeptide
SEQUENCE: 14
SGSTSNIGSN TVH                                                        13
```

-continued

```
SEQ ID NO: 15          moltype = AA   length = 8
FEATURE                Location/Qualifiers
source                 1..8
                       mol_type = protein
                       organism = synthetic construct
                       note = Synthetic Polypeptide
SEQUENCE: 15
TSNIGSNT                                                              8

SEQ ID NO: 16          moltype = AA   length = 13
FEATURE                Location/Qualifiers
source                 1..13
                       mol_type = protein
                       organism = synthetic construct
                       note = Synthetic Polypeptide
SEQUENCE: 16
SGSSSNIGGN TVH                                                        13

SEQ ID NO: 17          moltype = AA   length = 8
FEATURE                Location/Qualifiers
source                 1..8
                       mol_type = protein
                       organism = synthetic construct
                       note = Synthetic Polypeptide
SEQUENCE: 17
SSNIGGNT                                                              8

SEQ ID NO: 18          moltype = AA   length = 7
FEATURE                Location/Qualifiers
source                 1..7
                       mol_type = protein
                       organism = synthetic construct
                       note = Synthetic Polypeptide
SEQUENCE: 18
SDNQRPS                                                               7

SEQ ID NO: 19          moltype =    length =
SEQUENCE: 19
000

SEQ ID NO: 20          moltype = AA   length = 7
FEATURE                Location/Qualifiers
source                 1..7
                       mol_type = protein
                       organism = synthetic construct
                       note = Synthetic Polypeptide
SEQUENCE: 20
SDDQRPS                                                               7

SEQ ID NO: 21          moltype =    length =
SEQUENCE: 21
000

SEQ ID NO: 22          moltype = AA   length = 10
FEATURE                Location/Qualifiers
source                 1..10
                       mol_type = protein
                       organism = synthetic construct
                       note = Synthetic Polypeptide
SEQUENCE: 22
AAWDDSLNGV                                                            10

SEQ ID NO: 23          moltype = AA   length = 10
FEATURE                Location/Qualifiers
source                 1..10
                       mol_type = protein
                       organism = synthetic construct
                       note = Synthetic Polypeptide
SEQUENCE: 23
AAWDESLNGV                                                            10

SEQ ID NO: 24          moltype = AA   length = 126
FEATURE                Location/Qualifiers
source                 1..126
                       mol_type = protein
                       organism = synthetic construct
                       note = Synthetic Polypeptide
SEQUENCE: 24
QIQLVQSGGG VVQPGRSLRL SCAASGFTFS SYGMHWVRQA PGKGLEWVAV ISYDGSNKYY  60
```

```
ADSVKGRFTI SRDNSKNTLY LQMNSLRAED TAVYYCARDL LVRFLEWSHY YGMDVWGQGT    120
TVTVSS                                                               126

SEQ ID NO: 25              moltype = AA   length = 126
FEATURE                    Location/Qualifiers
source                     1..126
                           mol_type = protein
                           organism = synthetic construct
                           note = Synthetic Polypeptide
SEQUENCE: 25
QVQLVESGGG VVQPGRSLRL SCAASGFTFS SYGMHWVRQA PGKGLEWVAV ISYDGSNKYY    60
ADSVKGRFTI SRDNSKNTLY LQMNSLRAED TAVYYCARDL LVRFLEWSHY YGMDVWGQGT    120
TVTVSS                                                               126

SEQ ID NO: 26              moltype = AA   length = 126
FEATURE                    Location/Qualifiers
source                     1..126
                           mol_type = protein
                           organism = synthetic construct
                           note = Synthetic Polypeptide
SEQUENCE: 26
QIQLVQSGGG VVQPGRSLRL SCAASGFAFS SYGMHWVRQA PGKGLEWVAV ISYDGSIKYY    60
ADSVKGRFTI SRDNSKNTLY LQMNSLRAED TAVYYCARDL LVRFLEWSHK YGMDVWGQGT    120
TVTVSS                                                               126

SEQ ID NO: 27              moltype = AA   length = 126
FEATURE                    Location/Qualifiers
source                     1..126
                           mol_type = protein
                           organism = synthetic construct
                           note = Synthetic Polypeptide
SEQUENCE: 27
QVQLVESGGG VVQPGRSLRL SCAASGFAFS SYGMHWVRQA PGKGLEWVAV ISYDGSIKYY    60
ADSVKGRFTI SRDNSKNTLY LQMNSLRAED TAVYYCARDL LVRFLEWSHK YGMDVWGQGT    120
TVTVSS                                                               126

SEQ ID NO: 28              moltype = AA   length = 126
FEATURE                    Location/Qualifiers
source                     1..126
                           mol_type = protein
                           organism = synthetic construct
                           note = Synthetic Polypeptide
SEQUENCE: 28
QIQLVQSGGG VVQPGRSLRL SCAASGFAFS SYGMHWVRQA PGKGLEWVAV ISYDGNNKYY    60
ADSVKGRFTI SRDNSKNTLY LQMNSLRAED TAVYYCARDL LVRFLEWSHK YGMDVWGQGT    120
TVTVSS                                                               126

SEQ ID NO: 29              moltype = AA   length = 126
FEATURE                    Location/Qualifiers
source                     1..126
                           mol_type = protein
                           organism = synthetic construct
                           note = Synthetic Polypeptide
SEQUENCE: 29
QVQLVESGGG VVQPGRSLRL SCAASGFAFS SYGMHWVRQA PGKGLEWVAV ISYDGNNKYY    60
ADSVKGRFTI SRDNSKNTLY LQMNSLRAED TAVYYCARDL LVRFLEWSHK YGMDVWGQGT    120
TVTVSS                                                               126

SEQ ID NO: 30              moltype = AA   length = 109
FEATURE                    Location/Qualifiers
source                     1..109
                           mol_type = protein
                           organism = synthetic construct
                           note = Synthetic Polypeptide
SEQUENCE: 30
QPVLTQPPSA SGTPGQRVTI SCSGSSSNIG SNTVHWYQQL PGTAPKLLIY SDNQRPSGVP    60
DRFSGSKSGT SASLVISGLQ SDDEADYYCA AWDDSLNGVF GGGTKLTVL                109

SEQ ID NO: 31              moltype = AA   length = 109
FEATURE                    Location/Qualifiers
source                     1..109
                           mol_type = protein
                           organism = synthetic construct
                           note = Synthetic Polypeptide
SEQUENCE: 31
QSVLTQPPSA SGTPGQRVTI SCSGSSSNIG SNTVHWYQQL PGTAPKLLIY SDNQRPSGVP    60
DRFSGSKSGT SASLAISGLQ SEDEADYYCA AWDDSLNGVF GGGTKLTVL                109

SEQ ID NO: 32              moltype = AA   length = 109
```

-continued

```
FEATURE           Location/Qualifiers
source            1..109
                  mol_type = protein
                  organism = synthetic construct
                  note = Synthetic Polypeptide
SEQUENCE: 32
QPVLTQPPSA SGTPGQRVTI SCSGSTSNIG SNTVHWYQQL PGTAPKLLIY SDDQRPSGVP    60
DRFSGSKSGT SASLVISGLQ SDDEADYYCA AWDESLNGVF GGGTKLTVL              109

SEQ ID NO: 33     moltype = AA  length = 109
FEATURE           Location/Qualifiers
source            1..109
                  mol_type = protein
                  organism = synthetic construct
                  note = Synthetic Polypeptide
SEQUENCE: 33
QSVLTQPPSA SGTPGQRVTI SCSGSTSNIG SNTVHWYQQL PGTAPKLLIY SDDQRPSGVP    60
DRFSGSKSGT SASLAISGLQ SEDEADYYCA AWDESLNGVF GGGTKLTVL              109

SEQ ID NO: 34     moltype = AA  length = 109
FEATURE           Location/Qualifiers
source            1..109
                  mol_type = protein
                  organism = synthetic construct
                  note = Synthetic Polypeptide
SEQUENCE: 34
QPVLTQPPSA SGTPGQRVTI SCSGSSSNIG GNTVHWYQQL PGTAPKLLIY SDDQRPSGVP    60
DRFSGSKSGT SASLVISGLQ SDDEADYYCA AWDESLNGVF GGGTKLTVL              109

SEQ ID NO: 35     moltype = AA  length = 109
FEATURE           Location/Qualifiers
source            1..109
                  mol_type = protein
                  organism = synthetic construct
                  note = Synthetic Polypeptide
SEQUENCE: 35
QSVLTQPPSA SGTPGQRVTI SCSGSSSNIG GNTVHWYQQL PGTAPKLLIY SDDQRPSGVP    60
DRFSGSKSGT SASLAISGLQ SEDEADYYCA AWDESLNGVF GGGTKLTVL              109

SEQ ID NO: 36     moltype = AA  length = 98
FEATURE           Location/Qualifiers
source            1..98
                  mol_type = protein
                  organism = synthetic construct
                  note = Synthetic Polypeptide
SEQUENCE: 36
QVQLVESGGG VVQPGRSLRL SCAASGFTFS SYGMHWVRQA PGKGLEWVAV ISYDGSNKYY    60
ADSVKGRFTI SRDNSKNTLY LQMNSLRAED TAVYYCAR                          98

SEQ ID NO: 37     moltype = AA  length = 98
FEATURE           Location/Qualifiers
source            1..98
                  mol_type = protein
                  organism = synthetic construct
                  note = Synthetic Polypeptide
SEQUENCE: 37
QSVLTQPPSA SGTPGQRVTI SCSGSSSNIG SNTVNWYQQL PGTAPKLLIY SNNQRPSGVP    60
DRFSGSKSGT SASLAISGLQ SEDEADYYCA AWDDSLNG                          98

SEQ ID NO: 38     moltype = DNA  length = 378
FEATURE           Location/Qualifiers
source            1..378
                  mol_type = other DNA
                  organism = synthetic construct
                  note = Synthetic Polynucleotide
SEQUENCE: 38
cagatccagc tggtgcagtc tggggggaggc gtggtccagc ctgggaggtc cctgagactc    60
tcctgtgcag cgtctggatt caccttcagt agctatggca tgcactgggt ccgccaggct   120
ccaggcaagg ggctggagtg ggtggcagtt atatcatatg atggaagtaa taaatactat   180
gcagactccg tgaagggccg attcaccatc tccagagaca attccaagaa cacgctgtat   240
ctgcaaatga acagcctgag agccgaggac acggctgtgt attactgtgc gagagatctc   300
ctggtgcgat ttttggagtg gtcgcactac tacggtatgg acgtctgggg ccaagggacc   360
acggtcaccg tctcctca                                                378

SEQ ID NO: 39     moltype = DNA  length = 378
FEATURE           Location/Qualifiers
source            1..378
                  mol_type = other DNA
                  organism = synthetic construct
```

```
                              note = Synthetic Polynucleotide
SEQUENCE: 39
caggtgcagc tggtggagtc tggggggaggc gtggtccagc ctgggaggtc cctgagactc   60
tcctgtgcag cgtctggatt caccttcagt agctatggca tgcactgggt ccgccaggct   120
ccaggcaagg ggctggagtg ggtggcagtt atatcatatg atggaagtaa taaatactat   180
gcagactccg tgaagggccg attcaccatc tccagagaca attccaagaa cacgctgtat   240
ctgcaaatga acagcctgag agccgaggac acggctgtgt attactgtgc gagagatctc   300
ctggtgcgat ttttggagtg gtcgcactac tacggtatgg acgtctgggg ccaagggacc   360
acggtcaccg tctcctca                                                 378

SEQ ID NO: 40        moltype = DNA  length = 378
FEATURE              Location/Qualifiers
source               1..378
                     mol_type = other DNA
                     organism = synthetic construct
                     note = Synthetic Polynucleotide
SEQUENCE: 40
cagatccagc tggtgcagtc tggggggaggc gtggtccagc ctgggaggtc cctgagactc   60
tcctgtgcag cgtctggatt cgccttcagt agctatggca tgcactgggt ccgccaggct   120
ccaggcaagg ggctggagtg ggtggcagtt atatcatatg atggaagtat caaatactat   180
gcagactccg tgaagggccg attcaccatc tccagagaca attccaagaa cacgctgtat   240
ctgcaaatga acagcctgag agccgaggac acggctgtgt attactgtgc gagagatctc   300
ctggtgcgat ttttggagtg gtcgcacaag tacggtatgg acgtctgggg ccaagggacc   360
acggtcaccg tctcctca                                                 378

SEQ ID NO: 41        moltype = DNA  length = 378
FEATURE              Location/Qualifiers
source               1..378
                     mol_type = other DNA
                     organism = synthetic construct
                     note = Synthetic Polynucleotide
SEQUENCE: 41
caggtgcagc tggtggagtc tggggggaggc gtggtccagc ctgggaggtc cctgagactc   60
tcctgtgcag cgtctggatt cgccttcagt agctatggca tgcactgggt ccgccaggct   120
ccaggcaagg ggctggagtg ggtggcagtt atatcatatg atggaagtat caaatactat   180
gcagactccg tgaagggccg attcaccatc tccagagaca attccaagaa cacgctgtat   240
ctgcaaatga acagcctgag agccgaggac acggctgtgt attactgtgc gagagatctc   300
ctggtgcgat ttttggagtg gtcgcacaag tacggtatgg acgtctgggg ccaagggacc   360
acggtcaccg tctcctca                                                 378

SEQ ID NO: 42        moltype = DNA  length = 378
FEATURE              Location/Qualifiers
source               1..378
                     mol_type = other DNA
                     organism = synthetic construct
                     note = Synthetic Polynucleotide
SEQUENCE: 42
cagatccagc tggtgcagtc tggggggaggc gtggtccagc ctgggaggtc cctgagactc   60
tcctgtgcag cgtctggatt cgccttcagt agctatggca tgcactgggt ccgccaggct   120
ccaggcaagg ggctggagtg ggtggcagtt atatcatatg atggaaataa taaatactat   180
gcagactccg tgaagggccg attcaccatc tccagagaca attccaagaa cacgctgtat   240
ctgcaaatga acagcctgag agccgaggac acggctgtgt attactgtgc gagagatctc   300
ctggtgcgat ttttggagtg gtcgcacaag tacggtatgg acgtctgggg ccaagggacc   360
acggtcaccg tctcctca                                                 378

SEQ ID NO: 43        moltype = DNA  length = 378
FEATURE              Location/Qualifiers
source               1..378
                     mol_type = other DNA
                     organism = synthetic construct
                     note = Synthetic Polynucleotide
SEQUENCE: 43
caggtgcagc tggtggagtc tggggggaggc gtggtccagc ctgggaggtc cctgagactc   60
tcctgtgcag cgtctggatt cgccttcagt agctatggca tgcactgggt ccgccaggct   120
ccaggcaagg ggctggagtg ggtggcagtt atatcatatg atggaaataa taaatactat   180
gcagactccg tgaagggccg attcaccatc tccagagaca attccaagaa cacgctgtat   240
ctgcaaatga acagcctgag agccgaggac acggctgtgt attactgtgc gagagatctc   300
ctggtgcgat ttttggagtg gtcgcacaag tacggtatgg acgtctgggg ccaagggacc   360
acggtcaccg tctcctca                                                 378

SEQ ID NO: 44        moltype = DNA  length = 327
FEATURE              Location/Qualifiers
source               1..327
                     mol_type = other DNA
                     organism = synthetic construct
                     note = Synthetic Polynucleotide
SEQUENCE: 44
cagcctgtgc tgactcagcc accctcagcg tctgggaccc ccgggcagag ggtcaccatc   60
tcttgttctg gaagcagctc caacatcgga agtaatactg tccactggta ccagcaactc   120
```

```
ccaggaacgg ccccaaact cctcatctat agtgataatc agcgcccctc aggggtccct    180
gaccgattct ctggctccaa gtctggcacc tcagcctccc tggtcatcag tgggctccag    240
tctgacgatg aggctgatta ttactgtgca gcatgggatg acagcctgaa tggggtgttc    300
ggcggaggga ccaagctgac cgtccta                                        327

SEQ ID NO: 45          moltype = DNA  length = 327
FEATURE                Location/Qualifiers
source                 1..327
                       mol_type = other DNA
                       organism = synthetic construct
                       note = Synthetic Polynucleotide
SEQUENCE: 45
cagtctgtgc tgactcagcc accctcagcg tctgggaccc ccgggcagag ggtcaccatc    60
tcttgttctg gaagcagctc caacatcgga agtaatactg tccactggta ccagcaactc    120
ccaggaacgg ccccaaact cctcatctat agtgataatc agcgcccctc aggggtccct     180
gaccgattct ctggctccaa gtctggcacc tcagcctccc tggccatcag tgggctccag    240
tctgaggatg aggctgatta ttactgtgca gcatgggatg acagcctgaa tggggtgttc    300
ggcggaggga ccaagctgac cgtccta                                        327

SEQ ID NO: 46          moltype = DNA  length = 327
FEATURE                Location/Qualifiers
source                 1..327
                       mol_type = other DNA
                       organism = synthetic construct
                       note = Synthetic Polynucleotide
SEQUENCE: 46
cagcctgtgc tgactcagcc accctcagcg tctgggaccc ccgggcagag ggtcaccatc    60
tcttgttctg gaagcacctc caacatcgga agtaatactg tccactggta ccagcaactc    120
ccaggaacgg ccccaaact cctcatctat agtgatgatc agcgcccctc aggggtccct     180
gaccgattct ctggctccaa gtctggcacc tcagcctccc tggtcatcag tgggctccag    240
tctgacgatg aggctgatta ttactgtgca gcatgggatg agagcctgaa tggggtgttc    300
ggcggaggga ccaagctgac cgtccta                                        327

SEQ ID NO: 47          moltype = DNA  length = 327
FEATURE                Location/Qualifiers
source                 1..327
                       mol_type = other DNA
                       organism = synthetic construct
                       note = Synthetic Polynucleotide
SEQUENCE: 47
cagtctgtgc tgactcagcc accctcagcg tctgggaccc ccgggcagag ggtcaccatc    60
tcttgttctg gaagcacctc caacatcgga agtaatactg tccactggta ccagcaactc    120
ccaggaacgg ccccaaact cctcatctat agtgatgatc agcgcccctc aggggtccct     180
gaccgattct ctggctccaa gtctggcacc tcagcctccc tggccatcag tgggctccag    240
tctgaggatg aggctgatta ttactgtgca gcatgggatg agagcctgaa tggggtgttc    300
ggcggaggga ccaagctgac cgtccta                                        327

SEQ ID NO: 48          moltype = DNA  length = 327
FEATURE                Location/Qualifiers
source                 1..327
                       mol_type = other DNA
                       organism = synthetic construct
                       note = Synthetic Polynucleotide
SEQUENCE: 48
cagcctgtgc tgactcagcc accctcagcg tctgggaccc ccgggcagag ggtcaccatc    60
tcttgttctg gaagcagctc caacatcgga ggaaatactg tccactggta ccagcaactc    120
ccaggaacgg ccccaaact cctcatctat agtgatgatc agcgcccctc aggggtccct     180
gaccgattct ctggctccaa gtctggcacc tcagcctccc tggtcatcag tgggctccag    240
tctgacgatg aggctgatta ttactgtgca gcatgggatg agagcctgaa tggggtgttc    300
ggcggaggga ccaagctgac cgtccta                                        327

SEQ ID NO: 49          moltype = DNA  length = 327
FEATURE                Location/Qualifiers
source                 1..327
                       mol_type = other DNA
                       organism = synthetic construct
                       note = Synthetic Polynucleotide
SEQUENCE: 49
cagtctgtgc tgactcagcc accctcagcg tctgggaccc ccgggcagag ggtcaccatc    60
tcttgttctg gaagcagctc caacatcgga ggaaatactg tccactggta ccagcaactc    120
ccaggaacgg ccccaaact cctcatctat agtgatgatc agcgcccctc aggggtccct     180
gaccgattct ctggctccaa gtctggcacc tcagcctccc tggccatcag tgggctccag    240
tctgaggatg aggctgatta ttactgtgca gcatgggatg agagcctgaa tggggtgttc    300
ggcggaggga ccaagctgac cgtccta                                        327

SEQ ID NO: 50          moltype = AA  length = 452
FEATURE                Location/Qualifiers
source                 1..452
                       mol_type = protein
```

-continued

```
                        organism = synthetic construct
                        note = Synthetic Polypeptide
SEQUENCE: 50
QVQLVESGGG VVQPGRSLRL SCAASGFTFS SYGMHWVRQA PGKGLEWVAV ISYDGSNKYY   60
ADSVKGRFTI SRDNSKNTLY LQMNSLRAED TAVYYCARDL LVRFLEWSHY YGMDVWGQGT   120
TVTVSSASTK GPSVFPLAPC SRSTSESTAA LGCLVKDYFP EPVTVSWNSG ALTSGVHTFP   180
AVLQSSGLYS LSSVVTVPSS SLGTKTYTCN VDHKPSNTKV DKRVESKYGP PCPPCPAPEF   240
LGGPSVFLFP PKPKDTLMIS RTPEVTCVVV DVSQEDPEVQ FNWYVDGVEV HNAKTKPREE   300
QFNSTYRVVS VLTVLHQDWL NGKEYKCKVS NKGLPSSIEK TISKAKGQPR EPQVYTLPPS   360
QEEMTKNQVS LTCLVKGFYP SDIAVEWESN GQPENNYKTT PPVLDSDGSF FLYSRLTVDK   420
SRWQEGNVFS CSVMHEALHN HYTQKSLSLS LG                                 452

SEQ ID NO: 51          moltype = AA   length = 215
FEATURE                Location/Qualifiers
source                 1..215
                       mol_type = protein
                       organism = synthetic construct
                       note = Synthetic Polypeptide
SEQUENCE: 51
QSVLTQPPSA SGTPGQRVTI SCSGSSSNIG SNTVHWYQQL PGTAPKLLIY SDNQRPSGVP   60
DRFSGSKSGT SASLAISGLQ SEDEADYYCA AWDDSLNGVF GGGTKLTVLG QPKAAPSVTL   120
FPPSSEELQA NKATLVCLIS DFYPGAVTVA WKADSSPVKA GVETTTPSKQ SNNKYAASSY   180
LSLTPEQWKS HRSYSCQVTH EGSTVEKTVA PTECS                              215

SEQ ID NO: 52          moltype = AA   length = 352
FEATURE                Location/Qualifiers
source                 1..352
                       mol_type = protein
                       organism = Homo sapiens
SEQUENCE: 52
NENSEQKENV EKEGLCNACT WRQNTKSSRI EAIKIQILSK LRLETAPNIS KDVIRQLLPK   60
APPLRELIDQ YDVQRDDSSD GSLEDDDYHA TTETIITMPT ESDFLMQVDG KPKCCFFKFS   120
SKIQYNKVVK AQLWIYLRPV ETPTTVFVQI LRLIKPMKDG TRYTGIRSLK LDMNPGTGIW   180
QSIDVKTVLQ NWLKQPESNL GIEIKALDEN GHDLAVTFPG PGEDGLNPFL EVKVTDTPKR   240
SRRDFGLDCD EHSTESRCCR YPLTVDFEAF GWDWIIAPKR YKANYCSGEC EFVFLQKYPH   300
THLVHQANPR GSAGPCCTPT KMSPINMLYF NGKEQIIYGK IPAMVVDRCG CS           352

SEQ ID NO: 53          moltype = AA   length = 352
FEATURE                Location/Qualifiers
source                 1..352
                       mol_type = protein
                       organism = Rattus rattus
SEQUENCE: 53
NEDSEREANV EKEGLCNACA WRQNTRYSRI EAIKIQILSK LRLETAPNIS KDAIRQLLPR   60
APPLRELIDQ YDVQRDDSSD GSLEDDDYHA TTETIITMPT ESDFLMQADG KPKCCFFKFS   120
SKIQYNKVVK AQLWIYLRAV KTPTTVFVQI LRLIKPMKDG TRYTGIRSLK LDMSPGTGIW   180
QSIDVKTVLQ NWLKQPESNL GIEIKALDEN GHDLAVTFPG PGEDGLNPFL EVKVTDTPKR   240
SRRDFGLDCD EHSTESRCCR YPLTVDFEAF GWDWIIAPKR YKANYCSGEC EFVFLQKYPH   300
THLVHQANPR GSAGPCCTPT KMSPINMLYF NGKEQIIYGK IPAMVVDRCG CS           352

SEQ ID NO: 54          moltype = AA   length = 352
FEATURE                Location/Qualifiers
source                 1..352
                       mol_type = protein
                       organism = Mus musculus
SEQUENCE: 54
NEGSEREENV EKEGLCNACA WRQNTRYSRI EAIKIQILSK LRLETAPNIS KDAIRQLLPR   60
APPLRELIDQ YDVQRDDSSD GSLEDDDYHA TTETIITMPT ESDFLMQADG KPKCCFFKFS   120
SKIQYNKVVK AQLWIYLRPV KTPTTVFVQI LRLIKPMKDG TRYTGIRSLK LDMSPGTGIW   180
QSIDVKTVLQ NWLKQPESNL GIEIKALDEN GHDLAVTFPG PGEDGLNPFL EVKVTDTPKR   240
SRRDFGLDCD EHSTESRCCR YPLTVDFEAF GWDWIIAPKR YKANYCSGEC EFVFLQKYPH   300
THLVHQANPR GSAGPCCTPT KMSPINMLYF NGKEQIIYGK IPAMVVDRCG CS           352

SEQ ID NO: 55          moltype = AA   length = 277
FEATURE                Location/Qualifiers
source                 1..277
                       mol_type = protein
                       organism = Macaca fascicularis
SEQUENCE: 55
NENSEQKENV EKEGLCNACT WRQNTKSSRI EAIKIQILSK LRLETAPNIS KDAIRQLLPK   60
APPLRELIDQ YDVQRDDSSD GSLEDDDYHA TTETIITMPT ESDFLMQVDG KPKCCFFKFS   120
SKIQYNKVVK AQLWIYLRPV ETPTTVFVQI LRLIKPMKDG TRYTGIRSLK LDMNPGTGIW   180
QSIDVKTVLQ NWLKQPESNL GIEIKALDEN GHDLAVTFPG PGEDGLNPFL EVKVTDTPKR   240
SRRDFGLDCD EHSTESRCCR YPLTVDFEAF GWDWIIA                            277

SEQ ID NO: 56          moltype = AA   length = 4
FEATURE                Location/Qualifiers
source                 1..4
                       mol_type = protein
```

-continued

```
                            organism = synthetic construct
                            note = Synthetic Polypeptide
SEQUENCE: 56
RSRR                                                             4

SEQ ID NO: 57               moltype = AA   length = 4
FEATURE                     Location/Qualifiers
source                      1..4
                            mol_type = protein
                            organism = synthetic construct
                            note = Synthetic Polypeptide
SEQUENCE: 57
RVRR                                                             4

SEQ ID NO: 58               moltype = AA   length = 5
FEATURE                     Location/Qualifiers
source                      1..5
                            mol_type = protein
                            organism = synthetic construct
                            note = Synthetic Polypeptide
SEQUENCE: 58
CPPCP                                                            5

SEQ ID NO: 59               moltype = AA   length = 17
FEATURE                     Location/Qualifiers
source                      1..17
                            mol_type = protein
                            organism = synthetic construct
                            note = Synthetic Polypeptide
SEQUENCE: 59
HYYGMDVWGQ GTTVTVS                                               17

SEQ ID NO: 60               moltype = AA   length = 89
FEATURE                     Location/Qualifiers
source                      1..89
                            mol_type = protein
                            organism = synthetic construct
                            note = Synthetic Polypeptide
SEQUENCE: 60
QSVLTQPPSA SGTPGQRVTI SCSGSSSNIG SNTVNWYQQL PGTAPKLLIY SNNQRPSGVP  60
DRFSGSKSGT SASLAISGLQ SEDEADYYC                                   89

SEQ ID NO: 61               moltype = AA   length = 11
FEATURE                     Location/Qualifiers
source                      1..11
                            mol_type = protein
                            organism = synthetic construct
                            note = Synthetic Polypeptide
SEQUENCE: 61
VFGGGTKLTV L                                                     11

SEQ ID NO: 62               moltype = AA   length = 33
FEATURE                     Location/Qualifiers
source                      1..33
                            mol_type = protein
                            organism = synthetic construct
                            note = Synthetic Polypeptide
SEQUENCE: 62
PKAPPLRELI DQYDVQRDDS SDGSLEDDDY HAT                              33

SEQ ID NO: 63               moltype = AA   length = 34
FEATURE                     Location/Qualifiers
source                      1..34
                            mol_type = protein
                            organism = synthetic construct
                            note = Synthetic Polypeptide
SEQUENCE: 63
GLNPFLEVKV TDTPKRSRRD FGLDCDEHST ESRC                             34

SEQ ID NO: 64               moltype = AA   length = 80
FEATURE                     Location/Qualifiers
source                      1..80
                            mol_type = protein
                            organism = synthetic construct
                            note = Synthetic Polynucleotide
SEQUENCE: 64
VDLNENSEQK ENVEKEGLCN ACTWRQNTKS SRIEAIKIQI LSKLRLETAP NISKDVIRQL  60
LPKAPPLREL IDQYDVQRDD                                             80
```

-continued

```
SEQ ID NO: 65          moltype = AA   length = 418
FEATURE                Location/Qualifiers
source                 1..418
                       mol_type = protein
                       organism = synthetic construct
                       note = Synthetic Polynucleotide
SEQUENCE: 65
MDMRVPAQLL GLLLLWFSGV LGDYKDDDDK HHHHHHLEVL FQGPAEGPAA AAAAAAAAAA  60
AGVGGERSSR PAPSVAPEPD GCPVCVWRQH SRELRLESIK SQILSKLRLK EAPNISREVV  120
KQLLPKAPPL RELIDQYDVQ RDDSSDGSLE DDDYHATTET IITMPTESDF LMQVDGKPKC  180
CFFKFSSKIQ YNKVVKAQLW IYLRPVETPT TVFVQILRLI KPMKDGTRYT GIRSLKLDMN  240
PGTGIWQSID VKTVLQNWLK QPESNLGIEI KALDENGHDL AVTFPGPGED GLNPFLEVKV  300
TDTPKRSRRN LGLDCDEHSS ESRCCRYPLT VDFEAFGWDW IIAPKRYKAN YCSGQCEYMF  360
MQKYPHTHLV QQANPRGSAG PCCTPTKMSP INMLYFNDKQ QIIYGKIPGM VVDRCGCS    418
```

METHOD OF MAKING ANTI-PRO/LATENT MYOSTATIN ANTIBODIES

CROSS REFERENCE TO RELATED APPLICATION

This application claims priority under 35 U.S.C. § 119(e) of U.S. Provisional Patent Application No. 62/219,094, filed Sep. 15, 2015, and entitled "ANTI-PRO/LATENT-MYO-STATIN ANTIBODIES AND USES THEREOF", the contents of which are incorporated herein by reference for all purposes.

SEQUENCE LISTING

The instant application contains a Sequence Listing which has been submitted electronically in XML format and is hereby incorporated by reference in its entirety. Said XML copy, created on Nov. 28, 2022, is named 15094_0002-02000_SL.xml and is 75,036 bytes in size.

FIELD OF THE DISCLOSURE

Embodiments of the present disclosure may include modulators of growth factor activity. In some embodiments, such modulators may include antibodies and may modulate TGF-β family member activity and/or biology.

BACKGROUND OF THE DISCLOSURE

Myostatin is a secreted growth factor which negatively regulates muscle mass. Loss of function mutations in the Myostatin gene, leading to a hypermuscular phenotype, have been described in cattle, sheep, fish, dogs and humans. Myostatin expression is generally limited to skeletal muscle, with low levels of expression reported in adipose and cardiac tissues. Inhibition of Myostatin signaling leads to an increase in muscle size.

SUMMARY OF THE DISCLOSURE

Aspects of the disclosure relate, in some embodiments, to antibodies that bind specifically to forms of Myostatin (e.g., proMyostatin and/or latent Myostatin). For example, antibodies provided herein specifically bind to one or more of a pro-form, and/or a latent-form of Myostatin, such as pro-Myostatin and/or latent Myostatin. In certain aspects, the disclosure is based on the surprising discovery of antibodies provided herein that specifically bind pure, or substantially pure, proGDF8 (also referred to as proMyostatin). In some embodiments, antibodies provided herein inhibit Myostatin signaling. In some embodiments, inhibition of Myostatin signaling is useful for increasing muscle mass or preventing muscle atrophy. In some embodiments, antibodies provided herein bind to and prevent cleavage of Myostatin by a proprotein convertase and/or a tolloid protease. Preventing cleavage of proMyostatin or latent Myostatin, in some embodiments, prevents Myostatin activation. Further aspects of the disclosure relate to antibodies having an affinity to an antigen that is sensitive to pH. In some embodiments, such pH sensitive antibodies are effective for clearing antigens from serum. Furthermore, in some embodiments, antibodies provided herein are sweeping antibodies that can efficiently clear antigens (e.g., proMyostatin and/or latent Myostatin) from serum.

Aspects of the present disclosure include an antibody that comprises a heavy chain variable domain and a light chain variable domain, in which the heavy chain variable domain comprises a complementarity determining region 3 (CDRH3) comprising a sequence as set forth in any one of SEQ ID NOs: 10-11. In some embodiments, an antibody specifically binds to pro/latent-Myostatin. In some embodiments, the light chain variable domain comprises a complementarity determining region 3 (CDRL3) comprising a sequence as set forth in any one of SEQ ID NO: 22-23. In another embodiment, said antibody comprises six complementarity determining regions (CDRs): CDRH1, CDRH2, CDRH3, CDRL1, CDRL2, and CDRL3, wherein CDRH1 comprises a sequence as set forth in any one of SEQ ID NOs: 1-3, CDRH2 comprises a sequence as set forth in any one of SEQ ID NOs: 4-9, CDRH3 comprises a sequence as set forth in any one of SEQ ID NOs: 10-11, CDRL1 comprises a sequence as set forth in any one of SEQ ID NOs: 12-17, CDRL2 comprises a sequence as set forth in any one of SEQ ID NOs: 18-21, and CDRL3 comprises a sequence as set forth in any one of SEQ ID NOs: 22-23.

In some embodiments, said CDRH1 comprises a sequence as set forth in SEQ ID NO: 1 or 2, CDRH2 comprises a sequence as set forth in SEQ ID NO: 4 or 5, CDRH3 comprises a sequence as set forth in SEQ ID NO: 10, CDRL1 comprises a sequence as set forth in SEQ ID NO: 12 or 13, CDRL2 comprises a sequence as set forth in SEQ ID NO: 18 or 19, and CDRL3 comprises a sequence as set forth in SEQ ID NO: 22.

In another embodiment, said CDRH1 comprises a sequence as set forth in SEQ ID NO: 1 or 3, CDRH2 comprises a sequence as set forth in SEQ ID NO: 6 or 7, CDRH3 comprises a sequence as set forth in SEQ ID NO: 11. CDRL1 comprises a sequence as set forth in SEQ ID NO: 14 or 15, CDRL2 comprises a sequence as set forth in SEQ ID NO: 20 or 21, and CDRL3 comprises a sequence as set forth in SEQ ID NO: 23.

In other embodiments, CDRH1 comprises a sequence as set forth in SEQ ID NO: 1 or 3, CDRH2 comprises a sequence as set forth in SEQ ID NO: 8 or 9, CDRH3 comprises a sequence as set forth in SEQ ID NO: 11, CDRL1 comprises a sequence as set forth in SEQ ID NO: 16 or 17, CDRL2 comprises a sequence as set forth in SEQ ID NO: 20 or 21, and CDRL3 comprises a sequence as set forth in SEQ ID NO: 23.

In another embodiment, said antibody comprises a heavy chain variable domain sequence as set forth in any one of SEQ ID NOs: 25-29. In some embodiments, said antibody comprises a light chain variable domain sequence of as set forth in any one of SEQ ID NOs: 30-35.

Other aspects of the disclosure include an antibody that specifically binds to pro/latent-Myostatin and that comprises a heavy chain variable domain and a light chain variable domain, in which the light chain variable domain comprises a complementarity determining region 3 (CDRL3) comprising a sequence as set forth in any one of SEQ ID NO: 22-23. In some embodiments, said antibody comprises a light chain variable domain sequence of SEQ ID NO: 30.

Some aspects of the disclosure relate to a polypeptide having a sequence selected from the group consisting of SEQ ID NO: 24, SEQ ID NO: 25, SEQ ID NO: 26, SEQ ID NO: 27, SEQ ID NO: 28, and SEQ ID NO 29. In some embodiments, the polypeptide is a variable heavy chain domain. In some embodiments, the polypeptide is at least 75% (e.g., 80%, 85%, 90%, 95%, 98%, or 99%) identical to any one of the amino acid sequences set forth in SEQ ID NO: 24, SEQ ID NO: 25, SEQ ID NO: 26, SEQ ID NO: 27, SEQ ID NO: 28, or SEQ ID NO 29.

Some aspects of the disclosure relate to a polypeptide having a sequence selected from the group consisting of SEQ ID NO: 30, SEQ ID NO: 31, SEQ ID NO: 32, SEQ ID NO: 33, SEQ ID NO: 34, and SEQ ID NO 35. In some embodiments, the polypeptide is a variable light chain domain. In some embodiments, the polypeptide is at least 75% (e.g., 80%, 85%, 90%, 95%, 98%, or 99%) identical to any one of the amino acid sequences set forth in SEQ ID NO: 30, SEQ ID NO: 31, SEQ ID NO: 32, SEQ ID NO: 33, SEQ ID NO: 34, or SEQ ID NO 35.

Another aspect of the disclosure includes an antibody that competes for binding to pro/latent-Myostatin with an antibody described above. In some embodiments, said antibody binds to pro/latent-Myostatin at the same epitope as an antibody described above. In another embodiment, an antibody competes for binding to pro/latent-Myostatin with an equilibrium dissociation constant, Kd, between the antibody and pro/latent-Myostatin of is less than $10^{-6}$ M. In other embodiments, said antibody's Kd is in a range of $10^{-11}$ M to $10^{-6}$ M.

In some embodiments, an antibody is a humanized antibody, a diabody, a chimeric antibody, a Fab fragment, a F(ab')2 fragment, or an Fv fragment. In another embodiment, an antibody is a humanized antibody. In another embodiment, an antibody is a human antibody.

In some embodiments, an antibody comprises a framework having a human germline sequence. In another embodiment, an antibody comprises a heavy chain constant domain selected from the group consisting of IgG, IgG1, IgG2, IgG2A, IgG2B, IgG2C, IgG3, IgG4, IgA1, IgA2, IgD, IgM, and IgE constant domains. In some embodiments, an antibody comprises a constant domain of IgG4. In other embodiments, an antibody comprises a constant domain of IgG4 having a backbone substitution of Ser to Pro that produces an IgG1-like hinge and permits formation of inter-chain disulfide bonds. In another embodiment, an antibody is conjugated to an agent selected from the group consisting of a fluorescent agent, a luminescent agent, an enzymatic agent and a radioactive agent.

In another embodiment, an antibody specifically binds to pro/latent-Myostatin compared with mature myostatin. In some embodiments, an antibody specifically binds to pro/latent-Myostatin compared with another member of the transforming growth factor Beta family. In another embodiment, said member is GDF11 or Activin.

A further aspect of the disclosure includes an antibody that specifically binds pro/latent-Myostatin and that inhibits proteolytic formation of mature myostatin by a tolloid protease. In some embodiments, said antibody inhibits proteolytic formation of mature myostatin by a tolloid protease with an IC50 of less than 1 μM. In some embodiments, an antibody is cross-reactive with human and murine pro/latent-Myostatin. In other embodiments, the antibody specifically binds to pro/latent-Myostatin compared with GDF11 or Activin. In another embodiment, an antibody specifically binds to pro/latent-Myostatin compared with mature myostatin.

Another aspect of the disclosure encompasses a method of reducing myostatin receptor activation in cells present in a medium comprising pro/latent-Myostatin, the method comprising delivering to the medium an antibody described above in an amount effective for inhibiting proteolytic activation of the pro/latent-Myostatin. In some embodiments, the medium further comprises a proprotein convertase. In other embodiments, the medium further comprises a tolloid protease. In another embodiment, an antibody is delivered to the medium in an amount effective for inhibiting proteolytic activation of the pro/latent-Myostatin by the tolloid protease. In some embodiments, the cell is in vitro. In other embodiments, the cell is in vivo.

Another aspect of the disclosure includes a method of treating a subject having a myopathy, the method comprising administering to the subject an effective amount of an antibody described above. In some embodiments, the myopathy is a primary myopathy. In another embodiment, the primary myopathy comprises disuse atrophy. In other embodiments, the disuse atrophy is associated with hip fracture, elective joint replacement, critical care myopathy, spinal cord injury or stroke. In some embodiments, the myopathy is a secondary myopathy, in which muscle loss is secondary to a disease pathology. In other embodiments, the secondary myopathy comprises denervation, genetic muscle weakness or cachexia. In another embodiment, the secondary myopathy is a denervation associated with amyotrophic lateral sclerosis or spinal muscular atrophy. In some embodiments, the secondary myopathy is a genetic muscle weakness associated with a muscular dystrophy. In other embodiments, the secondary myopathy is a cachexia associated with renal failure, AIDS, a cardiac condition, cancer or aging.

Another aspect of the disclosure includes a method of treating a subject having a disease or condition related to aging. Exemplary diseases and conditions related to ageing include, without limitation, sarcopenia (age-related muscle loss), frailty, and androgen deficiency.

Another aspect of the disclosure includes a method of treating a subject having a disease or condition related to disuse atrophy/trauma. Exemplary diseases and conditions related to disuse atrophy/trauma include, without limitation, muscle weakness related to time spent in an intensive care unit (ICU), hip/joint replacement, hip fracture, stroke, bed rest, SCI, rotator cuff injury, knee replacement, bone fracture, and burns.

Another aspect of the disclosure includes a method of treating a subject having a neurodegenerative disease or condition. Exemplary neurodegenerative diseases or conditions include, without limitation, spinal muscular atrophy and amyotrophic lateral sclerosis (ALS).

Another aspect of the disclosure includes a method of treating a subject having a disease or condition related to Cachexia. Exemplary diseases and conditions related to cachexia include, without limitation, cancer, chronic heart failure, acquired immune deficiency syndrome (AIDS), chronic obstructive pulmonary disease (COPD), and chronic kidney disease (CKD).

Another aspect of the disclosure includes a method of treating a subject having a disease or condition related to rare diseases. Exemplary rare diseases and conditions include, without limitation, osteogenesis imperfecta, sporadic Inclusion body myositis, and acute lymphoblastic leukemia.

Another aspect of the disclosure includes a method of treating a subject having a disease or condition related to a metabolic disorder and/or body composition. In some embodiments, the disease or condition is obesity (e.g., severe obesity), Prader-Willi, type II diabetes, or anorexia. However, additional diseases or conditions related to metabolic disorders and/or body composition are within the scope of this disclosure.

Another aspect of the disclosure includes a method of treating a subject having a disease or condition related to congenital myopathies. Exemplary congenital myopathies include, without limitation, X-linked myotubular myopathy, autosomal dominant centronuclear myopathy, autosomal recessive centronuclear myopathy, nemaline myopathy, and congenital fiber-type disproportion myopathy.

Another aspect of the disclosure includes a method of treating a subject having a disease or condition related to muscular dystrophies. Exemplary muscular dystrophies include, without limitation, Duchenne's, Becker's, facioscapulohumeral (FSH), and Limb-Girdle muscular dystrophies.

Another aspect of the disclosure includes a method of treating a subject having a urogynecological related disease or condition, glottic disorders (stenosis), extraocular myopathy, carpel tunnel, Guillain-Barré, or osteosarcoma.

In some embodiments, treatment results in improved muscle strength in the subject. In other embodiments, treatment results in improved metabolic status in the subject.

In some embodiments, an antibody is administered at a dose in a range of 0.1 mg/kg to 100 mg/kg. In another embodiment, an antibody is administered at a dose in a range of 0.3 mg/kg to 30 mg/kg.

In some embodiments, an antibody is administered to the subject intravenously. In other embodiments, an antibody is administered to the subject subcutaneously. In another embodiment, an antibody is administered to the subject on multiple occasions. In some embodiments, said multiple administrations are performed at least monthly. In another embodiment, said multiple administrations are performed at least weekly.

A further aspect of the disclosure includes a composition comprising any antibody described above and a carrier. In some embodiments, said carrier is a pharmaceutically acceptable carrier. In other embodiments, an antibody and carrier are in a lyophilized form. In another embodiment, an antibody and carrier are in solution. In some embodiments, an antibody and carrier are frozen. In other embodiments, an antibody and carrier are frozen at a temperature less than or equal to −65° C.

Other aspects of the disclosure include an isolated nucleic acid encoding a protein comprising three complementarity determining regions (CDRs): CDRH1, CDRH2, and CDRH3, in which CDRH3 comprises a sequence as set forth in SEQ ID NO: 10 or 11. In some embodiments, said CDRH1 comprises a sequence as set forth in SEQ ID NO: 1, 2 or 3. In other embodiments, CDRH2 comprises a sequence as set forth in any one of SEQ ID NOs: 4-9.

Another aspect of the present disclosure includes an isolated nucleic acid encoding a protein comprising three complementarity determining regions (CDRs): CDRL1, CDRL2, and CDRL3, in which CDRL3 comprises a sequence as set forth in SEQ ID NO: 22. In some embodiments, said CDRL1 comprises a sequence as set forth in any one of SEQ ID NOs: 12-17. In other embodiments, CDRL2 comprises a sequence as set forth in any one of SEQ ID NOs: 18-21.

Further aspects of the present disclosure include an isolated nucleic acid comprising a sequence as set forth in any one of SEQ ID NOs: 38-49.

Another aspect of the disclosure includes an isolated cell comprising an isolated nucleic acid described above.

The present disclosure, in some aspects, includes methods of assessing a biological sample obtained from a subject having a myopathy. In some embodiments, the method comprises: preparing an immunological reaction mixture that comprises protein of a biological sample obtained from the subject and an antibody that specifically binds pro/latent—Myostatin; maintaining the immunological reaction mixture under conditions that permit binding complexes to form between the antibody and a pro/latent-Myostatin; and determining the extent of binding complex formation. In some embodiments, the method comprises: preparing an immunological reaction mixture that comprises protein of a biological sample obtained from the subject and an antibody that specifically binds pro-Myostatin; maintaining the immunological reaction mixture under conditions that permit binding complexes to form between the antibody and a pro-Myostatin; and determining the extent of binding complex formation. In some embodiments, the method comprises: preparing an immunological reaction mixture that comprises protein of a biological sample obtained from the subject and an antibody that specifically binds latent-Myostatin; maintaining the immunological reaction mixture under conditions that permit binding complexes to form between the antibody and a latent-Myostatin; and determining the extent of binding complex formation. In some embodiments, the method comprises: preparing an immunological reaction mixture that comprises protein of a biological sample obtained from the subject and an antibody that specifically binds mature-Myostatin; maintaining the immunological reaction mixture under conditions that permit binding complexes to form between the antibody and a mature-Myostatin; and determining the extent of binding complex formation.

In one aspect, disclosed herein is an isolated antibody comprising a heavy chain variable region comprising an amino acid sequence of SEQ ID NO:25 and a light chain variable region comprising an amino acid sequence of SEQ ID NO:31. In one embodiment, the antibody comprises a heavy chain comprising an amino acid sequence of SEQ ID NO:50. In another embodiment, the antibody comprises a light chain comprising an amino acid sequence of SEQ ID NO:51.

In another aspect, disclosed herein is an isolated antibody comprising a heavy chain variable region comprising a CDRH1 sequence comprising SEQ ID NO:1, a CDRH2 sequence comprising SEQ ID NO:6, and a CDRH3 sequence comprising SEQ ID NO: 11; and a light chain variable region comprising a CDRL1 sequence comprising SEQ ID NO:14, a CDRL2 sequence comprising SEQ ID NO:20, and a CDRL3 sequence comprising SEQ ID NO:23.

In one embodiment, the heavy chain variable region comprises a sequence of SEQ ID NO:26. In another embodiment, the light chain variable region comprises a sequence of SEQ ID NO:32.

In one embodiment, the heavy chain variable region comprises a sequence of SEQ ID NO:27. In another embodiment, the light chain variable region comprises a sequence of SEQ ID NO:33

In another aspect, disclosed herein is an isolated antibody comprising a heavy chain variable region comprising a CDRH1 sequence comprising SEQ ID NO:1, a CDRH2 sequence comprising SEQ ID NO:8, and a CDRH3 sequence comprising SEQ ID NO:11; and a light chain variable region comprising a CDRL1 sequence comprising SEQ ID NO:16, a CDRL2 sequence comprising SEQ ID NO:20, and a CDRL3 sequence comprising SEQ ID NO:23.

In one embodiment, the heavy chain variable region comprises a sequence of SEQ ID NO:28. In another embodiment, the light chain variable region comprises a sequence of SEQ ID NO:34.

In one embodiment, the heavy chain variable region comprises a sequence of SEQ ID NO:29. In one embodiment, the light chain variable region comprises a sequence of SEQ ID NO:35.

In one embodiment, the antibody is a human antibody. In one embodiment, the antibody comprises an IgG4 constant domain. In one embodiment, the antibody comprises an IgG4 constant domain having a backbone substitution of Ser to Pro that produces an IgG1-like hinge and permits formation of inter-chain disulfide bonds.

In one embodiment, the antibody specifically binds to pro/latent-myostatin. In one embodiment, the antibody specifically binds to pro-myostatin. In another embodiment, the antibody specifically binds to latent-myostatin. In one embodiment, the antibody does not bind to mature myostatin.

In one embodiment, the antibody inhibits proteolytic formation of mature myostatin by tolloid protease. In one embodiment, the antibody inhibits proteolytic formation of mature myostatin by tolloid protease with an IC50 of less than 1 µM.

In one embodiment, the antibody is cross-reactive with human and murine pro/latent-myostatin. In another embodiment, the antibody binds to pro/latent-myostatin but does not bind to GDF11 or activin.

In one aspect, disclosed herein is a method of reducing myostatin receptor activation in cells present in a medium comprising pro/latent-myostatin, the method comprising delivering to the medium an antibody described herein in an amount effective for inhibiting proteolytic activation of the pro/latent-myostatin. In one embodiment, the medium comprises a proprotein convertase. In another embodiment, the medium comprises a tolloid protease. In one embodiment, the cell is in vitro. In another embodiment, the cell is in vivo.

In another aspect, disclosed herein is a method of treating a subject having a myopathy, the method comprising administering to the subject an effective amount of an antibody disclosed herein.

In one embodiment, the myopathy is a primary myopathy. In another embodiment, the primary myopathy is disuse atrophy. In one embodiment, the disuse atrophy is associated with hip fracture, elective joint replacement, critical care myopathy, spinal cord injury, and/or stroke.

In another embodiment, the myopathy is a secondary myopathy in which muscle loss is secondary to a disease pathology. In one embodiment, the secondary myopathy comprises denervation, genetic muscle weakness, or cachexia. In another embodiment, the secondary myopathy is a denervation associated with amyotrophic lateral sclerosis or spinal muscular atrophy. In yet another embodiment, the secondary myopathy is a genetic muscle weakness associated with a muscular dystrophy. In one embodiment, the secondary myopathy is a cachexia associated with renal failure, AIDS, a cardiac condition, cancer, or aging.

In one embodiment, the administering results in improved muscle strength in the subject. In one embodiment, the administering results in improved metabolic status in the subject.

In one embodiment, the antibody is administered at a dose in a range of 0.1 mg/kg to 100 mg/kg. In another embodiment, the antibody is administered at a dose in a range of 0.3 mg/kg to 30 mg/kg.

In one embodiment, the antibody is administered to the subject intravenously. In another embodiment, the antibody is administered to the subject subcutaneously.

In one embodiment, the antibody is administered to the subject on multiple occasions. In one embodiment, the multiple administrations are performed at least monthly. In another embodiment, the multiple administrations are performed at least weekly.

In another aspect, disclosed herein is a pharmaceutical composition comprising an antibody disclosed herein and a pharmaceutically acceptable carrier. In one embodiment, the composition is a lyophilized composition. In another embodiment, the composition is a liquid composition. In one embodiment, the composition is frozen. In one embodiment, the composition is frozen at a temperature less than or equal to −65° C.

In another aspect, disclosed herein is a syringe comprising a pharmaceutical composition described herein.

In another aspect, disclosed herein is an isolated nucleic acid encoding an antibody comprising a heavy chain variable region comprising a nucleic acid sequence of SEQ ID NO:39 and a light chain variable region comprising a nucleic acid sequence of SEQ ID NO:45.

In another aspect, disclosed herein is an isolated nucleic acid encoding an antibody comprising a heavy chain variable region comprising a CDRH1 sequence comprising SEQ ID NO:1, a CDRH2 sequence comprising SEQ ID NO:6, and a CDRH3 sequence comprising SEQ ID NO:11; and a light chain variable region comprising a CDRL1 sequence comprising SEQ ID NO:14, a CDRL2 sequence comprising SEQ ID NO:20, and a CDRL3 sequence comprising SEQ ID NO:23.

In one embodiment, the heavy chain variable region comprises a sequence of SEQ ID NO:40. In one embodiment, the light chain variable region comprises a sequence of SEQ ID NO:46.

In one embodiment, the heavy chain variable region comprises a sequence of SEQ ID NO:41. In another embodiment, the light chain variable region comprises a sequence of SEQ ID NO:47.

In another aspect, disclosed herein is an isolated nucleic acid encoding an antibody comprising a heavy chain variable region comprising a CDRH1 sequence comprising SEQ ID NO:1, a CDRH2 sequence comprising SEQ ID NO:8, and a CDRH3 sequence comprising SEQ ID NO:11; and a light chain variable region comprising a CDRL1 sequence comprising SEQ ID NO:16, a CDRL2 sequence comprising SEQ ID NO:20, and a CDRL3 sequence comprising SEQ ID NO:23.

In one embodiment, the heavy chain variable region comprises a sequence of SEQ ID NO:42. In another embodiment, the light chain variable region comprises a sequence of SEQ ID NO:48.

In one embodiment, the heavy chain variable region comprises a sequence of SEQ ID NO:43. In another embodiment, the light chain variable region comprises a sequence of SEQ ID NO:49.

In another aspect, disclosed herein is an isolated cell comprising an isolated nucleic acid described herein.

BRIEF DESCRIPTION OF THE FIGURES

FIG. 1A shows Myostatin secreted as a proprotein, with an inhibitory prodomain followed by a C-terminal growth factor domain, which exists as a disulfide-linked dimer. FIG. 1B shows precursor protein assembled in an inactive conformation where the prodomain (dark gray) encloses the growth factor (light gray) with a "straightjacket" assembly. This figure is an adaption from the structure of latent TGFβ1 (Shi et al. Nature 2011).

FIG. 3C shows the activation of Myostatin involves two distinct protease events, generating three major Myostatin species. The biosynthetic precursor protein, proMyostatin, is processed by two separate proteases. Cleavage of proMyostatin (and proGDF11) is carried out by a proprotein convertase, such as Furin/PACE3 (Paired Basic Amino acid Cleaving Enzyme 3) or PCSK5 (Proprotein Convertase Subtilisin/Kexin type 5), which cuts at a conserved RXXR site between the prodomain and mature growth factor. This cleavage produces a latent complex, in which the mature growth factor is shielded from binding to its receptors by the prodomain. See FIG. 3B, which illustrates the potential inhibition of a tolloid protease, blocking further cleavage of proMyostatin. Activation and release of the active growth factor is accomplished after cleavage by an additional protease from the BMP/tolloid family, such as TLL-2 (Tolloid-like protein 2) or BMP1 (Bone Morphogenetic Protein 1).

FIG. 7A shows the mean gastrocnemius weight. FIG. 7B shows the mean pectoralis weight. FIG. 7C shows the mean soleus weight. FIG. 7D shows the mean triceps weight. Statistical evaluation was performed using a one-way ANOVA followed by Holm-Sidak's post hoc test in comparison to the Vehicle Control Group (Group 1). Data represent group means±SEM. **$p<0.01$. Bars indicate from left-to-right Groups 1-5.

FIG. 8A shows the mean tibialis anterior weight. FIG. 8B shows the mean diaphragm weight. FIG. 8C shows the mean quadriceps weight. Statistical evaluation was performed using a one-way ANOVA followed by Holm-Sidak's post hoc test in comparison to the Vehicle Control Group (Group 1). Data represent group means±SEM. *$p<0.05$. Bars indicate from left-to-right Groups 1-5.

FIG. 9A is a graph showing the calculated percent weight change from Day 0 in animals weighed twice weekly throughout the study. In FIG. 9B, animals underwent EchoMRI (QNMR) to measure body composition on days −4, 7, 14, 21, and 28 and percent lean mass change from Day 0 was calculated. Data represent group means±SEM. For both body weight and lean mass the mean percent change data for each group on day 28 of the study were analyzed using a one-way ANOVA followed by Holm-Sidak's post hoc test in comparison to the IgG Control Group (Group 2). *$p<0.0005$, $p<0.005$, *$p<0.05$, ns (not significant).

FIG. 10A shows the mean quadriceps weight, FIG. 10B shows the mean gastrocnemius weight, FIG. 10C shows the mean tibialis anterior weight, and FIG. 10D shows the mean diaphragm weight. Percent difference in mean muscle weights of the Ab1 treated groups compared to the IgG control group is noted above each bar. Statistical evaluation was performed using a one-way ANOVA followed by Holm-Sidak's post hoc test in comparison to the IgG Control Group (Group 2). Data represent group means±SEM. **$p<0.0001$, *$p<0.0005$, **$p<0.005$. *$p<0.05$, ns (not significant).

FIG. 11A shows the percent weight change from Day 0 calculated from animals weighed twice weekly throughout the study. (FIG. 11B) Animals underwent EchoMRI (QNMR) to measure body composition on days −1, 6, and 13 and percent lean mass change from Day −1 was calculated. PBS=phosphate buffered saline, Dex=dexamethasone, IgG (20)=IgG control antibody dosed at 20 mg/kg/wk, Ab1 (20)=Ab1 antibody dosed at 20 mg/kg/wk, and Ab1 (2)=Ab1 antibody dosed at 2 mg/kg/wk. Data represent group means±SEM. Mean percent change data for each group on day 14 (for body weight) and day 13 (for lean mass) were analyzed using a one-way ANOVA followed by a Dunnett's multiple comparisons test vs. group 1 (**$p<0.0001$, *$p<0.0005$, **$p<0.005$, *$p<0.05$) and vs. group 5 (++++$p<0.0001$, +++$p<0.0005$, ++$p<0.005$, +$p<0.05$). ns (not significant).

FIG. 12A shows the mean gastrocnemius weight (grams), FIG. 12B shows the mean quadriceps weight (grams), FIG. 12C shows the mean percent gastrocnemius weight change versus the control animals treated with PBS (IP) and normal drinking water (Group 1), and FIG. 12D shows the mean percent quadriceps weight change versus the control animals treated with PBS (IP) and normal drinking water (Group 1). PBS=phosphate buffered saline, Dex=dexamethasone, IgG (20)=IgG control antibody dosed at 20 mg/kg/wk, Ab1 (20)=Ab1 antibody dosed at 20 mg/kg/wk, and Ab1 (2)=Ab1 antibody dosed at 2 mg/kg/wk. For FIGS. 12A-12B, error bars represent standard deviation (SD). For FIGS. 12C-12D, error bars represent standard error of the mean (SEM). Statistical evaluation was performed using a one-way ANOVA followed by a Dunnett's multiple comparisons test vs. group 1 (**$p<0.0001$, *$p<0.0005$, **$p<0.005$, *$p<0.05$) and vs. group 5 (++++$p<0.0001$, +++$p<0.0005$, ++$p<0.005$, +$p<0.05$). ns (not significant). Bars indicate from left-to-right, PBS, water; PBS, dex; IgG Control; Ab1(20); and Ab1(2).

FIG. 13A shows the percent weight change from Day 0 calculated for animals who were weighed twice weekly throughout the study. FIG. 13B shows the percent lean mass change from Day −1 calculated from animals who underwent EchoMRI (QNMR) to measure body composition on days −1, 7, and 14. PBS=phosphate buffered saline, IgG (20)=IgG control antibody dosed at 20 mg/kg/wk, Ab1 (20)=Ab1 antibody dosed at 20 mg/kg/wk, and Ab1 (2)=Ab1 antibody dosed at 2 mg/kg/wk. Data represent group means±SEM.

FIG. 14A shows the mean gastrocnemius weight from the casted leg (grams), FIG. 14B shows the mean quadriceps weight from the casted leg (grams), FIG. 14C shows the mean percent gastrocnemius weight change versus the control animals treated with PBS (IP) and not casted (Group 1), and FIG. 14D shows the mean percent quadriceps weight change versus the control animals treated with PBS (IP) and not casted (Group 1). PBS=phosphate buffered saline, IgG (20)=IgG control antibody dosed at 20 mg/kg/wk, Ab1 (20)=Ab1 antibody dosed at 20 mg/kg/wk, and Ab1 (2)=Ab1 antibody dosed at 2 mg/kg/wk. For FIGS. 14A-14B, error bars represent standard deviation (SD). For FIGS. 14C-14D, error bars represent standard error of the mean (SEM). Statistical evaluation was performed using a one-way ANOVA followed by a Dunnett's multiple comparisons test vs. group 1 (**$p<0.0001$, *$p<0.0005$, **$p<0.005$, *$p<0.05$) and vs. group 5 (++++$p<0.0001$, +++$p<0.0005$, ++$p<0.005$, +$p<0.05$). ns (not significant). Bars indicate from left-to-right, PBS, no cast; PBS, casted; IgG Control (2), casted; Ab1(20), casted; and Ab1(2), casted.

FIG. 16A shows the domain structure of proMyostatin and latent Myostatin, with protease cleavage sites indicated. FIG. 16B shows partially proprotein convertase cleaved proMyostatin run on an SDS PAGE gel. Under reducing conditions, the protein bands consisted of the proMyostatin monomer (~50 kD), prodomain (~37 kD) and growth factor (12.5 kD).

FIG. 17A shows Ab1 binds specifically to proMyostatin and latent Myostatin, with no binding observed to other members of the TGFB superfamily, most notably the corresponding forms of GDF11. Ab1 was administered at a high concentration (50 ug/mL) to Forte-Bio BLT tips coated with the indicated antigen and the on and off rates were measured to obtain an approximate Kd value. The magnitude of biosensor response, indicating a binding event, is graphically represented by black bars, and the calculated Kd is indicated in orange. FIG. 17B shows that Ab1 blocks the activation of proMyostatin, but not proGDF11. Following an overnight proteolysis reaction with enzymes from both the proprotein-convertase and tolloid protease families, the release of mature growth factor was measured using a CAGA-based reporter assay in 293T cells. Results were compared to control reactions to calculate the fraction of proMyostatin or proGDF11 which was released in the assay.

FIGS. 18A-18C show the SCID dose response with the candidate antibodies. FIG. 18A shows the muscle weight of the gastrocnemius and FIG. 18B shows the muscle weight of the quadriceps. FIG. 18C shows the percent changes in mean muscle weight compared to the PBS control. The bars in FIGS. 18A-18B from left-to-right are: PBS; IgG Ctrl 20 mg/kg/wk; Ab1 20 mg/kg/wk; Ab1 2 mg/kg/wk; Ab1 0.5 mg/kg/wk; Ab2 20 mg/kg/wk; Ab2 2 mg/kg/wk; Ab2 0.5 mg/kg/wk; Ab4 20 mg/kg/wk; Ab4 2 mg/kg/wk; Ab4 0.5 mg/kg/wk; Ab6 20 mg/kg/wk; Ab6 2 mg/kg/wk; and Ab6 0.5 mg/kg/wk.

FIG. 20 is a schematic illustrating an assay that reconstitutes Myostatin activation in vitro.

FIGS. 21A-21B show the heavy chain (FIG. 21A; SEQ ID NO: 50) and light chain (FIG. 21B; SEQ ID NO: 51) of a humanized monoclonal antibody (Ab2) of the IgG4 subtype with Proline substituted for Serine. This generates an IgG1-like hinge sequence and minimizes the incomplete formation of inter-chain disulfide bridges which is characteristic of IgG4. The complementarity-determining regions (CDRs) are underlined. Bolded NST sequence: N-linked glycosylation consensus sequence site; Bolded DP sequences are potential cleavage sites; Bolded NX sequences, wherein X can be S, T, or G are potential deamidation sites; Bolded DX sequences, wherein X can be G, S, T, or SDG are potential isomerization sites; Bolded methionines are potential methionine oxidation sites; Bolded Q is an expected N-terminal pyroglutamic acid.

FIG. 23C shows the affinity-matured variants have a slower off-rate by octet as well.

FIGS. 24A-24B show sequence alignments of the variable heavy regions (FIG. 24A) and variable light regions (FIG. 24B) of parental Ab1 with affinity optimized variants, Ab3 and Ab5. Sequence identifiers from top to bottom correspond to SEQ ID NOs.: 24, 26, 28 (FIG. 24A). Sequence identifiers from top to bottom correspond to SEQ ID NOs.: 30, 32, 34 (FIG. 24B). Complementarity-determining regions (CDRs) are defined using the Kabat (underlined) and IMGT nomenclature (bold). Substitutions from parental Ab1 are shown in light gray.

FIG. 30A shows rats treated with Ab2 show increased lean mass compared to PBS- or IgG control-treated animals. Ab2 and IgG were administered intravenously at 10 mg/kg doses on day 0. Lean mass measured by qNMR (N=8 per group) at 7, 14, 21 and 28 days after dosing. FIG. 30B shows rectus femoris and tibialis anterior muscles were collected from all groups at the end of the study (N=8 per group) and weighed to determine muscle mass. Rats treated with Ab2 show an increase of 14% and 11% in rectus femoris and tibialis anterior muscle masses, respectively.

FIG. 31A shows treatment with Ab2 (top line) increases latent myostatin levels in rat serum by ~20-fold. FIG. 31B shows that in rat muscle (rectus femoris), Ab2 treatment leads to a 1.9×increase in the latent form of Myostatin. The bars from left to right correspond to proMyostatin, latent Myostatin, proMyostatin, and latent Myostatin. No statistically significant change in pro-Myostatin is observed in rat muscle. These data are from quantitative western analyses with n=3 samples per group.

FIG. 35A shows latent Myostatin is elevated in both Ab2- and AbMyo-treated muscles. However, elevation of latent Myostatin in AbMyo-treated muscles returns to baseline by day 28, while those in Ab2 treated muscles remain elevated until at least this time (P<0.003 vs. AbMyo treatment). FIG. 35B shows a similar trend is observed with proMyostatin, though the difference between the Ab2 and AbMyo treated groups at day 28 is not statistically significant (P=0.068).

DETAILED DESCRIPTION

Figure 1A:
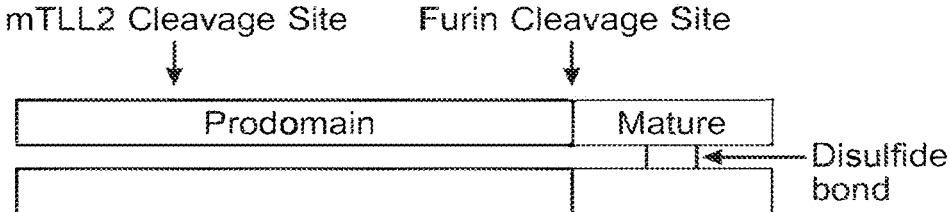
FIGS. 1A-1B show Myostatin domain structure and pro-Myostatin assembly.
Figure 1B:
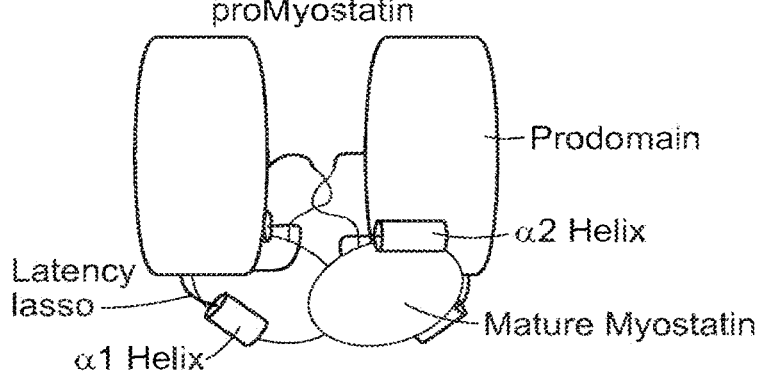

Myostatin is a member of the TGFβ superfamily, and belongs to a subfamily including two members: Myostatin (also known as GDF8) and GDF11. Like other members of the TGFβ superfamily, Myostatin and GDF11 are both initially expressed as inactive precursor polypeptides (termed proMyostatin and proGDF11, respectively). The domain structure and nomenclature are shown in FIG. 1A. FIG. 1B illustrates a cartoon model of the overall structure of proMyostatin, where the mature growth factor is held locked in a cage comprised of two alpha helices connected by a loop termed the "latency lasso".

Figure 2:
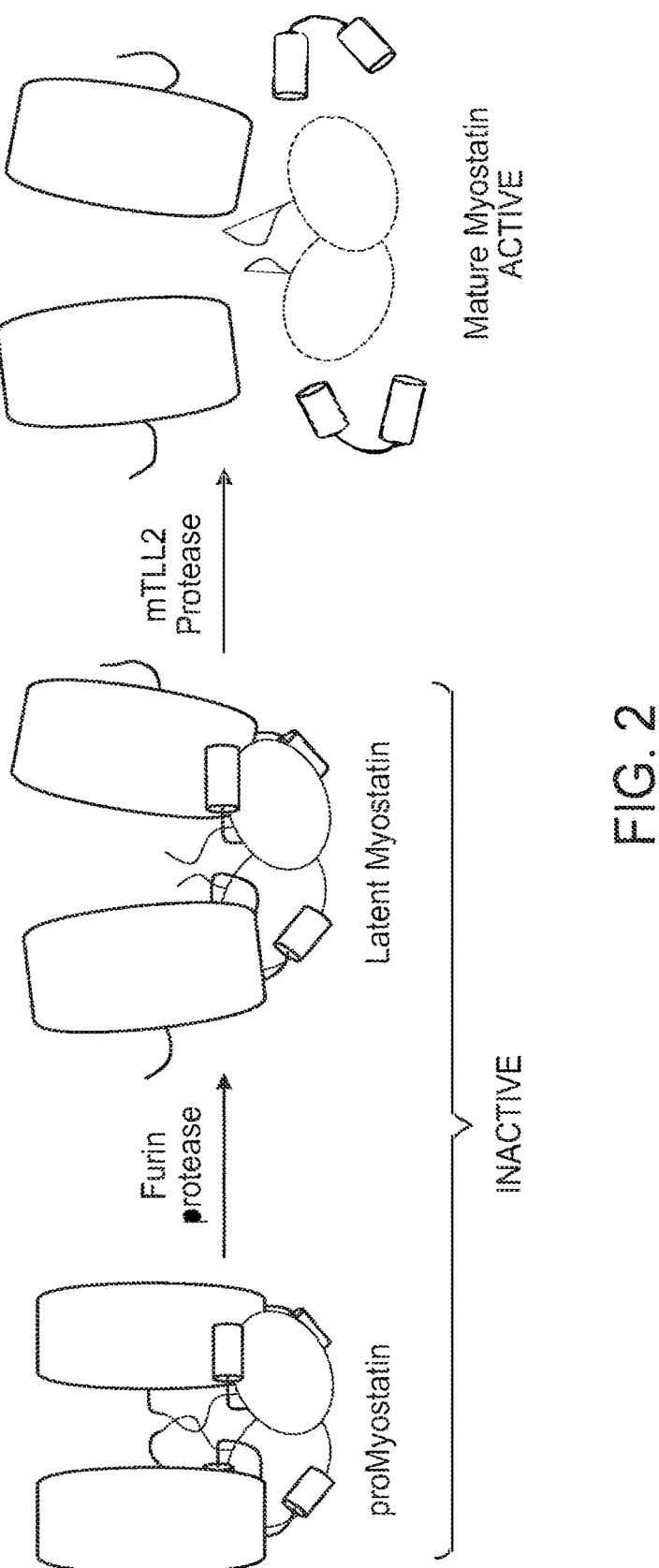
FIG. 2 shows the activation of Myostatin involves two distinct protease events, generating three major Myostatin species. The biosynthetic precursor protein, proMyostatin, is processed by two separate proteases. Cleavage of proMyostatin (and proGDF11) is carried out by a proprotein convertase, such as Furin/PACE3 (Paired Basic Amino acid Cleaving Enzyme 3) or PCSK5 (Proprotein Convertase Subtilisin/Kexin type 5), which cuts at a conserved RXXR site between the prodomain and mature growth factor. This cleavage produces a latent complex, in which the mature growth factor is shielded from binding to its receptors by the prodomain. Activation and release of the active growth factor is accomplished after cleavage by an additional protease from the BMP/tolloid family, such as TLL-2 (Tolloid-like protein 2) or BMP1 (Bone Morphogenetic Protein 1). These cleavage events yield a mature form of Myostatin, which may be referred to as Active Myostatin or Mature Myostatin.

Activation and release of the mature growth factor is accomplished by several discrete protease cleavage events, outlined in FIG. 2. The first cleavage step of proMyostatin and proGDF11 is carried out by a proprotein convertase, which cuts at a conserved RXXR site between the prodomain and mature growth factor. This cleavage produces a latent complex, in which the mature growth factor is shielded from binding to its receptors by the prodomain. Activation and release of the mature, active Myostatin growth factor is accomplished after cleavage by an additional protease from the BMP/tolloid family, such as mTLL-2 (FIG. 2).

Exemplary proGDF8 sequences in the human, rat, mouse and cynomolgus are provided below. In these proGDF8 sequences, a proprotein convertase cleavage site is indicated in bold and a tolloid protease site is indicated by underlining. In some embodiments, the proprotein convertase cleavage site comprises amino acid residues 240 to 243 of SEQ ID NOs: 52-55. In some embodiments, the tolloid protease site comprises amino acid residues 74-75 of SEQ ID NOs: 52-55. It should be appreciated that the exemplary proGDF8 sequences provided herein are not intended to be limiting and additional proGDF8 sequences from other species, including any isoforms thereof, are within the scope of this disclosure.

```
proGDF8 (human):
                                (SEQ ID NO: 52)
NENSEQKENVEKEGLCNACTWRQNTKSSRIEAIKIQILSKLRLETAPNIS

KDVIRQLLPKAPPLRELIDQYDVQRDDSSDGSLEDDDYHATTETIITMPT

ESDFLMQVDGKPKCCFFKFSSKIQYNKVVKAQLWIYLRPVETPTTVFVQI

LRLIKPMKDGTRYTGIRSLKLDMNPGTGIWQSIDVKTVLQNWLKQPESNL

GIEIKALDENGHDLAVTFPGPGEDGLNPFLEVKVTDTPKRSRRDFGLDCD

EHSTESRCCRYPLTVDFEAFGWDWIIAPKRYKANYCSGECEFVFLQKYPH

THLVHQANPRGSAGPCCTPTKMSPINMLYFNGKEQIIYGKIPAMVVDRCG

CS.

proGDF8 (rat):
                                (SEQ ID NO: 53)
NEDSEREANVEKEGLCNACAWRQNTRYSRIEAIKIQILSKLRLETAPNIS

KDAIRQLLPRAPPLRELIDQYDVQRDDSSDGSLEDDDYHATTETIITMPT

ESDFLMQADGKPKCCFFKFSSKIQYNKVVKAQLWIYLRAVKTPTTVFVQI

LRLIKPMKDGTRYTGIRSLKLDMSPGTGIWQSIDVKTVLQNWLKQPESNL

GIEIKALDENGHDLAVTFPGPGEDGLNPFLEVKVTDTPKRSRRDFGLDCD

EHSTESRCCRYPLTVDFEAFGWDWIIAPKRYKANYCSGECEFVFLQKYPH

THLVHQANPRGSAGPCCTPTKMSPINMLYFNGKEQIIYGKIPAMVVDRCG

CS.

proGDF8 (mouse):
                                (SEQ ID NO: 54)
NEGSEREENVEKEGLCNACAWRQNTRYSRIEAIKIQILSKLRLETAPNIS

KDAIRQLLPRAPPLRELIDQYDVQRDDSSDGSLEDDDYHATTETIITMPT

ESDFLMQADGKPKCCFFKFSSKIQYNKVVKAQLWIYLRPVKTPTTVFVQI

LRLIKPMKDGTRYTGIRSLKLDMSPGTGIWQSIDVKTVLQNWLKQPESNL

GIEIKALDENGHDLAVTFPGPGEDGLNPFLEVKVTDTPKRSRRDFGLDCD
```

```
-continued
EHSTESRCCRYPLTVDFEAFGWDWIIAPKRYKANYCSGECEFVFLQKYPH

THLVHQANPRGSAGPCCTPTKMSPINMLYFNGKEQIIYGKIPAMVVDRCG

CS.

proGDF8 (cynomolgus):
                                (SEQ ID NO: 55)
NENSEQKENVEKEGLCNACTWRQNTKSSRIEAIKIQILSKLRLETAPNIS

KDAIRQLLPKAPPLRELIDQYDVQRDDSSDGSLEDDDYHATTETIITMPT

ESDFLMQVDGKPKCCFFKFSSKIQYNKVVKAQLWIYLRPVETPTTVFVQI

LRLIKPMKDGTRYTGIRSLKLDMNPGTGIWQSIDVKTVLQNWLKQPESNL

GIEIKALDENGHDEAVTFPGPGEDGLNPFLEVKVTDTPKRSRRDFGLDCD

EHSTESRCCRYPLTVDFEAFGWDWIIA.
```

Myostatin and GDF11 share a relatively high degree of conservation between their mature growth factor domains, with ninety percent identity, but are much less well conserved in their prodomain regions with less than fifty percent amino acid identity between the two. Myostatin and GDF11 bind and signal through the same receptors consisting of a Type I receptor (ALK4/5) in association with a type II receptor (ACTRIIA/B). Engagement of Myostatin with Type I and Type II receptors initiates a signaling cascade leading to SMAD phosphorylation and transcriptional activation of muscle atrophy genes. The relatively high degree of conservation in the mature growth factors has made it challenging to identify reagents, such as monoclonal antibodies, that can differentiate between mature Myostatin and GDF11.

In some embodiments, pro/latent-Myostatin antibodies are provided herein that specifically bind to a chimeric construct that contains the growth factor domain and N terminal propeptide portion of GDF11 and the C terminal portion of the propeptide of GDF8.

This chimeric construct, as forth below, is referred as GDF11 Arm8.

```
> GDF11Arm8
                                (SEQ ID NO: 65)
MDMRVPAQLLGLLLLWFSGVLGDYKDDDDKHHHHHHLEVLFQGPAEGPAA

AAAAAAAAAAGVGGERSSRPAPSVAPEPDGCPVCVWRQHSRELRLESIK

SQILSKLRLKEAPNISREVVKQLLPKAPPLRELIDQYDVQRDDSSDGSLE

DDDYHATTETIITMPTESDFLMQVDGKPKCCFFKFSSKIQYNKVVKAQLW

IYLRPVETPTTVFVQILRLIKPMKDGTRYTGIRSLKLDMNPGTGIWQSID

VKTVLQNWLKQPESNLGIEIKALDENGHDLAVTFPGPGEDGLNPFLEVKV

TDTPKRSRRNLGLDCDEHSSESRCCRYPLTVDFEAFGWDWIIAPKRYKAN

YCSGQCEYMFMQKYPHTHLVQQANPRGSAGPCCTPTKMSPINMLYFNDKQ

QIIYGKIPGMVVDRCGCS
```

Role of Myostatin in Myopathies

Skeletal muscle accounts for approximately 40% of body mass and is a dynamic organ, turning over at a rate of 1-2% per day. Muscle atrophy is a highly regulated catabolic process which occurs during periods of disuse (e.g. disuse atrophy) and/or in response to heightened systemic inflammation (cachexia). In disuse atrophy, which can occur during prolonged periods of immobilization such as during bed rest, muscle loss occurs rapidly. For example, during a hospital stay of one week, an average patient loses ~1.3 kg of muscle mass.

Muscle atrophy causes significant morbidity in a wide range of clinical conditions. In diseases of denervation like amyotrophic lateral sclerosis (ALS) or spinal muscular atrophy (SMA) and genetic diseases including muscular dystrophies, loss of muscle strength and function are highly disabling clinical manifestations for which there are no adequate treatments. In cachexia syndromes due to renal failure, AIDS, cardiac conditions, or cancer, muscle wasting often undermines successful treatment of the primary condition. Muscle loss also results as a natural process of aging and in its most severe form is categorized as sarcopenia, a pervasive condition among the elderly that is increasingly being recognized as a pathology warranting intervention. Lastly, a major driver of muscle atrophy is disuse. Immobilization causes rapid and significant muscle loss in a large group of conditions such as hip fracture, elective joint replacement, spinal cord injury, critical care myopathy and stroke. While varied in their cause, these indications share a characteristic of muscle weakness, which leads to significant disability, lengthy physical rehabilitation and recovery times and impairment of quality of life.

There has been an unmet medical need in muscle atrophy conditions. Accordingly, in some embodiments, methods are provided herein for treating muscle atrophy. In some embodiments, methods provided herein relate to the treatment of a primary myopathy. In some embodiments, methods provided herein relate to the treatment of secondary myopathy, such as, for example, diseases of denervation, genetic muscle weakness and cachexia, conditions in which muscle loss is secondary to the disease pathology. In some embodiments, methods provided herein for the treatment of primary myopathies, such as disuse atrophy (e.g., associated with hip fracture or spinal cord injury (SCI)), result in increase in muscle mass, strength and function in a subject.

Myostatin Pathway Inhibition

There are several Myostatin pathway antagonists in various stages of clinical development towards the treatment of muscle-related conditions. Such pathway antagonists target either the mature growth factor or its type II receptor, and most antagonize the signaling of multiple TGFβ family members. For example, a number of current clinical candidates block additional growth factors such as Activin A, GDF11, and BMPs 9 and 10, which are regulators of reproductive biology, wound healing, erythropoiesis and blood vessel formation, respectively. Aspects of this disclosure relate to a recognition that blocking these factors in addition to Myostatin will potentially limit the population of patients who can safely undergo therapy due to unacceptable side-effects.

Accordingly, provided herein are antibodies capable of binding to proMyostatin and/or latent Myostatin, thereby inhibiting Myostatin activity, and uses thereof for treating diseases and disorders associated with myopathy. In some embodiments, given the prevalence of the latent complex in circulation, treatments are provided herein that specifically target more abundant and longer-lived Myostatin precursors e.g., proMyostatin and latent Myostatin, rather than the mature growth factor. Without wishing to be bound by any particular theory, antibodies provided herein may prevent the proteolytic activation of proMyostatin and/or latent Myostatin into mature Myostatin which is considered the "active" form of Myostatin, capable of activating the Myostatin pathway, e.g., by binding Type I (ALK4/5) and Type II (ACTRIIA/B) receptors.

As used herein, the term "pro/latent-Myostatin" refers to proMyostatin, latent Myostatin, or both. In some embodiments, an anti-pro/latent-Myostatin antibody binds specifically to proMyostatin. In some embodiments, an anti-pro/latent-Myostatin antibody binds specifically to latent Myostatin. In some embodiments, an anti-pro/latent-Myostatin antibody binds specifically to both latent Myostatin and proMyostatin. It should be appreciated that "latent Myostatin" and "proMyostatin" may also be referred to herein as "latent GDF8" and "proGDF8", respectively.

As used herein, the term "mature myostatin" refers to a mature, biologically active form of myostatin. In some embodiments, mature myostatin is capable of myostatin receptor binding and/or activation. Activation and release of mature myostatin in vivo from its pro-myostatin form is accomplished by several discrete protease cleavage events. To begin with, "pro-myostatin" is cleaved by a proprotein convertase, resulting in "latent-myostatin," in which the mature myostatin is shielded from binding to its receptors by a portion of the prodomain. Activation and release of mature myostatin is accomplished after cleavage of latent-myostatin by an additional protease from the BMP/tolloid family, such as mTLL-2. See, for example, FIGS. 1A, 1B, and 2. As used herein, the term "mature myostatin" can refer to both full-length mature myostatin, as well as fragments of the full-length mature myostatin which retain biological activity. Exemplary mature myostatin sequences, variants thereof, and methods of generating mature myostatin are well known in the art and described in more detail herein.

The term "pro-myostatin," also known as "proGDF8," refers to an inactive precursor of mature myostatin which comprises a disulfide-linked homodimer, each molecule of the homodimer comprising the amino terminal prodomain covalently bound to the carboxyl terminal mature myostatin domain. In one embodiment, "pro-myostatin" has not been cleaved by either a proprotein convertase, or a protease from the BMP/tolloid family. Exemplary pro-myostatin sequences, variants thereof, and methods of generating pro-myostatin are well known in the art and described in more detail herein.

As used herein the term "latent-myostatin" refers to an inactive precursor of mature myostatin which comprises a disulfide-linked homodimer, each molecule of the homodimer comprising the amino terminal prodomain non-covalently bound to the carboxyl terminal mature myostatin domain. In one embodiment, "latent-myostatin" is generated from a pro-myostatin that has been cleaved by a proprotein convertase, but which has not been cleaved by a protease from the BMP/tolloid family. In another embodiment, "latent-myostatin" can be generated by combining the prodomain and the carboxy terminal mature myostatin domain in vitro and allowing them to fold properly. See, for example, Sengle et al., J. Biol. Chem., 286(7):5087-5099, 2011. Exemplary latent-myostatin sequences, variants thereof, and methods of generating latent-myostatin are well known in the art and described in more detail herein.

As used herein, the term "pro/latent-myostatin" refers to pro-myostatin, latent-myostatin, or both pro-myostatin and latent-myostatin. In one embodiment, an antibody disclosed herein binds to pro-myostatin. In another embodiment, an antibody disclosed herein binds to latent-myostatin. In another embodiment, an antibody disclosed herein binds to pro-myostatin and latent-myostatin.

As used herein, the term "pure pro-myostatin" or "pure pro-GDF8" refers to a composition comprising pro-myostatin that is free, or substantially free, of other forms of myostatin, such as latent-myostatin and mature myostatin. In one embodiment, an antibody disclosed herein specifically binds pure pro-myostatin. In other words, such an antibody binds to pro-myostatin in a composition which lacks the other forms of myostation, latent-myostatin and mature myostatin.

As used herein, the term "proprotein convertase cleavage site" refers to a site where pro-myostatin is cleaved by a proprotein convertase. In one embodiment, a proprotein convertase cleavage site is a conserved RXXR site between the prodomain and the biologically active domain, or mature myostatin. See, for example, FIGS. 1A, 1B, and 2.

As used herein, the term "BMP/tolloid protease family cleavage site" refers to a site where latent myostatin is cleaved by a BMP/tolloid protease family member. In one embodiment, a BMP/tolloid protease family member is mTLL-2. See, for example, FIGS. 1A, 1B, and 2.

Antibodies that Bind Pro/Latent-Myostatin

The present disclosure is based, at least in part, on the surprising discovery that certain pro/latent-Myostatin-specific antibodies (e.g., an antibody referred to herein as Ab1), prevented proteolytic activation of pro/latent-Myostatin into mature Myostatin. Furthermore, inhibition of Myostatin activation using such antibodies was effective for increasing muscle mass in both dexamethasone and casting induced muscle atrophy mouse models. Aspects of the disclosure provide antibodies (e.g., antibodies and antigen binding fragments) that bind to pro/latent-Myostatin and inhibit proteolytic activation of pro/latent-Myostatin into mature Myostatin.

An antibody (interchangeably used in plural form) is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody" encompasses not only intact (e.g., full-length) polyclonal or monoclonal antibodies, but also antigen-binding fragments thereof (such as Fab, Fab', F(ab')2, Fv), single chain (scFv), mutants thereof, fusion proteins comprising an antibody portion, humanized antibodies, chimeric antibodies, diabodies, linear antibodies, single chain antibodies, multispecific antibodies (e.g., bispecific antibodies) and any other modified configuration of the immunoglobulin molecule that comprises an antigen recognition site of the required specificity, including glycosylation variants of antibodies, amino acid sequence variants of antibodies, and covalently modified antibodies. An antibody includes an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

An "isolated antibody", as used herein, is intended to refer to an antibody that is substantially free of other antibodies having different antigenic specificities (e.g., an isolated antibody that specifically binds pro/latent-myostatin is substantially free of antibodies that specifically bind antigens other than pro/latent-myostatin). An isolated antibody that specifically binds pro/latent-myostatin may, however, have cross-reactivity to other antigens, such as pro/latent-myostatin molecules from other species. Moreover, an isolated antibody may be substantially free of other cellular material and/or chemicals.

The term "human antibody", as used herein, is intended to include antibodies having variable and constant regions derived from human germline immunoglobulin sequences and fragments thereof. The human antibodies of the disclosure may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "epitope" includes any polypeptide determinant capable of specific binding to an immunoglobulin or T-cell receptor. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. An epitope is a region of an antigen that is bound by an antibody. In certain embodiments, an antibody is said to specifically bind an antigen when it preferentially recognizes its target antigen in a complex mixture of proteins and/or macromolecules.

Antibodies described herein are capable of binding to a pro/latent-Myostatin, thereby inhibiting the proteolytic activation of pro/latent-Myostatin into mature Myostatin. In some instances, antibodies described herein can inhibit the proteolytic activation of pro/latent-Myostatin by at least 20%, e.g., 30%, 40%, 50%, 60%, 70%, 80%, 90%, 95%, or higher. In some instances, antibodies described herein can inhibit the proteolytic cleavage of proMyostatin by a proprotein convertase (e.g., furin) by at least 20%, e.g., 30%, 40%, 50%, 60%, 70%, 80%, 90%, 95%, or higher. In some instances antibodies described herein can inhibit the proteolytic cleavage of proMyostatin or latent Myostatin by a tolloid protease (e.g., mTLL2) by at least 20%, e.g., 30%, 40%, 50%, 60%, 70%, 80%, 90%, 95%, or higher. The inhibitory activity of an anti-pro/latent-Myostatin antibody can be measured by routine methods, for example, by Western blot analysis as described in Example 1 and FIG. 3. However, it should be appreciated that additional methods may be used for measuring the inhibitory activity of an anti-pro/latent-Myostatin antibody on proteolytic cleavage of pro/latent-Myostatin. In some embodiments, inhibition of pro/latent-Myostatin cleavage (e.g., by a proprotein convertase and/or tolloid protease) may be reflected as an inhibition constant (Ki), which provides a measure of inhibitor potency, and which it is the concentration of inhibitor (e.g., an anti-pro/latent-Myostatin antibody) required to reduce protease activity (e.g., of a proprotein convertase or tolloid protease) by half and is not dependent on enzyme or substrate concentrations.

In some embodiments, a proprotein convertase comprises (i) a catalytic domain that hydrolyzes a peptide bond of a protein containing a proprotein convertase cleavage site, and (ii) a binding pocket that binds to an rTGF with a proprotein convertase cleavage site. Examples of proprotein convertases for use in accordance with the present disclosure include, without limitation, PCSK5/6, PACE4, PACE7 and PACE3 (e.g., furin). A proprotein convertase, in some embodiments, is obtained from any mammal including, without limitation, humans, monkeys or rodents (e.g., mice, rats, hamsters).

In some embodiments, a proprotein convertase is homologous to a proprotein convertase selected from the group consisting of: PCSK5/6, PACE4, PACE7 and PACE3 (e.g., furin). For example a proprotein convertase may be at least 70% identical, at least 80% identical, at least 90% identical, at least 95% identical, at least 96% identical, at least 97% identical, at least 98% identical, at least 99% identical, at least 99.5% identical, or at least about 99.9% identical to PCSK5/6, PACE4, PACE7 or PACE3 (e.g., furin).

A proprotein convertase cleavage site, in some embodiments, is an amino sequence that can be cleaved by a proprotein convertase (e.g., PCSK5/6, PACE4, PACE7 and PACE3). In some embodiments, the proprotein convertase cleavage site comprises the amino acid sequence R-X-X-R, where R is arginine and X is any amino acid. In some embodiments, the proprotein convertase cleavage site comprises the amino acid sequence R-X-(K/R)-R, where R is arginine, K is lysine and X is any amino acid. In some embodiments, the proprotein convertase cleavage site comprises the amino acid sequence is R-V-R-R (SEQ ID NO: 57), where R is arginine and V is valine. Exemplary proprotein convertase cleavage sites for human, rat, mouse, and cynomolgus myostatin are shown, in bold, in SEQ ID NOs: 52-55. In some embodiments, the proprotein convertase cleavage site comprises the amino acid sequence RSRR (SEQ ID NO: 56).

In some embodiments, tolloid proteases for use in accordance with the present disclosure include, without limitation, BMP-1, mTLL-1 and mTLL-2. A tolloid protease may be obtained from any mammal including, without limitation, humans, monkeys, or rodents (e.g., mice, rats, hamsters). In some embodiments, a tolloid protease is homologous to a tolloid protease selected from the group consisting of: BMP-1, mTLL-1 and mTLL-2. For example a tolloid protease may be at least 70% identical, at least 80% identical, at least 90% identical, at least 95% identical, at least 96% identical, at least 97% identical, at least 98% identical, at least 99% identical, at least 99.5% identical, or at least about 99.9% identical to BMP-1, mTLL-1 and mTLL-2.

A tolloid protease cleavage site, in some embodiments, is an amino sequence that can be cleaved by a tolloid (e.g., BMP-1, mTLL-1 and mTLL-2). Exemplary tolloid protease cleavage sites for human, rat, mouse, and cynomolgus myostatin are shown, in underlining, in SEQ ID NOs: 52-55. In some embodiments, the tolloid cleavage site comprises the amino acid sequence QR, where Q is glutamine and R is arginine.

In some embodiments, antibodies described herein are capable of binding to a pro/latent-Myostatin, thereby inhibiting Myostatin activity. In some instances, the antibodies described herein can inhibit Myostatin signaling by at least 20%, e.g., 30%, 40%, 50%, 60%, 70%, 80%, 90%, 95%, or higher. In some embodiments, inhibition of Myostatin signaling can be measured by routine methods, for example, using a Myostatin activation assay as described in Example 1. However, it should be appreciated that additional methods may be used for measuring Myostatin signaling activity.

It should be appreciated that the extent of proteolytic cleavage of myostatin, e.g., by a proprotein convertase and/or a tolloid protease, can be measured and/or quantified using any suitable method. In some embodiments, the extent of proteolytic cleavage of myostatin is measured and/or quantified using an enzyme-linked immunosorbent assay (ELISA). For example, an ELISA may be used to measure the level of released growth factor (e.g., mature myostatin). As another example, an antibody that specifically binds to proMyostatin, latent Myostatin and/or mature Myostatin can be used in an ELISA to measure the level of a specific form of myostatin (e.g., pro/latent/mature-Myostatin), to quantify the extent of proteolytic cleavage of myostatin. In some embodiments, the extent of proteolytic cleavage of myostatin is measured and/or quantified using immunoprecipitation followed by SDS-PAGE or mass spectrometry of tryptic peptides, fluorescence anisotropy-based techniques, FRET assays, hydrogen-deuterium-exchange mass spectrometry, and/or NMR spectroscopy.

In some embodiments, antibodies, also known as immunoglobulins, are tetrameric glycosylated proteins composed of two light (L) chains of approximately 25 kDa each and two heavy (H) chains of approximately 50 kDa each. Two types of light chain, termed lambda and kappa, may be found in antibodies. Depending on the amino acid sequence of the constant domain of heavy chains, immunoglobulins can be assigned to five major classes: A, D, E, G, and M, and several of these may be further divided into subclasses (isotypes), e.g., $IgG_1$, $IgG_2$, $IgG_3$, $IgG_4$, $IgA_1$, and $IgA_2$. Each light chain typically includes an N-terminal variable (V) domain ($V_L$) and a constant (C) domain ($C_L$). Each heavy chain typically includes an N-terminal V domain ($V_H$), three or four C domains ($C_H$1-3), and a hinge region. The $C_H$ domain most proximal to $V_H$ is designated as $C_H$1. The $V_H$ and $V_L$ domains consist of four regions of relatively conserved sequences called framework regions (FR1, FR2, FR3, and FR4), which form a scaffold for three regions of hypervariable sequences (complementarity determining regions, CDRs). The CDRs contain most of the residues responsible for specific interactions of the antibody with the antigen. CDRs are referred to as CDR1, CDR2, and CDR3. Accordingly, CDR constituents on the heavy chain are referred to as CDRH1, CDRH2, and CDRH3, while CDR constituents on the light chain are referred to as CDRL1, CDRL2, and CDRL3. The CDRs typically refer to the Kabat CDRs, as described in Sequences of Proteins of Immunological Interest, US Department of Health and Human Services (1991), eds. Kabat et al. Another standard for characterizing the antigen binding site is to refer to the hypervariable loops as described by Chothia. See, e.g., Chothia, D. et al. (1992) J. Mol. Biol. 227:799-817; and Tomlinson et al. (1995) EMBO J. 14:4628-4638. Still another standard is the AbM definition used by Oxford Molecular's AbM antibody modeling software. See, generally, e.g., Protein Sequence and Structure Analysis of Antibody Variable Domains. In: Antibody Engineering Lab Manual (Ed.: Duebel, S, and Kontermann, R., Springer-Verlag, Heidelberg). Embodiments described with respect to Kabat CDRs can alternatively be implemented using similar described relationships with respect to Chothia hypervariable loops or to the AbM-defined loops, or combinations of any of these methods.

In some embodiments, anti-pro/latent-Myostatin antibodies of the present disclosure and the nucleic acid molecules of the present disclosure that encode the antibodies include the CDR amino acid sequences shown in Table 1.

TABLE 1

| Antibody | CDRH1 (SEQ ID NOs: 1-3) | CDRH2 (SEQ ID NOs: 4-9) | CDRH3 (SEQ ID NOs: 10-11) | CDRL1 (SEQ ID NOs: 12-17) | CDRL2 (SEQ ID NOs: 18-21) | CDRL3 (SEQ ID NOs: 22-23) |
|---|---|---|---|---|---|---|
| Ab1<br>Kabat:<br>IMGT: | SSYGMH (SEQ ID NO: 1)<br>GFTTSSYGMH (SEQ ID NO: 2) | VISYDGSNKYY ADSVKG (SEQ ID NO: 4)<br>ISYDGSN (SEQ ID NO: 5) | DLLVRFLEWSH YYGMDV (SEQ ID NO: 10) | SGSSSNIGSNTV H (SEQ ID NO: 12)<br>SSNIGSNT (SEQ ID NO: 13) | SDNQRPS (SEQ ID NO: 18)<br>SDN (SEQ ID NO: 19) | AAWDDSLNGV (SEQ ID NO: 22) |
| Ab3<br>Kabat:<br>IMGT: | SSYGMH (SEQ ID NO: 1)<br>GFAFSSYGMH (SEQ ID NO: 3) | VISYDGSIKYYA DSVKG (SEQ ID NO: 6)<br>ISYDGSI (SEQ ID NO: 7) | DLLVRFLEWSH KYGMDV (SEQ ID NO: 11) | SGSTSNIGSNTV H (SEQ ID NO: 14)<br>TSNIGSNT (SEQ ID NO: 15) | SDDQRPS (SEQ ID NO: 20)<br>SDD (SEQ ID NO: 21) | AAWDESLNGV (SEQ ID NO: 23) |
| Ab5<br>Kabat:<br>IMGT: | SSYGMH (SEQ ID NO: 1)<br>GFAFSSYGMH (SEQ ID NO: 3) | VISYDGNNKYY ADSVKG (SEQ ID NO: 8)<br>ISYDGNN (SEQ ID NO: 9) | DLLVRFLEWSH KYGMDV (SEQ ID NO: 11) | SGSSSNIGGNTV H (SEQ ID NO: 16)<br>SSNIGGNT (SEQ ID NO: 17) | SDDQRPS (SEQ ID NO: 20)<br>SDD (SEQ ID NO: 21) | AAWDESLNGV (SEQ ID NO: 23) |

In Table 1, the single sequences of CDRH3 and CDRL3 reflect Kabat and IMGT.

In some embodiments, anti-pro/latent-Myostatin binding agents (e.g., antibodies) of the disclosure include any antibody (including antigen binding fragments) that includes a CDRH1, CDRH2, CDRH3, CDRL1, CDRL2, or CDRL3, or combinations thereof, as provided for any one of the antibodies shown in Table 1. In some embodiments, anti-pro/latent-Myostatin binding agents include the CDRH1, CDRH2, CDRH3, CDRL1, CDRL2, and CDRL3 of any one of the antibodies shown in Table 1. The disclosure also includes any nucleic acid sequence that encodes a molecule comprising a CDRH1, CDRH2, CDRH3, CDRL1, CDRL2, or CDRL3 as provided for any one of the antibodies shown in Table 1. Antibody heavy and light chain CDR3 domains may play a particularly important role in the binding specificity/affinity of an antibody for an antigen. Accordingly, the anti-pro/latent-Myostatin binding agents of the disclosure, or the nucleic acid molecules thereof, may include at least the heavy and/or light chain CDR3s of antibodies as shown in Table 1.

Aspects of the disclosure relate to a monoclonal antibody or antigen binding fragment, that binds to pro/latent-Myostatin protein and that comprises six complementarity determining regions (CDRs): CDRH1, CDRH2, CDRH3, CDRL1, CDRL2, and CDRL3.

In some embodiments, CDRH1 comprises a sequence as set forth in any one of SEQ ID NOs: 1-3. In some embodiments, CDRH2 comprises a sequence as set forth in any one of SEQ ID NOs: 4-9. In some embodiments, CDRH3 comprises a sequence as set forth in any one of SEQ ID NOs: 10-11. CDRL1 comprises a sequence as set forth in any one of SEQ ID NOs: 12-17. In some embodiments, CDRL2 comprises a sequence as set forth in any one of SEQ ID NOs: 18-21. In some embodiments, CDRL3 comprises a sequence as set forth in any one of SEQ ID NOs: 22-23.

In some embodiments (e.g., as for anti-pro/latent-Myostatin antibody Ab1, shown in Table 1), CDRH1 comprises a sequence as set forth in SEQ ID NO: 1 or 2, CDRH2 comprises a sequence as set forth in SEQ ID NO: 4 or 5. CDRH3 comprises a sequence as set forth in SEQ ID NO: 10, CDRL1 comprises a sequence as set forth in SEQ ID NO: 12, or 13, CDRL2 comprises a sequence as set forth in SEQ ID NO: 18 or 19, and CDRL3 comprises a sequence as set forth in SEQ ID NO: 22, and the antibody binds to pro/latent-Myostatin.

In some embodiments (e.g., as for anti-pro/latent-Myostatin antibody Ab3, shown in Table 1), CDRH1 comprises a sequence as set forth in SEQ ID NO: 1 or 3, CDRH2 comprises a sequence as set forth in SEQ ID NO: 6 or 7, CDRH3 comprises a sequence as set forth in SEQ ID NO: 11, CDRL1 comprises a sequence as set forth in SEQ ID NO: 14, or 15, CDRL2 comprises a sequence as set forth in SEQ ID NO: 20 or 21, and CDRL3 comprises a sequence as set forth in SEQ ID NO: 23, and the antibody binds to pro/latent-Myostatin.

In some embodiments (e.g., as for anti-pro/latent-Myostatin antibody Ab5, shown in Table 1), CDRH1 comprises a sequence as set forth in SEQ ID NO: 1 or 3, CDRH2 comprises a sequence as set forth in SEQ ID NO: 8 or 9, CDRH3 comprises a sequence as set forth in SEQ ID NO: 11, CDRL1 comprises a sequence as set forth in SEQ ID NO: 16, or 17, CDRL2 comprises a sequence as set forth in SEQ ID NO: 20 or 21, and CDRL3 comprises a sequence as set forth in SEQ ID NO: 23, and the antibody binds to pro/latent-Myostatin. In some examples, any of the anti-pro/latent-Myostatin binding agents (e.g., antibodies) of the disclosure include any antibody (including antigen binding fragments) having one or more CDR (e.g., CDRH or CDRL) sequences substantially similar to CDRH1, CDRH2, CDRH3, CDRL1, CDRL2, and/or CDRL3. For example, the antibodies may include one or more CDR sequences as shown in Table 1 (SEQ ID NOs: 1-23) containing up to 5, 4, 3, 2, or 1 amino acid residue variations as compared to the corresponding CDR region in any one of SEQ ID NOs: 1-23. The complete amino acid and nucleic acid sequences for the heavy chain variable region and light chain variable region of the antibodies listed in Table 1 are provided below.

Heavy chain variable region - Ab1 parental
                                    (SEQ ID NO: 24)
QIQLVQSGGGVVQPGRSLRLSCAASGFTFSSYGMHWVRQAPGKGLEWVAVI

SYDGSNKYYADSVKGRFTISRDNSKNTLYLQMNSLRAEDTAVYYCARDLLV

RFLEWSHYYGMDVWGQGTTVTVSS (SEQ ID NO: 38)
CAGATCCAGCTGGTGCAGTCTGGGGGAGGCGTGGTCCAGCCTGGGAGGTCC

CTGAGACTCTCCTGTGCAGCGTCTGGATTCACCTTCAGTAGCTATGGCATG

-continued

CACTGGGTCCGCCAGGCTCCAGGCAAGGGGCTGGAGTGGGTGGCAGTTATA

TCATATGATGGAAGTAATAAATACTATGCAGACTCCGTGAAGGGCCGATTC

ACCATCTCCAGAGACAATTCCAAGAACACGCTGTATCTGCAAATGAACAGC

CTGAGAGCCGAGGACACGGCTGTGTATTACTGTGCGAGAGATCTCCTGGTG

CGATTTTTGGAGTGGTCGCACTACTACGGTATGGACGTCTGGGGCCAAGGG

ACCACGGTCACCGTCTCCTCA

Heavy chain variable region - Ab2 germline
(SEQ ID NO: 25)
QVQLVESGGGVVQPGRSLRLSCAASGFTFSSYGMHWVRQAPGKGLEWVAVI

SYDGSNKYYADSVKGRFTISRDNSKNTLYLQMNSLRAEDTAVYYCARDLLV

RFLEWSHYYGMDVWGQGTTVTVSS (SEQ ID NO: 39)
CAGGTGCAGCTGGTGGAGTCTGGGGGAGGCGTGGTCCAGCCTGGGAGGTCC

CTGAGACTCTCCTGTGCAGCGTCTGGATTCACCTTCAGTAGCTATGGCATG

CACTGGGTCCGCCAGGCTCCAGGCAAGGGGCTGGAGTGGGTGGCAGTTATA

TCATATGATGGAAGTAATAAATACTATGCAGACTCCGTGAAGGGCCGATTC

ACCATCTCCAGAGACAATTCCAAGAACACGCTGTATCTGCAAATGAACAGC

CTGAGAGCCGAGGACACGGCTGTGTATTACTGTGCGAGAGATCTCCTGGTG

CGATTTTTGGAGTGGTCGCACTACTACGGTATGGACGTCTGGGGCCAAGGG

ACCACGGTCACCGTCTCCTCA

Heavy chain variable region - Ab3 parental
(SEQ ID NO: 26)
QIQLVQSGGGVVQPGRSLRLSCAASGFAFSSYGMHWVRQAPGKGLEWVAVI

SYDGSIKYYADSVKGRFTISRDNSKNTLYLQMNSLRAEDTAVYYCARDLLV

RFLEWSHKYGMDVWGQGTTVTVSS (SEQ ID NO: 40)
CAGATCCAGCTGGTGCAGTCTGGGGGAGGCGTGGTCCAGCCTGGGAGGTCC

CTGAGACTCTCCTGTGCAGCGTCTGGATTCGCCTTCAGTAGCTATGGCATG

CACTGGGTCCGCCAGGCTCCAGGCAAGGGGCTGGAGTGGGTGGCAGTTATA

TCATATGATGGAAGTATCAAATACTATGCAGACTCCGTGAAGGGCCGATTC

ACCATCTCCAGAGACAATTCCAAGAACACGCTGTATCTGCAAATGAACAGC

CTGAGAGCCGAGGACACGGCTGTGTATTACTGTGCGAGAGATCTCCTGGTG

CGATTTTTGGAGTGGTCGCACAAGTACGGTATGGACGTCTGGGGCCAAGGG

ACCACGGTCACCGTCTCCTCA

Heavy chain variable region - Ab4 germline
(SEQ ID NO: 27)
QVQLVESGGGVVQPGRSLRLSCAASGFAFSSYGMHWVRQAPGKGLEWVAVI

SYDGSIKYYADSVKGRFTISRDNSKNTLYLQMNSLRAEDTAVYYCARDLLV

RFLEWSHKYGMDVWGQGTTVTVSS (SEQ ID NO: 41)
CAGGTGCAGCTGGTGGAGTCTGGGGGAGGCGTGGTCCAGCCTGGGAGGTCC

CTGAGACTCTCCTGTGCAGCGTCTGGATTCGCCTTCAGTAGCTATGGCATG

CACTGGGTCCGCCAGGCTCCAGGCAAGGGGCTGGAGTGGGTGGCAGTTATA

TCATATGATGGAAGTATCAAATACTATGCAGACTCCGTGAAGGGCCGATTC

ACCATCTCCAGAGACAATTCCAAGAACACGCTGTATCTGCAAATGAACAGC

-continued

CTGAGAGCCGAGGACACGGCTGTGTATTACTGTGCGAGAGATCTCCTGGTG

CGATTTTTGGAGTGGTCGCACAAGTACGGTATGGACGTCTGGGGCCAAGGG

ACCACGGTCACCGTCTCCTCA

Heavy chain variable region - Ab5 parental
(SEQ ID NO: 28)
QIQLVQSGGGVVQPGRSLRLSCAASGFAFSSYGMHWVRQAPGKGLEWVAVI

SYDGNNKYYADSVKGRFTISRDNSKNTLYLQMNSLRAEDTAVYYCARDLLV

RFLEWSHKYGMDVWGQGTTVTVSS (SEQ ID NO: 42)
CAGATCCAGCTGGTGCAGTCTGGGGGAGGCGTGGTCCAGCCTGGGAGGTCC

CTGAGACTCTCCTGTGCAGCGTCTGGATTCGCCTTCAGTAGCTATGGCATG

CACTGGGTCCGCCAGGCTCCAGGCAAGGGGCTGGAGTGGGTGGCAGTTATA

TCATATGATGGAAATAATAAATACTATGCAGACTCCGTGAAGGGCCGATTC

ACCATCTCCAGAGACAATTCCAAGAACACGCTGTATCTGCAAATGAACAGC

CTGAGAGCCGAGGACACGGCTGTGTATTACTGTGCGAGAGATCTCCTGGTG

CGATTTTTGGAGTGGTCGCACAAGTACGGTATGGACGTCTGGGGCCAAGGG

ACCACGGTCACCGTCTCCTCA

Heavy chain variable region - Ab6 germline
(SEQ ID NO: 29)
QVQLVESGGGVVQPGRSLRLSCAASGFAFSSYGMHWVRQAPGKGLEWVAVI

SYDGNNKYYADSVKGRFTISRDNSKNTLYLQMNSLRAEDTAVYYCARDLLV

RFLEWSHKYGMDVWGQGTTVTVSS (SEQ ID NO: 43)
CAGGTGCAGCTGGTGGAGTCTGGGGGAGGCGTGGTCCAGCCTGGGAGGTCC

CTGAGACTCTCCTGTGCAGCGTCTGGATTCGCCTTCAGTAGCTATGGCATG

CACTGGGTCCGCCAGGCTCCAGGCAAGGGGCTGGAGTGGGTGGCAGTTATA

TCATATGATGGAAATAATAAATACTATGCAGACTCCGTGAAGGGCCGATTC

ACCATCTCCAGAGACAATTCCAAGAACACGCTGTATCTGCAAATGAACAGC

CTGAGAGCCGAGGACACGGCTGTGTATTACTGTGCGAGAGATCTCCTGGTG

CGATTTTTGGAGTGGTCGCACAAGTACGGTATGGACGTCTGGGGCCAAGGG

ACCACGGTCACCGTCTCCTCA

Light chain variable region - Ab1 parental
(SEQ ID NO: 30)
QPVLTQPPSASGTPGQRVTISCSGSSSNIGSNTVHWYQQLPGTAPKLLIYS

DNQRPSGVPDRFSGSKSGTSASLVISGLQSDDEADYYCAAWDDSLNGVFGG

GTKLTVL (SEQ ID NO: 44)
CAGCCTGTGCTGACTCAGCCACCCTCAGCGTCTGGGACCCCCGGGCAGAGG

GTCACCATCTCTTGTTCTGGAAGCAGCTCCAACATCGGAAGTAATACTGTC

CACTGGTACCAGCAACTCCCAGGAACGGCCCCCAAACTCCTCATCTATAGT

GATAATCAGCGCCCCTCAGGGGTCCCTGACCGATTCTCTGGCTCCAAGTCT

GGCACCTCAGCCTCCCTGGTCATCAGTGGGCTCCAGTCTGACGATGAGGCT

GATTATTACTGTGCAGCATGGGATGACAGCCTGAATGGGGTGTTCGGCGGA

GGGACCAAGCTGACCGTCCTA

-continued

Light chain variable region - Ab2 germline
```
                                   (SEQ ID NO: 31)
QSVLTQPPSASGTPGQRVTISCSGSSSNIGSNTVHWYQQLPGTAPKLLIYS

DNQRPSGVPDRFSGSKSGTSASLAISGLQSEDEADYYCAAWDDSLNGVFGG

GTKLTVL
```
```
                                   (SEQ ID NO: 45)
CAGTCTGTGCTGACTCAGCCACCCTCAGCGTCTGGGACCCCCGGGCAGAGG

GTCACCATCTCTTGTTCTGGAAGCAGCTCCAACATCGGAAGTAATACTGTC

CACTGGTACCAGCAACTCCCAGGAACGGCCCCCAAACTCCTCATCTATAGT

GATAATCAGCGCCCCTCAGGGGTCCCTGACCGATTCTCTGGCTCCAAGTCT

GGCACCTCAGCCTCCCTGGCCATCAGTGGGCTCCAGTCTGAGGATGAGGCT

GATTATTACTGTGCAGCATGGGATGACAGCCTGAATGGGGTGTTCGGCGGA

GGGACCAAGCTGACCGTCCTA
```

Light chain variable region - Ab3 parental
```
                                   (SEQ ID NO: 32)
QPVLTQPPSASGTPGQRVTISCSGSTSNIGSNTVHWYQQLPGTAPKLLIYS

DDQRPSGVPDRFSGSKSGTSASLVISGLQSDDEADYYCAAWDESLNGVFGG

GTKLTVL
```
```
                                   (SEQ ID NO: 46)
CAGCCTGTGCTGACTCAGCCACCCTCAGCGTCTGGGACCCCCGGGCAGAGG

GTCACCATCTCTTGTTCTGGAAGCACCTCCAACATCGGAAGTAATACTGTC

CACTGGTACCAGCAACTCCCAGGAACGGCCCCCAAACTCCTCATCTATAGT

GATGATCAGCGCCCCTCAGGGGTCCCTGACCGATTCTCTGGCTCCAAGTCT

GGCACCTCAGCCTCCCTGGTCATCAGTGGGCTCCAGTCTGACGATGAGGCT

GATTATTACTGTGCAGCATGGGATGAGAGCCTGAATGGGGTGTTCGGCGGA

GGGACCAAGCTGACCGTCCTA
```

Light chain variable region - Ab4 germline
```
                                   (SEQ ID NO: 33)
QSVLTQPPSASGTPGQRVTISCSGSTSNIGSNTVHWYQQLPGTAPKLLIYS

DDQRPSGVPDRFSGSKSGTSASLAISGLQSEDEADYYCAAWDESLNGVFGG

GTKLTVL
```
```
                                   (SEQ ID NO: 47)
CAGTCTGTGCTGACTCAGCCACCCTCAGCGTCTGGGACCCCCGGGCAGAGG

GTCACCATCTCTTGTTCTGGAAGCACCTCCAACATCGGAAGTAATACTGTC

CACTGGTACCAGCAACTCCCAGGAACGGCCCCCAAACTCCTCATCTATAGT

GATGATCAGCGCCCCTCAGGGGTCCCTGACCGATTCTCTGGCTCCAAGTCT

GGCACCTCAGCCTCCCTGGCCATCAGTGGGCTCCAGTCTGAGGATGAGGCT

GATTATTACTGTGCAGCATGGGATGAGAGCCTGAATGGGGTGTTCGGCGGA

GGGACCAAGCTGACCGTCCTA
```

Light chain variable region - Ab5 parental
```
                                   (SEQ ID NO: 34)
QPVLTQPPSASGTPGQRVTISCSGSSSNIGGNTVHWYQQLPGTAPKLLIYS

DDQRPSGVPDRFSGSKSGTSASLVISGLQSDDEADYYCAAWDESLNGVFGG

GTKLTVL
```
```
                                   (SEQ ID NO: 48)
CAGCCTGTGCTGACTCAGCCACCCTCAGCGTCTGGGACCCCCGGGCAGAGG

GTCACCATCTCTTGTTCTGGAAGCAGCTCCAACATCGGAGGAAATACTGTC
```

-continued
```
CACTGGTACCAGCAACTCCCAGGAACGGCCCCCAAACTCCTCATCTATAGT

GATGATCAGCGCCCCTCAGGGGTCCCTGACCGATTCTCTGGCTCCAAGTCT

GGCACCTCAGCCTCCCTGGTCATCAGTGGGCTCCAGTCTGACGATGAGGCT

GATTATTACTGTGCAGCATGGGATGAGAGCCTGAATGGGGTGTTCGGCGGA

GGGACCAAGCTGACCGTCCTA
```

Light chain variable region - Ab6 germline
```
                                   (SEQ ID NO: 35)
QSVLTQPPSASGTPGQRVTISCSGSSSNIGGNTVHWYQQLPGTAPKLLIYS

DDQRPSGVPDRFSGSKSGTSASLAISGLQSEDEADYYCAAWDESLNGVFGG

GTKLTVL
```
```
                                   (SEQ ID NO: 49)
CAGTCTGTGCTGACTCAGCCACCCTCAGCGTCTGGGACCCCCGGGCAGAGG

GTCACCATCTCTTGTTCTGGAAGCAGCTCCAACATCGGAGGAAATACTGTC

CACTGGTACCAGCAACTCCCAGGAACGGCCCCCAAACTCCTCATCTATAGT

GATGATCAGCGCCCCTCAGGGGTCCCTGACCGATTCTCTGGCTCCAAGTCT

GGCACCTCAGCCTCCCTGGCCATCAGTGGGCTCCAGTCTGAGGATGAGGCT

GATTATTACTGTGCAGCATGGGATGAGAGCCTGAATGGGGTGTTCGGCGGA

GGGACCAAGCTGACCGTCCTA
```

Ab2-Heavy Chain
```
                                   (SEQ ID NO: 50)
QVQLVESGGGVVQPGRSLRLSCAASGFTFSSYGMHWVRQAPGKGLEWVAVI

SYDGSNKYYADSVKGRFTISRDNSKNTLYLQMNSLRAEDTAVYYCARDLLV

RFLEWSHYYGMDVWGQGTTVTVSSASTKGPSVFPLAPCSRSTSESTAALGC

LVKDYFPEPVTVSWNSGALTSGVHTFPAVLQSSGLYSLSSVVTVPSSSLGT

KTYTCNVDHKPSNTKVDKRVESKYGPPCPPCPAPEFLGGPSVFLFPPKPKD

TLMISRTPEVTCVVVDVSQEDPEVQFNWYVDGVEVHNAKTKPREEQFNSTY

RVVSVLTVLHQDWLNGKEYKCKVSNKGLPSSIEKTISKAKGQPREPQVYTL

PPSQEEMTKNQVSLTCLVKGFYPSDIAVEWESNGQPENNYKTTPPVLDSDG

SFFLYSRLTVDKSRWQEGNVFSCSVMHEALHNHYTQKSLSLSLG
```

Ab2-Light Chain
```
                                   (SEQ ID NO: 51)
QSVLTQPPSASGTPGQRVTISCSGSSSNIGSNTVHWYQQLPGTAPKLLIYS

DNQRPSGVPDRFSGSKSGTSASLAISGLQSEDEADYYCAAWDDSLNGVFGG

GTKLTVLGQPKAAPSVTLFPPSSEELQANKATLVCLISDFYPGAVTVAWKA

DSSPVKAGVETTTPSKQSNNKYAASSYLSLTPEQWKSHRSYSCQVTHEGST

VEKTVAPTECS
```

In some embodiments, anti-pro/latent-Myostatin antibodies of the disclosure include any antibody that includes a heavy chain variable domain of any one of SEQ ID NOs: 24-29 or a light chain variable domain of any one of SEQ ID NOs: 30-35. In some embodiments, anti-pro/latent-Myostatin antibodies of the disclosure include any antibody that includes the heavy chain variable and light chain variable pairs of SEQ ID NOs: 24 and 30; 25 and 31; 26 and 32; 27 and 33; 28 and 34; or 29 and 35).

Aspects of the disclosure provide anti-pro/latent-Myostatin antibodies having a heavy chain variable and/or a light chain variable amino acid sequence homologous to any of those described herein. In some embodiments, the anti-pro/ latent-Myostatin antibody comprises a heavy chain variable sequence or a light chain variable sequence that is at least 75% (e.g., 80%, 85%, 90%, 95%, 98%, or 99%) identical to the heavy chain variable sequence of any of SEQ ID NOs: 24-29 or a light chain variable sequence of any one of SEQ ID NOs: 30-35. In some embodiments, the homologous heavy chain variable and/or a light chain variable amino acid sequences do not vary within any of the CDR sequences provided herein. For example, in some embodiments, the degree of sequence variation (e.g., 75%, 80%, 85%, 90%, 95%, 98%, or 99%) may occur within a heavy chain variable and/or a light chain variable sequence excluding any of the CDR sequences provided herein.

The "percent identity" of two amino acid sequences is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, word length=3 to obtain amino acid sequences homologous to the protein molecules of interest. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used.

In some embodiments, conservative mutations can be introduced into the CDRs or framework sequences at positions where the residues are not likely to be involved in interacting with pro/latent-Myostatin as determined based on the crystal structure. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g. Molecular Cloning: A Laboratory Manual, J. Sambrook, et al., eds., Second Edition, Cold Spring Harbor Laboratory Press, Cold Spring Harbor, New York, 1989, or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

In some embodiments, the antibodies provided herein comprise mutations that confer desirable properties to the antibodies. For example, to avoid potential complications due to Fab-arm exchange, which is known to occur with native IgG4 mAbs, the antibodies provided herein may comprise a stabilizing 'Adair' mutation (Angal S., et al., "A single amino acid substitution abolishes the heterogeneity of chimeric mouse/human (IgG4) antibody," *Mol Immunol* 30, 105-108; 1993), where serine 228 (EU numbering; residue 241 Kabat numbering) is converted to proline resulting in an IgG1-like (CPPCP (SEQ ID NO: 58)) hinge sequence. Accordingly, any of the antibodies may include a stabilizing 'Adair' mutation or the amino acid sequence CPPCP (SEQ ID NO: 58).

Anti-pro/latent-Myostatin binding agents of this disclosure may optionally comprise antibody constant regions or parts thereof. For example, a $V_L$ domain may be attached at its C-terminal end to a light chain constant domain like Cκ or Cλ. Similarly, a $V_H$ domain or portion thereof may be attached to all or part of a heavy chain like IgA, IgD, IgE, IgG, and IgM, and any isotype subclass. Antibodies may include suitable constant regions (see, for example, Kabat et al., Sequences of Proteins of Immunological Interest, No. 91-3242, National Institutes of Health Publications, Bethesda, Md. (1991)). Therefore, antibodies within the scope of this may disclosure include $V_H$ and $V_L$ domains, or an antigen binding portion thereof, combined with any suitable constant regions.

In certain embodiments, the $V_H$ and/or $V_L$ domains may be reverted to germline sequence, e.g., the FR of these domains are mutated using conventional molecular biology techniques to match those produced by the germline cells. For example, the $V_H$ and/or $V_L$ domains may be reverted to germline sequence of IgHV3-30 (SEQ ID NO: 36) and/or IgLV1-44 (SEQ ID NO: 37), respectively. It should be appreciated that any of the $V_H$ and/or $V_L$ domains may be reverted to any suitable germline sequence. In other embodiments, the FR sequences remain diverged from the consensus germline sequences.

```
IgHV3-30
                                    (SEQ ID NO: 36)
QVQLVESGGGVVQPGRSLRLSCAASGFTFSSYGMHWVRQAPGKGLEWVAV

ISYDGSNKYYADSVKGRFTISRDNSKNTLYLQMNSLRAEDTAVYYCAR

IgLV1-44
                                    (SEQ ID NO: 37)
QSVLTQPPSASGTPGQRVTISCSGSSSNIGSNTVNWYQQLPGTAPKLLIY

SNNQRPSGVPDRFSGSKSGTSASLAISGLQSEDEADYYCAAWDDSLNG
```

In some embodiments, anti-pro/latent-Myostatin antibodies or antigen binding fragments may or may not include the framework region of the antibodies shown in SEQ ID NOs: 24-35. In some embodiments, anti-pro-latent-Myostatin antibodies are murine antibodies and include murine framework region sequences.

In some embodiments, an anti-pro/latent-Myostatin antibodies of the disclosure can bind to pro/latent-Myostatin with relatively high affinity, e.g., with a Kd less than $10^{-6}$ M, $10^{-7}$ M, $10^{-8}$ M, $10^{-9}$ M, $10^{-10}$M, $10^{-11}$ M or lower. For example, anti-pro/latent-Myostatin antibodies can bind to pro/latent-Myostatin with an affinity between 5 pM and 500 nM, e.g., between 50 pM and 100 nM, e.g., between 500 pM and 50 nM. The disclosure also includes antibodies or antigen binding fragments that compete with any of the antibodies described herein for binding to pro/latent-Myostatin and that have an affinity of 50 nM or lower (e.g., 20 nM or lower, 10 nM or lower, 500 pM or lower, 50 pM or lower, or 5 pM or lower). The affinity and binding kinetics of the anti-pro/latent-Myostatin antibody can be tested using any suitable method including but not limited to biosensor technology (e.g., OCTET or BIACORE).

An antibody that "specifically binds" to a target antigen, binds to the target antigen with greater affinity, avidity, more readily, and/or with greater duration than it binds to non-target antigens. In some embodiments, antibodies are disclosed herein that specifically binds pro/latent-Myostatin. in some embodiments any of the antibodies provided herein bind at or near a tolloid cleavage site or at or near a tolloid docking site of pro/latent-Myostatin. In some embodiments, an antibody binds near a tolloid cleavage site or near a tolloid docking site if it binds within 15 or fewer amino acid residues of the tolloid cleavage site or tolloid docking site. In some embodiments, any of the antibodies provided herein bind within 1, 2, 3, 4, 5, 6, 7, 8, 9, 10, 11, 12, 13, 14 or 15 amino acid residues of a tolloid cleavage site or tolloid docking site. In some embodiments, an antibody binds at or near a tolloid cleavage site of GDF8. For example, an antibody may bind an amino acid sequence as set forth in SEQ ID NO: 62 PKAPPL-RELIDQYDVQRDDSSDGSLEDDDYHAT (SEQ ID NO: 62). In other embodiments, any of the antibodies provided herein bind at or near a proprotein convertase cleavage site or at or near a proprotein convertase docking site of pro/latent-Myostatin. In some embodiments, an antibody binds near a proprotein convertase cleavage site or near a proprotein convertase docking site if it binds within 15 or fewer amino acid residues of the proprotein convertase cleavage site or proprotein convertase docking site. In some embodiments, any of the antibodies provided herein bind within 1, 2, 3, 4, 5, 6, 7, 8, 9, 10, 11, 12, 13, 14 or 15 amino acid residues of a proprotein convertase cleavage site or proprotein convertase docking site. In some embodiments, an antibody binds at or near a proprotein convertase cleavage site of GDF8. For example, an antibody may bind an amino acid sequence as set forth in SEQ ID NO: 63.

```
                                              (SEQ ID NO: 63)
        GLNPFLEVKVTDTPKRSRRDFGLDCDEHSTESRC
```

In one example, the anti-pro/latent-Myostatin antibodies described herein specifically bind pro/latent-Myostatin as compared to other forms of Myostatin and/or other members of the TGFβ family of growth factors. Members of the TGFβ family of growth factors include, without limitation AMH, ARTN, BMP10, BMP15, BMP2, BMP3, BMP4, BMP5, BMP6, BMP7, BMP8A, BMP8B, GDF1, GDF10, GDF11, GDF15, GDF2, GDF3, GDF3A, GDF5, GDF6, GDF7, GDF8, GDF9, GDNF, INHA, INHBA, INHBB, INHBC, INHBE, LEFTY1, LEFTY2, NODAL, NRTN, PSPN, TGFβ1, TGFβ2, and TGFβ3 protein. Such antibodies may bind pro/latent-Myostatin at a much higher affinity as compared to other members of the TGFβ family of growth factors (e.g., at least 2-fold, 5-fold, 10-fold, 50-fold, 100-fold, 200-fold, 500-fold, or 1,000-fold higher). In some embodiments, such antibodies may bind pro/latent-Myostatin with an affinity of at least 1,000 greater as compared to other members of the TGFβ family of growth factors. In some embodiments, antibodies provided herein may bind to pro/latent-Myostatin at a much higher affinity as compared to one or more forms of GDF11 or mature Myostatin (e.g., at least 2-fold, 5-fold, 10-fold, 50-fold, 100-fold, 200-fold, 500-fold, or 1,000-fold higher). In some embodiments, antibodies provided herein may bind to pro/latent-Myostatin with an affinity of at least 1,000 greater as compared to one or more forms of GDF11 (e.g., proGDF11, latent GDF11 or mature GDF11) or mature Myostatin Alternatively, or in addition, antibodies may exhibit a much higher inhibitory activity against proteolytic cleavage of pro/latent-Myostatin (e.g., by a proprotein convertase or tolloid protease) as compared with other members of the TGFβ family, such as pro/latent GDF11 (e.g., at least 2-fold, 5-fold, 10-fold, 50-fold, 100-fold, 200-fold, 500-fold, 1,000-fold higher).

In some embodiments, antibodies bind an antigen but cannot effectively eliminate the antigen from the plasma. Thus, in some embodiments, the concentration of the antigen in the plasma may be increased by reducing the clearance of the antigen. However, in some embodiments, antibodies (e.g., sweeping antibodies) provided herein have an affinity to an antigen that is sensitive to pH. Such pH sensitive antibodies may bind to the antigen in plasma at neutral pH and dissociate from the antigen in an acidic endosome, thus reducing antibody-mediated antigen accumulation and/or promoting antigen clearance from the plasma.

Aspects of the disclosure relate to sweeping antibodies. As used herein "sweeping antibodies" refer to antibodies having both pH-sensitive antigen binding and at least a threshold level of binding to cell surface neonatal Fc receptor (FcRn) at neutral or physiological pH. In some embodiments, sweeping antibodies bind to the neonatal Fc receptor FcRn at neutral pH. For example sweeping antibodies may bind to the FcRn at a pH ranging from 7.0 to 7.6. In some embodiments, sweeping antibodies can bind to an antigen at an antigen binding site and bind to a cellular FcRn via an Fc portion of the antibody. In some embodiments, sweeping antibodies may then be internalized, releasing antigen in an acidic endosome, which may be degraded. In some embodiments, a sweeping antibody, no longer bound to the antigen, may then be released (e.g., by exocytosis) by the cell back into the serum.

In some embodiments, FcRn in the vascular endothelia (e.g., of a subject) extends the half-life of a sweeping antibody. In some embodiments, vascular endothelial cells internalize sweeping antibodies, which in some embodiments are bound to an antigen such as Myostatin (e.g., proMyostatin, latent Myostatin or primed Myostatin). In some embodiments, a sweeping antibody is recycled back into the bloodstream. In some embodiments, a sweeping antibody has an increased half-life (e.g., in the serum of a subject) as compared to its conventional counterpart. In some embodiments, a conventional counterpart of a sweeping antibody refers the antibody from which the sweeping antibody was derived (e.g., prior to engineering the Fc portion of the conventional antibody to bind FcRn with greater affinity at pH 7). In some embodiments, a sweeping antibody has a half-life in the serum of a subject that is at least 1%, 5%, 10%, 15%, 20%, 25%, 35%, 50%, 75%, 100%, 150%, 200% or 250% longer as compared to its conventional counterpart.

In some embodiments, an Fc portion of a sweeping antibody binds FcRn. In some embodiments, the Fc portion of a sweeping antibody binds to FcRn at a pH of 7.4 with a Kd ranging from $10^{-3}$ M to $10^{-8}$ M. In some embodiments, a sweeping antibody binds to FcRn at a pH of 7.4 with a Kd ranging from $10^{-3}$ M to $10^{-7}$ M, from $10^{-3}$ M to $10^{-6}$ M, from $10^{-3}$ M to $10^{-5}$ M, from $10^{-3}$ M to $10^{-4}$ M, from $10^{-4}$ M to $10^{-8}$ M, from $10^{-4}$ M to $10^{-7}$ M, from $10^{-4}$ M to $10^{-6}$ M, from $10^{-4}$ M to $10^{-5}$ M, from $10^{-5}$ M to $10^{-8}$ M, from $10^{-5}$ M to $10^{-7}$ M, from $10^{-5}$ M to $10^{-6}$ M, from $10^{-6}$ M to $10^{-8}$ M, from $10^{-6}$ M to $10^{-7}$ M, or from $10^{-7}$ M to $10^{-8}$ M. In some embodiments, FcRn binds to the CH2-CH3 hinge region of a sweeping antibody. In some embodiments, FcRn binds to the same region as proteinA or protein G. In some embodiments, FcRn binds to a different binding site from FcγRs. In some embodiments, the amino acid residues AA of a sweeping antibody Fc region are required for binding to FcRn. In some embodiments, the amino acid residues AA of a sweeping antibody Fc region affect binding to FcRn.

In some embodiments, any of the antibodies provided herein are engineered to bind FcRn with greater affinity. In some embodiments, any of the antibodies provided herein are engineered to bind FcRn with greater affinity at pH 7.4. In some embodiments, the affinity of sweeping antibodies to FcRn is increased to extend their pharmacokinetic (PK) properties as compared to their conventional counterparts. For example, in some embodiments, sweeping antibodies elicit less adverse reactions due to their efficacy at lower doses. In some embodiments, sweeping antibodies are administered less frequently. In some embodiments, transcytosis of sweeping antibodies to certain tissue types are increased. In some embodiments, sweeping antibodies enhance efficiency of trans-placental delivery. In some embodiments, sweeping antibodies are less costly to produce.

In some embodiments, any of the antibodies provided herein are engineered to bind FcRn with lower affinity. In some embodiments, any of the antibodies provided herein are engineered to bind FcRn with lower affinity at pH 7.4. In some embodiments, the affinity of sweeping antibodies to FcRn is decreased to shorten their pharmacokinetic (PK) properties as compared to their conventional counterparts. For example, in some embodiments, sweeping antibodies are more rapidly cleared for imaging and/or radioimmunotherapy. In some embodiments, sweeping antibodies promote clearance of endogenous pathogenic antibodies as a treatment for autoimmune diseases. In some embodiments, sweeping antibodies reduce the risk of adverse pregnancy outcome, which may be caused by trans-placental transport of material fetus-specific antibodies.

In some embodiments, sweeping antibodies have decreased affinity to an antigen at low pH as compared to a neutral or physiological pH (e.g., pH 7.4). In some embodiments, sweeping antibodies have a decreased affinity to an antigen at an acidic pH (e.g. a pH ranging from 5.5 to 6.5) as compared to a physiological pH (e.g., pH 7.4). It should be appreciated that any of the antibodies provided herein can be engineered to dissociate from the antigen depending on changes in pH (e.g., pH sensitive antibodies). In some embodiments, sweeping antibodies provided herein are engineered to bind antigen dependent on pH. In some embodiments, sweeping antibodies provided herein are engineered to bind FcRn dependent on pH. In some embodiments, sweeping antibodies provided herein are internalized by endocytosis. In some embodiments, sweeping antibodies provided here are internalized by FcRn binding. In some embodiments, endocytosed sweeping antibodies release antigen in an endosome. In some embodiments, sweeping antibodies are recycled back to the cell surface. In some embodiments, sweeping antibodies remain attached to cells. In some embodiments, endocytosed sweeping antibodies are recycled back to the plasma. It should be appreciated that the Fc portion of any of the antibodies provided herein may be engineered to have different FcRn binding activity. In some embodiments, FcRn binding activity affects the clearance time of an antigen by a sweeping antibody. In some embodiments, sweeping antibodies may be long-acting or rapid-acting sweeping antibodies.

In some embodiments, converting a conventional therapeutic antibody into a sweeping antibody reduces the efficacious dose. In some embodiments, converting a conventional therapeutic antibody into a sweeping antibody reduces the efficacious dose by at least 1%, 2%, 5%, 10%, 20%, 30%, 40%, 50%, 60%, 70%, 80%, 90%, 95%, or 99%. In some embodiments, converting a conventional therapeutic antibody into a sweeping antibody reduces the efficacious dose by at least 1.5 fold, 2 fold, 3 fold, 4 fold, 5 fold, 6 fold, 8 fold, 10 fold, 15 fold, 20 fold, 50 fold or 100 fold.

In some embodiments, selecting an appropriate dose of a sweeping antibody for therapy may be performed empirically. In some embodiments, a high dose of a sweeping antibody may saturate FcRn, resulting in antibodies which stabilize antigen in serum without being internalized. In some embodiments, a low dose of a sweeping antibody may not be therapeutically effective. In some embodiments, sweeping antibodies are administered once a day, once a week, once every two weeks, once every three weeks, once every four weeks, once every 6 weeks, once every 8 weeks, once every 10 weeks, once every 12 weeks, once every 16 weeks, once every 20 weeks, or once every 24 weeks.

In some embodiments, any of the antibodies provided herein may be modified or engineered to be sweeping antibodies. In some embodiments, any of the antibodies provided herein may be converted into a sweeping antibody using any suitable method. For example, suitable methods for making sweeping antibodies have been previously described in Igawa et al., (2013) "Engineered Monoclonal Antibody with Novel Antigen-Sweeping Activity In Vivo," *PLoS ONE* 8(5): e63236; and Igawa et al., "pH-dependent antigen-binding antibodies as a novel therapeutic modality," *Biochimica et Biophysica Acta* 1844 (2014) 1943-1950; the contents of each of which are hereby incorporated by reference. It should be appreciated, however, that the methods for making sweeping antibodies as provided herein are not meant to be limiting. Thus, additional methods for making sweeping antibodies are within the scope of this disclosure.

Some aspects of the disclosure are based on the recognition that the affinity (e.g., as expressed as Kd) of any of the anti-pro/latent-Myostatin antibodies provided herein are sensitive to changes in pH. In some embodiments, the antibodies provided herein have an increased Kd of binding to pro/latent-Myostatin at a relatively low pH (e.g., a pH ranging from 4.0-6.5) as compared to a relatively high pH (e.g., a pH ranging from 7.0-7.4). In some embodiments, the antibodies provided herein have a Kd of binding to pro/latent-Myostatin ranging from $10^{-3}$ M, $10^{-4}$ M, $10^{-5}$ M, $10^{-6}$M, $10^{-7}$ M, $10^{-8}$ M when the pH is between 4.0 and 6.5. In some embodiments, the antibodies provided herein have a Kd of binding to pro/latent-Myostatin ranging from $10^{-6}$ M, $10^{-7}$ M, $10^{-8}$ M, $10^{-9}$ M, $10^{-10}$ M, $10^{-11}$ M when the pH is between 7.0 and 7.4. In some embodiments, the antibodies provided herein have a Kd of binding to pro/latent-Myostatin that is at least 2 fold, at least 10 fold, at least 50 fold, at least 100 fold, at least 500 fold, at least 1000 fold, at least 5000 fold, or at least 10000 fold greater at a pH between 4.0 and 6.5 as compared to a pH between 7.0 and 7.4.

In some embodiments, pro/latent-Myostatin antibodies are provided herein that do not specifically bind to an epitope within the amino acid sequence set forth as (SEQ ID NO: 64). In some embodiments, pro/latent-Myostatin antibodies provided herein do not specifically bind to the same epitope as an antibody described in Table 2a, 11a, 11b, or 13 of International Patent Application Publication No. WO 2016/098357, which was published on Jun. 23, 2016, and which is based on International Patent Application No. PCT/JP2015/006323, which was filed on Dec. 18, 2015. In some embodiments, pro/latent-Myostatin antibodies provided herein do not compete or do not cross-compete for binding to the same epitope as an antibody described in Table 2a, 11a, 11b, or 13 of International Patent Application Publication No. WO 2016/098357, which was published on Jun. 23, 2016, and which is based on International Patent Application No. PCT/JP2015/006323, which was filed on Dec. 18, 2015. In some embodiments, pro/latent-Myostatin antibodies provided herein do not specifically bind to the same epitope as an antibody comprising a VH and a VL pair described in Table 2a, 11a, 11b, or 13 of International Patent Application Publication No. WO 2016/098357, which was published on Jun. 23, 2016, and which is based on International Patent Application No. PCT/JP2015/006323, which was filed on Dec. 18, 2015. In some embodiments, pro/ latent-Myostatin antibodies provided herein do not compete or do not cross-compete for binding to the same epitope as an antibody comprising a VH and a VL pair described in Table 2a, 11a, 11b, or 13 of International Patent Application Publication No. WO 2016/098357, which was published on Jun. 23, 2016, and which is based on International Patent Application No. PCT/JP2015/006323, which was filed on Dec. 18, 2015.

Polypeptides

Some aspects of the disclosure relate to a polypeptide having a sequence selected from the group consisting of SEQ ID NO: 24, SEQ ID NO: 25, SEQ ID NO: 26, SEQ ID NO: 27, SEQ ID NO: 28, and SEQ ID NO 29. In some embodiments, the polypeptide is a variable heavy chain domain. In some embodiments, the polypeptide is at least 75% (e.g., 80%, 85%, 90%, 95%, 98%, or 99%) identical to any one of the amino acid sequences set forth in SEQ ID NO: 24, SEQ ID NO: 25, SEQ ID NO: 26, SEQ ID NO: 27, SEQ ID NO: 28, or SEQ ID NO 29.

Some aspects of the disclosure relate to a polypeptide having a sequence selected from the group consisting of SEQ ID NO: 30, SEQ ID NO: 31, SEQ ID NO: 32, SEQ ID NO: 33, SEQ ID NO: 34, and SEQ ID NO 35. In some embodiments, the polypeptide is a variable light chain domain. In some embodiments, the polypeptide is at least 75% (e.g., 80%, 85%, 90%, 95%, 98%, or 99%) identical to any one of the amino acid sequences set forth in SEQ ID NO: 30, SEQ ID NO: 31, SEQ ID NO: 32, SEQ ID NO: 33, SEQ ID NO: 34, or SEQ ID NO 35.

Antibodies that Compete with Anti-Pro/Latent-Myostatin Antibodies

Aspects of the disclosure relate to antibodies that compete or cross-compete with any of the antibodies provided herein. The term "compete", as used herein with regard to an antibody, means that a first antibody binds to an epitope of a protein (e.g., latent Myostatin) in a manner sufficiently similar to the binding of a second antibody, such that the result of binding of the first antibody with its epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its epitope or ligand, whether to the same, greater, or lesser extent, the antibodies are said to "cross-compete" with each other for binding of their respective epitope(s). Both competing and cross-competing antibodies are within the scope of this disclosure. Regardless of the mechanism by which such competition or cross-competition occurs (e.g., steric hindrance, conformational change, or binding to a common epitope, or portion thereof), the skilled artisan would appreciate that such competing and/or cross-competing antibodies are encompassed and can be useful for the methods and/or compositions provided herein.

Aspects of the disclosure relate to antibodies that compete or cross-compete with any of the antibodies provided herein. In some embodiments, an antibody binds at or near the same epitope as any of the antibodies provided herein. In some embodiments, an antibody binds near an epitope if it binds within 15 or fewer amino acid residues of the epitope. In some embodiments, any of the antibodies provided herein bind within 1, 2, 3, 4, 5, 6, 7, 8, 9, 10, 11, 12, 13, 14 or 15 amino acid residues of an epitope that is bound by any of the antibodies provided herein.

In another embodiment, an antibody competes or cross-competes for binding to any of the antigens provided herein (e.g., pro/latent-Myostatin) with an equilibrium dissociation constant, Kd, between the antibody and the protein of less than $10^{-6}$ M. In other embodiments, an antibody competes or cross-competes for binding to any of the antigens provided herein with a Kd in a range from $10^{-11}$ M to $10^{-6}$ M.

Aspects of the disclosure relate to antibodies that compete for binding to pro/latent-Myostatin with any of the antibodies provided herein. In some embodiments, the antibody binds to pro/latent-Myostatin at the same epitope as any of the antibodies provided herein. For example, in some embodiments any of the antibodies provided herein bind at or near a tolloid cleavage site or at or near a tolloid docking site of pro/latent-Myostatin. In other embodiments, any of the antibodies provided herein bind at or near a proprotein convertase cleavage site or at or near a proprotein convertase docking site of pro/latent-Myostatin. In another embodiment, an antibody competes for binding to pro/latent-Myostatin with an equilibrium dissociation constant, Kd, between the antibody and pro/latent-Myostatin of less than $10^{-6}$ M. In other embodiments, the an antibody that competes with any of the antibodies provided herein binds to pro/latent-Myostatin with a Kd in ranging from $10^{-11}$ M to $10^{-6}$ M.

Any of the antibodies provided herein can be characterized using any suitable methods. For example, one method is to identify the epitope to which the antigen binds, or "epitope mapping." There are many suitable methods for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which an antibody binds. The epitope can be a linear epitope, i.e., contained in a single stretch of amino acids, or a conformational epitope formed by a three-dimensional interaction of amino acids that may not necessarily be contained in a single stretch (primary structure linear sequence). Peptides of varying lengths (e.g., at least 4-6 amino acids long) can be isolated or synthesized (e.g., recombinantly) and used for binding assays with an antibody. In another example, the epitope to which the antibody binds can be determined in a systematic screen by using overlapping peptides derived from the target antigen sequence and determining binding by the antibody. According to the gene fragment expression assays, the open reading frame encoding the target antigen is fragmented either randomly or by specific genetic constructions and the reactivity of the expressed fragments of the antigen with the antibody to be tested is determined. The gene fragments may, for example, be produced by PCR and then transcribed and translated into protein in vitro, in the presence of radioactive amino acids. The binding of the antibody to the radioactively labeled antigen fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. In an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant of a target antigen in which various fragments of the pro/latent-Myostatin polypeptide have been replaced (swapped) with sequences from a closely related, but antigenically distinct protein, such as another member of the TGFβ protein family (e.g., GDF11). By assessing binding of the antibody to the mutant pro/latent-Myostatin, the importance of the particular antigen fragment to antibody binding can be assessed.

Alternatively, competition assays can be performed using other antibodies known to bind to the same antigen to determine whether an antibody binds to the same epitope as the other antibodies. Competition assays are well known to those of skill in the art. Any of the suitable methods, e.g., the epitope mapping methods as described herein, can be applied to determine whether an anti-pro/latent-Myostatin antibody binds one or more of the specific residues/segments in pro/latent-Myostatin as described herein. Further, the interaction of the antibody with one or more of those defined residues in pro/latent-Myostatin can be determined by routine technology. For example, a crystal structure can be determined, and the distances between the residues in pro/latent-Myostatin and one or more residues in the antibody can be determined accordingly. Based on such distance, whether a specific residue in pro/latent-Myostatin interacts with one or more residues in the antibody can be determined. Further, suitable methods, such as competition assays and target mutagenesis assays can be applied to determine the preferential binding of a candidate anti-pro/latent-Myostatin antibody to pro/latent-Myostatin as compared to another target such as a mutant pro/latent-Myostatin.

Production of Antibodies that Bind Pro/Latent-Myostatin

Numerous methods may be used for obtaining antibodies, or antigen binding fragments thereof, of the disclosure. For example, antibodies can be produced using recombinant DNA methods. Monoclonal antibodies may also be produced by generation of hybridomas (see e.g., Kohler and Milstein (1975) Nature, 256: 495-499) in accordance with known methods. Hybridomas formed in this manner are then screened using standard methods, such as enzyme-linked immunosorbent assay (ELISA) and surface plasmon resonance (e.g., OCTET or BIACORE) analysis, to identify one or more hybridomas that produce an antibody that specifically binds to a specified antigen. Any form of the specified antigen may be used as the immunogen, e.g., recombinant antigen, naturally occurring forms, any variants or fragments thereof, as well as antigenic peptide thereof (e.g., any of the epitopes described herein as a linear epitope or within a scaffold as a conformational epitope). One exemplary method of making antibodies includes screening protein expression libraries that express antibodies or fragments thereof (e.g., scFv), e.g., phage or ribosome display libraries. Phage display is described, for example, in Ladner et al., U.S. Pat. No. 5,223,409; Smith (1985) Science 228:1315-1317; Clackson et al. (1991) Nature, 352: 624-628; Marks et al. (1991) J. Mol. Biol., 222: 581-597WO92/18619; WO 91/17271; WO 92/20791; WO 92/15679; WO 93/01288; WO 92/01047; WO 92/09690; and WO 90/02809.

In addition to the use of display libraries, the specified antigen (e.g., proMyostatin) can be used to immunize a non-human animal, e.g., a rodent, e.g., a mouse, hamster, or rat. In one embodiment, the non-human animal is a mouse. In another embodiment, a monoclonal antibody is obtained from the non-human animal, and then modified, e.g., chimeric, using suitable recombinant DNA techniques. A variety of approaches for making chimeric antibodies have been described. See e.g., Morrison et al., Proc. Natl. Acad. Sci. U.S.A. 81:6851, 1985; Takeda et al., Nature 314:452, 1985, Cabilly et al., U.S. Pat. No. 4,816,567; Boss et al., U.S. Pat. No. 4,816,397; Tanaguchi et al., European Patent Publication EP171496; European Patent Publication 0173494, United Kingdom Patent GB 2177096B.

For additional antibody production techniques, see Antibodies: A Laboratory Manual, eds. Harlow et al., Cold Spring Harbor Laboratory, 1988. The present disclosure is not necessarily limited to any particular source, method of production, or other special characteristics of an antibody.

Some aspects of the present disclosure relate to host cells transformed with a polynucleotide or vector. Host cells may be a prokaryotic or eukaryotic cell. The polynucleotide or vector which is present in the host cell may either be integrated into the genome of the host cell or it may be maintained extrachromosomally. The host cell can be any prokaryotic or eukaryotic cell, such as a bacterial, insect, fungal, plant, animal or human cell. In some embodiments, fungal cells are, for example, those of the genus Saccharomyces, in particular those of the species S. cerevisiae. The term "prokaryotic" includes all bacteria which can be transformed or transfected with a DNA or RNA molecules for the expression of an antibody or the corresponding immunoglobulin chains. Prokaryotic hosts may include gram negative as well as gram positive bacteria such as, for example, E. coli, S. typhimurium, Serratia marcescens and Bacillus subtilis. The term "eukaryotic" includes yeast, higher plants, insects and vertebrate cells, e.g., mammalian cells, such as NSO and CHO cells. Depending upon the host employed in a recombinant production procedure, the antibodies or immunoglobulin chains encoded by the polynucleotide may be glycosylated or may be non-glycosylated. Antibodies or the corresponding immunoglobulin chains may also include an initial methionine amino acid residue.

In some embodiments, once a vector has been incorporated into an appropriate host, the host may be maintained under conditions suitable for high level expression of the nucleotide sequences, and, as desired, the collection and purification of the immunoglobulin light chains, heavy chains, light/heavy chain dimers or intact antibodies, antigen binding fragments or other immunoglobulin forms may follow; see, Beychok, Cells of Immunoglobulin Synthesis, Academic Press, N.Y., (1979). Thus, polynucleotides or vectors are introduced into the cells which in turn produce the antibody or antigen binding fragments. Furthermore, transgenic animals, preferably mammals, comprising the aforementioned host cells may be used for the large scale production of the antibody or antibody fragments.

The transformed host cells can be grown in fermenters and cultured using any suitable techniques to achieve optimal cell growth. Once expressed, the whole antibodies, their dimers, individual light and heavy chains, other immunoglobulin forms, or antigen binding fragments, can be purified according to standard procedures of the art, including ammonium sulfate precipitation, affinity columns, column chromatography, gel electrophoresis and the like; see, Scopes, "Protein Purification", Springer Verlag, N.Y. (1982). The antibody or antigen binding fragments can then be isolated from the growth medium, cellular lysates, or cellular membrane fractions. The isolation and purification of the, e.g., microbially expressed antibodies or antigen binding fragments may be by any conventional means such as, for example, preparative chromatographic separations and immunological separations such as those involving the use of monoclonal or polyclonal antibodies directed, e.g., against the constant region of the antibody.

Aspects of the disclosure relate to a hybridoma, which provides an indefinitely prolonged source of monoclonal antibodies. As an alternative to obtaining immunoglobulins directly from the culture of hybridomas, immortalized hybridoma cells can be used as a source of rearranged heavy chain and light chain loci for subsequent expression and/or genetic manipulation. Rearranged antibody genes can be reverse transcribed from appropriate mRNAs to produce cDNA. In some embodiments, heavy chain constant region can be exchanged for that of a different isotype or eliminated altogether. The variable regions can be linked to encode single chain Fv regions. Multiple Fv regions can be linked to confer binding ability to more than one target or chimeric heavy and light chain combinations can be employed. Any appropriate method may be used for cloning of antibody variable regions and generation of recombinant antibodies.

In some embodiments, an appropriate nucleic acid that encodes variable regions of a heavy and/or light chain is obtained and inserted into an expression vectors which can be transfected into standard recombinant host cells. A variety of such host cells may be used. In some embodiments, mammalian host cells may be advantageous for efficient processing and production. Typical mammalian cell lines useful for this purpose include CHO cells, 293 cells, or NSO cells. The production of the antibody or antigen binding fragment may be undertaken by culturing a modified recombinant host under culture conditions appropriate for the growth of the host cells and the expression of the coding sequences. The antibodies or antigen binding fragments may be recovered by isolating them from the culture. The expression systems may be designed to include signal peptides so that the resulting antibodies are secreted into the medium; however, intracellular production is also possible.

The disclosure also includes a polynucleotide encoding at least a variable region of an immunoglobulin chain of the antibodies described herein. In some embodiments, the variable region encoded by the polynucleotide comprises at least one complementarity determining region (CDR) of the VH and/or VL of the variable region of the antibody produced by any one of the above described hybridomas.

Polynucleotides encoding antibody or antigen binding fragments may be, e.g., DNA, cDNA, RNA or synthetically produced DNA or RNA or a recombinantly produced chimeric nucleic acid molecule comprising any of those polynucleotides either alone or in combination. In some embodiments, a polynucleotide is part of a vector. Such vectors may comprise further genes such as marker genes which allow for the selection of the vector in a suitable host cell and under suitable conditions.

In some embodiments, a polynucleotide is operatively linked to expression control sequences allowing expression in prokaryotic or eukaryotic cells. Expression of the polynucleotide comprises transcription of the polynucleotide into a translatable mRNA. Regulatory elements ensuring expression in eukaryotic cells, preferably mammalian cells, are well known to those skilled in the art. They may include regulatory sequences that facilitate initiation of transcription and optionally poly-A signals that facilitate termination of transcription and stabilization of the transcript. Additional regulatory elements may include transcriptional as well as translational enhancers, and/or naturally associated or heterologous promoter regions. Possible regulatory elements permitting expression in prokaryotic host cells include, e.g., the PL, Lac, Trp or Tac promoter in E. coli, and examples of regulatory elements permitting expression in eukaryotic host cells are the AOX1 or GAL1 promoter in yeast or the CMV-promoter, SV40-promoter, RSV-promoter (Rous sarcoma virus), CMV-enhancer, SV40-enhancer or a globin intron in mammalian and other animal cells.

Beside elements which are responsible for the initiation of transcription such regulatory elements may also include transcription termination signals, such as the SV40-poly-A site or the tk-poly-A site, downstream of the polynucleotide. Furthermore, depending on the expression system employed, leader sequences capable of directing the polypeptide to a cellular compartment or secreting it into the medium may be added to the coding sequence of the polynucleotide and have been described previously. The leader sequence(s) is (are) assembled in appropriate phase with translation, initiation and termination sequences, and preferably, a leader sequence capable of directing secretion of translated protein, or a portion thereof, into, for example, the extracellular medium. Optionally, a heterologous polynucleotide sequence can be used that encode a fusion protein including a C- or N-terminal identification peptide imparting desired characteristics, e.g., stabilization or simplified purification of expressed recombinant product.

In some embodiments, polynucleotides encoding at least the variable domain of the light and/or heavy chain may encode the variable domains of both immunoglobulin chains or only one. Likewise, a polynucleotides may be under the control of the same promoter or may be separately controlled for expression. Furthermore, some aspects relate to vectors, particularly plasmids, cosmids, viruses and bacteriophages used conventionally in genetic engineering that comprise a polynucleotide encoding a variable domain of an immunoglobulin chain of an antibody or antigen binding fragment; optionally in combination with a polynucleotide that encodes the variable domain of the other immunoglobulin chain of the antibody.

In some embodiments, expression control sequences are provided as eukaryotic promoter systems in vectors capable of transforming or transfecting eukaryotic host cells, but control sequences for prokaryotic hosts may also be used. Expression vectors derived from viruses such as retroviruses, vaccinia virus, adeno-associated virus, herpes viruses, or bovine papilloma virus, may be used for delivery of the polynucleotides or vector into targeted cell population (e.g., to engineer a cell to express an antibody or antigen binding fragment). A variety of appropriate methods can be used to construct recombinant viral vectors. In some embodiments, polynucleotides and vectors can be reconstituted into liposomes for delivery to target cells. The vectors containing the polynucleotides (e.g., the heavy and/or light variable domain(s) of the immunoglobulin chains encoding sequences and expression control sequences) can be transferred into the host cell by suitable methods, which vary depending on the type of cellular host.

Modifications

Antibodies or antigen binding fragments of the disclosure may be modified with a detectable label, including, but not limited to, an enzyme, prosthetic group, fluorescent material, luminescent material, bioluminescent material, radioactive material, positron emitting metal, nonradioactive paramagnetic metal ion, and affinity label for detection and isolation of pro/latent-Myostatin. The detectable substance may be coupled or conjugated either directly to the polypeptides of the disclosure or indirectly, through an intermediate (such as, for example, a linker) using suitable techniques. Non-limiting examples of suitable enzymes include horseradish peroxidase, alkaline phosphatase, β-galactosidase, glucose oxidase, or acetylcholinesterase; non-limiting examples of suitable prosthetic group complexes include streptavidin/biotin and avidin/biotin; non-limiting examples of suitable fluorescent materials include biotin, umbelliferone, fluorescein, fluorescein isothiocyanate, rhodamine, dichlorotriazinylamine fluorescein, dansyl chloride, or phycoerythrin; an example of a luminescent material includes luminol; non-limiting examples of bioluminescent materials include luciferase, luciferin, and aequorin; and examples of suitable radioactive material include a radioactive metal ion, e.g., alpha-emitters or other radioisotopes such as, for example, iodine ($^{131}$I, $^{125}$I, $^{123}$I, $^{121}$I), carbon ($^{14}$C), sulfur ($^{35}$S), tritium ($^{3}$H), indium ($^{115m}$In, $^{113m}$In, $^{112}$In, $^{111}$In), and technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, Lu, $^{159}$Gd, $^{149}$Pm, $^{140}$La, $^{175}$Yb, $^{166}$Ho, $^{90}$Y, $^{47}$Sc, $^{86}$R, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, and tin ($^{113}$Sn, $^{117}$Sn). The detectable substance may be coupled or conjugated either directly to the anti-pro/latent-Myostatin antibodies of the disclosure or indirectly, through an intermediate (such as, for example, a linker) using suitable techniques. Anti-pro/latent-Myostatin antibodies conjugated to a detectable substance may be used for diagnostic assays as described herein.

Pharmaceutical Compositions

One or more of the anti-pro/latent-Myostatin antibodies can be mixed with a pharmaceutically acceptable carrier (excipient), including buffer, to form a pharmaceutical composition for use in alleviating a disease or disorder that is associated with myopathy. "Acceptable" means that the carrier must be compatible with the active ingredient of the composition (and preferably, capable of stabilizing the active ingredient) and not deleterious to the subject to be treated. Examples of pharmaceutically acceptable excipients (carriers), including buffers, would be apparent to the skilled artisan and have been described previously. See, e.g., Remington: The Science and Practice of Pharmacy 20th Ed. (2000) Lippincott Williams and Wilkins, Ed. K. E. Hoover. In one example, a pharmaceutical composition described herein contains more than one anti-pro/latent-Myostatin antibodies that recognize different epitopes/residues of the target antigen.

The pharmaceutical compositions to be used in the present methods can comprise pharmaceutically acceptable carriers, excipients, or stabilizers in the form of lyophilized formulations or aqueous solutions. (Remington: The Science and Practice of Pharmacy 20th Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURON- ICS™ or polyethylene glycol (PEG). Pharmaceutically acceptable excipients are further described herein.

In some examples, the pharmaceutical composition described herein comprises liposomes containing the anti-pro/latent-Myostatin antibody, which can be prepared by any suitable method, such as described in Epstein, et al., Proc. Natl. Acad. Sci. USA 82:3688 (1985); Hwang, et al., Proc. Natl. Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The anti-pro/latent-Myostatin antibody may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Exemplary techniques have been described previously, see, e.g., Remington, The Science and Practice of Pharmacy 20th Ed. Mack Publishing (2000).

In other examples, the pharmaceutical composition described herein can be formulated in sustained-release format. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(v nyl-alcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(–)-3-hydroxybutyric acid.

The pharmaceutical compositions to be used for in vivo administration must be sterile. This is readily accomplished by, for example, filtration through sterile filtration membranes. Therapeutic antibody compositions are generally placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient can be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present disclosure, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 mg to about 500 mg of the active ingredient of the present disclosure. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, nonionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%.

The emulsion compositions can be those prepared by mixing an anti-proMyostatin antibody with Intralipid™ or the components thereof (soybean oil, egg phospholipids, glycerol and water).

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect. Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Use of Anti-Pro/Latent-Myostatin Antibodies for Treating Diseases/Disorders

The anti-pro/latent-Myostatin antibodies described herein are effective in treating a disease or disorder associated with myopathy. As used herein, the term "myopathy" refers to a muscular disease in which the muscle fibers do not function properly, typically resulting in muscular weakness. Myopathies include muscular diseases that are neuromuscular or musculoskeletal in nature. In some embodiments, the myopathy is an inherited myopathy. Inherited myopathies include, without limitation, dystrophies, myotonias, congenital myopathies (e.g., nemaline myopathy, multi/minicore myopathy, and centronuclear myopathy), mitochondrial myopathies, familial periodic myopathies, inflammatory myopathies and metabolic myopathies (e.g., glycogen storage diseases and lipid storage disorder). In some embodiments, the myopathy is an acquired myopathy. Acquired myopathies include, without limitation, external substance induced myopathy (e.g., drug-induced myopathy and glucocorticoid myopathy, alcoholic myopathy, and myopathy due to other toxic agents), myositis (e.g., dermatomyositis, polymositis and inclusion body myositis), myositis ossificans, rhabdomyolysis, and myoglobinurias, and disuse atrophy. In some embodiments, the myopathy is disuse atrophy, which may be caused by bone fracture (e.g. a hip fracture) or by nerve injury (e.g., spinal cord injury (SCI)). In some embodiments the myopathy is related to a disease or disorder such as amyotrophic lateral sclerosis (ALS), spinal muscular atrophy (SMA), cachexia syndromes due to renal failure, AIDS, cardiac conditions and/or cancer. In some embodiments the myopathy is related to ageing.

An aspect of the disclosure includes a method of treating a subject having a myopathy, the method comprising administering to the subject an effective amount of an antibody described above. In some embodiments, the myopathy is a primary myopathy. In another embodiment, the primary myopathy comprises disuse atrophy. In other embodiments, the disuse atrophy is associated with hip fracture, elective joint replacement, critical care myopathy, spinal cord injury or stroke. In some embodiments, the myopathy is a secondary myopathy, in which muscle loss is secondary to a disease pathology. In other embodiments, the secondary myopathy comprises denervation, genetic muscle weakness or cachexia. In another embodiment, the secondary myopathy is a denervation associated with amyotrophic lateral sclerosis or spinal muscular atrophy. In some embodiments, the secondary myopathy is a genetic muscle weakness associated with a muscular dystrophy. In other embodiments, the secondary myopathy is a cachexia associated with renal failure, AIDS, a cardiac condition, cancer or aging.

Another aspect of the disclosure includes a method of treating a subject having a disease or condition related to aging. Exemplary diseases and conditions related to ageing include, without limitation, sarcopenia (age-related muscle loss), frailty, and androgen deficiency.

Another aspect of the disclosure includes a method of treating a subject having a disease or condition related to disuse atrophy/trauma. Exemplary diseases and conditions related to disuse atrophy/trauma include, without limitation, muscle weakness related to time spent in an intensive care unit (ICU), hip/joint replacement, hip fracture, stroke, bed rest, SCI, rotator cuff injury, knee replacement, bone fracture, and burns.

Another aspect of the disclosure includes a method of treating a subject having a neurodegenerative disease or condition. Exemplary neurodegenerative diseases or conditions include, without limitation, spinal muscular atrophy and amyotrophic lateral sclerosis (ALS).

Another aspect of the disclosure includes a method of treating a subject having a disease or condition related to Cachexia. Exemplary diseases and conditions related to cachexia include, without limitation, cancer, chronic heart failure, acquired immune deficiency syndrome (AIDS), chronic obstructive pulmonary disease (COPD), and chronic kidney disease (CKD).

Another aspect of the disclosure includes a method of treating a subject having a disease or condition related to rare diseases. Exemplary rare diseases and conditions include, without limitation, osteogenesis imperfecta, sporadic Inclusion body myositis, and acute lymphoblastic leukemia.

Another aspect of the disclosure includes a method of treating a subject having a disease or condition related to a metabolic disorder and/or body composition. In some embodiments, the disease or condition is obesity (e.g., severe obesity), Prader-Willi, type II diabetes, or anorexia. However, additional diseases or conditions related to metabolic disorders and/or body composition would be apparent to the skilled artisan and are within the scope of this disclosure.

Another aspect of the disclosure includes a method of treating a subject having a disease or condition related to congenital myopathies. Exemplary congenital myopathies include, without limitation, X-linked myotubular myopathy, autosomal dominant centronuclear myopathy, autosomal recessive centronuclear myopathy, nemaline myopathy, and congenital fiber-type disproportion myopathy.

Another aspect of the disclosure includes a method of treating a subject having a disease or condition related to muscular dystrophies. Exemplary muscular dystrophies include, without limitation, Duchenne's, Becker's, facioscapulohumeral (FSH), and Limb-Girdle muscular dystrophies.

Another aspect of the disclosure includes a method of treating a subject having a urogynecological related disease or condition, glottic disorders (stenosis), extraocular myopathy, carpel tunnel, Guillain-Barré, or osteosarcoma.

To practice the method disclosed herein, an effective amount of the pharmaceutical composition described above can be administered to a subject (e.g., a human) in need of the treatment via a suitable route, such as intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes. Commercially available nebulizers for liquid formulations, including jet nebulizers and ultrasonic nebulizers are useful for administration. Liquid formulations can be directly nebulized and lyophilized powder can be nebulized after reconstitution. Alternatively, anti-pro/latent-Myostatin antibodies can be aerosolized using a fluorocarbon formulation and a metered dose inhaler, or inhaled as a lyophilized and milled powder.

The subject to be treated by the methods described herein can be a mammal, more preferably a human. Mammals include, but are not limited to, farm animals, sport animals, pets, primates, horses, dogs, cats, mice and rats. A human subject who needs the treatment may be a human patient having, at risk for, or suspected of having a disease/disorder associated with myopathy, such as those noted above. A subject having a pro/latent-Myostatin-associated disease or disorder can be identified by routine medical examination, e.g., laboratory tests, organ functional tests, CT scans, or ultrasounds. A subject suspected of having any of such disease/disorder might show one or more symptoms of the disease/disorder. A subject at risk for the disease/disorder can be a subject having one or more of the risk factors for that disease/disorder.

"An effective amount" as used herein refers to the amount of each active agent required to confer therapeutic effect on the subject, either alone or in combination with one or more other active agents. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons. In some embodiments, an effective amount refers to the amount of an antibody, or antigen-binding portion thereof, which is sufficient to reduce or ameliorate the severity and/or duration of a disorder or one or more symptoms thereof, prevent the advancement of a disorder, cause regression of a disorder, prevent the recurrence, development, onset or progression of one or more symptoms associated with a disorder, detect a disorder, or enhance or improve the prophylactic or therapeutic effect(s) of another therapy (e.g., prophylactic or therapeutic agent).

In some embodiments, in the context of administration of a pro/latent-Myostatin antibody to a subject, an effective amount is an amount effective to increase mass of a target muscle in the subject compared with a control muscle mass. In some embodiments, the increase in muscle mass is an increase of at least 1.1-fold, at least 1.2-fold, at least 1.3-fold, at least 1.4-fold, at least 1.5-fold, at least 1.6-fold, at least 1.7-fold, at least 1.8-fold, at least 1.9-fold, at least 2-fold, at least 4-fold, at least 5-fold or more compared with a control muscle mass. In some embodiments, the increase in muscle mass is an increase in a range of 1-fold to 5-fold, 2-fold to 10-fold, 1-fold to 1.5-fold, 1-fold to 2-fold, etc. compared with a control muscle mass.

As used herein, the term "control muscle mass" refers to a reference standard useful for evaluating effects of a condition (e.g., treatment with a pro/latent-Myostatin antibody) on the mass of a target muscle in a subject. In some embodiments, a control muscle mass is a predetermined value. In some embodiments, a control muscle mass is experimentally determined. In some embodiments, a control muscle mass is the mass of a target muscle in a subject who has not been administered the pro/latent-Myostatin antibody. In some embodiments, a control muscle mass is the mass (e.g., the average mass) of a target muscle in a population of subjects who have not been administered the pro/latent-Myostatin antibody. In some embodiments, a control muscle mass is the mass of a target muscle in a subject prior to (e.g., immediately prior to) being administered the pro/latent-Myostatin antibody. In some embodiments, a control muscle mass is the mass of a target muscle in a subject who has been administered, in place of the pro/latent-Myostatin antibody, a normal antibody (e.g., of the same isotype as the pro/latent-Myostatin antibody) that has been obtained from an animal that has not been exposed to the antigen to which the pro/latent-Myostatin antibody is directed. In some embodiments, a control muscle mass is the mass of a target muscle in a subject who has been administered, in place of the pro/latent-Myostatin antibody, a vehicle, e.g., saline.

In some embodiments, in the context of administration of a pro/latent-Myostatin antibody to a subject, an effective amount is an amount effective to increase force generation capacity (e.g., a maximal force generation as determined in vitro with a muscle lever system adapted with a horizontal perfusion bath) of a target muscle in the subject compared with a control force generation capacity. In some embodiments, the increase in force generation capacity is an increase of at least 1.1-fold, at least 1.2-fold, at least 1.3-fold, at least 1.4-fold, at least 1.5-fold, at least 1.6-fold, at least 1.7-fold, at least 1.8-fold, at least 1.9-fold, at least 2-fold, at least 4-fold, at least 5-fold or more compared with a control force generation capacity. In some embodiments, the increase in force generation capacity is an increase in a range of 1-fold to 5-fold, 2-fold to 10-fold, 1-fold to 1.5-fold, 1-fold to 2-fold, etc. compared with a control force generation capacity.

As used herein, the term "control force generation capacity" refers to a reference standard useful for evaluating effects of a condition (e.g., treatment with a pro/latent-Myostatin antibody) on the force generation capacity of a muscle in a subject. In some embodiments, a control force generation capacity is a predetermined value. In some embodiments, a control force generation capacity is experimentally determined. In some embodiments, a control force generation capacity is the force generation capacity of a target muscle in a subject who has not been administered the pro/latent-Myostatin antibody. In some embodiments, a control force generation capacity is the force generation capacity (e.g., the average force generation capacity) of a target muscle in a population of subjects who have not been administered the pro/latent-Myostatin antibody. In some embodiments, a control force generation capacity is the force generation capacity of a target muscle in a subject prior to (e.g., immediately prior to) being administered the pro/latent-Myostatin antibody. In some embodiments, a control force generation capacity is the force generation capacity of a target muscle in a subject who has been administered, in place of the pro/latent-Myostatin antibody, a normal antibody (e.g., of the same isotype as the pro/latent-Myostatin antibody) that has been obtained from an animal that has not been exposed to the antigen to which the pro/latent-Myostatin antibody is directed. In some embodiments, a control force generation capacity is the force generation capacity of a target muscle in a subject who has been administered, in place of the pro/latent-Myostatin antibody, a vehicle, e.g., saline.

Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of a disease/disorder associated with myopathy. Alternatively, sustained continuous release formulations of an anti-pro/latent-Myostatin may be appropriate. Various formulations and devices for achieving sustained release would be apparent to the skilled artisan and are within the scope of this disclosure.

In one example, dosages for an anti-pro/latent-Myostatin antibody as described herein may be determined empirically in individuals who have been given one or more administration(s) of the antibody. Individuals are given incremental dosages of the antagonist. To assess efficacy of the antagonist, an indicator of the disease/disorder can be followed.

Generally, for administration of any of the antibodies described herein, an initial candidate dosage can be about 2 mg/kg. For the purpose of the present disclosure, a typical daily dosage might range from about any of 0.1 µg/kg to 3 µg/kg to 30 µg/kg to 300 µg/kg to 3 mg/kg, to 30 mg/kg to 100 mg/kg or more, depending on the factors mentioned above. For repeated administrations over several days or longer, depending on the condition, the treatment is sustained until a desired suppression of symptoms occurs or until sufficient therapeutic levels are achieved to alleviate a disease or disorder associated with pro/latent-Myostatin, or a symptom thereof. An exemplary dosing regimen comprises administering an initial dose of about 2 mg/kg, followed by a weekly maintenance dose of about 1 mg/kg of the antibody, or followed by a maintenance dose of about 1 mg/kg every other week. However, other dosage regimens may be useful, depending on the pattern of pharmacokinetic decay that the practitioner wishes to achieve. For example, dosing from one-four times a week is contemplated. In some embodiments, dosing ranging from about 3 µg/mg to about 2 mg/kg (such as about 3 µg/mg, about 10 µg/mg, about 30 µg/mg, about 100 µg/mg, about 300 µg/mg, about 1 mg/kg, and about 2 mg/kg) may be used. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, every 4 months, every 5 months, every 6 months, every 8 months, every 10 months, every year, or longer. The progress of this therapy is easily monitored by conventional techniques and assays. The dosing regimen (including the antibody used) can vary over time.

In some embodiments, for an adult patient of normal weight, doses ranging from about 0.3 to 5.00 mg/kg may be administered. The particular dosage regimen, e.g., dose, timing and repetition, will depend on the particular individual and that individual's medical history, as well as the properties of the individual agents (such as the half-life of the agent, and other relevant considerations).

For the purpose of the present disclosure, the appropriate dosage of an anti-pro/latent-Myostatin antibody will depend on the specific antibody (or compositions thereof) employed, the type and severity of the disease/disorder, whether the antibody is administered for preventive or therapeutic purposes, previous therapy, the patient's clinical history and response to the antagonist, and the discretion of the attending physician. In some embodiments, a clinician will administer an anti-pro/latent-Myostatin antibody, until a dosage is reached that achieves the desired result. Administration of an anti-pro/latent-Myostatin antibody can be continuous or intermittent, depending, for example, upon the recipient's physiological condition, whether the purpose of the administration is therapeutic or prophylactic, and other factors known to skilled practitioners. The administration of an anti-pro/latent-Myostatin antibody may be essentially continuous over a preselected period of time or may be in a series of spaced dose, e.g., either before, during, or after developing a disease or disorder associated with pro/latent-Myostatin.

As used herein, the term "treating" refers to the application or administration of a composition including one or more active agents to a subject, who has a disease/disorder associated with myopathy, a symptom of the disease/disorder, or a predisposition toward the disease/disorder, with the purpose to cure, heal, alleviate, relieve, alter, remedy, ameliorate, improve, or affect the disorder, the symptom of the disease, or the predisposition toward the disease/disorder.

Alleviating a disease/disorder associated with pro/latent-Myostatin includes delaying the development or progression of the disease, or reducing disease severity. Alleviating the disease does not necessarily require curative results. As used therein, "delaying" the development of a disease/disorder associated with pro/latent-Myostatin means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques. However, development also refers to progression that may be undetectable. For purpose of this disclosure, development or progression refers to the biological course of the symptoms. "Development" includes occurrence, recurrence, and onset. As used herein "onset" or "occurrence" of a disease/disorder associated with myopathy includes initial onset and/or recurrence.

In some embodiments, the anti-pro/latent-Myostatin antibody described herein is administered to a subject in need of the treatment at an amount sufficient to inhibit the proteolytic activation of pro/latent-Myostatin to active Myostatin by at least 20% (e.g., 30%, 40%, 50%, 60%, 70%, 80%, 90% or greater) in vivo. In other embodiments, an antibody is administered in an amount effective in reducing the pro/latent-Myostatin or latent Myostatin level by at least 20% (e.g., 30%, 40%, 50%, 60%, 70%, 80%, 90% or greater).

Conventional methods, known to those of ordinary skill in the art of medicine, can be used to administer the pharmaceutical composition to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods.

Injectable compositions may contain various carriers such as vegetable oils, dimethyllactamide, dimethylformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the antibody and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution.

In one embodiment, an anti-pro/latent-Myostatin antibody is administered via site-specific or targeted local delivery techniques. Examples of site-specific or targeted local delivery techniques include various implantable depot sources of the anti-pro/latent-Myostatin antibody or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO00/53211 and U.S. Pat. No. 5,981,568.

Targeted delivery of therapeutic compositions containing a polynucleotide, or expression vector can also be used. Receptor-mediated DNA delivery techniques are described in, for example, Findeis et al., Trends Biotechnol. (1993) 11:202; Chiou et al., Gene Therapeutics: Methods And Applications Of Direct Gene Transfer (J. A. Wolff, ed.) (1994); Wu et al., J. Biol. Chem. (1988) 263:621; Wu et al., J. Biol. Chem. (1994) 269:542; Zenke et al., Proc. Natl. Acad. Sci. USA (1990) 87:3655; Wu et al., J. Biol. Chem. (1991) 266:338.

Therapeutic compositions containing a polynucleotide (e.g., those encoding the anti-pro/latent-Myostatin antibodies described herein) are administered in a range of about 100 ng to about 200 mg of DNA for local administration in a gene therapy protocol. In some embodiments, concentration ranges of about 500 ng to about 50 mg, about 1 sg to about 2 mg, about 5 μg to about 500 μg, and about 20 μg to about 100 μg of DNA or more can also be used during a gene therapy protocol.

The therapeutic polynucleotides and polypeptides described herein can be delivered using gene delivery vehicles. The gene delivery vehicle can be of viral or non-viral origin (see generally, Jolly, Cancer Gene Therapy (1994) 1:51; Kimura, Human Gene Therapy (1994) 5:845; Connelly, Human Gene Therapy (1995) 1:185; and Kaplitt, Nature Genetics (1994) 6:148). Expression of such coding sequences can be induced using endogenous mammalian or heterologous promoters and/or enhancers. Expression of the coding sequence can be either constitutive or regulated.

Suitable viral-based vectors for delivery of a desired polynucleotide (e.g., encoding an antibody disclosed herein) and expression in a desired cell are within the scope of this disclosure. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther. (1992) 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther. (1992) 3:147); ligand-linked DNA (see, e.g., Wu, J. Biol. Chem. (1989) 264: 16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP Patent No. 0524968. Additional approaches are described in Philip, Mol. Cell. Biol. (1994) 14:2411, and in Woffendin, Proc. Natl. Acad. Sci. (1994) 91:1581.

The particular dosage regimen, e.g., dose, timing and repetition, used in the method described herein will depend on the particular subject and that subject's medical history.

In some embodiments, more than one anti-pro/latent-Myostatin antibodies, or a combination of an anti-pro/latent-Myostatin antibody and another suitable therapeutic agent, may be administered to a subject in need of the treatment. The antagonist can be the same type or different from each other. The anti-pro/latent-Myostatin antibody can also be used in conjunction with other agents that serve to enhance and/or complement the effectiveness of the agents.

Treatment efficacy for a disease/disorder associated with myopathy can be assessed using any suitable methods. For example, treatment efficacy for a disease/disorder associated with myopathy can be assessed by evaluating muscle weakness (e.g., assessing the pattern and severity of weakness), electromyography, evaluating blood chemistries (e.g., assessing electrolytes, assessing endocrine causes, measuring creatinine kinase level, determining erythrocyte sedimentation rate and performing antinuclear antibody assays), and evaluating biopsies (e.g., by histologic, histochemical, electron microscopic, biochemical, and genetic analysis).

Kits for Use in Alleviating Diseases/Disorders Associated with Myopathy

The present disclosure also provides kits for use in alleviating diseases/disorders associated with myopathy. Such kits can include one or more containers comprising an anti-pro/latent-Myostatin antibody, e.g., any of those described herein.

In some embodiments, the kit can comprise instructions for use in accordance with any of the methods described herein. The included instructions can comprise a description of administration of the anti-pro/latent-Myostatin antibody to treat, delay the onset, or alleviate a target disease as those described herein. The kit may further comprise a description of selecting an individual suitable for treatment based on identifying whether that individual has the target disease. In still other embodiments, the instructions comprise a description of administering an antibody to an individual at risk of the target disease.

The instructions relating to the use of an anti-pro/latent-Myostatin antibody generally include information as to dosage, dosing schedule, and route of administration for the intended treatment. The containers may be unit doses, bulk packages (e.g., multi-dose packages) or sub-unit doses. Instructions supplied in the kits of the disclosure are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, delaying the onset and/or alleviating a disease or disorder associated with myopathy. Instructions may be provided for practicing any of the methods described herein.

The kits of this disclosure are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an anti-pro/latent-Myostatin antibody as those described herein.

Kits may optionally provide additional components such as buffers and interpretive information. Normally, the kit comprises a container and a label or package insert(s) on or associated with the container. In some embodiments, the disclosure provides articles of manufacture comprising contents of the kits described above.

Assays for Detecting Pro/Latent-Myostatin

In some embodiments, methods and compositions provided herein relate to a method for detecting pro/latent-Myostatin in a sample obtained from a subject. As used herein, a "subject" refers to an individual organism, for example, an individual mammal. In some embodiments, the subject is a human. In some embodiments, the subject is a non-human mammal. In some embodiments, the subject is a non-human primate. In some embodiments, the subject is a rodent. In some embodiments, the subject is a sheep, a goat, a cattle, a cat, or a dog. In some embodiments, the subject is a vertebrate, an amphibian, a reptile, a fish, an insect, a fly, or a nematode. In some embodiments, the subject is a research animal. In some embodiments, the subject is genetically engineered, e.g., a genetically engineered non-human subject. The subject may be of either sex and at any stage of development. In some embodiments, the subject is a patient or a healthy volunteer.

In some embodiments, a method for detecting a pro/latent-Myostatin in a sample obtained from a subject involves (a) contacting the sample with the anti-pro/latent-Myostatin antibody under conditions suitable for binding of the antibody to the antigen, if the antigen is present in the sample, thereby forming binding complexes; and (b) determining the level of the antibody or antigen binding fragment bound to the antigen (e.g., determining the level of the binding complexes).

As used herein a binding complex refers to a biomolecular complex of antibody (including antigen binding fragments) bound to antigen (e.g., pro/latent-Myostatin protein). Binding complexes may comprise antibodies with a single specificity or two or more antibodies or antigen binding fragments with different specificities. In one embodiment, a binding complex comprises two or more antibodies recognizing different antigenic sites on the same antigen. In some instances, an antibody may be bound to an antigen, having bound to it other biomolecules such as RNA, DNA, polysaccharides or proteins. In one embodiment, a binding complex comprises two or more antibodies recognizing different antigens. In some embodiments, an antibody in a binding complex (e.g., an immobilized antibody bound to antigen), may itself by bound, as an antigen, to an antibody (e.g., a detectably labeled antibody). Thus, binding complexes may, in some instances, comprise multiple antigens and multiple antibodies or antigen binding fragments.

Antigens present in binding complexes may or may not be in their native in situ conformation. In some embodiments, a binding complex is formed between an antibody and a purified protein antigen, or isolated proteins comprising antigen, in which the antigen is not in its native in situ conformation. In some embodiments, a binding complex is formed between an antibody and a purified protein antigen, in which the antigen is not in its native in situ conformation and is immobilized on solid support (e.g., a PVDF membrane). In some embodiments, a binding complex is formed with an antibody and, for example, a cell surface protein that is present in situ in a native confirmation (e.g., on the surface of a cell).

Antibodies in binding complexes may or may not be detectably labeled. In some embodiments, binding complexes comprise detectably labeled antibodies and non-labeled antibodies. In some embodiments, binding complexes comprise detectably labeled antigen. In some embodiments, antibodies, in binding complexes, are immobilized to one or more solid supports. In some embodiments, antigens, in binding complexes, are immobilized to one or more solid supports. Exemplary solid supports are disclosed herein and will be apparent to one of ordinary skill in the art. The foregoing examples of binding complexes are not intended to be limiting. Other examples of binding complexes will be apparent to one or ordinary skill in the art.

In any of the detection, diagnosis, and monitoring methods, the antibody, (including antigen binding fragments) or antigen may be conjugated to a solid support surface, either directly or indirectly. Methods for conjugation to solid supports are standard and can be accomplished via covalent and non-covalent interactions. Non-limiting examples of conjugation methods include: adsorption, cross-linking, protein A/G—antibody interactions, and streptavidin-biotin interactions. Other methods of conjugation will be readily apparent to one of ordinary skill in the art.

In some aspects, detection, diagnosis, and monitoring methods include comparing the level of the antibody (including antigen binding fragments) bound to the antigen (e.g., pro/latent-Myostatin) to one or more reference standards. The reference standard may be, for example, the level of a corresponding pro/latent-Myostatin in a subject that does or does not have a pro/latent-Myostatin. In one embodiment, the reference standard is the level of pro/latent-Myostatin detected in a sample that does not contain pro/latent-Myostatin (e.g., a background level). Alternatively, a background level can be determined from a sample that contains a particular pro/latent-Myostatin, by contacting the sample with non-specific antibodies (e.g., antibodies obtained from non-immune serum). Then again, the reference standard may be the level of pro/latent-Myostatin detected in a sample that does contain pro/latent-Myostatin (e.g., a positive control). In some cases, the reference standard may be a series of levels associated with varying concentrations of pro/latent-Myostatin in a sample and useful for quantifying the concentration of pro/latent-Myostatin in the test sample. The foregoing examples of reference standards are not limiting and other suitable reference standard will be readily apparent to one of ordinary skill in the art. In some embodiments, the level of the antibody bound to pro/latent-Myostatin is compared to the level of mature Myostatin. In some instances the level of pro/latent-Myostatin is compared to mature Myostatin to determine the ratio of inactive to active Myostatin in the sample.

The level of pro/latent-Myostatin may be measured, as provided herein, from a biological sample. A biological sample refers to any biological material which may be obtained from a subject or cell. For example, a biological sample may be whole blood, plasma, serum, saliva, cerebrospinal fluid, urine, cells (or cell lysate) or tissue (e.g., normal tissue or tumor tissue). In some embodiments, a biological sample is a fluid sample. In some embodiments, a biological sample is a solid tissue sample. For example, a tissue sample may include, without limitation skeletal muscle, cardiac muscle, adipose tissue as well as tissue from other organs. In some embodiments, a biological sample is a biopsy sample. In some embodiments, a solid tissue sample may be made into a fluid sample using routine methods in the art.

A biological sample may also include one or more cells of a cell line. In some embodiments, a cell line includes human cells, primate cells (e.g., vero cells), rat cells (e.g., GH3 cells, OC23 cells) or mouse cells (e.g., MC3T3 cells). There are a variety of human cell lines, including, without limitation, human embryonic kidney (HEK) cells, HeLa cells, cancer cells from the National Cancer Institute's 60 cancer cell lines (NCI60), DU145 (prostate cancer) cells, Lncap (prostate cancer) cells, MCF-7 (breast cancer) cells, MDA-MB-438 (breast cancer) cells, PC3 (prostate cancer) cells, T47D (breast cancer) cells, THP-1 (acute myeloid leukemia) cells, U87 (glioblastoma) cells, SHSY5Y human neuroblastoma cells (cloned from a myeloma) and Saos-2 (bone cancer) cells.

A further embodiment relates to a method for monitoring a disease, a condition, or any treatment thereof (e.g., myopathy or myopathy treatment) in a subject having, or at risk of having, the disease or condition comprising: (a) obtaining a biological sample from the subject, (b) determining the level of a pro/latent-Myostatin in the biological sample using an antibody that detects pro/latent-Myostatin, and (c) repeating steps (a) and (b) on one or more occasions. Myostatin has been used as a biomarker for muscle atrophy, however, the currently available commercial methods and reagents (e.g., antibodies used in ELISAs and Western Blots) are either not specific for Myostatin, detect only mature myostatin or do not detect myostatin at all. Thus, provided herein are methods and reagents (e.g., antibodies) for detecting pro/latent-Myostatin in the context of diseases and/or conditions (e.g., muscle atrophy) for diagnostic purposes. As one example, the level of pro/latent-Myostatin may be measured in a subject, or biological sample therefrom, to detect or monitor the progression of a disease or condition. As another example, the level of pro/latent-Myostatin may be measured in a subject, or biological sample therefrom, to monitor the response to a treatment for a disease or condition. It should be appreciated that the level of pro/latent-Myostatin may be monitored over any suitable period of time, which may differ depending on the disease or condition, the subject has or any treatment regimen that the subject may be subject to.

Another embodiment relates to a diagnostic composition comprising any one of the above described antibodies, antigen binding fragments, polynucleotides, vectors or cells and optionally suitable means for detection. The antibodies are, for example, suited for use in immunoassays in which they can be utilized in liquid phase or bound to a solid phase carrier. Examples of immunoassays which can utilize the antibody are competitive and non-competitive immunoassays in either a direct or indirect format. Examples of such immunoassays are the Enzyme Linked Immunoassay (ELISA), radioimmunoassay (RIA), the sandwich (immunometric assay), flow cytometry, the western blot assay, immunoprecipitation assays, immunohistochemistry, immuno-microscopy, lateral flow immuno-chromatographic assays, and proteomics arrays. The antigens and antibodies can be bound to many different solid supports (e.g., carriers, membrane, columns, proteomics array, etc.). Examples of solid support materials include glass, polystyrene, polyvinyl chloride, polyvinylidene difluoride, polypropylene, polyethylene, polycarbonate, dextran, nylon, amyloses, natural and modified celluloses, such as nitrocellulose, polyacrylamides, agaroses, and magnetite. The nature of the support can be either fixed or suspended in a solution (e.g., beads).

By a further embodiment, antibodies (including antigen binding fragments) provided herein may also be used in a method for evaluating pro/latent-Myostatin expression in a subject by obtaining a biological sample from the subject which may be a tissue sample, a blood sample or any other appropriate body fluid sample. The procedure may comprise contacting the blood sample (whole blood, serum, plasma), a tissue sample, or protein sample isolated therefrom, with an antibody, under conditions enabling the formation of binding complexes between antibody and antigen. The level of such binding complexes may then be determined by any suitable method. In some embodiments, the biological sample is contacted with the antibody under conditions suitable for binding of the antibody to a pro/latent-Myostatin protein, if the antigen is present in the sample, and formation of binding complexes consisting of antibody, bound to the antigen. This contacting step is typically performed in a reaction chamber, such as a tube, plate well, membrane bath, cell culture dish, microscope slide, and the like. In some embodiments, an antibody is immobilized on a solid support. In some embodiments, the antigen is immobilized on a solid support. In some embodiments, the solid support is the surface of the reaction chamber. In some embodiments, the solid support is of a polymeric membrane (e.g., nitrocellulose strip, Polyvinylidene Difluoride (PVDF) membrane, etc.). Other appropriate solid supports may be used.

In some embodiments, an antibody is immobilized on the solid support prior to contacting with the antigen. In other embodiments, immobilization of the antibody is performed after formation of binding complexes. In still other embodiments, antigen is immobilized on a solid support prior to formation of binding complexes. A detection reagent is added to the reaction chamber to detect immobilized binding complexes. In some embodiments, the detection reagent comprises a detectably labeled secondary antibody directed against the antigen. In some embodiments, the primary antibody is itself detectable labeled, and is thereby the detection reagent.

In one aspect, detection methods comprise the steps of immobilizing antibodies to a solid support; applying a sample (e.g., a biological sample or isolated protein sample) to the solid support under conditions that permit binding of antigen to the antibodies, if present in the sample; removing the excess sample from the solid support; applying detectably labeled antibodies under conditions that permit binding of the detectably labeled antibodies to the antigen-bound immobilized antibodies; washing the solid support and assaying for the presence of label on the solid support.

In some embodiments, the antigen is immobilized on the solid support, such as a PVDF membrane, prior to contacting with the antibody in a reaction chamber (e.g., a membrane bath). A detection reagent is added to the reaction chamber to detect immobilized binding complexes. In some embodiments, the detection reagent comprises a detectably labeled secondary antibody directed against the antigen. In some embodiments, the detection reagent comprises a detectably labeled secondary antibody directed against the primary antibody. As disclosed herein, the detectable label may be, for example, a radioisotope, a fluorophore, a luminescent molecule, an enzyme, a biotin-moiety, an epitope tag, or a dye molecule. In some embodiments, the primary antibody is itself detectable labeled, and is thereby the detection reagent. Suitable detectable labels are described herein, and will be readily apparent to one of ordinary skill in the art.

Accordingly, diagnostic kits, suitable for home or clinical use (point of care service), are provided that comprise (a) detectably labeled and/or non-labeled antibodies, as antigen binding reagents (e.g., pro/latent-Myostatin binding reagents); (b) a detection reagent; and, optionally, (c) complete instructions for using the reagents to detect antigens in a sample. In some embodiments, the diagnostic kit includes the antibody, and/or pro/latent-Myostatin immobilized on a solid support. Any of the solid supports described herein are suitable for incorporation in the diagnostic kits. In a preferred embodiment, the solid support is the surface of a reaction chamber of a plate well. Typically, the plate well is in a multi-well plate having a number of wells selected from: 6, 12, 24, 96, 384, and 1536, but it is not so limited. In other embodiments, the diagnostic kits provide a detectably labeled antibody. Diagnostic kits are not limited to these embodiments and other variations in kit composition will be readily apparent to one of ordinary skill in the art.

The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1: Generation and Selection of Antibodies

Antibody Summary

Ab2 is a fully human anti-pro/latent-Myostatin monoclonal antibody of the IgG4/lambda isotype that binds to human pro- and latent-myostatin with high affinity ($K_d$=3420 μM by ForteBio BLI). The antibody is capable of inhibiting the proteolytic activation of pro/latent-Myostatin with IC50 values in the 0.5 micromolar range (which is at or near the limit of the assay). The theoretical molecular weight of the polypeptide is 144,736 Da and its theoretical pI is 6.7. Affinity optimization using antibody display was performed to identify higher affinity variants Ab4 and Ab6. The affinity optimized variants are similarly constructed on the human IgG4/lambda isotype frameworks.

TABLE 2

| Biochemical properties of candidate anti-Pro/latent-Myostatin antibodies | | |
| --- | --- | --- |
| Antibody | Affinity (Octet) pM | Theoretical MW (Da) *aglycosylated | Calculated pI |
| Ab1 | 4760 | 144809.8 | 6.9 |
| Ab2 | 3420 | 144735.6 | 6.7 |
| Ab4 | 472 | 144661.7 | 6.7 |
| Ab6 | 331 | 144629.5 | 6.7 |

Platform and Identification of Parental Antibody

The parental Ab1 antibody was identified via selection of a naïve phage display library using pro- and latent-myostatin as the primary antigens for selection. Phage selection and initial screening were performed using a library displaying conventional scFv in a format similar to that described by McCafferty et al. (McCafferty et al., 1990). Each round of selection consisted of pre-clearing (for removal of nonspecific phage antibodies), incubation with antigen, washing, elution and amplification. Selections were performed via multiple rounds using both solid phase (biotinylated anti-gens coated on immunotubes) and solution phase (bioti-nylated antigens, captured using streptavidin coated beads) panning strategies.

In total, 10,000 individual scFv clones were screened for binding to pro- or latent-myostatin through two separate campaigns. The first program utilized pro/latent-Myostatin as an antigen, while a second campaign used latent Myostatin as an antigen. DNA for scFv clones of interest were sequenced and 216 unique clones were identified. Positive binding scFv clones were counter-screened for binding to proGDF11 as well as to a panel of unrelated proteins to confirm specificity for pro/latent-Myostatin. From the panel of unique scFv clones, 101 (of 134 GDF8 specific clones) were converted to full length IgG (IgG1 isotype) for addi-tional characterization.

Full-length IgG antibodies were further characterized by ELISA for binding to the human and murine pro- and latent-forms of myostatin and GDF11. Antibodies were also screened for binding to the Myostatin prodomain, proTGFβ (human and murine), the mature growth factor of Myostatin, the GDF11 mature growth factor, the Activin A growth factor, and proActivin A. Lead antibodies were selected based on their cross-reactivity with pro- and latent human and murine Myostatin, with no interactions with GDF11, Activin, or TGFβ proteins.

Two forms of epitope binning were employed. First, chimeric constructs which swapped portions of the prodo-mains of Myostatin and GDF11 were designed and pro-duced. These chimeric proteins were assayed for interaction with screening antibodies by ELISA. Epitope binning was carried out using a ForteBio BLI instrument, in which the biotinylated pro/latent-Myostatin antibody was immobilized on a streptavidin coated biosensor chip, and cross-blocking of antibodies was evaluated by sensor response. These epitope binning experiments, along with data from the ELISA binding experiments, allowed for the segregation of our functionally active lead antibodies (see below) into three distinct epitope groups (see Table 3).

Conditioned medium from cells overexpressing either mTll2 (the tolloid protease require for Myostatin activation) or Furin (the proprotein convertase which cleaves the mature growth factor from the prodomain) were produced. Follow-ing pre-incubation with the test antibody, pro/latent-Myo-statin or latent Myostatin was incubated with either a mixture of mTll2 and Furin conditioned media (proMyosta-tin) or mTll2 conditioned media (latent Myostatin). Follow-ing an overnight proteolysis reaction, the release of mature growth factor was measured using a CAGA-based reporter assay in 293T cells. Antibodies were further validated by dose response, in the same assay, the results of which are shown in Table 3.

Five parental antibodies (Table 3) demonstrated consis-tently potent selectivity and activity in all of the above assays and were further chosen for further characterization in vivo (discussed in Example 2). For consistency, the binding and activity of these antibodies towards pro/latent-Myostatin is summarized, as Ab8 does not recognize latent myostatin.

Figures 3A, 3B:
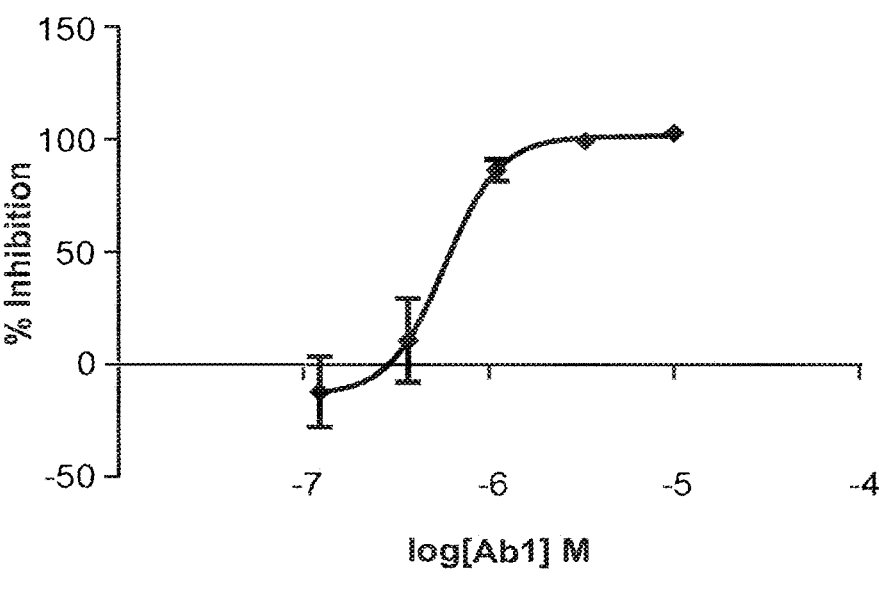
FIGS. 3A-3C show that Ab1 blocks cleavage of proMyostatin by members of the tolloid family of proteases. Latent Myostatin samples, preincubated with increasing amounts of Ab1, were analyzed in a myostatin activation assay. Following analysis of myostatin release by reporter assay (FIG. 3A), samples were then run under reducing conditions and probed by western blot with an antibody raised towards the prodomain of Myostatin (FIG. 3B). An ~18 kDa band (box), corresponding to the ARM portion of the prodomain generated after tolloid cleavage, decreased proportionally with increasing doses of Ab1. The latent and proMyostatin standards (45 ng loaded) show the migration of proMyostatin at ~50 kDa, and the prodomain at ~37 kDa.
Figure 3C:
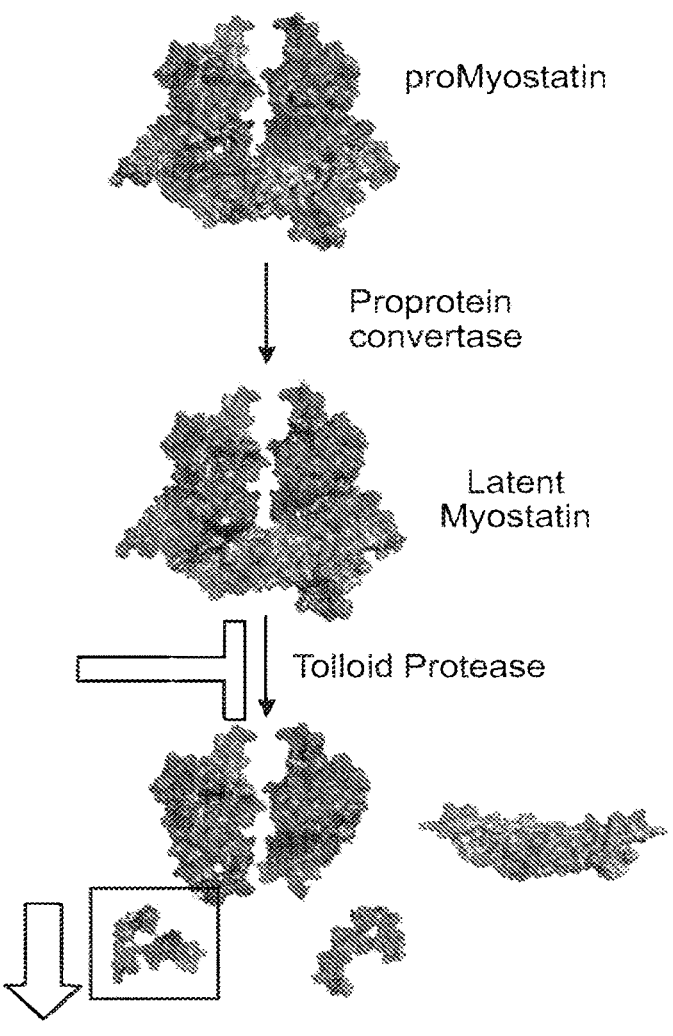

To determine the mechanism of action of antibody can-didates, samples were analyzed by western blotting using a polyclonal antibody raised against the prodomain of myo-statin, as shown in FIG. 3. This allowed for tracking of a fragment (boxed) of the myostatin prodomain which is generated after mTll2 cleavage. A dose-dependent decrease was seen in the generation of this fragment as the concen-tration of Ab1 is increased. This experiment indicates that the antibodies in epitope bin 1 act by blocking the cleavage of pro- and latent-myostatin by the tolloid family of pro-teases.

Based on the in vitro and in vivo activity of the active anti-pro/latent-Myostatin antibodies, Ab1 was selected as the lead for further optimization, including affinity matura-tion, germlining and manufacturability analysis.

Optimization of Ab1

The Ab1 antibody was selected for further optimization. The affinity for pro/latent-Myostatin was optimized using yeast display. Additionally, the sequence of Ab1 was germ-

TABLE 3

| | | | | | | |
|---|---|---|---|---|---|---|
| | | Human proGDF8 IC50$^2$ (μM) Reporter assay | Murine proGDF8 IC50$^2$ (μM) Reporter assay | % body weight increase in 6 weeks 25 mg/kg/week | % lean mass increase in 4 weeks 20 mg/kg/week | |
| Clone ID | proGDF8 Kd (μM) (octet) | | | | | Epitope bin |
| Ab1 | 11.5 | 0.996 | 1.46 | 14.58* | 14.1* | 1 |
| Ab7 | 28 | 0.983 | 1.68 | 12.42* | ND | 1 |
| Ab8 | 0.5 | 6.037 | 139$^1$ | 10.33* | 7.4 | 2 |
| Ab9 | 22 | 12.16 | 19.86 | 7.44 | ND | 3 |
| Ab10 | 0.3 | 0.772 | ND | ND | 14.3* | 1 |

Ranking of five anti-pro/latent-Myostatin IgG1 antibodies

*Statistical significance by one-way ANOVA with Dunnett.

Ab8 does not bind latent myostatin, only proMyostatin. Murine pro/latent-Myostatin preparations have ~40% latent material which reduces the apparent efficacy in functional assays.

ND: Not determined.

In order to evaluate the ability of antibodies to bind and inhibit the activation of pro/latent-Myostatin, a number of biochemical and cellular assays were established. Binding kinetics to pro- and latent-Myostatin was measured by ForteBio Octet, in which the biotinylated substrate protein was immobilized on streptavidin coated sensor chips. The equilibrium dissociation constants of candidates from screening are shown in Table 3.

To measure the ability of the IgGs to inhibit Myostatin signaling, a Myostatin activation assay was developed.

lined to reduce the potential immunogenicity liability of non-germline amino acid positions within the human vari-able regions frameworks.

Affinity Optimization of Ab1 by Yeast Display

Figure 23A:
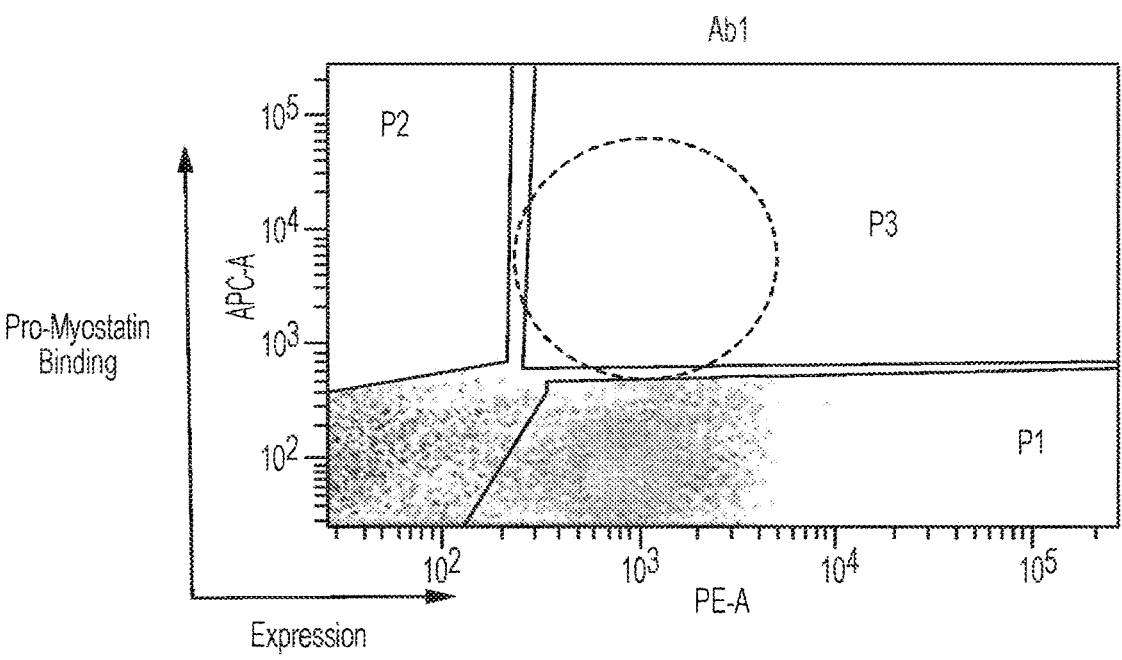
FIGS. 23A-23C show the optimization of Ab1. Optimized candidates which bind specifically to proMyostatin were chosen, resulting in dozens of clones with increased affinity. FACS was performed to show the increased binding of the yeast clones (FIG. 23B) compared to Ab1 (FIG. 23A).
Figure 23B:
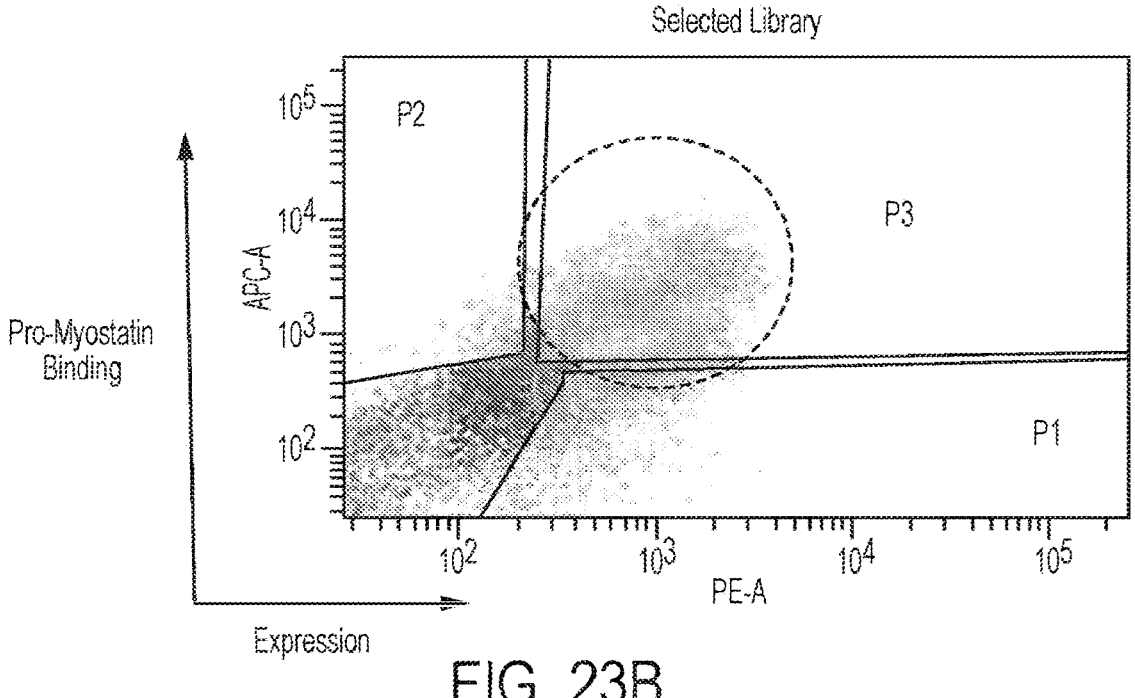
Figure 23C:
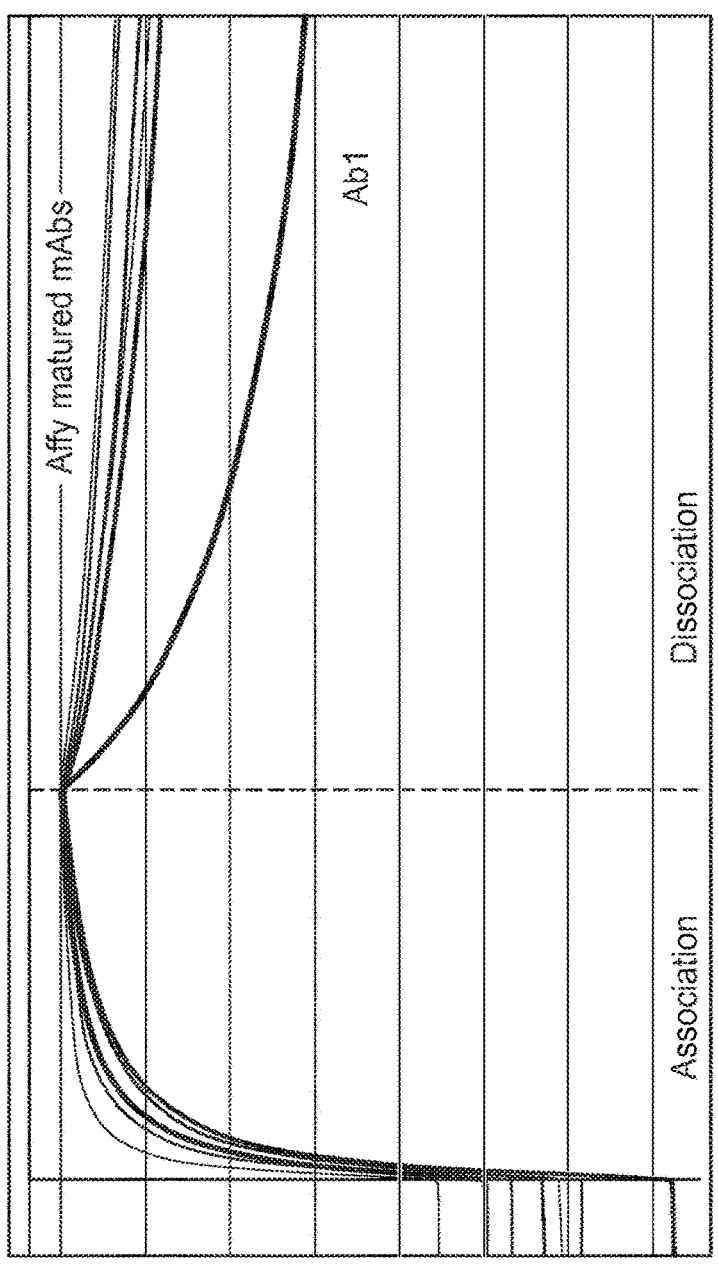

The Ab1 parental antibody was optimized for binding to pro/latent-Myostatin using an scFv display approach based in yeast. Briefly, three different scFv libraries were created to introduce point mutations to selected CDR positions based on the amino acid frequency observed in natural human antibody repertoires using antibody deep sequencing corresponding to the human frameworks utilized by Ab1. Each library contained scFv based on the Ab1 sequence with single point mutations introduced in each CDR such that each variant of the resulting heavy chain or light chain would have three total substitutions, one in each CDR. The three libraries were used for FACS-based sorting and selection to identify pools of clones with higher binding affinity for pro/latent-Myostatin (FIG. 23). Direct binding of yeast expressed scFv clones was used to select antibodies for conversion to full length IgG expressed in mammalian cell culture.

Many of the higher affinity scFv clones identified in the yeast campaign contained a substitution at position 28 of the heavy chain. For some clones, substitution of threonine to asparagine resulted in the incorporation of a non-canonical N-glycosylation motif within CDRH1. As N-glycosylation within the variable region of an antibody may be undesirable, any clone which contained a glycosylation motif was further substituted to contain alanine at this position.

The binding kinetics to pro- and latent-Myostatin were then assessed by octet for each of the affinity optimized constructs and compared to that of the parental Ab1 (discussed in Example 2). All of the clones showed significantly increased binding affinity for Myostatin, and two, Ab3 and Ab5, were selected based on the selective binding profile over GDF11.

Primary Sequence and Backbone of Anti-Pro/Latent-Myostatin Antibodies

The sequence alignment of the variable regions of parental Ab1 with its affinity optimized variants is shown below. Complementarity-determining regions (CDRs) are defined using the Kabat (underlined) and IMGT nomenclature (bold). Substitutions from parental Ab1 are shown in lower case text (below and FIG. 24A-24B).

Antibody Engineering and Rationale for Isotype Selection

In some embodiments, an antibody useful for myostatin blockade will lack effector function. Thus for the humanized construct, an IgG4-Fc region was selected. Antibodies of the IgG4 isotype poorly bind complement C1q and therefore do not significantly activate complement. These antibodies also bind weakly to Fcγ receptors, leading to inefficient or absent antibody-dependent cell-mediated cytotoxicity (ADCC).

To avoid potential complication due to Fab-arm exchange, which is known to occur with native IgG4 mAbs, Ab1 and its variants were engineered with the stabilizing 'Adair' mutation (Angal, 1993), where serine 228 (EU numbering; residue 241 Kabat numbering) is converted to proline resulting in an IgG1-like (CPPCP (SEQ ID NO: 58)) hinge sequence. This engineered Fc-sequence is used in the production of the approved antibodies Keytruda, Mylotarg and Tysabri, as well as in a number of current late-stage clinical candidate mAbs.

Germlining and Immunogenicity Risk Assessment

The Ab1 parental antibody and its variants are fully human IgG4 (S228P), lambda antibodies derived from phage display. The Fc portion of the antibody contains a single stabilizing mutation to prevent Fab arm exchange (described above). The IgG4 Fc is not expected to have measurable binding to Fc gamma receptors (see Example 2).

Figure 22:
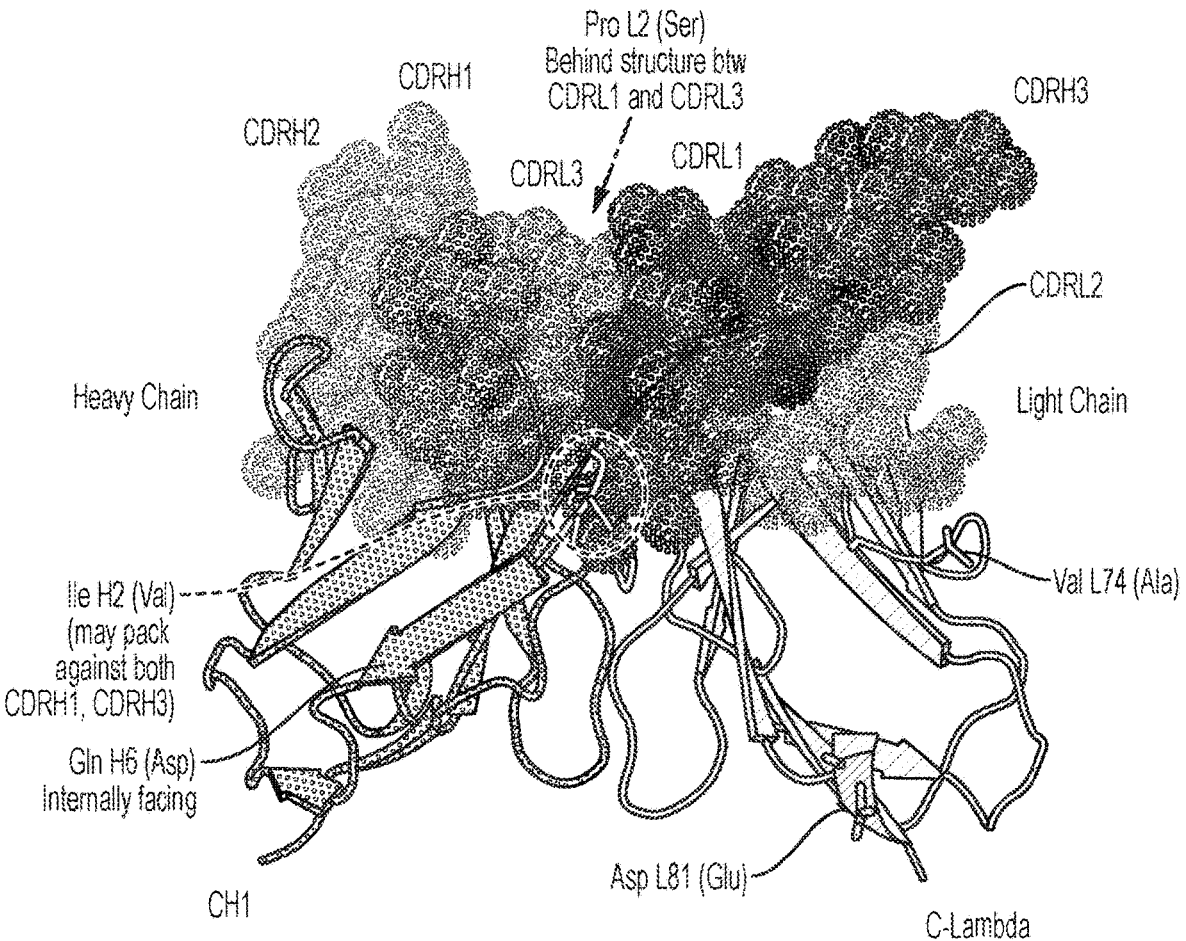
FIG. 22 is a schematic showing the reduced immunogenicity risk by germlining. 24H4 (WT) contains 5 non-germline amino acids within framework regions, as indicated in the schematic.

The variable framework regions of Ab1 as isolated from the fully human naïve phage library contains five non-germline amino acids (see below and FIG. 22). Complementarity determining regions (CDRs) are defined using the Kabat nomenclature and are underlined. Non-germline residues are shown in lower case.

```
                    A. Heavy Chain Variable Region

FRAMEWORK 1              CDR1        FRAMEWORK 2
Ab1 parental  QIQLVQSGGGVVQPGRSLRLSCAASGFTFSSYGMHWVRQAPGKGLEWVA
Ab 3          QIQLVQSGGGVVQPGRSLRLSCAASGFaFSSYGMHWVRQAPGKGLEWVA
Ab5           QIQLVQSGGGVVQPGRSLRLSCAASGFaFSSYGMHWVRQAPGKGLEWVA CDR2                FRAMEWORK 3
Ab1 parental  VISYDGSNKYYADSVKGRFTISRDNSKNTLYLQMNSLRAEDTAVYYCAR
Ab3           VISYDGSiKYYADSVKGRFTISRDNSKNTLYLQMNSLRAEDTAVYYCAR
Ab5           VISYDGnNKYYADSVKGRFTISRDNSKNTLYLQMNSLRAEDTAVYYCAR CDR3           FRAMEWORK 4
Ab1 parental  DLLVRFLEWSHYYGMDVWGQGTTVTVSS  (SEQ ID NO: 24)
Ab3           DLLVRFLEWSHYYGMDVWGQGTTVTVSS  (SEQ ID NO: 26)
Ab5           DLLVRFLEWSHYYGMDVWGQGTTVTVSS  (SEQ ID NO: 28)

B. Light Chain Variable Region

FRAMEWORK 1            CDR1        FRW2
Ab1 parental  QPVLTQPPSASGTPGQRVTISCSGSSSNIGSNTVHWYQQLPGTAPKLLIY
Ab3           QPVLTQPPSASGTPGQRVTISCSGStSNIGSNTVHWYQQLPGTAPKLLIY
Ab5           QPVLTQPPSASGTPGQRVTISCSGSSSNIGgNTVHWYQQLPGTAPKLLIY CDR2            FRAMEWORK 3
Ab1 parental  SDNQRPSGVPDRFSGSKSGTSASLVISGLQSDDEADYYC
Ab3           SDdQRPSGVPDRFSGSKSGTSASLVISGLQSDDEADYYC
Ab5           SDdQRPSGVPDRFSGSKSGTSASLVISGLQSDDEADYYC CDR3        FRAMEWORK 4
Ab1 parental  AAWDDSLNGVFGGGTKLTVL  (SEQ ID NO: 30)
Ab3           AAWDeSLNGVFGGGTKLTVL  (SEQ ID NO: 32)
Ab5           AAWDeSLNGVFGGGTKLTVL  (SEQ ID NO: 34)
```

```
                        A. Heavy Chain Variable Region

<-------------FR1------------><CDR><-----FR2----><-----CDR2------>
Ab1         QIQLVQSGGGVVQPGRSLRLSCAASGFTFSSYGMHWVRQAPGKGLEWVAVISYDGSNKYYADSVKG
IgHV3-30    .v...e.........................................................

<-------------FR3-------------><------CDR3-----><---FR4--->
Ab1         RFTISRDNSKNTLYLQMNSLRAEDTAVYYCARDLLVRFLEWSHYYGMDVWGQGTTVTVSS
            (SEQ ID NO: 24)

IgHV3-30    ................................... (SEQ ID NO: 36)
JH6                                                ................
            (SEQ ID NO: 59)
```

```
                        B. Light Chain Variable Region

<---------FR1---------><----CDR1---><-----FR2------><CDR2->
Ab1         QPVLTQPPSASGTPGQRVTISCSGSSSNIGSNTVHWYQQLPGTAPKLLIYSDNQRPS
IgLV1-44    .s...............................n................n.....

<--------------FR3-------------><--CDR3--><---FR4-->
Ab1         GVPDRFSGSKSGTSASLVISGLQSDDEADYYCAAWDDSLNGVFGGGTKLTVL
            (SEQ ID NO: 30)

IgLV1-44    .................a......e....... (SEQ ID NO: 60)
JL1/2/3                                 ........... (SEQ ID NO: 61)
```

To mitigate the potential for immunogenicity, additional variants of Ab1 molecules were created which substitute the non-germline framework residues to their corresponding germline amino acids. In some embodiments, the substitution pertaining to Ab1 may be similarly applied to Ab3 and Ab4, or any antibody disclosed herein for which germlining is appropriate.

A sequence alignment of variable regions of Ab1 with its affinity optimized variants is shown below. A.) heavy chain, B.) light chain. Complementarity determining regions (CDRs) are defined using the Kabat (underlined) and IMGT nomenclature (bold). Framework regions substitutions present in parental Ab1 are shown in lower case.

```
                        A. Heavy Chain Variable Region

FRAMEWORK 1              CDR1          FRAMEWORK 2
IgHV3-30    QIQLVESGGGVVQPGRSLRLSCAASGFTFSSYGMHWVRQAPGKGLEWVA
Ab1         QlQLVqSGGGVVQPGRSLRLSCAASGFTFSSYGMHWVRQAPGKGLEWVA
Ab2         QVQLVESGGGVVQPGRSLRLSCAASGFTFSSYGMHWVRQAPGKGLEWVA
Ab4         QVQLVESGGGVVQPGRSLRLSCAASGFAFSSYGMHWVRQAPGKGLEWVA
Ab6         QVQLVESGGGVVQPGRSLRLSCAASGFAFSSYGMHWVRQAPGKGLEWVA

CDR2              FRAMEWORK 3
IgHV3-30    VISYDGSNKYYADSVKGRFTISRDNSKNTLYLQMNSLRAEDTAVYYCAR
Ab1         VISYDGSNKYYADSVKGRFTISRDNSKNTLYLQMNSLRAEDTAVYYCAR
Ab2         VISYDGSNKYYADSVKGRFTISRDNSKNTLYLQMNSLRAEDTAVYYCAR
Ab4         VISYDGSIKYYADSVKGRFTISRDNSKNTLYLQMNSLRAEDTAVYYCAR
Ab6         VISYDGNNKYYADSVKGRFTISRDNSKNTLYLQMNSLRAEDTAVYYCAR

CDR3              FRAMEWORK 4
IgHV3-30    -------------------------- (SEQ ID NO: 36)
Ab1         DLLVRFLEWSHYYGMDVWGQGTTVTVSS (SEQ ID NO: 24)
Ab2         DLLVRFLEWSHYYGMDVWGQGTTVTVSS (SEQ ID NO: 25)
Ab4         DLLVRFLEWSHKYGMDVWGQGTTVTVSS (SEQ ID NO: 27)
Ab6         DLLVRFLEWSHKYGMDVWGQGTTVTVSS (SEQ ID NO: 29)
```

```
                        B. Light Chain Variable Region

FRAMEWORK 1              CDR1          FRW2
IgLV1-44    QSVLTQPPSASGTPGQRVTISCSGSSSNIGSNTVNWYQQLPGTAPKLLIY
Ab1         QpVLTQPPSASGTPGQRVTISCSGSSSNIGSNTVHWYQQLPGTAPKLLIY
Ab2         QSVLTQPPSASGTPGQRVTISCSGSSSNIGSNTVHWYQQLPGTAPKLLIY
Ab4         QSVLTQPPSASGTPGQRVTISCSGSTSNIGSNTVHWYQQLPGTAPKLLIY
Ab6         QSVLTQPPSASGTPGQRVTISCSGSSSNIGGNTVHWYQQLPGTAPKLLIY

CDR2              FRAMEWORK 3
IgLV1-44    SNNQRPSGVPDRFSGSKSGTSASLAISGLQSEDEADYYC
Ab1         SDNQRPSGVPDRFSGSKSGTSASLVISGLQSdDEADYYC
Ab2         SDNQRPSGVPDRFSGSKSGTSASLAISGLQSEDEADYYC
Ab4         SDDQRPSGVPDRFSGSKSGTSASLAISGLQSEDEADYYC
Ab6         SDDQRPSGVPDRFSGSKSGTSASLAISGLQSEDEADYYC
```

-continued

```
          CDR3          FRAMEWORK 4
IgLV1-44  -------------------- (SEQ ID NO: 60)
Ab1       AAWDDSLNGVFGGGTKLTVL (SEQ ID NO: 30)
Ab2       AAWDDSLNGVFGGGTKLTVL (SEQ ID NO: 31)
Ab4       AAWDESLNGVFGGGTKLTVL (SEQ ID NO: 33)
Ab6       AAWDESLNGVFGGGTKLTVL (SEQ ID NO: 35)
```

Three of the five substitutions were found to be away from CDR regions and therefore have no impact on binding. A Proline at position 2 of the light chain packs against CDRL3 and substitution to germline Serine actually improves binding to pro/latent-Myostatin by stabilizing the CDR conformation.

The overall antibody is greater than 99% human (calculated as 100% minus the % non-germline AA excluding CDRH3). There are no chemical conjugations. The heavy chain CDRH2 sequence contains a potential isomerization liability (Asp-Gly) which is also present in the germline IgHV3-30 sequence.

Example 2: Pharmacological Characterization

In Vitro Pharmacological Assays

A total of 24 optimized Ab1 variants were expressed and purified as IgG4 and assayed for improved binding and functional activity. The changes to these molecules included germlining mutations to the parental variable region, along with mutations in the CDRs which conferred increased binding to pro/latent-Myostatin in the affinity maturation screen (see Example 1).

The Ab1 variants were screened in several different ELISA-based assays, in which the binding to the proMyostatin and latent Myostatin proteins (human, murine, and cynomolgus) was re-assessed, along with a large screen of negative control proteins to verify that non-specific binding was not introduced as a result of the affinity maturation. Negative controls included GDF11 proteins (proGDF11, latent GDF11 and mature GDF11), TGFβ proteins, and Activin proteins (proActivin). Additionally, the antibodies were assessed for polyspecificity (which can lead to rapid clearance) in a screen similar to that published previously (Hotzel et al., 2012). Any antibodies with significant interactions to negative control proteins, or with baculovirus particles in the polyspecificity screen were not considered further as candidates for a development program.

The 24 optimized variants of Ab1 were also assessed in the proMyostatin activation assay to determine their functional efficacy, and EC50 values from dose response curves were compared to the parental Ab1 antibody. Most antibodies had equivalent or improved EC50 values, with a few displaying reduced efficacy in this assay. Those with reduced efficacy in the activity assay were excluded from further analysis.

Three variants of Ab1 with improved binding to pro- and latent myostatin while retaining specificity for pro- and latent myostatin were identified. Binding and activity data for these three variants and the parental Ab1 molecule are summarized in Tables 4-7, sequences are shown in Example 1.

TABLE 4

Binding characteristics of antibodies to human/cynomolgus/mouse proMyostatin to parental Ab1 IgG4.

| | Ab1 | | | |
| | Activity Assay - 293T cells | Kinetics Analysis - Fortebio Octet | | |
| | EC50 (µM) | kon (1/Ms) | kdis (1/s) | Kd (M) |
|---|---|---|---|---|
| Human | 0.274 | 4.18E+05 | 1.99E−03 | 4.76E−09 |
| Cynomolgus | 0.5842 | 3.05E+05 | 1.75E−03 | 5.75E−09 |
| Mouse | 0.8386 | 2.37E+05 | 2.62E−03 | 1.10E−08 |

TABLE 5

Binding characteristics of antibodies to human/cynomolgus/mouse proMyostatin to Ab1 IgG4 with the correct germline residues replaced (Ab2) for non-germlined residues.

| | Ab2 | | | |
| | Activity Assay - 293T cells | Kinetics Analysis - Fortebio Octet | | |
| | EC50 (µM) | kon (1/Ms) | kdis (1/s) | Kd (M) |
|---|---|---|---|---|
| Human | 0.248 | 4.57E+05 | 1.56E−03 | 3.42E−09 |
| Cynomolgus | 0.6168 | 2.78E+05 | 1.41E−03 | 5.08E−09 |
| Mouse | 0.7138 | 2.35E+05 | 1.97E−03 | 8.39E−09 |

TABLE 6

Binding characteristics of antibodies to human/cynomolgus/mouse proMyostatin to Ab3 IgG4 containing the corrected germline residues (Ab4).

| | Ab4 | | | |
| | Activity Assay - 293T cells | Kinetics Analysis - Fortebio Octet | | |
| | EC50 (µM) | kon (1/Ms) | kdis (1/s) | Kd (M) |
|---|---|---|---|---|
| Human | 0.179 | 4.98E+05 | 2.35E−04 | 4.72E−10 |
| Cynomolgus | 0.4451 | 3.01E+05 | 2.34E−04 | 7.76E−10 |
| Mouse | 0.4466 | 2.53E+05 | 2.72E−04 | 1.08E−09 |

TABLE 7

Binding characteristics of antibodies to human/cynomolgus/mouse proMyostatin to Ab5 IgG4 containing the corrected germline residues (Ab6).

| | Ab6 | | | |
| | Activity Assay - 293T cells | Kinetics Analysis - Fortebio Octet | | |
| | EC50 (µM) | kon (1/Ms) | kdis (1/s) | Kd (M) |
| Human | 0.151 | 5.27E+05 | 2.51E−04 | 4.77E−10 |
| Cynomolgus | 0.4037 | 3.50E+05 | 2.57E−04 | 7.35E−10 |
| Mouse | 0.3068 | 2.94E+05 | 2.81E−04 | 9.54E−10 |

Cell-Based, Ex Vivo and In Vivo Biological Activity Assays

Figures 4, 5:
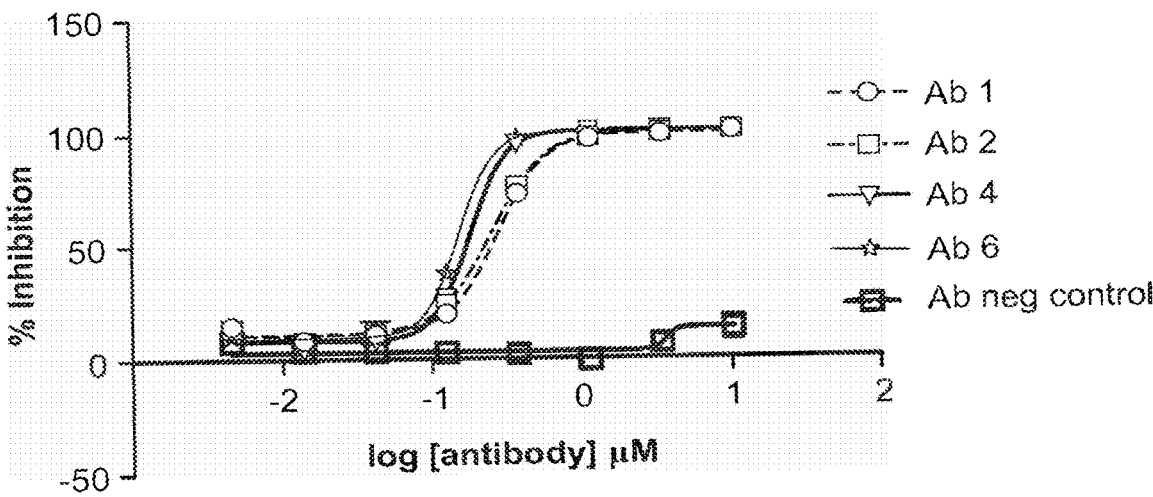
FIG. 4 shows the performance of the parental Ab1 antibody and other candidates in the cell-based reporter assay. Following an overnight proteolysis reaction with enzymes from both the proprotein-convertase and tolloid protease families, the release of mature growth factor was measured using a CAGA-based reporter assay in 293T cells. Results were compared to control reactions to calculate the fraction of proMyostatin or proGDF11 which was released in the assay. Standard deviation for an average of 3 replicates is shown, but not visible on the graph for most data points due to their low magnitude.
FIG. 5 shows graphically that Ab1, Ab2, Ab4, and Ab6 antibodies do not inhibit proGDF11 activation.

Ab1 optimized variants were assessed in the GDF8 activation assay in a dose response study. In these experiments, 0.5 µM proMyostatin was pre-incubated with increasing amounts of the test article. Following this pre-incubation step, conditioned media from HEK293 cells overexpressing the mTll2 and Furin proteases was added to release the mature growth factor from proMyostatin. Following incubation at 30° C. overnight, the material was added to 293T cells carrying a SMAD-based luciferase reporter plasmid, and the activity of the released material was recorded. Data from a screen are shown in FIG. 4.

Selectivity for Myostatin Over Other TGFβ Family Members

The selectivity of the candidate antibodies were also assessed by both binding and functional assays to verify the lack of cross reactivity to other members of the TGFβ family. Human Myostatin and GDF11 share 90% identity in the mature growth factor domain, and 47% identity in the prodomain regions. From the epitope mapping studies, it was determined that the parental Ab1 molecule recognizes an epitope on the prodomain of proMyostatin and latent myostatin because ELISA assays have shown binding of this antibody to a construct consisting of the prodomain of myostatin. Even though the prodomains of myostatin and GDF11 share less than 50% identity, and we do not expect significant cross reactivity, the specificity of the lead antibodies was carefully assessed.

A sensitive assay for detecting interactions between the antibodies of interest and negative control reagents was developed. In this assay, biotinylated proGDF11 or biotinylated proMyostatin was immobilized on a ForteBio BLI streptavidin-coated sensor tip, which was applied to wells containing 30 µg/mL of antibody. Interactions of the analyte with the protein immobilized on the chip are measured by the magnitude of the response of the biosensor chip. The biosensor response after 5 minutes of association (a saturating signal for proGDF8) was compared between the two antigens, and expressed as the percent response for GDF8 binding. All antibodies had minimal interactions with proGDF11, compared to the robust binding events measured for proMyostatin.

TABLE 8

Interactions with proGDF11 at high concentrations of the candidate molecules

| | GDF11 response, expressed as a percentage of GDF8 response |
| Ab1 | 1.33% |
| Ab2 | 0.81% |

TABLE 8-continued

Interactions with proGDF11 at high concentrations of the candidate molecules

| | GDF11 response, expressed as a percentage of GDF8 response |
| Ab4 | 2.51% |
| Ab6 | 2.07% |

The antibody candidates were also evaluated in a GDF11 activation assay. In this assay, 50 nM proGDF11 is preincubated with increasing concentrations of the antibody. Following preincubation, conditioned medium from HEK293 cells overexpressing BMP-1 (a tolloid family protease) and PCSK5 (a furin family member specific for GDF11) was added to proteolytically activate proGDF11. Following overnight incubation at 30° C., the reaction mixtures are assessed for GDF11 activity in a SMAD-based reporter cell line. As is shown in Table 8, the anti-myostatin antibodies do not inhibit proGDF11 activation, while a positive control antibody imparts dose-dependent inhibition of GDF11 activation.

Binding affinities of antibody candidates were determined using the FortdBio Octet QKe dip and read label free assay system utilizing bio-layer interferometry. Antigens were immobilized to biosensors (streptavidin-coated biosensors for proGDF8, proGDF11 and proActivin; direct amine coupling for all others) in each experiment and the antibodies/constructs were presented in solution at high concentration (50 µg/mL) to measure binding interactions.

Binding affinities of antibodies were determined using the FortéBio Octet QKe dip and read label free assay system utilizing bio-layer interferometry. Human proGDF8, latent GDF8, proGDF11 and proActivin were biotinylated and immobilized to streptavidin-coated biosensors (FortéBio). Mature growth factors were immobilized via direct amine coupling to amine reactive tips according to manufacturer's instructions (FortéBio). In each experiment, the antibodies/constructs were presented in solution at a single high concentration (50 µg/mL) to measure binding interactions. Growth factors were purchased from R&D systems and biotinylated proteins were produced as described.

TABLE 9a

Comparison of antibodies for binding to different forms of several TGFβ family members.

| | Ab2 | Ab4 | Ab6 | Ab1 |
| --- | --- | --- | --- | --- |
| Pro GDF8 | 7.35E−09 | 9.24E−10 | 8.89E−10 | 6.23E−09 |
| Latent GDF8 | 7.84E−09 | 1.10E−09 | 1.12E−09 | 9.06E−09 |
| Mature GDF8 | — | — | — | — |
| Pro GDF11 | — | *1.25E−07 | *6.07E−08 | — |
| Mature GDF11 | — | — | — | — |
| Pro Activin A | — | — | — | — |
| Mature Activin A | — | — | — | — |
| BMP 9 | — | — | — | — |
| BMP10 | — | — | — | — |
| Mature TGFB1 | — | — | — | — |

*Non-specific binding.

Results from the antigen binding study are summarized in Table 9a. Experiments with no detectable binding are noted by a minus sign (−). There are some calculated Kd values that were fitted to data with poor binding response, which is indicated in the table as weak non-specific binding (*).

As the proGDF8 sample used in Table 9a contained approximately 10-15% latent GDF8, a separate experiment was used to confirm proGDF8 binding to human and murine GDF8 antigens specifically. In addition, primed GDF8, in which proGDF8 is proteolytically cleaved by both a pro-protein convertase and tolloid protease was also assessed for binding affinity to Ab2 and AbMyo. For these experiments, a homogenous preparation of human proGDF8 was purified from stably integrated 293 cells cultured in the presence of 30 µM decanoyl-RVKR-CMV. Primed human GDF8 was produced by in-vitro cleavage of proGDF8 utilizing condi-tioned media from mTll2-overexpressing cells and purified Furin protease. In the binding experiments with these pro-teins, 150 nM of Ab2 or AbMyo was used to saturate the immobilization sites on human Fc capture tips (FortéBio), and the association and dissociation of 150 nM analyte was evaluated.

Analysis of binding affinities to murine proteins were also assessed and are reported in Table 9b. Murine proGDF8 protein was produced by removing all mature and latent murine GDF8 from the sample via negative selection with an antibody that tightly recognizes latent and mature GDF8 (AbMyo2), 50 nM of antibody was used to saturate an anti-human Fc capture tip (FortéBio). Initially, all antibodies were tested against a single 200 nM concentration of murine proGDF8, murine latent GDF8, and mature GDF8. If bind-ing was observed, a Kd value was determined by immobi-lizing the antibody as previously described and using analyte in titration from 200 to 0.82 nM by 3-fold dilutions. The Kd was determined using a global fit with FortéBio data analy-sis software 8.2. For binding to mature myostatin, 5 ug/mL of growth factor (R&D systems) was coupled to amine reactive sensor tips (FortéBio) in acetate buffer at pH 5. All antibodies were initially tested at 333 nM for binding to this myostatin-coupled sensor. Antibodies that showed binding were then tested in concentrations ranging from 333 to 1.37 nM by 3 fold dilutions. A global fit was used to determine the Kd of the interaction using FortéBio data analysis 8.2.

TABLE 9b

Comparison of antibodies for binding to different forms of human and murine GDF8.

|  | Ab2 | AbMyo |
|---|---|---|
| Human Pro GDF8 | 2.9E-09 | — |
| Human latent GDF8 | 2.4E-9 | 3.87E-10 |
| Human primed GDF8 | 8.66E-09 | 8.83E-10 |
| Mature GDF8 | — | 4.7E-11 |
| Murine ProGDF8 | 2.3E-09 | — |
| Murine Latent GDF8 | 2.0E-09 | <1E-12 |

Results from an antigen binding study are summarized in Table 9b. Experiments with no detectable binding are noted by a minus sign (–). Some values, labeled as <1 E-12, had very slow dissociation rates making the high affinity unable to be quantified. Surprisingly, AbMyo was unable to recog-nize recombinant proGDF8, which is different than results reported in Latres et al 2015, in which the authors reported association of AbMyo with proGDF8 in an immunoprecipi-tation experiment from serum of mice that were dosed with the antibody which could produce artifacts. Another surpris-ing result is the interaction between Ab2 and primed GDF8, a complex of GDF8 with tolloid-cleaved prodomain. This result is unexpected because Ab2 blocks tolloid cleavage of the prodomain and suggests that the interaction of Ab2 with proGDF8 and latent GDF8 does not require an intact tolloid cleavage site.

Evaluation of Fc-Region Functionality

In some embodiments, anti-pro/latent-Myostatin therapy involves binding to a soluble target (pro/latent-Myostatin) and preventing proteolytic activation. In some embodi-ments, antibody dependent cell-mediated cytotoxicity and complement fixation are not involved in this process. Ab1 and its related variants were engineered to contain an IgG4-Fc region. It is understood that IgG4 antibodies gen-erally lack effector function due to their weak binding to complement component C1q and Fcγ receptors.

To demonstrate the reduced capacity for effector function, Ab1 and related antibodies were tested for binding to CD64 (FcgRI) and C1q by ELISA. For comparison, an IgG1 variant of Ab1 was also prepared. In this assay, all IgG4 antibodies showed significantly weaker binding (10 to 20-fold) to CD64 and C1q compared to IgG1. The relative binding values at the EC50 are listed in Table 10.

TABLE 10

Relative binding affinities of Ab2 and related antibodies to CD64.

| Antibody | Isotype | Relative CD64 Binding @ EC50 (%) | Relative C1q Binding @ EC50 (%) |
|---|---|---|---|
| Ab1-G1 | IgG1 | 100 | 100 |
| Ab1 | IgG4 (S228P) | 10 | ND |
| Ab2 | IgG4 (S228P) | 5 | 8 |
| Ab3 | IgG4 (S228P) | 5 | 5 |
| Ab5 | IgG4 (S228P) | 8 | 9 |

Not determined

The apparent binding affinities of Ab1 and its related variants to CD64 and C1q are similar to other IgG4 clinical candidate antibodies, and are considerably reduced com-pared to antibodies of the IgG1 isotype. Based on the biology of IgG4 antibodies, it is therefore concluded that the anti-pro/latent-Myostatin antibodies will not induce appre-ciable effector function in vivo.

Efficacy in Animal Models

Based on in vitro characterization, four antibodies were chosen to test in an in vivo study (Ab7, Ab1, Ab8 and Ab9). The objective of the study was to assess the ability of these four candidate antibodies to modulate muscle mass mice. Five (5) groups of ten (10) female SCID mice received test article administration by intraperitoneal (IP) injection once per week on Days 0, 7, 14, 21, 28, and 35. Prior to test article administration (Day 0), all animals underwent grip strength evaluation. Grip strength evaluation was also performed on the last day of the study (Day 42). On Day 0, blood was collected via retro-orbital bleed for assessment of complete blood counts (CBC). Following dosing, animals were evalu-ated daily for body weight and general health observations. On Day 42, following grip strength assessment, animals were sacrificed via $CO_2$ overdose and blood was collected via cardiac puncture for CBC assessment. Additional blood was collected for the preparation of plasma. Various tissues were isolated and weighed. The muscles collected were: gastrocnemius, pectoralis, soleus, triceps, tibialis anterior, quadriceps (rectus femoris) and diaphragm. The organs collected were: heart, kidney, spleen, liver and inguinal white adipose tissue. All tissues were weighed and snap frozen except for the gastrocnemius muscles which were fixed in formalin (leg 1) and OCT (leg 2) for histologic analysis.

Summary

Figure 6:
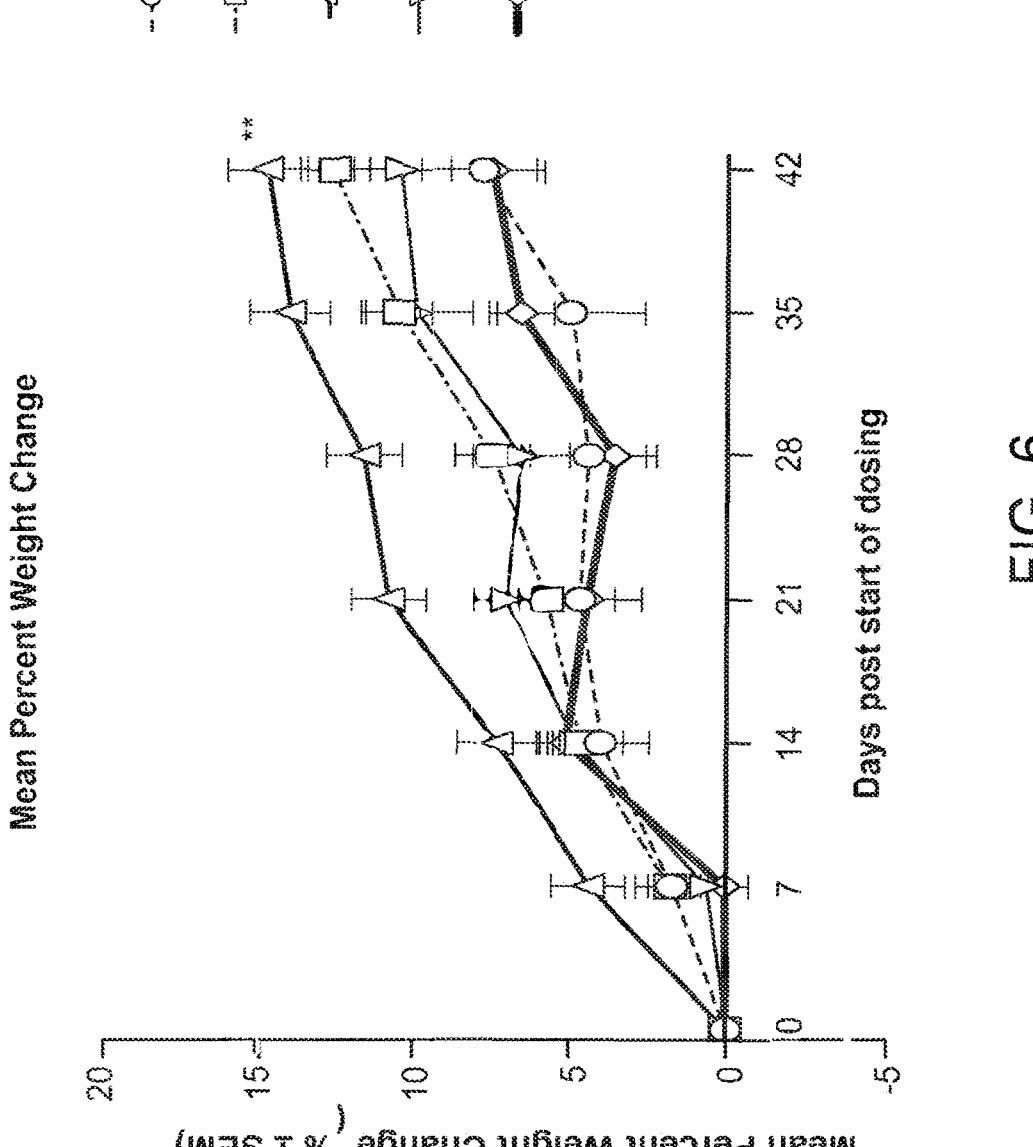
FIG. 6 shows results of an assay evaluating mean percent body weight change. Animals were weighed daily and the percent weight change from Day 0 was calculated. Data represent group means±SEM. The mean percent change data for each group on day 42 of the study were analyzed using a one-way ANOVA followed by Holm-Sidak's post hoc test in comparison to the PBS Control Group, **$p<0.01$.

The mean daily percent weight change data for animals in study SCH-02 are shown in FIG. 6. Animals in all five groups gained weight on a weekly basis. Animals treated with the antibody Ab1 had the largest increase in body weight (14.6%) as depicted in FIG. 6. Only animals treated with Ab1 had a statistically significant increase in mean percent body weight change in comparison to animals in the vehicle (PBS) control group (FIG. 6).

Figures 7A, 7B, 7C, 7D:
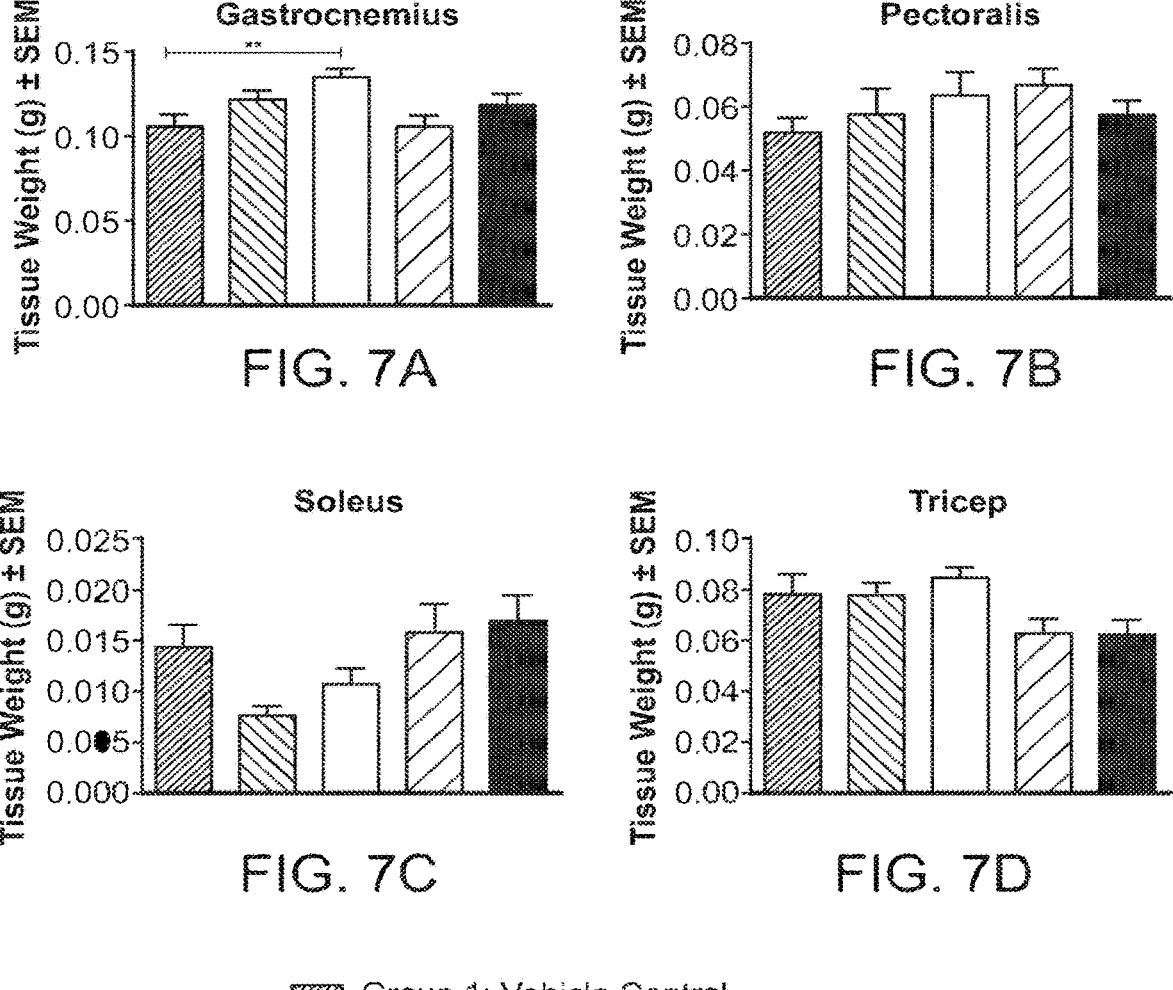
FIGS. 7A-7D show results of an assay evaluating tissue weights.
Figures 8A, 8B, 8C:
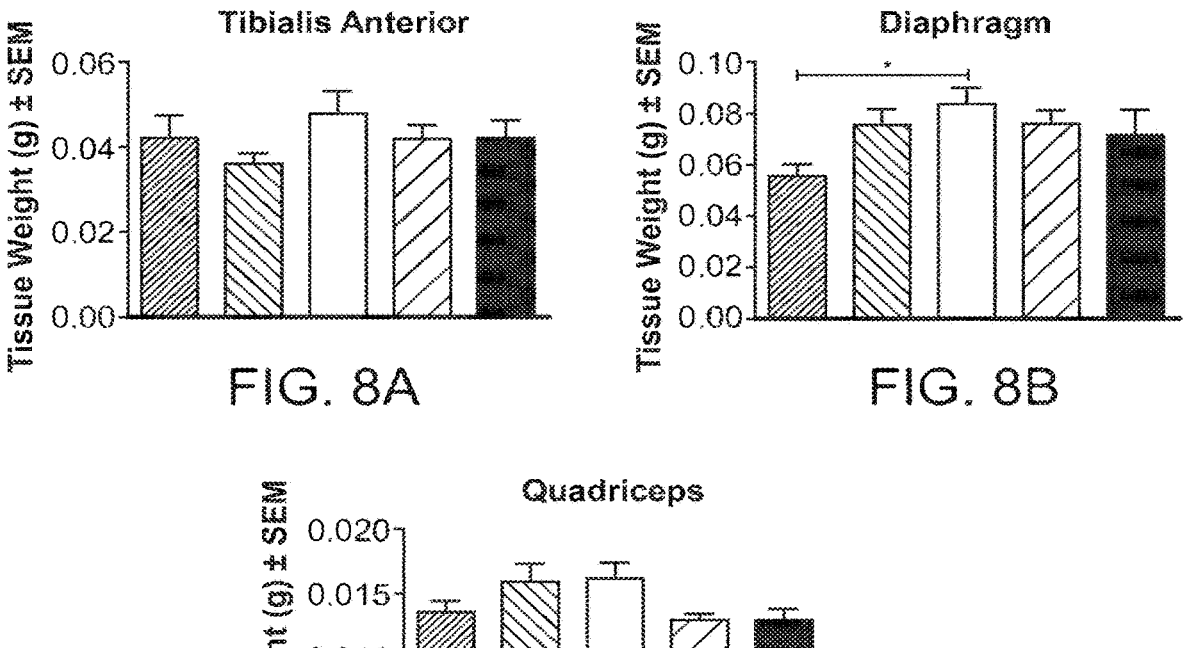
FIGS. 8A-8C show results of an assay evaluating tissue weights.

The weights for the dissected muscles are plotted in FIGS. 7 and 8. Animals treated with Ab1 had statistically significant increases in gastrocnemius (FIG. 7A) and diaphragm (FIG. 8B) weights compared to vehicle (PBS) control treated animals, 27.6% and 49.8%, respectively. Additional muscles from Ab1 treated animals showed increases in weight compared to the PBS control, but these differences were not statistically significant. There were no statistically significant differences between treatment groups for the mean tissue weights of heart, spleen, kidney, liver, and adipose tissue.

SCID Dose Response Study

In the in vivo study (above) animals dosed with Ab1 at 25 mg/kg once weekly for 6 weeks showed statistically significant increases in body weight and muscle weights (gastrocnemius and diaphragm) compared to animals dosed with the vehicle (PBS). This muscle enhancing activity of Ab1 was next investigated in more detail in a dose response study in SCID mice. In this study, whether the magnitude of the effect on muscle mass could be increased by increasing the dose of Ab1 to as high as 60 mg/kg/wk and whether the magnitude of the effect on muscle mass could be decreased by decreasing the dose of Ab1 to as low as 2 mg/kg/wk were examined. In this study, the activity of Ab1 was compared to two more antibodies (Ab8, which was originally tested in the study described above Ab10).

Ten (10) groups of ten (10) female SCID mice received test article administration by intraperitoneal (IP) injection (10 ml/kg) twice per week on Days 0, 3, 7, 10, 14, 17, 21, and 24. The doses of test articles were as follows: Ab1 (30 mg/kg, 10 mg/kg, 3 mg/kg and 1 mg/kg), Ab10 (10 mg/kg and 3 mg/kg), and Ab8 (10 mg/kg and 3 mg/kg). Control groups were dosed with PBS and IgG-control (30 mg/kg). Treatment groups are described in Table 11. Animals were 10 weeks old at the start of the study. Body weight was measured on day −4 and twice per week throughout the study, corresponding with dosing days. Body mass composition parameters (fat mass, lean mass and water content) were measured by Echo MRI (QNMR) on days −4, 7, 14, 21 and 28. Thirty (30) days after the first dose of antibody, animals were sacrificed via $CO_2$ overdose and blood was collected via cardiac puncture for CBC assessment and plasma preparation. Additionally, upon study termination, various tissues were isolated and weighed. The muscles collected were: gastrocnemius, soleus, tibialis anterior, quadriceps (rectus femoris) and diaphragm. Muscles were dissected from both the right and left legs of study mice. For analysis the weights of the individual muscles from both legs were combined and the average muscle weight in grams was calculated. The other tissues collected were: heart, kidney, spleen, liver and adipose tissue. All tissues were weighed and then snap frozen except for the gastrocnemius muscles which were fixed in formalin (left leg) and OCT (right leg) for histologic analysis.

TABLE 11

| Treatment Group | Test Article dose | # doses per week | Total dose per week | Animal IDs |
|---|---|---|---|---|
| 1 | PBS Control | 2 | 0 | 1-10 |
| 2 | IgG Control (30 mg/kg) | 2 | 60 mg/kg/wk | 11-20 |
| 3 | Ab1 (30 mg/kg) | 2 | 60 mg/kg/wk | 21-30 |
| 4 | Ab1 (10 mg/kg) | 2 | 20 mg/kg/wk | 31-40 |
| 5 | Ab1 (3 mg/kg) | 2 | 6 mg/kg/wk | 41-50 |
| 6 | Ab1 (1 mg/kg) | 2 | 2 mg/kg/wk | 51-60 |
| 7 | Ab10 (10 mg/kg) | 2 | 20 mg/kg/wk | 61-70 |
| 8 | Ab10 (3 mg/kg) | 2 | 6 mg/kg/wk | 71-80 |
| 9 | Ab8 (10 mg/kg) | 2 | 20 mg/kg/wk | 81-90 |
| 10 | Ab8 (3 mg/kg) | 2 | 6 mg/kg/wk | 91-100 |

Figure 9A:
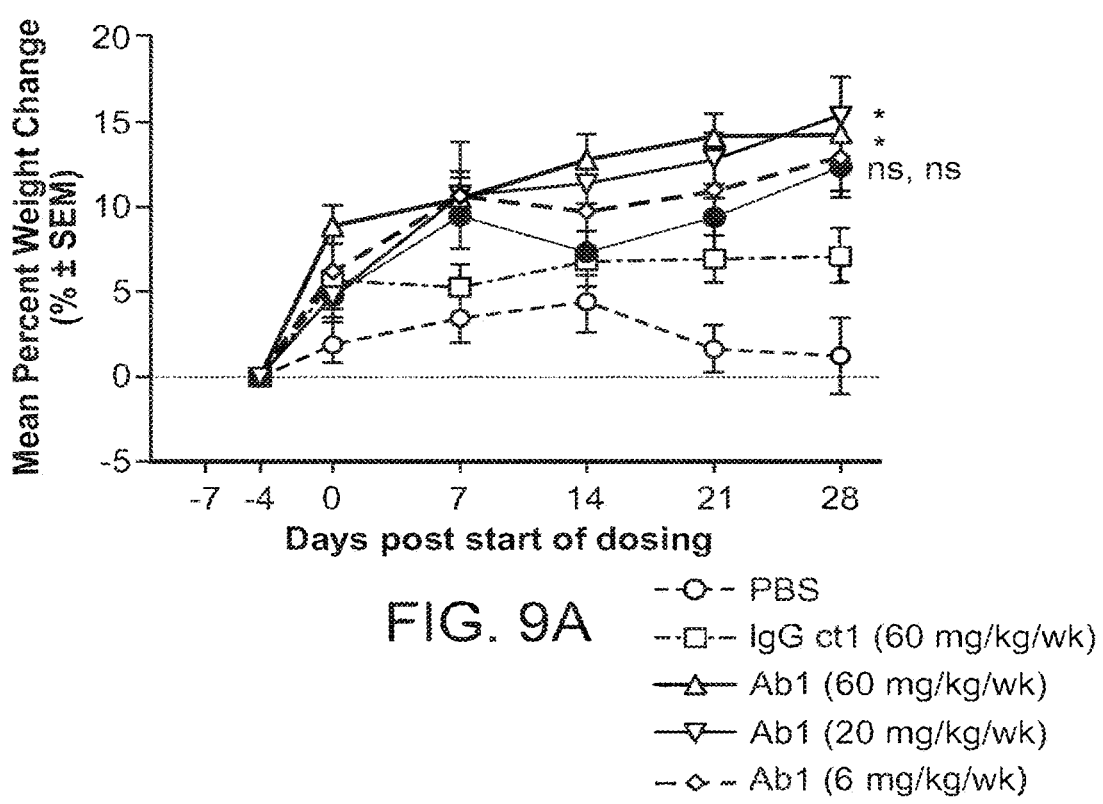
FIGS. 9A-9B show results of an assay evaluating mean percent body weight and lean mass change.
Figure 9B:
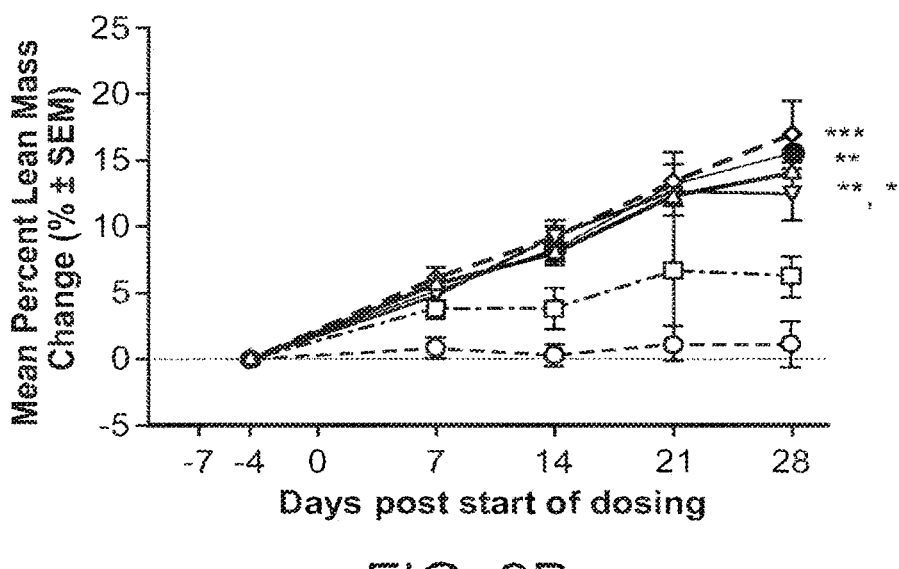

Mean percent weight change and mean percent lean mass change data for animals treated with vehicle (PBS), IgG control and different doses of Ab1 are shown in FIG. 9. Animals treated with Ab1 at 20 and 60 mg/kg/wk doses had significant increases in body weight on day 28 of the study compared to IgG control treated animals, 15.3% and 14.4%, respectively (FIG. 9A). All four groups of animals treated with Ab1 (60, 20, 6 and 2 mg/kg/wk doses) had statistically significant increases in lean mass on day 28 of the study compared to IgG control treated animals, 14.1%, 12.4%, 17.1%, and 15.5%, respectively (FIG. 9B).

Figures 10A, 10B:
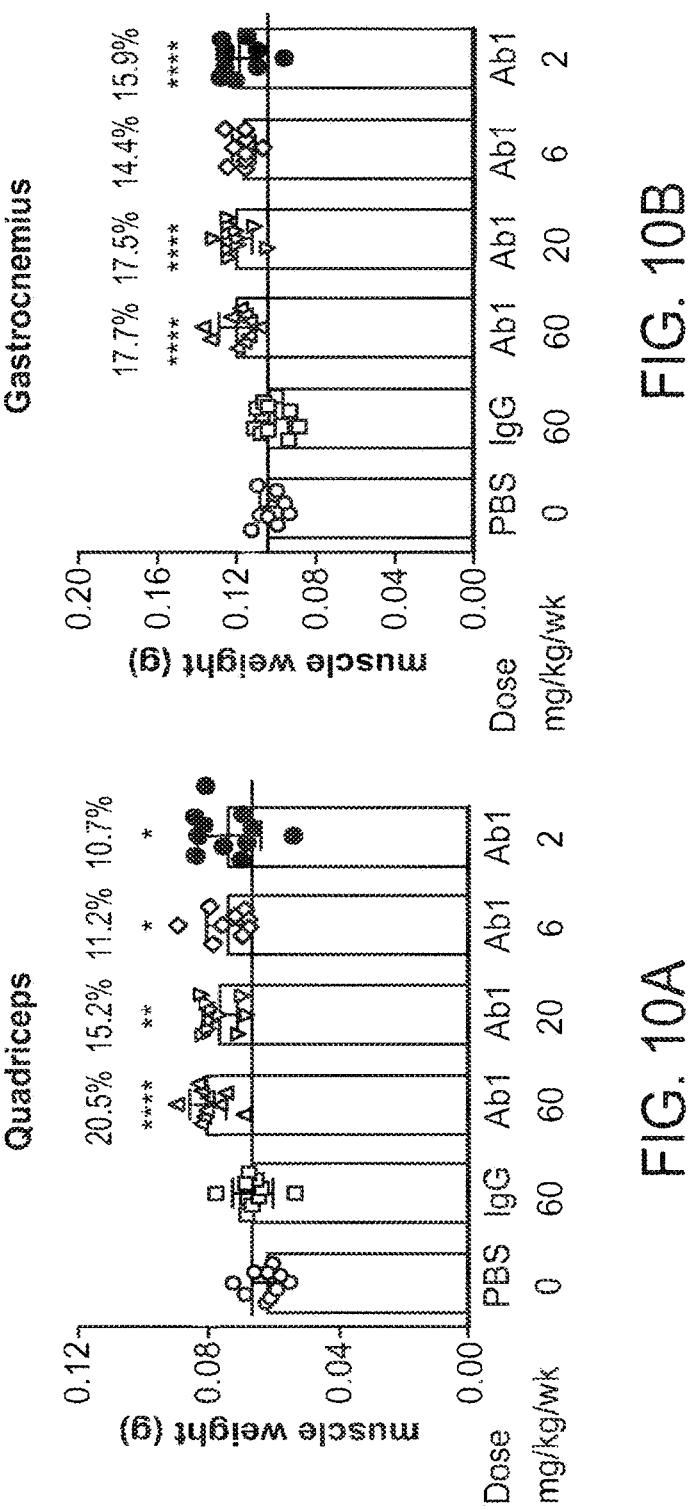
FIGS. 10A-10D are graphs showing results of an assay evaluating muscle weights.
Figures 10C, 10D:
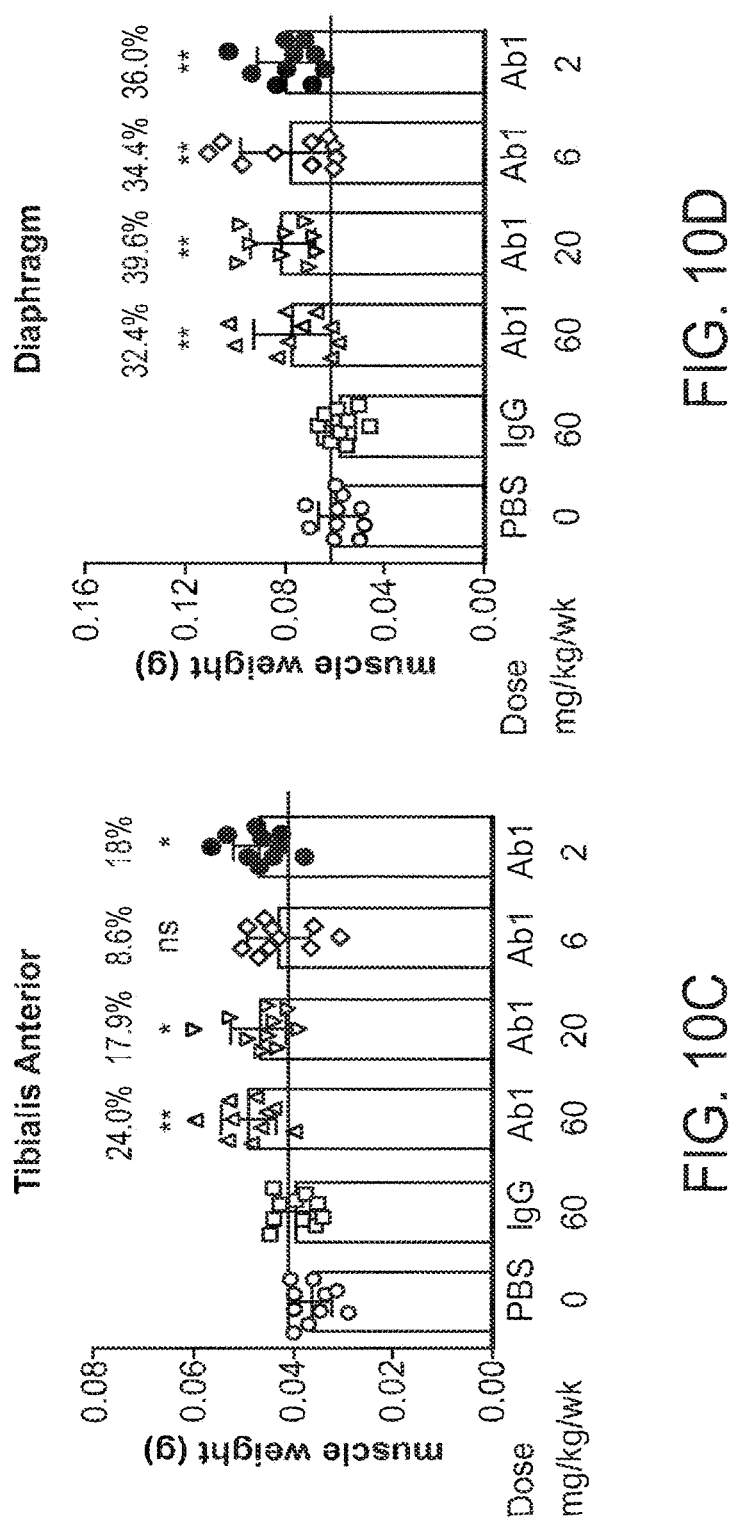

The weights for four muscles (quadriceps, gastrocnemius, tibialis anterior and diaphragm) are plotted in FIG. 10. The soleus muscle was also dissected, but the small size of the muscle resulted in an extremely variable data set. Animals treated with all doses of Ab1 had statistically significant increases in muscle weights compared to IgG control animals (FIG. 10). The mean percent changes in muscle mass compared to IgG control are shown above the corresponding bar on each muscle graph. Mean percent weight changes for quadriceps muscle ranged from 20.5% for the highest dose to 10.7% for the lowest dose (FIG. 10A). Mean percent weight changes for gastrocnemius muscle ranged from 17.7% for the highest dose to 15.9% for the lowest dose (FIG. 10B). Mean percent weight changes for tibialis anterior muscle ranged from 24.0% for the highest dose to 18.0% for the lowest dose (FIG. 10C). Mean percent weight changes for diaphragm muscle were greater than 30% for all dose groups (FIG. 10D). There were no statistically significant differences between treatment groups for the mean tissue weights of heart, spleen, kidney, liver, and adipose tissue.

Ab1 Treatment in a Dexamethasone Induced Muscle Atrophy Model

Given the ability of the anti-myostatin antibody Ab1 to build muscle mass in healthy SCID mice, it was determined whether Ab1 treatment could also protect animals from treatments that induce muscle atrophy. A model of corticosteroid-induced muscle atrophy was established by treating animals for two weeks with dexamethasone in their drinking water. The dose chosen (2.5 mg/kg/day) was able to induce significant decreases in lean body mass and the mass of individual hindlimb muscles. In the following experiment, animals were treated with different doses of Ab1 to determine if it could protect animals from this dexamethasone-induced muscle atrophy.

In this study, eight (8) groups of ten (10) male mice (C57BL/6) were enrolled in the study at 13.5 weeks of age. Starting on day 0 of the study, mice were given either normal drinking water (groups 1-4) or water containing dexamethasone (groups 5-8). Test articles were administered by intra-peritoneal (IP) injection (10 m/kg) twice per week on Days 0, 3, 7, and 10. The test articles and doses were as follows: PBS (groups 1 and 5), 10 mg/kg IgG Ctl (groups 2 and 6), 10 mg/kg Ab1 (groups 3 and 7), and 1 mg/kg Ab1 (groups 4 and 8). Treatment groups are described in Table 12. Body weight was measured at least twice per week throughout the study. Body mass composition parameters (fat mass, lean mass and water content) were measured by Echo MRI (QNMR) on days −1, 6, and 13. Fourteen (14) days after the first dose of antibody, animals were sacrificed via $CO_2$ overdose and blood was collected via cardiac puncture for plasma preparation. Additionally, upon study termination, various tissues were isolated and weighed. The muscles collected were: gastrocnemius, soleus, tibialis anterior, quadriceps (rectus femoris) and diaphragm. Muscles were dissected from both the right and left legs of study mice. For analysis the weights of the individual muscles from both legs were combined and the average muscle weight in grams was calculated. The other tissues collected were: heart, kidney, spleen, liver and adipose tissue. All tissues were weighed and then snap frozen except for the gastrocnemius muscles which were fixed in formalin (left leg) and OCT (right leg) for histologic analysis.

TABLE 12

Treatment groups for Dexamethazone-induced atrophy model study

| Treatment Group | Dexamethasone in drinking water | Test Article dose | # doses per week | Total dose per week | Animal IDs |
|---|---|---|---|---|---|
| 1 | none | PBS Control | 2 | 0 | 1-10 |
| 2 | none | IgG Control (10 mg/kg) | 2 | 20 mg/kg/wk | 11-20 |
| 3 | none | Ab1 (10 mg/kg) | 2 | 20 mg/kg/wk | 21-30 |
| 4 | none | Ab1 (1 mg/kg) | 2 | 2 mg/kg/wk | 31-40 |
| 5 | 2.5 mg/kg/day | PBS Control | 2 | 0 | 51-60 |
| 6 | 2.5 mg/kg/day | IgG Control (10 mg/kg) | 2 | 20 mg/kg/wk | 61-70 |
| 7 | 2.5 mg/kg/day | Ab1 (10 mg/kg) | 2 | 20 mg/kg/wk | 71-80 |
| 8 | 2.5 mg/kg/day | Ab1 (1 mg/kg) | 2 | 2 mg/kg/wk | 81-90 |

Figures 11A, 11B:
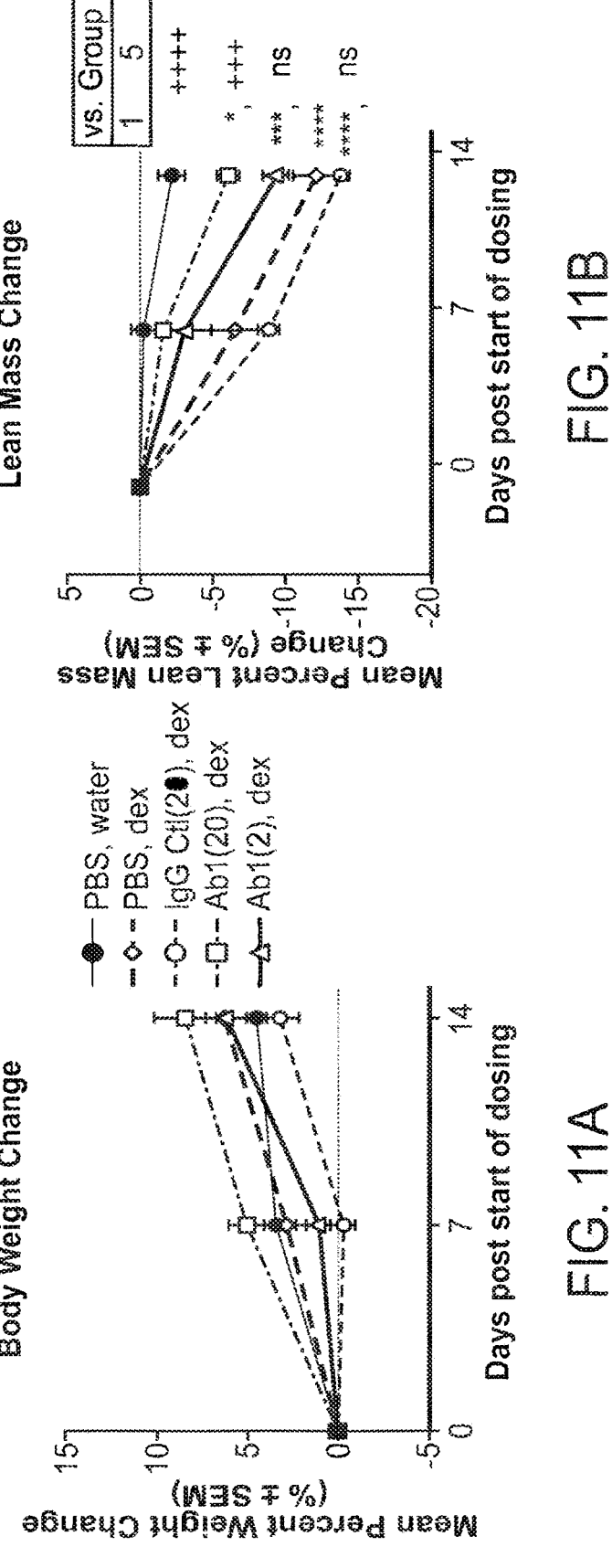
FIGS. 11A-11B show results of an assay evaluating mean percent body weight and lean mass change.

In this experiment it was determined whether treatment of mice with the anti-myostatin antibody Ab1 could protect animals from corticosteroid induced muscle atrophy. During the study body weight was measured twice weekly and lean mass by QNMR on days −1, 6 and 13. The mean percent weight change and mean percent lean mass change data for animals in the non-diseased control group (group 1) and the dexamethasone treated groups (groups 5-8) are shown in FIG. 11. There were no significant differences in mean percent body weight change between any of these treatment groups on day 14 (FIG. 11A). Treatment of mice with dexamethasone for two weeks led to a significant decrease in lean body mass (groups 5 and 6) compared to a control group (group 1) that was given normal drinking water (FIG. 11B). However, mice treated with both dexamethasone and the antibody Ab1 at 20 mg/kg/wk (group 7) showed no significant difference in percent change in lean body mass on day 14 of the study compared to the control group (group 1). Animals treated with Ab1 at 20 mg/kg/wk, but not 2 mg/kg/wk, showed a significant difference in percent change in lean body mass on day 14, when compared to either of the dexamethasone treated control groups (groups 5 and 6).

Figures 12A, 12B:
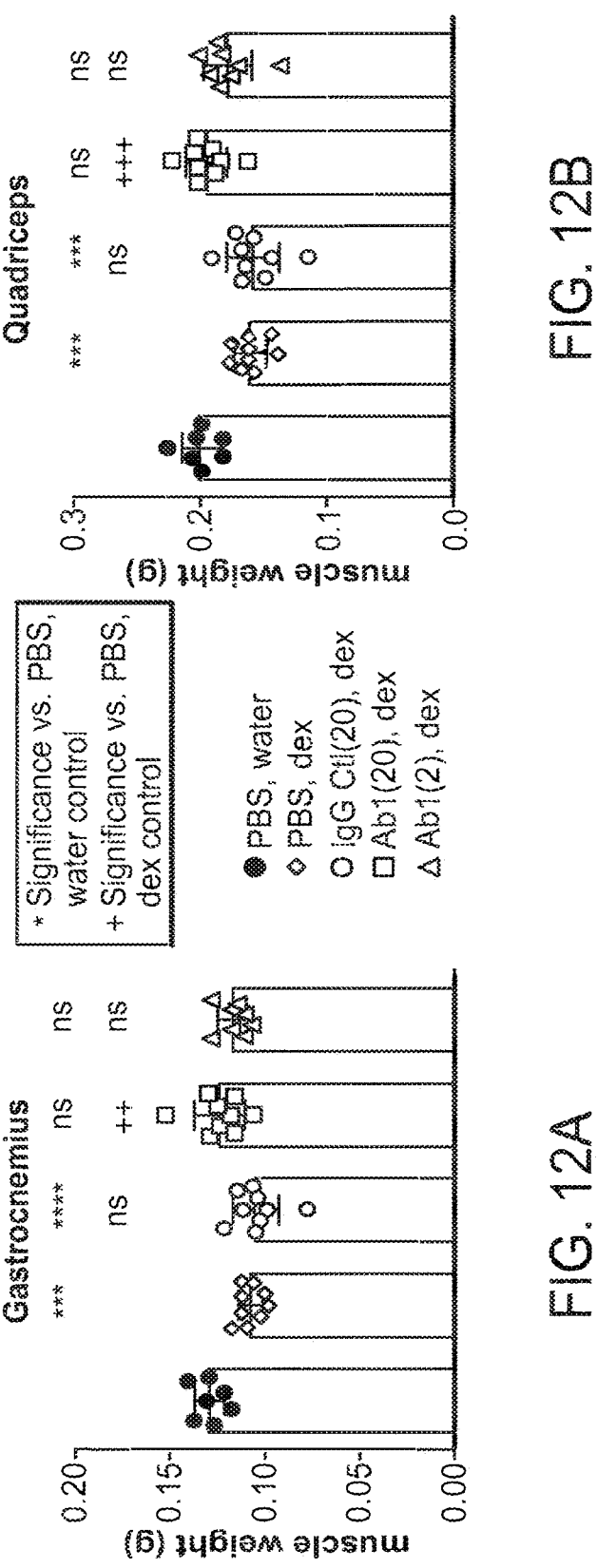
FIGS. 12A-12D are graphs showing results of an assay evaluating the weights of different muscles.
Figures 12C, 12D:
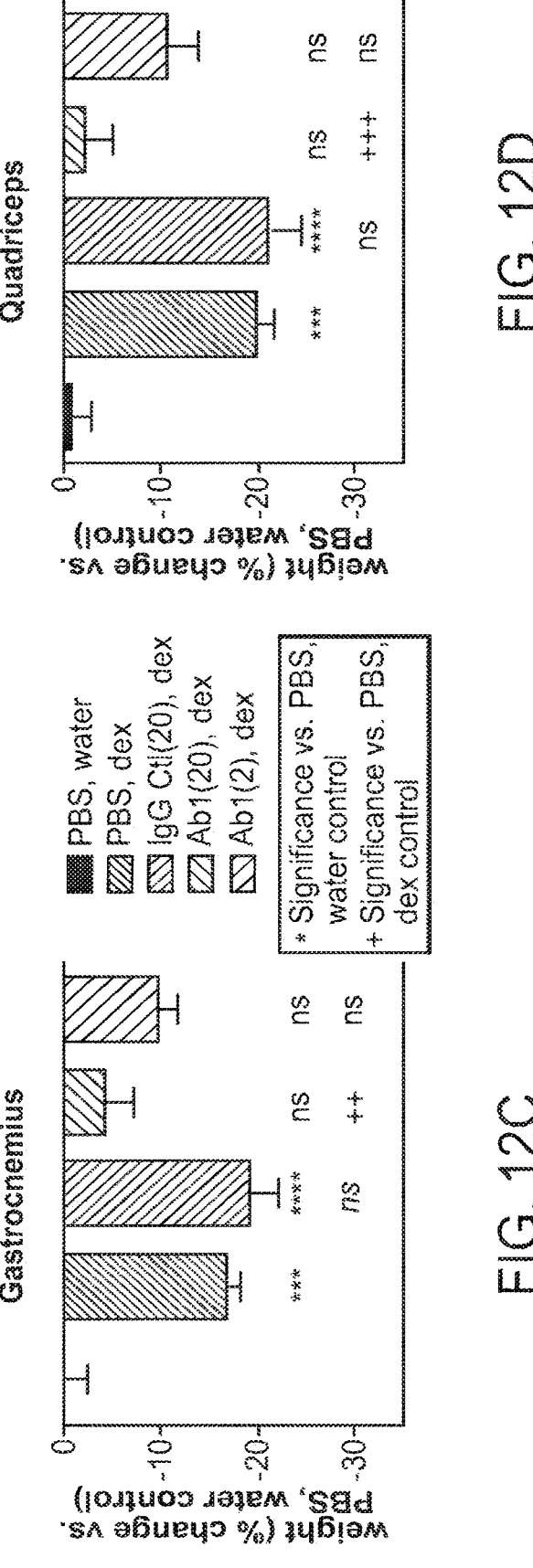

At the end of the two week treatment with dexamethasone and the test articles, individual muscles were dissected and weighed. The weight data for two muscles (gastrocnemius and quadriceps) are plotted in FIGS. 12A-12B. Animals that received dexamethasone via their drinking water and also received either PBS or IgG Control antibody showed significant atrophy in gastrocnemius and quadriceps muscles (groups 5 and 6) compared to the non-diseased control group (group 1). Animals treated with both dexamethasone and Ab1 at 20 mg/kg/wk (group 7), but not 2 mg/kg/wk, showed a significant difference in muscle weights when compared to either of the dexamethasone treated control groups (groups 5 and 6). In addition, mice treated with both dexamethasone and the antibody Ab1 at 20 mg/kg/wk (group 7) showed no significant difference in gastrocnemius and quadriceps weights when compared to the non-diseased control group (group 1). The mean percent difference in muscle weight of each group compared to the mean muscle weight of the control group (group 1, PBS and water) is shown in FIGS. 12C-12D. The percent decreases in gastrocnemius mass induced by dexamethasone treatment in the PBS and IgG Ctl groups were 16.5% and 18.9%, respectively. In contrast, animals treated with both dexamethasone and 20 mg/kg/wk of Ab1 only had a 4.0% decrease in gastrocnemius muscle mass which was not statistically different from the non-diseased control group (group 1). While animals treated with both dexamethasone and 2 mg/kg/wk Ab1 (group 8) only had a 10% decrease in gastrocnemius muscle mass, the muscle mass decrease for this group was not statistically different than the decreases for the PBS and IgG control groups (groups 5 and 6). Similar results were seen for the quadriceps muscle (FIG. 12D).

Ab1 Treatment in a Casting Induced Muscle Atrophy Model

Given the ability of the anti-myostatin antibody Ab1 to build muscle mass in healthy SCID mice, whether Ab1 treatment could also protect animals from treatments that induce muscle atrophy was investigated. A model of disuse atrophy was established by casting the right leg of mice for two weeks. Casting the right leg with the foot in a plantar flexion position for this time period was able to induce significant decreases in the mass of individual hindlimb muscles. In the following experiment animals were treated with different doses of Ab1 to determine the extent to which it protects animals from this casting induced muscle atrophy.

TABLE 13

Treatment groups for casting-induced atrophy model study

| Treatment Group | Casting | Test Article dose | # doses per week | Total dose per week | Animal IDs |
|---|---|---|---|---|---|
| 1 | No cast | PBS Control | 2 | 0 | 1-10 |
| 2 | No cast | IgG Control (10 mg/kg) | 2 | 20 mg/kg/wk | 11-20 |
| 3 | No cast | Ab1 (10 mg/kg) | 2 | 20 mg/kg/wk | 21-30 |
| 4 | No Cast | Ab1 (1 mg/kg) | 2 | 2 mg/kg/wk | 31-40 |
| 5 | Casted | PBS Control | 2 | 0 | 51-60 |
| 6 | Casted | IgG Control (10 mg/kg) | 2 | 20 mg/kg/wk | 61-70 |
| 7 | Casted | Ab1 (10 mg/kg) | 2 | 20 mg/kg/wk | 71-80 |
| 8 | Casted | Ab1 (1 mg/kg) | 2 | 2 mg/kg/wk | 81-90 |

In this study, eight (8) groups of ten (10) male mice (C57BL/6) were enrolled in the study at 14.5 weeks of age. Starting on day 0 of the study, mice were placed under anesthesia and a cast was applied to the right hindlimb with the foot in a plantar flexion position (groups 5-8). The control groups (groups 1-4) were also placed under anesthesia but no cast was placed on the hindlimb. Test articles were administered by intraperitoneal (EP) injection (10 mi/kg) twice per week on Days 0, 3, 7, and 10. The test articles and doses were as follows: PBS (groups 1 and 5), 10 mg/kg IgG Ct1 (groups 2 and 6), 10 mg/kg Ab1 (groups 3 and 7), and 1 mg/kg Ab1 (groups 4 and 8). Treatment groups are described in Table 13. Body weight was measured at least twice per week throughout the study. Body mass composition parameters (fat mass, lean mass and water content) were measured by Echo MRI (QNMR) on days –1, 7, and 14. Fourteen (14) days after the first dose of antibody, animals were sacrificed via $CO_2$ overdose and blood was collected via cardiac puncture for plasma preparation.

Additionally, various tissues were isolated and weighed. The muscles collected were: gastrocnemius, soleus, plantaris, tibialis anterior, and quadriceps (rectus femoris). For analysis the weights of the individual muscles from the right hindlimb of the animals were collected. The other tissues collected were: heart, adipose and spleen. All tissues were weighed and then snap frozen except for the gastrocnemius muscles which were fixed in formalin for histologic analysis.

Summary

Figures 13A, 13B:
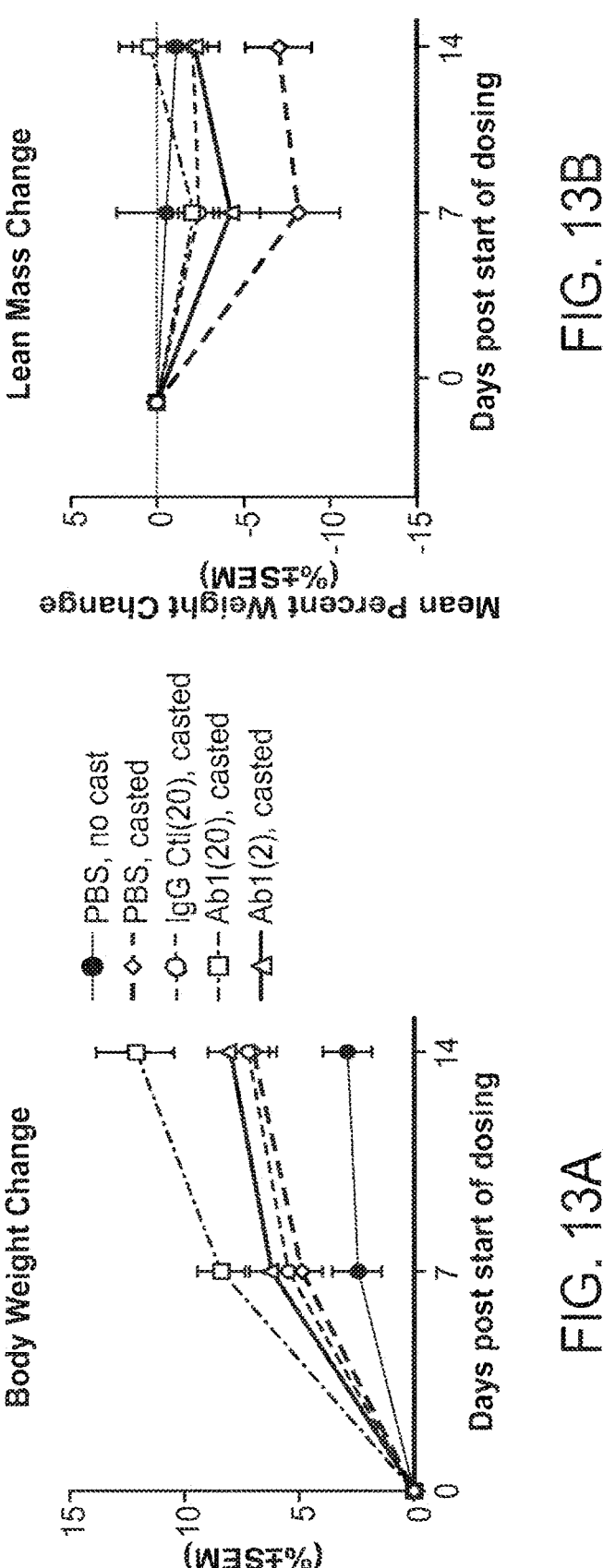
FIGS. 13A-13B show results of an assay evaluating the mean percent body weight and lean mass change.

In this experiment, whether treatment of mice with the anti-myostatin antibody Ab1 could protect mice from disuse muscle atrophy induced by casting of the right hindlimb was tested. During the study, body weight was measured twice weekly and lean mass was measured by QNMR on days –1, 7 and 14. The mean percent weight change and mean percent lean mass change data for animals in the non-diseased control group (group 1) and the groups that were casted for two weeks (groups 5-8) are shown in FIG. 13. Casting of the right hind limb did not have any negative effects on body weight gain (FIG. 13A) and any differences in lean mass of groups were not significant (FIG. 13B).

Figures 14A, 14B:
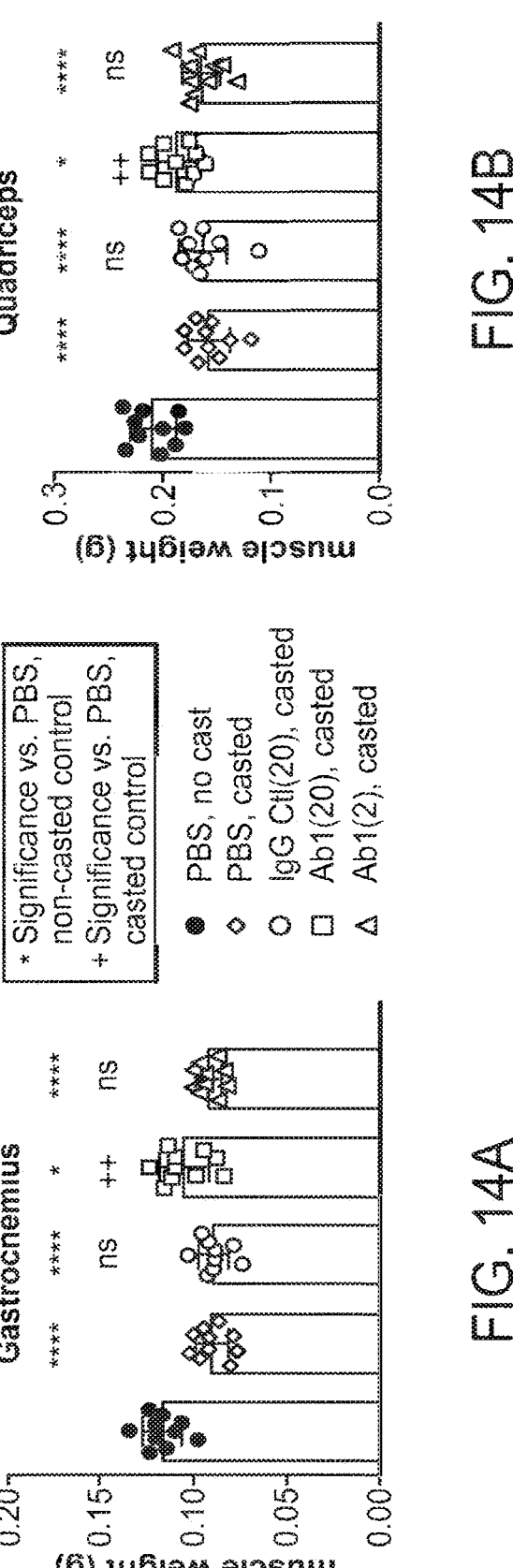
FIGS. 14A-14D show results of an assay evaluating muscle weights.
Figures 14C, 14D:
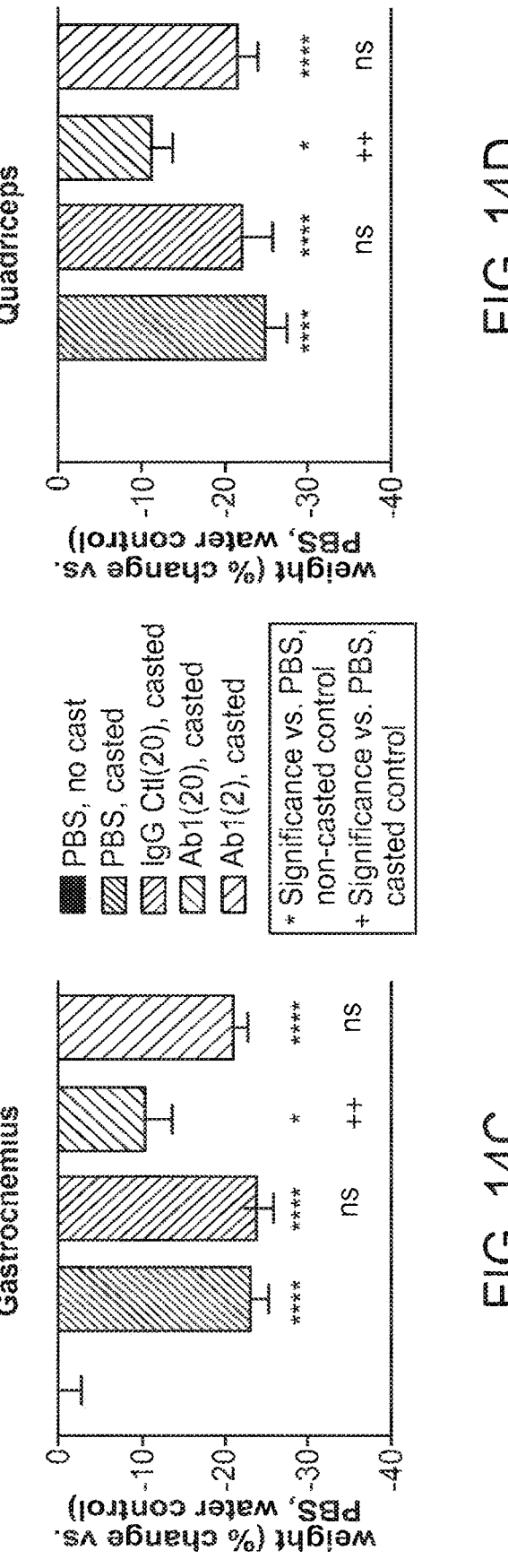

At the end of the two week study individual muscles were dissected and weighed. The weight data for two muscles (gastrocnemius and quadriceps) are plotted in FIGS. 14A-14B). Animals that had their leg casted and also received either PBS or IgG Control antibody showed significant atrophy in gastrocnemius and quadriceps muscles (groups 5 and 6) compared to the non-casted control group (group 1). Animals that were both casted and dosed with Ab1 at 20 mg/kg/wk (group 7), but not 2 mg/kg/wk, showed a significant difference in muscle weights when compared to either of the casted control groups (groups 5 and 6). In addition, casted mice that were treated with the antibody Ab1 at 20 mg/kg/wk (group 7) showed no significant difference in gastrocnemius and quadriceps weights when compared to the non-casted control group (group 1). The mean percent difference in muscle weight of each group compared to the mean muscle weight of the non-casted control group (group 1) is shown in FIGS. 14C-14D. The percent decreases in gastrocnemius mass induced by casting in the PBS and IgG Ct1 groups were 22.8% and 23.5%, respectively. In contrast, casted mice that were treated with 20 mg/kg/wk of Ab only had a 10.0% decrease in gastrocnemius muscle mass. This difference was found to be statistically different from the casted control groups that received PBS and IgG Ct1 antibody (group 5 and 6). The muscle mass decrease for the casted mice treated with 2 mg/kg/wk Ab1 was not statistically different than the decreases for the PBS and IgG control groups (groups 5 and 6). Similar results were seen for the quadriceps muscle (FIG. 14D).

Figure 16B:
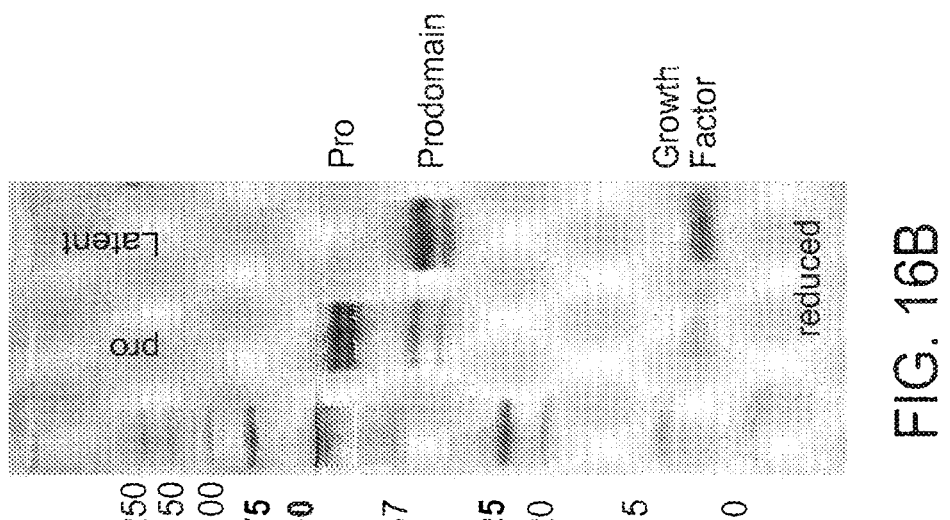
FIGS. 16A-16B show the domain structure and evaluation of Myostatin precursor forms.
Figure 16A:
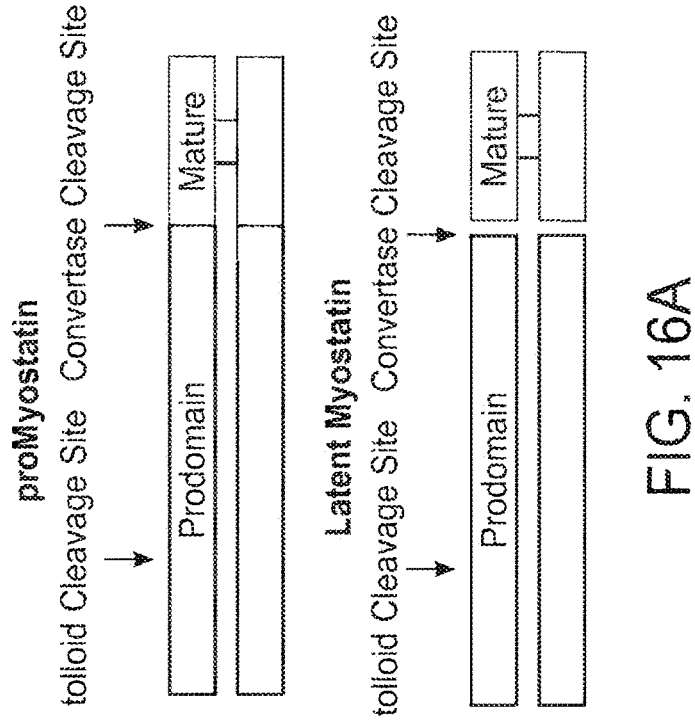

The domain structure of proMyostatin and latent Myostatin, with protease cleavage sites indicated, is shown in FIG. 16A. An example of partially proprotein convertase cleaved proMyostatin run on an SDS PAGE gel is shown in FIG. 16B. Under reducing conditions, the protein bands consisted of the proMyostatin monomer (~50 kD), prodomain (~37 kD) and growth factor (12.5 kD).

Figure 17B:
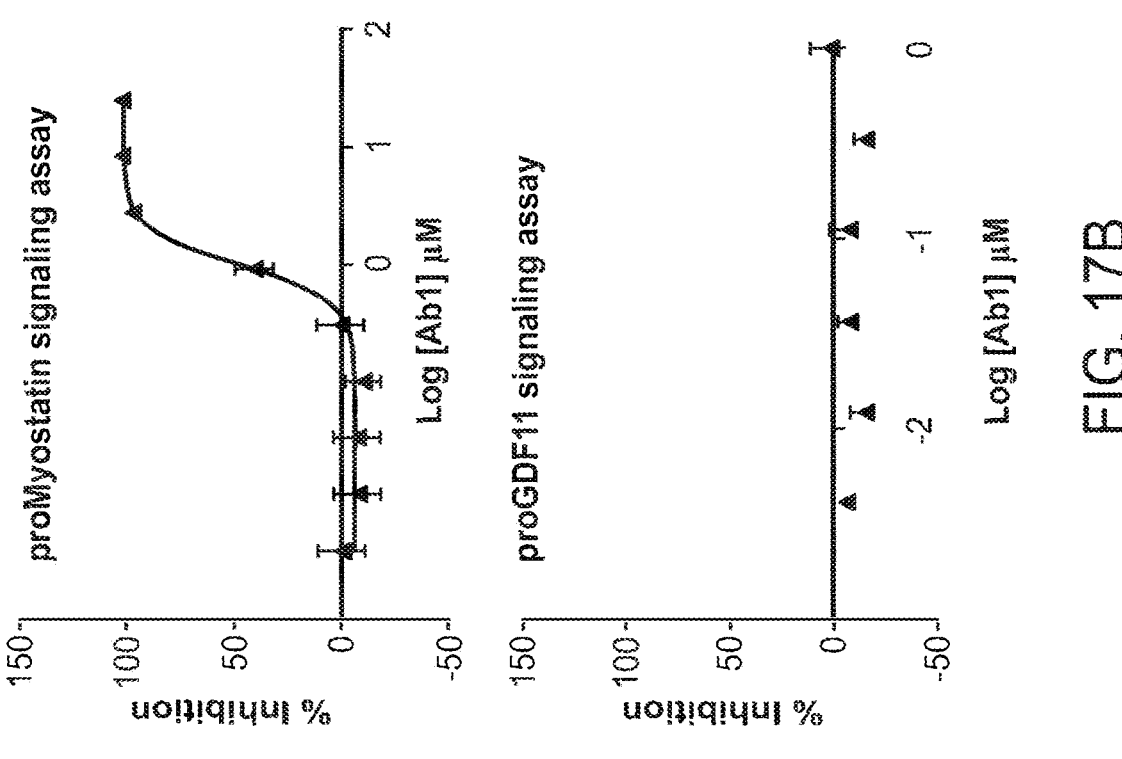
FIGS. 17A-17B show Ab1 is specific for Myostatin.
Figure 17A:
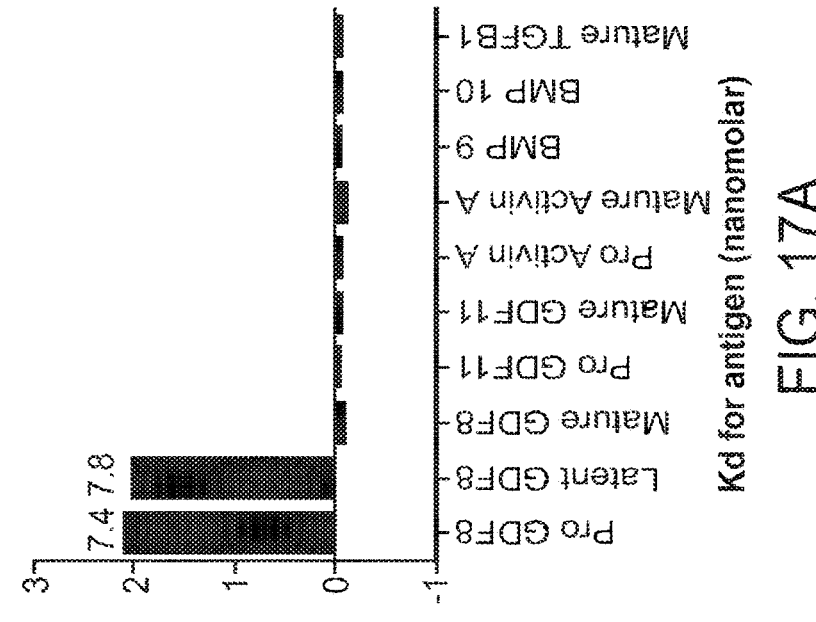

Ab1 binds specifically to proMyostatin and latent Myostatin, with no binding observed to other members of the TGFβ superfamily, most notably the corresponding forms of GDF11 (FIG. 17A). Ab1 was administered at a high concentration (50 ug/mL) to Forte-Bio BLI tips coated with the indicated antigen and the on and off rates were measured to obtain an approximate Kd value. The magnitude of biosensor response, indicating a binding event, is graphically represented by black bars, and the calculated Kd is indicated in orange. Furthermore Ab1 blocks the activation of proMyostatin, but not proGDF11 (FIG. 17B).

SCID Dose Response Study with Ab1, Ab2, Ab4 and Ab6

The previous in vivo studies with Ab1 have demonstrated that Ab1 can increase muscle mass in healthy animals as well as prevent muscle loss in mouse models of muscle atrophy (dexamethasone and casting induced atrophy). Antibody engineering efforts identified three antibodies with in vitro characteristics that were better than Ab1. In this study, in SCID mice, the in vivo activity of these antibodies was compared at three different doses to the already established activity of Ab1.

Fourteen (14) groups of eight (8) female SCID mice received test article administration by intraperitoneal (IP) injection (10 ml/kg) twice per week on Days 0, 3, 7, 10, 14, 17, 21, and 24. The doses of test articles were as follows: Ab1, Ab2, Ab4 and Ab6 were given at 3 different doses (10 mg/kg, 1 mg/kg, and 0.25 mg/kg) and the IgG-Ct1 antibody was given at 10 mg/kg. Treatment groups are described in Table 14. Animals were 10 weeks old at the start of the study. Body weight was measured twice per week throughout the study, corresponding with dosing days. Body mass composition parameters (fat mass, lean mass and water content) were measured by Echo MRI (QNMR) on days 0, 7, 14, 21 and 28. Twenty-eight (28) days after the first dose of antibody, animals were sacrificed via $CO_2$ overdose and blood was collected via cardiac puncture for plasma preparation.

Additionally, various tissues were isolated and weighed. The muscles collected were: gastrocnemius, soleus, tibialis anterior, quadriceps (rectus femoris), extensor digitorum longus, and diaphragm. Muscles were dissected from both the right and left legs of study mice. For analysis the weights of the individual muscles from both legs were combined and the average muscle weight in grams was calculated. The other tissues collected were: heart, kidney, spleen, liver and adipose tissue. All tissues were weighed and then snap frozen except for the left gastrocnemius muscles which was fixed in formalin for histologic analysis.

TABLE 14

| Treatment Group | Test Article dose | # doses per week | Total dose per week | Animal IDs |
|---|---|---|---|---|
| colspan=5 | Treatment groups for dose response model study | | | |
| 1 | PBS Control | 2 | 0 | 1-8 |
| 2 | IgG Control (10 mg/kg) | 2 | 20 mg/kg/wk | 9-16 |
| 3 | Ab1 (10 mg/kg) | 2 | 20 mg/kg/wk | 17-24 |
| 4 | Ab1 (1 mg/kg) | 2 | 2 mg/kg/wk | 25-32 |

TABLE 14-continued

| | Treatment groups for dose response model study | | | |
|---|---|---|---|---|
| Treatment Group | Test Article dose | # doses per week | Total dose per week | Animal IDs |
| 5 | Ab1 (0.25 mg/kg) | 2 | 0.5 mg/kg/wk | 33-40 |
| 6 | Ab2 (10 mg/kg) | 2 | 20 mg/kg/wk | 41-48 |
| 7 | Ab2 (1 mg/kg) | 2 | 2 mg/kg/wk | 49-56 |
| 8 | Ab2 (0.25 mg/kg) | 2 | 0.5 mg/kg/wk | 57-64 |
| 9 | Ab4 (10 mg/kg) | 2 | 20 mg/kg/wk | 65-72 |
| 10 | Ab4 (1 mg/kg) | 2 | 2 mg/kg/wk | 73-80 |
| 11 | Ab4 (0.25 mg/kg) | 2 | 0.5 mg/kg/wk | 81-88 |
| 12 | Ab6 (10 mg/kg) | 2 | 20 mg/kg/wk | 89-96 |
| 13 | Ab6 (1 mg/kg) | 2 | 2 mg/kg/wk | 97-104 |
| 14 | Ab6 (0.25 mg/kg) | 2 | 0.5 mg/kg/wk | 105-112 |

Figure 15:
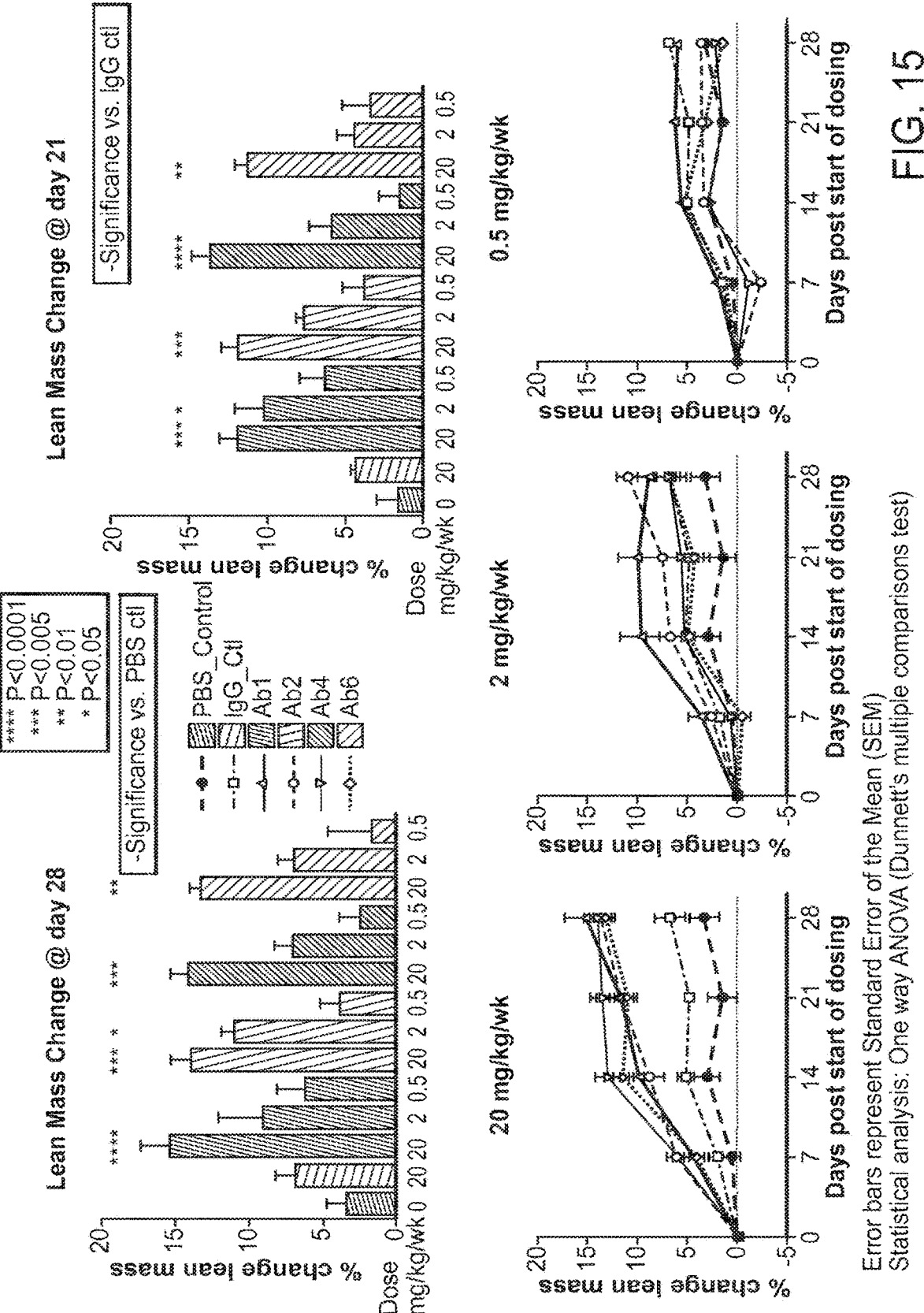
FIG. 15 shows results of an assay evaluating the lean mass change at Day 21 (top right) and Day 28 (top left). It also depicts the percent change in lean mass at three different doses, 20 mg/kg/wk (bottom left), 2 mg/kg/wk (bottom middle), and 0.5 mg/kg/wk (bottom right) of the tested antibodies, PBS control, and IgG control. Statistical evaluation was performed using a one-way ANOVA followed by a Dunnett's multiple comparisons test vs. group 1 (**$p<0.0001$, *$p<0.005$, **$p<0.01$, *$p<0.05$) and vs. the IgG control. For the top two panels, bars from left-to-right are: PBS; IgG Ctrl 20 mg/kg/wk; Ab1 20 mg/kg/wk; Ab1 2 mg/kg/wk; Ab1 0.5 mg/kg/wk; Ab2 20 mg/kg/wk; Ab2 2 mg/kg/wk; Ab2 0.5 mg/kg/wk; Ab4 20 mg/kg/wk; Ab4 2 mg/kg/wk; Ab4 0.5 mg/kg/wk; Ab6 20 mg/kg/wk; Ab6 2 mg/kg/wk; and Ab6 0.5 mg/kg/wk. For the bottom left panel (20 mg/kg/wk), the data points corresponding to day 28 post dosing, from top to bottom, correspond to Ab1, Ab4, Ab2, Ab6, IgG control, and PBS. For the bottom center panel (2 mg/kg/wk), the data points corresponding to day 28 post dosing, from top to bottom, correspond to Ab2, Ab1, Ab6, Ab4, IgG control, and PBS. For the bottom right panel (0.5 mg/kg/wk), the data points, corresponding to day 28 post dosing, from top to bottom, correspond to IgG control Ab1, Ab2, PBS, Ab4, and Ab6.

Mean percent lean mass changes (from day 0) data for animals treated with vehicle (PBS), IgG control, and different doses of Ab1, Ab2, Ab4 and Ab6 are shown in FIG. 15. Animals treated with Ab1, Ab2, Ab4, and Ab6 at a 20 mg/kg/wk dose level had significant increases in lean mass on day 21 and day 28 of the study compared to IgG control and vehicle (PBS) treated animals. Animals treated with Ab1 and Ab2 at a 2 mg/kg/wk dose level also had significant changes in lean mass at day 21 and 28 of the study. There were no significant changes in lean mass from the control groups for animals treated with Ab1, Ab2, Ab4 and Ab6 at a 0.5 mg/kg/wk dose level.

At the end of the study (day 28) muscles were collected and weighed. The weights for quadriceps (rectus femoris) and gastrocnemius muscles are plotted in FIGS. 18A and 18B. Animals treated with Ab1, Ab2, Ab4, and Ab6 at a 20 mg/kg/wk dose level had significant increases in gastrocnemius and quadriceps (rectus femoris) muscle weights compared to vehicle (PBS) treated animals. Animals treated with Ab2 and Ab4 at a 2 mg/kg/wk dose level also had significant changes in gastrocnemius muscle weights. Animals treated with Ab2 at a 2 mg/kg/wk dose level also had significant changes in quadriceps (rectus femoris) muscle weights. There were no significant changes in muscle mass from the control groups for animals treated with Ab1, Ab2, Ab4 and Ab6 at a 0.5 mg/kg/wk dose level. Percent differences in gastrocnemius and quadriceps (rectus femoris) muscle weights (when compared to the vehicle group) of animals treated with different doses of Ab1, Ab2, Ab4 and Ab6 are listed in FIG. 18C.

Duration of Action Study with Ab1 in SCID Mice

The ability of Ab1 to increase lean mass in SCID mice after a single dose and after 3 weekly doses was tested. Seven (7) groups of eight (8) female SCID mice received test article administration by intraperitoneal (IP) injection (10 ml/kg) either once at day 0 (groups 1-4) or once per week on days 0, 7 and 14 (groups 5-7). See Table 15. Antibodies (IgG control, Ab1 and AbMyo) were dosed at 10 mg/kg. Animals were 10 to 11 weeks old at the start of the study. Body weight was measured twice per week throughout the study, corresponding with dosing days. Body mass composition parameters (fat mass, lean mass and water content) were measured by Echo MRI (QNMR) on days 0, 7, 14, and 21.

TABLE 15

| | Treatment groups and dosing frequency. | | |
|---|---|---|---|
| Treatment Group | Test Article | Dose (mg/kg) | Dosing Frequency |
| 1 | PBS Control | 0 | Once |
| 2 | IgG CTL | 10 | Once |
| 3 | Ab1 | 10 | Once |
| 4 | AbMyo | 10 | Once |
| 5 | IgG CTL | 10 | Once Weekly |
| 6 | Ab1 | 10 | Once Weekly |
| 7 | AbMyo | 10 | Once Weekly |

Figure 19:
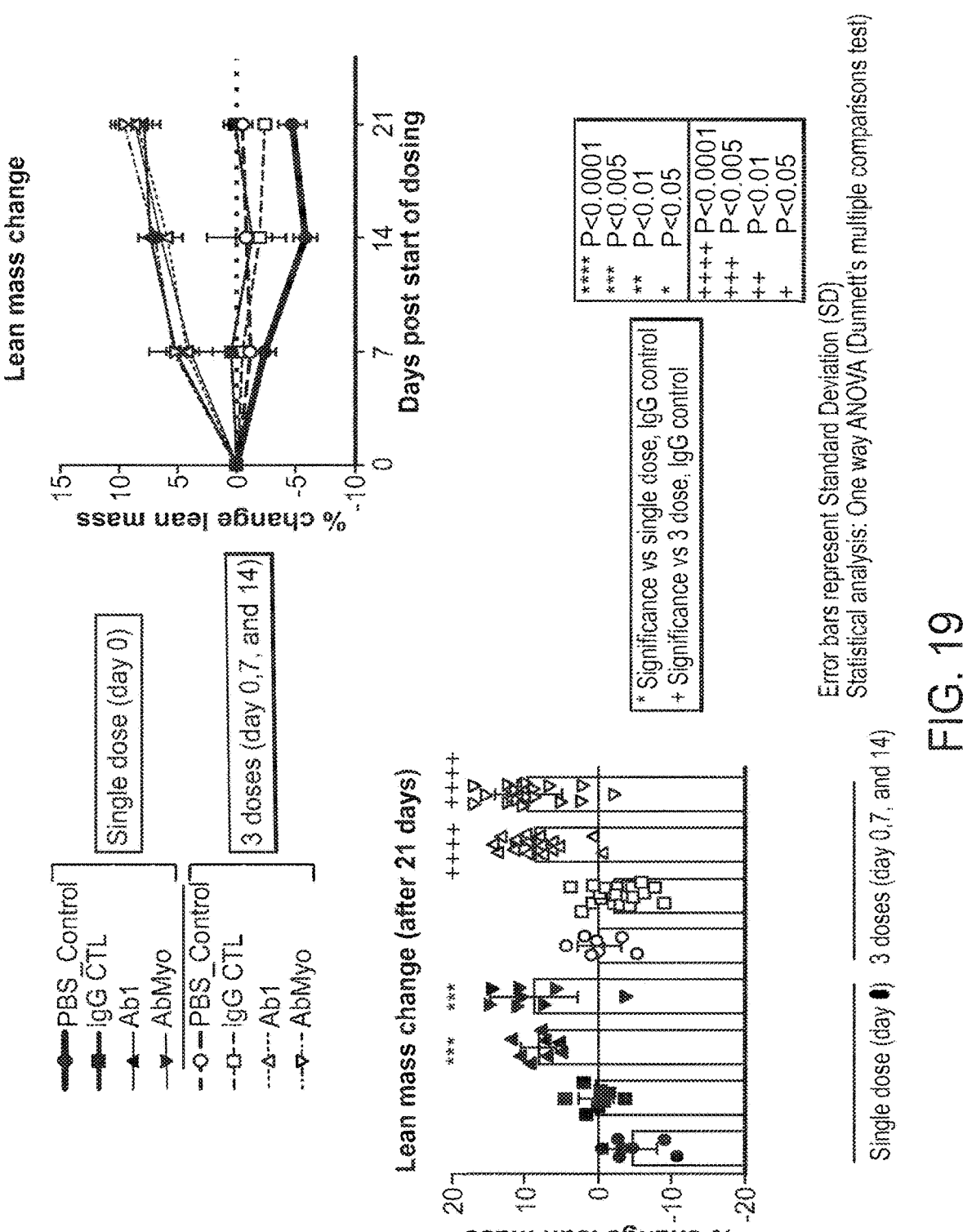
FIG. 19 shows the results of a duration of action study comparing Ab1 to an existing myostatin antibody (AbMyo). PBS was used as a negative control; IgG was used as a positive control. The lean mas change was examined under different dosing protocols after 21 days.

Mean percent lean mass change data for animals treated with vehicle (PBS), IgG control, Ab1, AbMyo are shown in FIG. 19. The data are expressed as change in lean mass from day 0 of the study. At 21 days after a single dose of test article, animals treated with Ab1 (group 3) had significant increases in lean mass (compared to IgG control animals-group 1) that were indistinguishable from the lean mass changes after 3 doses of Ab1 (group 6). These changes in lean mass were also comparable to changes seen in animals treated with a single dose (group 4) or with 3 weekly doses (group 7) of AbMyo.

Example 3: Chemistry/Pharmaceutical Sciences

Ab2 is a humanized monoclonal antibody of the IgG4 subtype with Proline substituted for Serine at position 228. This generates an IgG1-like hinge sequence and minimizes the incomplete formation of inter-chain disulfide bridges which is characteristic of IgG4. The complete amino acid sequence of the heavy and light chains of Ab2 are shown below. The complementarity-determining regions (CDRs) are underlined. Bolded NST sequence: N-linked glycosylation consensus sequence site; Bolded DP sequences are potential cleavage sites; Bolded NX sequences, wherein X can be S, T, or G are potential deamidation sites; Bolded DX sequences, wherein X can be G, S, T, or SDG are potential isomerization sites; Bolded methionines are potential methionine oxidation sites; Bolded Q is an expected N-terminal pyroglutamic acid (FIGS. 21A-21B).

Molecular modeling of Ab1 identified several potential sites of post-translational modifications. Two asparagines in the light chain and seven asparagines in the heavy chain are susceptible to deamidation. Two of these residues are located within CDR regions of the heavy chain.

Native IgG4 mAbs may have incomplete formation of inter-heavy chain disulfide bridges, with the two half molecules (each containing one heavy and one light chain) maintained in the intact antibody structure by noncovalent interactions. IgG4 molecules may be prone to exchange of half-molecules in vitro and in vivo, and the level of half molecules must be consistent across manufacturing batches. The substitution of Ser to Pro in the backbone of the IgG4 structure results in an IgG1-like hinge sequence, thereby enabling the formation of inter-chain disulfide bonds and markedly stabilizing the antibody structure. The integrity and stability of the hinge region is monitored during development with extended characterization, using such assays as non-reducing capillary electrophoresis and quantitation of free sulfhydryls. The potential for chain swapping is monitored in vivo.

US 12,582,712 B2

77
78

Summary

A pro/latent-Myostatin-specific antibody that blocks the activation of proMyostatin and/or latent myostatin is provided herein. Administration of this activation-blocking antibody to healthy mice increases lean body mass and muscle size, with only a single dose needed to sustain the muscle-enhancing effect over a 1 month period. Additionally, antibody administration protects healthy mice from muscle atrophy in two separate models of muscle wasting. The data demonstrate that blocking myostatin activation promotes robust muscle growth and prevents muscle atrophy in vivo, and represents an alternative mechanism for therapeutic interventions of muscle wasting.

Example 4: Analysis of Pro- and Latent-Myostatin in Muscle Atrophy

Western blots were performed to determine the presence of pro and latent Myostatin in muscle tissue and in circulation during muscle atrophy as well as during normal conditions. A standard model of muscle atrophy involves treating mice with 2.5 mg/kg/week Dexamethasone (dosed in drinking water) and muscle and plasma were collected after 2 weeks of treatment. This model regularly leads to 15-25% decrease in muscle mass over the course of treatment. Control muscle and plasma were collected at the same time from mice not treated with Dexamethasone. Rectus femoris, tibialis anterior, and soleus muscles were dissected out, flash frozen in liquid nitrogen, and stored at −80 C until ready to use. Muscle lysates were generated by pulverization, followed by lysis in T-PER buffer supplemented with protease and phosphatase inhibitors. Plasma was collected by standard methods and stored at −80 C.

Figures 25, 26:
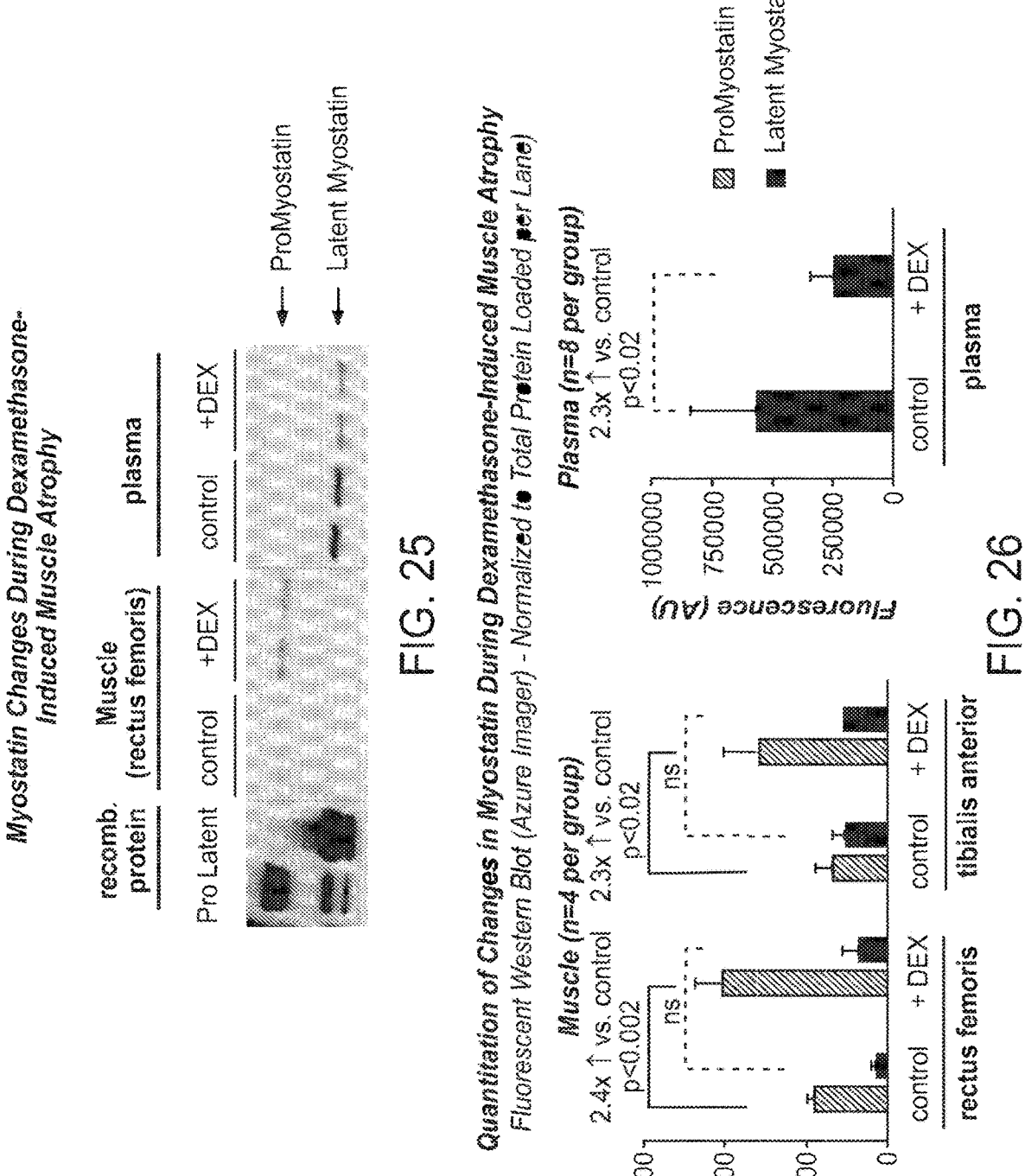
FIG. 25 shows the expression of pro- and latent-Myostatin in muscle and plasma from normal and atrophic mice.
FIG. 26 shows the quantitation of changes in pro and latent Myostatin in muscle and plasma. The bars from left to right show proMyostatin, latent myostatin, proMyostatin, latent myostatin, and latent myostatin.

Multiple samples containing equal concentrations of protein were separated by PAGE gels and Western blotted onto PVDF membrane. For muscle lysates, 10-50 ng total protein was loaded onto the gel. Plasma was diluted 1:10 in PBS and 10 μl of each sample was loaded onto the gel. As size standards, 0.1-1 ng recombinant pro and/or latent Myostatin were also loaded onto the gel. Identification of Myostatin protein was accomplished using an antibody recognizing the prodomain of Myostatin (AF1539, R&D Systems). This analysis shows that proMyostatin is the predominant form in muscle, while the latent Myostatin is the primary form in Plasma (FIG. 25). Furthermore, it was demonstrated that, in mice with muscle atrophy induced by Dexamethasone, proMyostatin is increased in muscle tissue, while latent Myostatin is decreased in plasma.

To confirm these results, the Western blots were repeated using fluorescent labeling and detection (Azure Biosystems). The relative levels of each of the Myostatin forms in plasma and in rectus femoris and tibialis anterior muscles from normal and Dexamethasone-treated mice were quantified. These data confirm the results described above, showing a 2- to 2.5-fold increase in proMyostatin in both muscles, and a 2.3-fold decrease in latent Myostatin in plasma (FIG. 26).

Figure 28A:
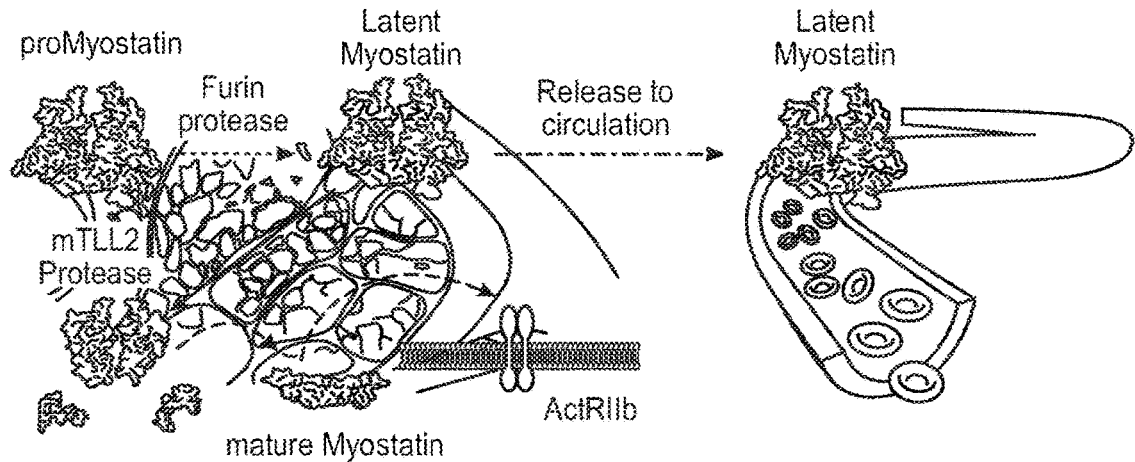
FIGS. 28A-28B provide a model for Myostatin flux in normal and atrophic muscle. In normal muscle (FIG. 28A), proMyostatin is produced in muscle and converted to latent Myostatin through cleavage by Furin protease, which may occur either inside or outside of the cell. Some fraction of the latent Myostatin in muscle is then released into the circulation, forming a circulating pool of latent Myostatin. In muscle atrophy (FIG. 28B), an increase in the active Myostatin growth factor is caused by upregulation of proMyostatin levels in muscle and increased conversion of latent Myostatin to the active growth factor. As a consequence, circulating latent Myostatin is decreased as the muscle pool of latent Myostatin is redirected towards formation of mature Myostatin by mTLL2 cleavage.
Figure 28B:
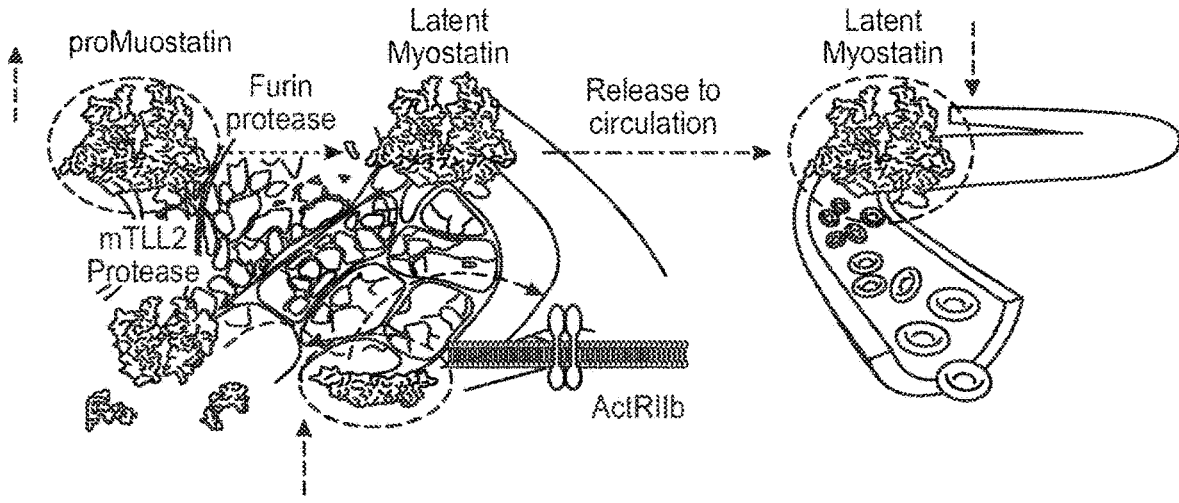

Based on these data, a model for Myostatin "flux" in normal and diseased muscle is given. As demonstrated, in normal muscle (FIG. 28A), proMyostatin is produced in muscle and converted to latent Myostatin through cleavage by Furin protease, which may occur either inside or outside of the cell (Anderson et al., 2008). Some fraction of the latent Myostatin in muscle is then released into the circulation, forming a circulating pool of latent Myostatin. In muscle atrophy, an increase in the active Myostatin growth factor is produced, driving muscle atrophy. This increase is thought to be caused by the upregulation of proMyostatin levels in muscle and the increased conversion of latent Myostatin to the active growth factor (FIG. 28B). The data outlined here directly support the first step of this model, showing increased proMyostatin in muscle. The data also support the second step as decreased muscle mass in Dexamethasone-treated mice was observed, indicating an increased production of mature Myostatin, without a concomitant increase in latent Myostatin in muscle. Accordingly, the level of Myostatin is plasma was decreased, suggesting an increased conversion to mature Myostatin.

Example 5: Immunoprecipitation from Murine Serum and Muscle Tissue

Figure 27:
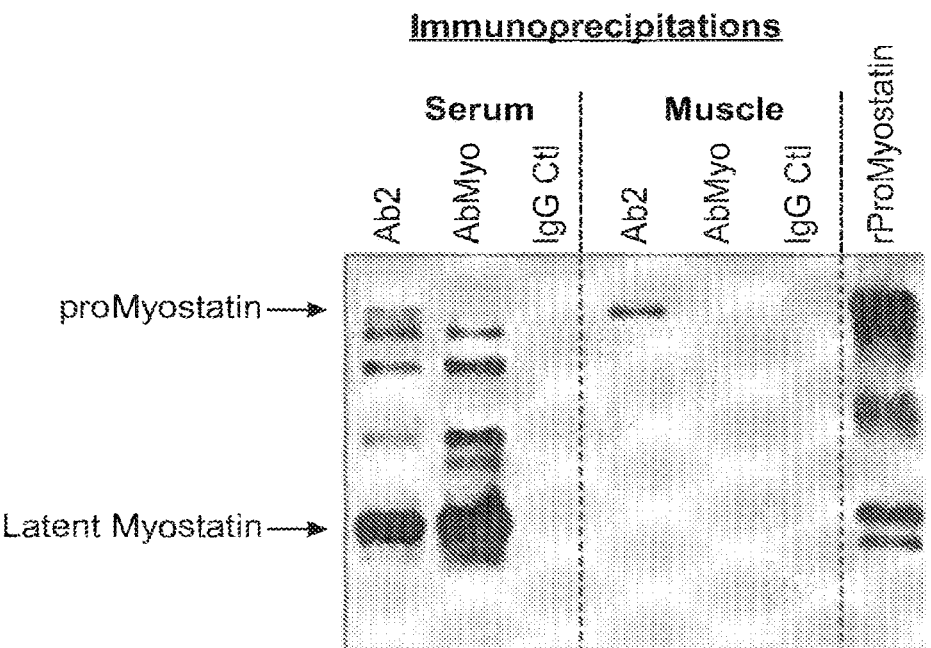
FIG. 27 shows that Ab2 uniquely recognizes proMyostatin and latent Myostatin, binding to the major forms of Myostatin in both serum and muscle. Non-reducing Western blot for prodomain (darker gray) and the mature growth factor (lighter gray). Recombinant proMyostatin (rProMyostatin) shows the migration of proMyostatin and myostatin prodomain (latent myostatin) on the gel, highlighted by arrows. In serum, both Ab2 and AbMyo bind to latent Myostatin (prodomain band) and multiple partially processed precursors, however only Ab2 recognized proMyostatin (top band). In muscle, Ab2 precipitated proMyostatin, with no interaction of AbMyo with proMyostatin in the muscle tissue.

Immunoprecipitations were performed to determine the presence of proMyostatin in circulation, and to investigate the binding of Ab2 and AbMyo to endogenous myostatin precursors in serum and muscle. Ab2 recognizes the major form of Myostatin in muscle. Results shown in FIG. 27 demonstrate that a pool of serum proMyostatin precipitates with Ab2, suggesting that there is extracellular proMyostatin present in vivo. In addition to binding to proMyostatin, latent Myostatin, and other partially processed forms of myostatin in serum, Ab2 immunoprecipitated proMyostatin from muscle extracts. In contrast, AbMyo efficiently bound to latent Myostatin and partially processed precursors in serum, with no detectable interactions with proMyostatin in the muscle. Given that the muscle is the site where myostatin signaling occurs, this could provide important advantages to the Ab2 mechanism of action.

Homogenized muscle lysate was prepared as follows: frozen mouse quadriceps were pulverized using a CryoPrep pulverizer (Covaris, Woburn Mass.). The pulverized muscle was then resuspended to a concentration of 50 mg/mL in M-Per buffer (ThermoFisher Scientific) with 1×Halt™ Protease and Phosphatase Inhibitor Cocktail without EDTA (ThermoFisher Scientific) The tissue was then crushed using a plastic pestle, (Bio-Plas Cat #4030-PB) and homogenized further with repeated pipetting with a cut-off pipette tip. Muscle samples were then incubated 30 minutes at 4C with end-over-end rotation. Finally, samples were centrifuged at 16,100 g for 10 minutes to pellet the insoluble fraction. The soluble fraction was aspirated off and used in downstream experiments.

For immunoprecipitation, Ab2, IgG Ct1, or AbMyo antibodies were covalently conjugated to agarose beads using the Thermo Scientific Pierce™ Co-Immunoprecipitation Kit according to the manufacturer's specifications. 75 ug of each antibody was conjugated to 50 uL of bead slurry, and 30 ug of antibody was utilized in each immunoprecipitation. The immunoprecipitation was performed against 3 mL of pooled normal mouse serum (Bioreclamation) or 1.05 mL of homogenized soluble mouse quadriceps prepared as described above. Antibody conjugated beads and samples were incubated at 4C with end-over-end rocking overnight. After incubation, the beads were recovered by passing the entire sample volume through the spin filters included in the co-immunoprecipitation kit using the QIAvac 24 Plus vacuum manifold. (Qiagen) The beads were then washed 3× with 200 uL of IP lysis/wash buffer, and once with 100 μL of 1× conditioning buffer according to the specifications of the kit. Elutions were performed with 50 μL of elution buffer for five minutes and were then mixed with 5p L of 1M Tris, pH 9.5 in the collection tube.

Myostatin species pulled down by the test antibodies were visualized by Western blotting utilizing AF1539, (R&D systems) ab124721, (Abcam) Alexa Fluor® 680 AffiniPure Donkey Anti-Sheep IgG (H+L), (Jackson ImmunoResearch) and IRDye® 800CW Donkey anti-Rabbit IgG (H+L) (LI-COR Biosciences) Thermo Scientific. SEA BLOCK blocking buffer was utilized for the blocking and primary antibody incubations.

Example 6: Increased Muscle Mass and Altered Myostatin Protein Expression in Rats Treated with Ab2

Study Design

Seven to eight week old female Sprague-Dawley rats were administered a single intravenous dose of either Ab2 (10 mg/kg), a nonfunctional human IgG control antibody (10 mg/kg), or an equivalent volume of phosphate buffered saline (PBS). During the course of the study, serum was collected from 3 rats per group at 4 hours, 48 hours, 7 days, 14 days, 21 days, and 28 days after dosing. Collection was done by standard methods and samples were stored at −80° C. Lean mass was measured by quantitative nuclear magnetic resonance (qNMR) at baseline (prior to day 0 dosing) and on days 7, 14, 21, and 28 (8 rats/group) and skeletal muscles (rectus femoris, tibialis anterior, and soleus) were collected at the end of study (day 28), weighed, and flash frozen in liquid nitrogen for storage at −80° C.

Results

Figure 29:
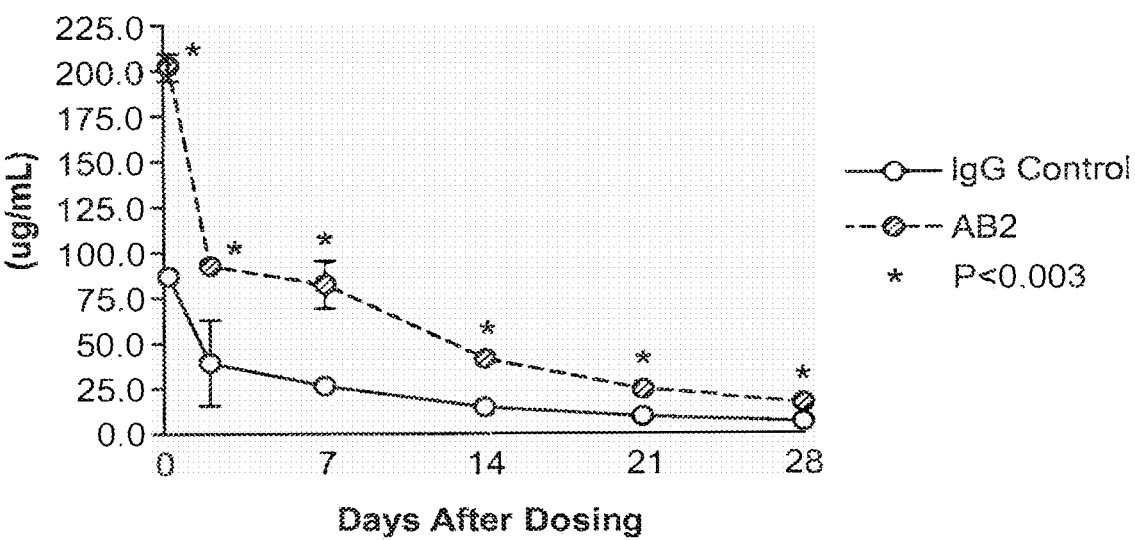
FIG. 29 shows detection of Ab2 (top line) and IgG control (bottom line) antibody in serum from dosed rats. Ab2 exhibits elevated levels in the circulation as compared to the IgG control, with an average of 17.1 μg/ml of Ab2 in serum at the end of the study. Ab2 levels determined by human IgG-specific ELISA with known quantities of each antibody used as a reference standard.

Drug exposure was measured in serum samples using an ELISA specific to human IgG with known quantities of each drug used as a reference standard. As shown in FIG. 29, 4 hours after injection, both Ab2 and the IgG control antibody are detected in rat serum. As the study progresses, Ab2 exhibits elevated circulating drug levels compared to the IgG control, with an average of 17.1 µg/ml drug in serum at the end of the study.

Figure 30A:
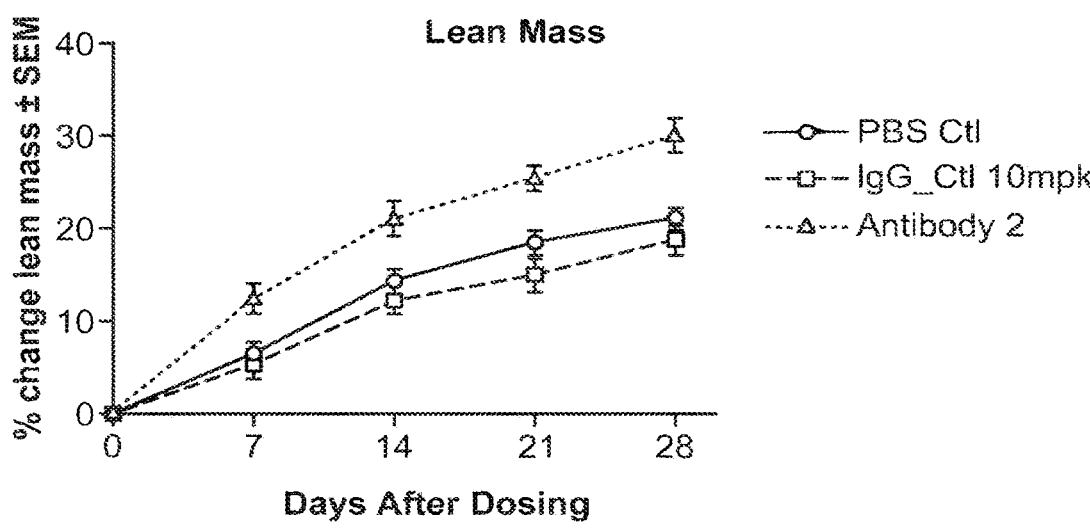
FIGS. 30A-30B shows pharmacodynamic effects of Ab2 in treated rats.
Figure 30B:
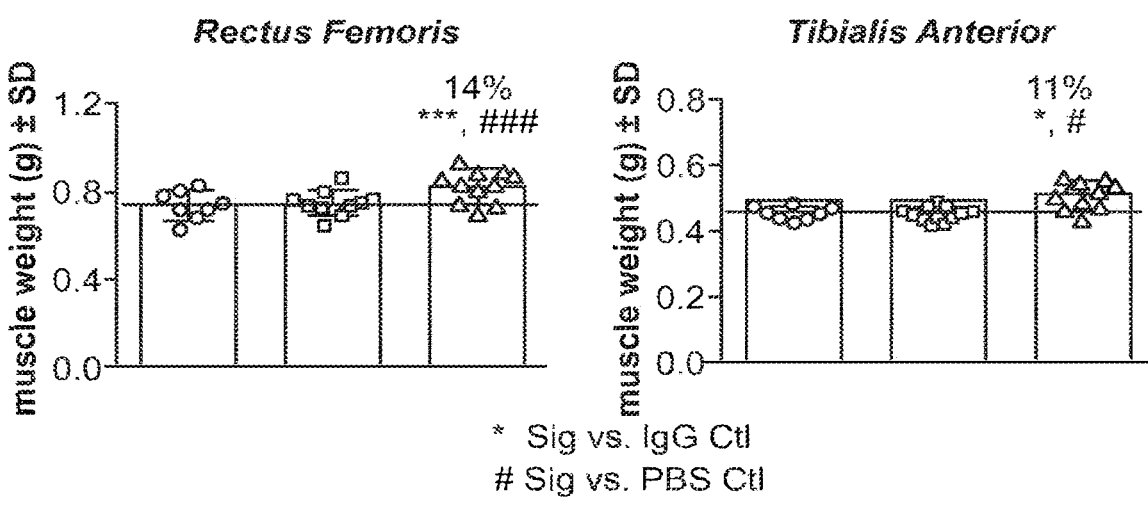

Pharmacodynamic effects of Ab2 treatment were assessed both by measuring lean mass (by qNMR) during the course of the study and by determining the weights of dissected muscle at the end of the study. FIG. 30A shows lean mass measurements during the course of the study, where rats treated with Ab2 demonstrate a clear increase in lean mass compared to rats treated with PBS or with human IgG Control antibody. Muscle mass was measured by collecting and weighing whole skeletal muscles at the end of the study (28 days). As shown in FIG. 30B, rats treated with Ab2 show an increase of 14% and 11% in rectus femoris and tibialis anterior muscle masses, respectively. Together, these data indicate that treatment of rats with a single dose of Ab2 leads to long-lasting increases in muscle mass.

Relative levels of pro and latent Myostatin was determined by quantitative western blotting of muscle lysate or serum samples. Muscle lysates were generated from flash frozen muscle samples by pulverization, followed by lysis in T-PER buffer supplemented with protease and phosphatase inhibitors. After lysis, samples containing equal concentrations of protein were separated by PAGE gels and Western blotted onto low fluorescence PVDF membrane. For muscle lysates, 10-50 ng total protein was loaded onto the gel. Plasma was diluted 1:10 in PBS and 10 µl of each sample loaded onto the gel. As size standards, 0.1-1 ng recombinant pro and/or latent Myostatin were also loaded onto the gel. Identification of Myostatin protein was accomplished using an antibody recognizing the prodomain of latent Myostatin (AF1539, R&D Systems), followed by detection with a fluorescently labeled secondary antibody. For all western blot analyses, a minimum of three samples per group were assayed.

Figure 31A:
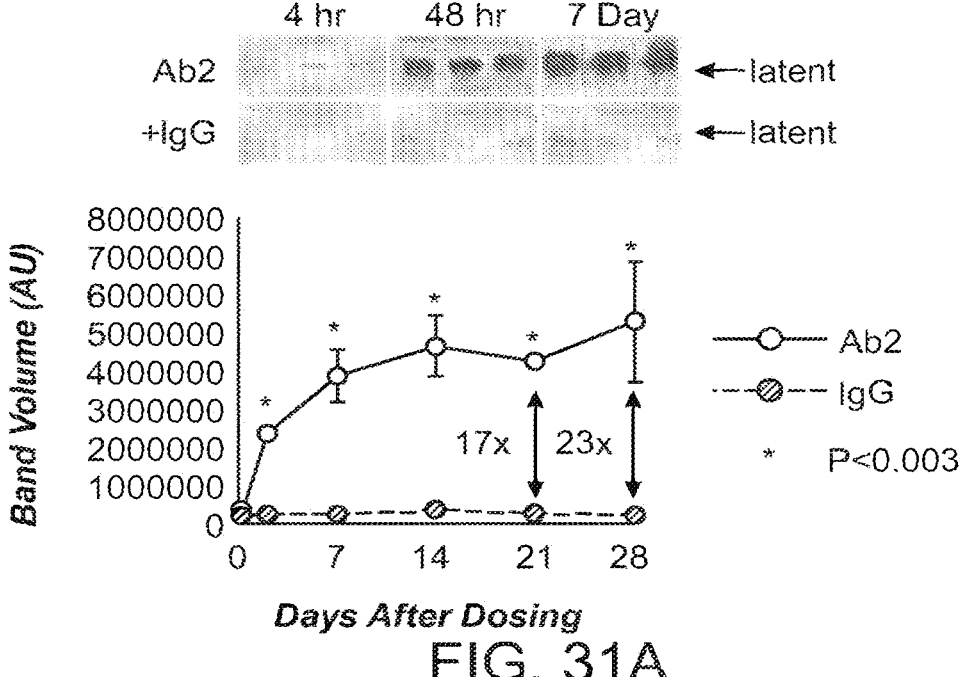
FIGS. 31A-31B shows pro/latent-Myostatin pro/latent-Myostatin levels in Ab2-treated rats.
Figure 31B:
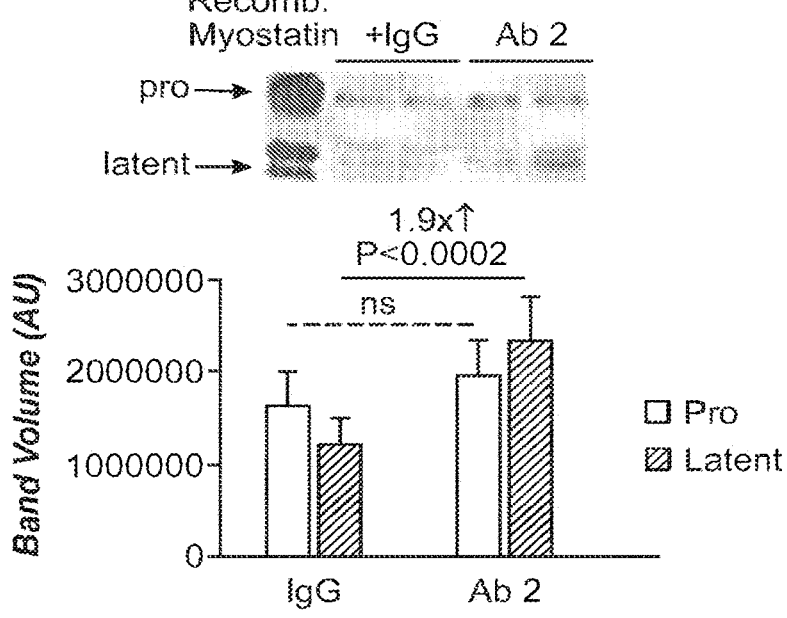

Treatment with Ab2 increases latent myostatin levels in rat serum by ~20-fold (FIG. 31A) compared to IgG control-treated rats. These data are consistent with effects seen with other antibody drugs, reflecting binding of the drug target in circulation. In rat muscle (rectus femoris), Ab2 treatment leads to a 1.9× increase (vs. IgG control-treated rats) in the latent form of Myostatin. No statistically significant change in proMyostatin is observed. These data indicate that Ab2 binds its target, pro/latent Myostatin, and alters Myostatin processing in muscle as well as in circulation. It was also observed that Ab2 treatment increases latent, but not pro-Myostatin in Rat muscle (FIG. 31B).

Example 7: Increased Muscle Mass and Alteration of Myostatin Protein Expression in Mice Treated with Ab2 and Comparison to a Comparator Anti-Myostatin Antibody Study Design Ten week old male SCID mice were administered a single intraperitoneal dose (5 mg/kg) of either Ab2, a nonfunctional human IgG control antibody, or a comparator antibody (AbMyo) that acts by blocking the Myostatin/receptor interaction. During the course of the study, serum and skeletal muscle were collected at 1 hour, 4 hours, 48 hours, 7 days, 14 days, 21 days, 28 days, and 56 days after dosing. Serum collection was done by standard methods and samples were stored at −80° C. Skeletal muscles (rectus femoris, tibialis anterior, and soleus) were collected, weighed, and flash frozen in liquid nitrogen for storage at −80° C. Lean mass was measured by quantitative nuclear magnetic resonance (qNMR) at baseline (prior to day 0 dosing) and weekly throughout the course of the study.

Results

Figure 32:
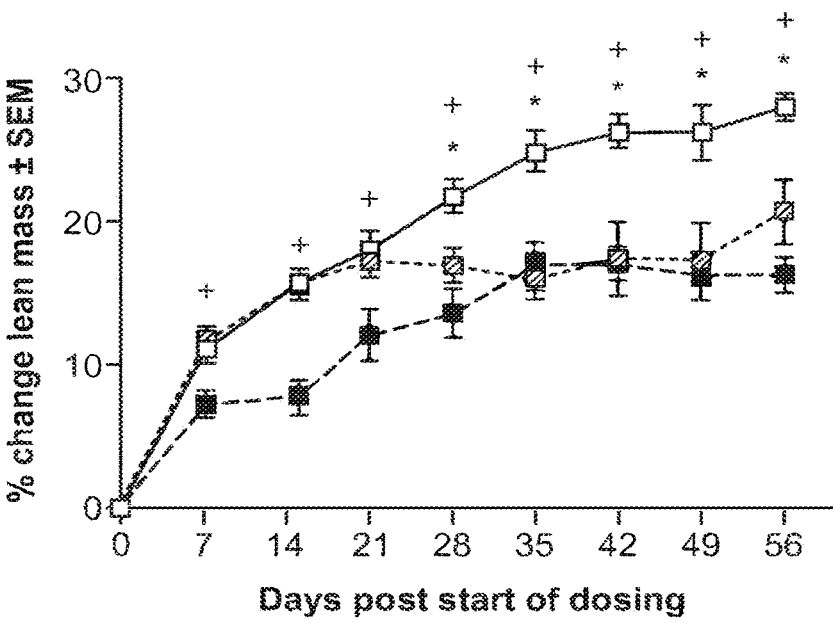
FIG. 32 shows treatment with Ab2 (Ab2) or with the comparator antibody (AbMyo) leads to increased lean mass by as early 7 days after antibody dosing. Increases in lean mass are equivalent for Ab2 and AbMyo until 21 days after dosing. By 28 days after dosing, however, increases in lean mass are lost in the AbMyo-treated group, while increases in the Ab2-treated group are maintained throughout the duration of the study. The top line corresponds to Ab2, the middle line correspond to AbMyo, and the bottom line corresponds to IgG Control (5 mg/kg).

Pharmacodynamic effects of Ab2 treatment were assessed by measuring lean mass (by qNMR) during the course of the study. FIG. 32 shows lean mass measurements during the course of the study, where mice treated with Ab2 demonstrate a clear increase in lean mass compared to mice treated with human IgG Control antibody. For the first three weeks of the study, mice treated with the comparator antibody (AbMyo) show increases in lean mass equivalent to those in the Ab2 group. However, by 28 days after dosing, AbMyo-treated mice do not maintain increased lean mass. In contrast, mice in the Ab2-treated group maintain their increased lean mass throughout the duration of the study (56 days). These data suggest that Ab2 has a longer duration of action that AbMyo.

Figure 33:
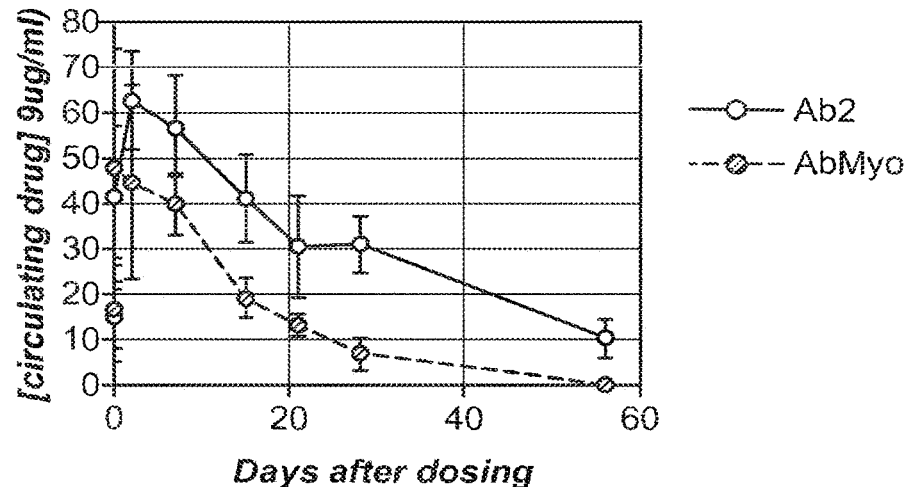
FIG. 33 shows that after a single, 5 mg/kg dose of Ab2 (top line) or of comparator antibody (AbMyo; bottom line), serum levels of drug were measured using an anti-human IgG ELISA. Drug is detected in serum as early as 1 hour after dosing, and levels>1 μg/ml of both antibodies can be detected throughout the study. However, Ab2 exhibits a significantly longer half-life and inferred area under the curve (AUCINF) than AbMyo, suggesting that, at similar doses, Ab2 exhibits significantly greater exposure than AbMyo.

Drug exposure was measured in serum samples using an ELISA specific to human IgG with known quantities of each drug used as a reference standard. As shown in FIG. 33, as early as 1 hour after injection, both Ab2 and the comparator antibody (AbMyo) are detected in serum and levels>1 µg/ml of both antibodies can be detected throughout the study. However, Ab2 exhibits a significantly longer half-life and inferred area under the curve (AUCINF) than AbMyo, suggesting that, at similar doses, Ab2 exhibits significantly greater exposure than AbMyo.

Relative levels of pro and latent Myostatin was determined by quantitative western blotting of muscle lysate or serum samples. Muscle lysates were generated from flash frozen muscle samples by pulverization, followed by lysis in T-PER buffer supplemented with protease and phosphatase inhibitors. After lysis, samples containing equal concentrations of protein were separated by PAGE gels and Western blotted onto low fluorescence PVDF membrane. For muscle lysates, 10-50 ng total protein was loaded onto the gel. Plasma was diluted 1:10 in PBS and 10 μl of each sample loaded onto the gel. As size standards, 0.1-1 ng recombinant pro and/or latent Myostatin were also loaded onto the gel. Identification of Myostatin protein was accomplished using an antibody recognizing the prodomain of latent Myostatin (AF1539, R&D Systems), followed by detection with a fluorescently labeled secondary antibody. For all western blot analyses, a minimum of three samples per group were assayed.

Figure 34:
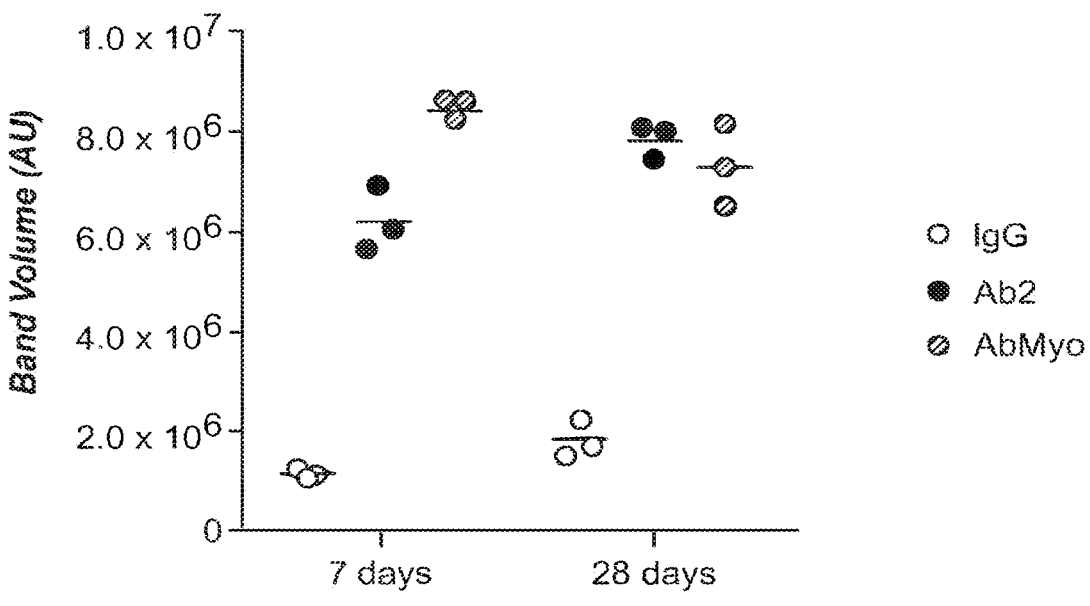
FIG. 34 shows serum Myostatin was measured in drug treated mice and in controls using fluorescent western blotting. Despite the increased serum exposure of Ab2, serum latent Myostatin levels in both Ab2- and AbMyo-treated mice were similar. These data suggest that the circulating levels of free drug are sufficiently in excess to the level of target that the increased serum exposure of Ab2 does not lead to a greater increase in circulating latent Myostatin than is observed in the AbMyo group. Groups of data from left to right correspond to IgG, Ab2, AbMyo, IgG, Ab2, and AbMyo.

Serum Myostatin was measured in drug treated mice and in controls using fluorescent western blotting. Despite the increased serum exposure of Ab2, serum latent Myostatin levels in both Ab2- and AbMyo-treated mice were similar (FIG. 34). These data suggest that the circulating levels of free drug (not bound to target) are sufficiently greater than the level of target, such that the increased serum exposure of Ab2 does not translate to larger increases in circulating latent Myostatin than those observed with AbMyo.

Figure 35A:
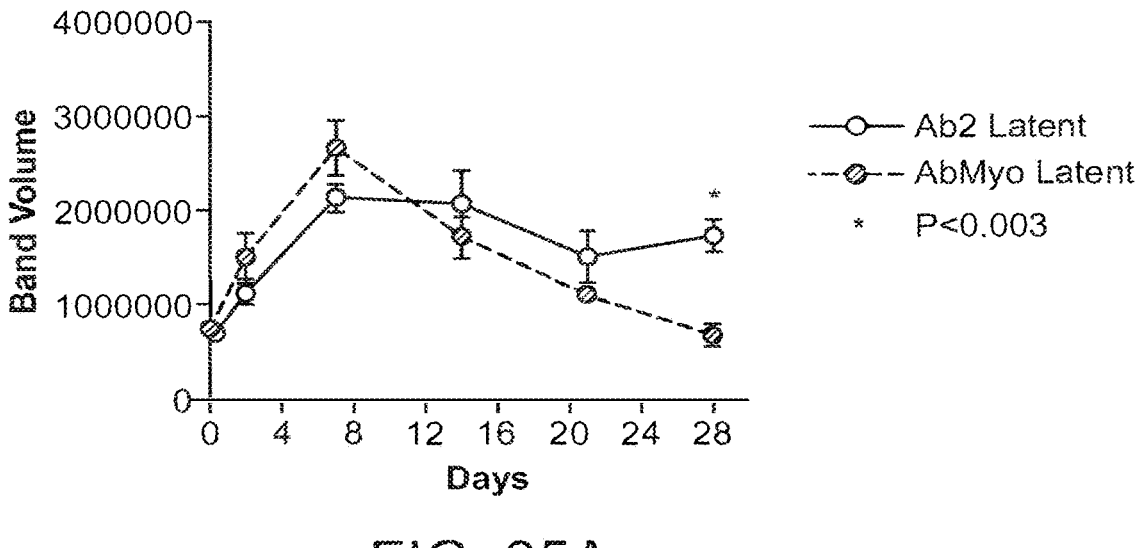
FIGS. 35A-35B shows relative levels of latent and pro-Myostatin were measured in mouse muscle lysates by fluorescent western blot.
Figure 35B:
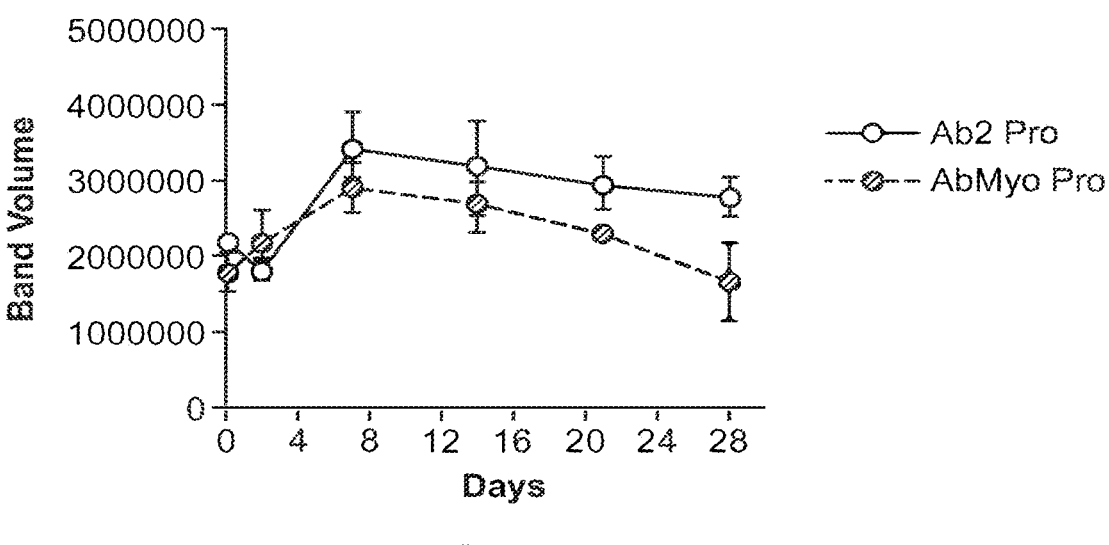

Myostatin levels in muscle (rectus femoris) were also evaluated by fluorescent western blotting. Relative levels of latent and proMyostatin were measured in mouse muscle lysates by fluorescent western blot. Latent Myostatin is elevated in both Ab2 and AbMyo treated muscles (FIG. 35A). However, elevation of latent Myostatin in AbMyo-treated muscles returns to baseline by day 28, while those in Ab2 treated muscles remain elevated until at least this time (P<0.003 vs. AbMyo treatment). A similar trend is observed with proMyostatin (FIG. 35B), though the difference is not statistically significant (P=0.068). These data suggest a longer duration of action of Ab2 at site of drug action, the skeletal muscle.

Example 8: Ab2 Increases Muscle Force Generation

In this Example, the effects of Ab2 on muscle force generation were evaluated. Briefly, male C57BL/6J mice were intraperitoneally administered IgG (20 mg/kg), Ab2 having a constant region of mouse IgG1 isotype (20 mg/kg), or PBS once per week for 4 weeks (n=10 per group).

At study termination, muscles were dissected and weighted, and in vitro muscle performance of the Extensor Digitorum Longus (EDL) muscle was measured in vitro with a 305C muscle lever system (Aurora Scientific Inc., Aurora, CAN) adapted with a horizontal perfusion bath. The muscle was placed in an ice-cold physiological buffered solution and a silk suture tied to the proximal tendon. The muscle was placed in the horizontal bath of the 305C muscle lever system and perfused with physiological buffer oxygenated with 95% $O_2$/5% $CO_2$ and kept at 37° C.

Sutures were tied to a fixed post on one side, and the lever arm on the other. A series of 1 Hz and 100 Hz field stimulations (0.2 ms pulse, 100 ms duration) at 0.01 Hz frequency were delivered via platinum electrodes flanking the muscle to ensure that the sutures are tight and that the maximal developed force is stable. Once stable, direct muscle stimulation—force vs. frequency was measured. Platinum wire electrodes are placed proximal and distal to the muscle belly.

Twitch tension was monitored with a 1 ms pulse and voltage increased until maximal force is achieved. A series of stimulations were then performed at increasing frequency of stimulation (1 ms pulse, 250 ms train duration): 1, 10, 20, 40, 60, 80, 100, 150 Hz, followed by a final stimulation at 1 Hz.

Figures 36A, 36B:
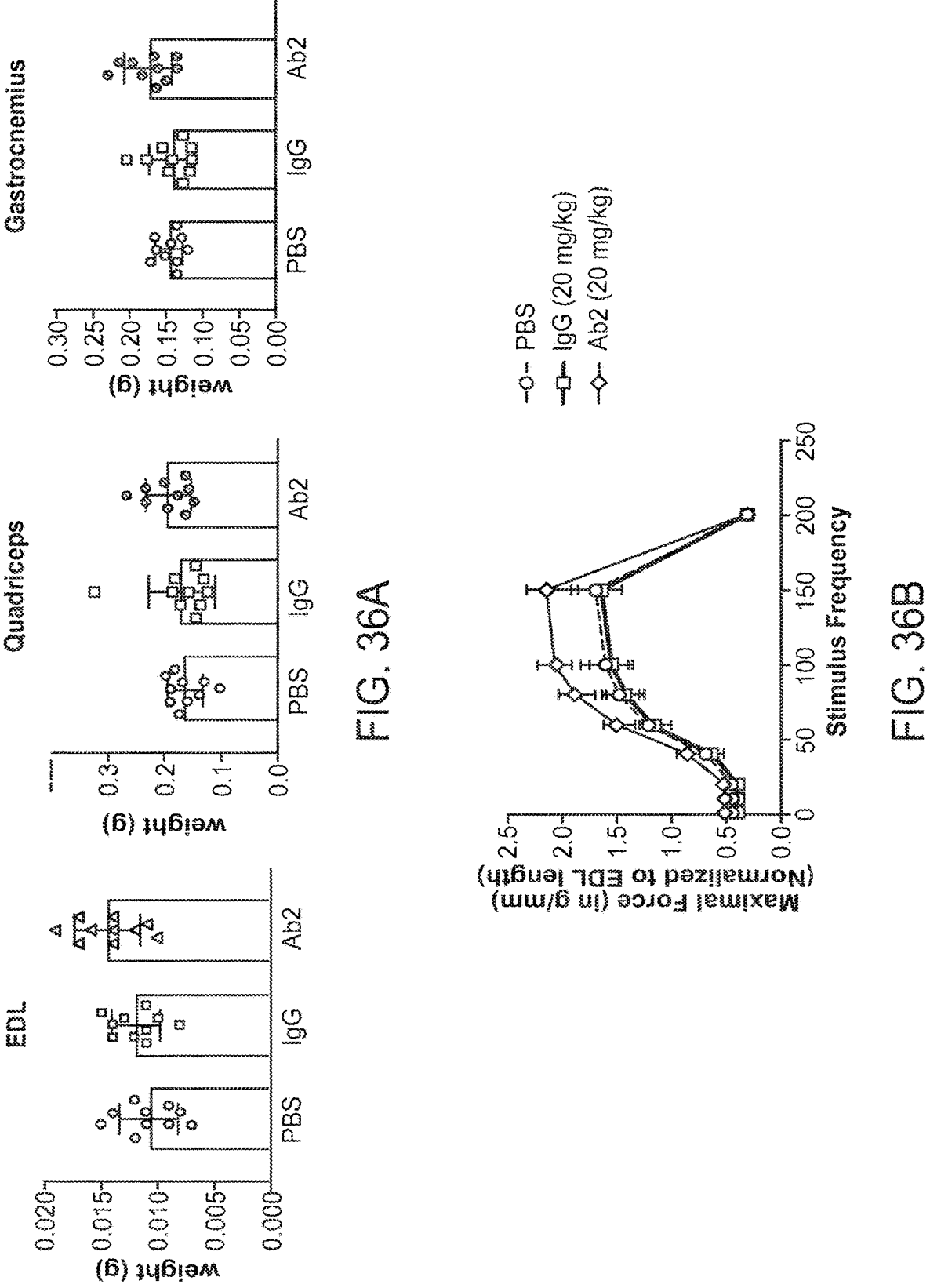
FIG. 36A shows effects of treatment with Ab2 on muscle mass and function in mice.
FIG. 36B shows effects of treatment with Ab2 on maximal force generation in mice.

As depicted in FIG. 36A, following 4 weeks of treatment with Ab2, muscle mass and function was increased. Mean EDL weight increased by 33%, and mean gastrocnemius and quadriceps weights increased by 19%.

As depicted in FIG. 36B, maximal force generation increased by 30% following 4 weekly doses of Ab2.

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used. Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present disclosure.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/ or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

What is claimed is:

1. A method of making an antibody comprising:

(i) culturing a host cell comprising a polynucleotide or polynucleotides encoding an antibody comprising a heavy chain amino acid sequence of SEQ ID NO: 50 and a light chain amino acid sequence of SEQ ID NO: 51 under conditions sufficient to produce the antibody; and (ii) purifying the antibody from the host cell.

2. The method of claim 1, further comprising confirming that the antibody inhibits proteolytic formation of mature myostatin by tolloid protease.

3. The method of claim 1, further comprising confirming that the antibody inhibits proteolytic formation of mature myostatin by tolloid protease with an IC50 of less than 1 μM.

4. The method of claim 1, further comprising formulating the antibody for intravenous administration.

5. The method of claim 1, further comprising formulating the antibody in a concentration suitable for administration at 0.3 to 30 mg/kg.

6. The method of claim 1, further comprising lyophilizing the antibody or formulating the antibody in an aqueous solution.

7. The method of claim 1, further comprising formulating the antibody in a pharmaceutical composition comprising at least one pharmaceutically acceptable carrier, excipient, or stabilizer.

8. The method of claim 7, wherein the at least one pharmaceutically acceptable carrier, excipient, or stabilizer comprises histidine.

\* \* \* \* \*